US011166465B2

(12) United States Patent
von Maltzahn et al.

(10) Patent No.: US 11,166,465 B2
(45) Date of Patent: *Nov. 9, 2021

(54) METHODS OF USE OF SEED-ORIGIN ENDOPHYTE POPULATIONS

(71) Applicant: Indigo Ag, Inc., Boston, MA (US)

(72) Inventors: Geoffrey von Maltzahn, Boston, MA (US); Richard Bailey Flavell, Thousand Oaks, CA (US); Gerardo V. Toledo, Belmont, MA (US); Slavica Djonovic, Malden, MA (US); Luis Miguel Marquez, Belmont, MA (US); David Morris Johnston, Cambridge, MA (US); Yves Alain Millet, Newtonville, MA (US); Jeffrey Lyford, Hollis, NH (US); Alexander Naydich, Cambridge, MA (US); Craig Sadowski, Somerville, MA (US)

(73) Assignee: Indigo Ag, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/657,929

(22) Filed: Oct. 18, 2019

(65) Prior Publication Data

US 2020/0281210 A1 Sep. 10, 2020

Related U.S. Application Data

(63) Continuation of application No. 16/024,029, filed on Jun. 29, 2018, now Pat. No. 10,499,652, which is a continuation of application No. 15/436,592, filed on Feb. 17, 2017, now Pat. No. 10,058,101, which is a continuation of application No. 15/145,687, filed on May 3, 2016, now Pat. No. 9,622,485, which is a continuation of application No. 15/017,531, filed on Feb. 5, 2016, now Pat. No. 9,532,573, which is a continuation of application No. 14/704,891, filed on May 5, 2015, now Pat. No. 9,288,995, which is a continuation of application No. 14/316,469, filed on Jun. 26, 2014, now Pat. No. 9,113,636.

(60) Provisional application No. 61/935,761, filed on Feb. 4, 2014, provisional application No. 61/959,854, filed on Sep. 4, 2013, provisional application No. 61/959,870, filed on Sep. 4, 2013, provisional application No. 61/959,859, filed on Sep. 4, 2013, provisional application No. 61/959,861, filed on Sep. 4, 2013, provisional application No. 61/959,857, filed on Sep. 4, 2013, provisional application No. 61/959,858, filed on Sep. 4, 2013, provisional application No. 61/957,255, filed on Jun. 26, 2013.

(51) Int. Cl.
*A01N 63/20* (2020.01)
*A01N 25/00* (2006.01)
*A01C 1/06* (2006.01)
*G01N 33/50* (2006.01)
*A01C 1/00* (2006.01)

(52) U.S. Cl.
CPC ............... *A01N 63/20* (2020.01); *A01C 1/06* (2013.01); *G01N 33/5097* (2013.01); *A01C 1/00* (2013.01)

(58) Field of Classification Search
None
See application file for complete search history.

(56) References Cited

U.S. PATENT DOCUMENTS

| | | |
|---|---|---|
| 2,200,532 A | 5/1940 | Bond |
| 4,940,834 A | 7/1990 | Hurley et al. |
| 5,041,290 A | 8/1991 | Gindrat et al. |
| 5,113,619 A | 5/1992 | Leps et al. |
| 5,229,291 A | 7/1993 | Nielsen et al. |
| 5,292,507 A | 3/1994 | Charley |
| 5,415,672 A | 5/1995 | Fahey et al. |
| 5,730,973 A | 3/1998 | Morales et al. |
| 5,919,447 A | 7/1999 | Marrone et al. |
| 5,994,117 A | 11/1999 | Bacon et al. |
| 6,072,107 A | 6/2000 | Latch et al. |
| 6,077,505 A | 6/2000 | Parke et al. |
| 6,337,431 B1 | 1/2002 | Tricoli et al. |
| 6,495,133 B1 | 12/2002 | Xue |
| 6,602,500 B1 | 8/2003 | Kharbanda et al. |
| 6,681,186 B1 | 1/2004 | Denisov et al. |
| 6,689,880 B2 | 2/2004 | Chen et al. |
| 6,823,623 B2 | 11/2004 | Minato et al. |
| 7,037,879 B2 | 5/2006 | Imada et al. |

(Continued)

FOREIGN PATENT DOCUMENTS

| | | |
|---|---|---|
| CA | 1041788 A | 11/1978 |
| CA | 1229497 A | 11/1987 |

(Continued)

OTHER PUBLICATIONS

Thomashow, M. F., "So What's New in the Field of Plant Cold Acclimation? Lots!," Plant Physiol., 2001, pp. 89-93, vol. 125.

(Continued)

*Primary Examiner* — Medina A Ibrahim
(74) *Attorney, Agent, or Firm* — Goodwin Procter LLP

(57) ABSTRACT

This application relates to methods and materials for providing a benefit to a seed or seedling of an agricultural plant (e.g., an agricultural grass plant), or the agricultural plant derived from the seed or seedling. For example, this application provides purified bacterial populations that include novel seed-origin bacterial endophytes, and synthetic combinations of seeds and/or seedlings (e.g., cereal seeds and/or seedlings) with heterologous seed-derived bacterial endophytes.

20 Claims, 5 Drawing Sheets

Specification includes a Sequence Listing.

(56) References Cited

U.S. PATENT DOCUMENTS

| | | |
|---|---|---|
| 7,084,331 B2 | 8/2006 | Isawa et al. |
| 7,335,816 B2 | 2/2008 | Kraus et al. |
| 7,341,868 B2 | 3/2008 | Chopade et al. |
| 7,485,451 B2 | 2/2009 | VanderGheynst et al. |
| 7,555,990 B2 | 7/2009 | Beaujot |
| 7,632,985 B2 | 12/2009 | Malven et al. |
| 7,763,420 B2 | 7/2010 | Stritzker et al. |
| 7,906,313 B2 | 3/2011 | Henson et al. |
| 7,977,550 B2 | 7/2011 | West et al. |
| 8,143,045 B2 | 3/2012 | Miasnikov et al. |
| 8,455,198 B2 | 6/2013 | Gao et al. |
| 8,455,395 B2 | 6/2013 | Miller et al. |
| 8,465,963 B2 | 6/2013 | Rolston et al. |
| 8,728,459 B2 | 5/2014 | Isawa et al. |
| 8,975,489 B2 | 3/2015 | Craven |
| 9,049,814 B2 | 6/2015 | Marx et al. |
| 9,113,636 B2 | 8/2015 | von Maltzahn et al. |
| 9,277,751 B2 | 3/2016 | Sword |
| 9,288,995 B2 | 3/2016 | von Maltzahn et al. |
| 9,295,263 B2 | 3/2016 | von Maltzahn et al. |
| 9,364,005 B2 | 6/2016 | Miller et al. |
| 9,408,394 B2 | 8/2016 | von Maltzahn et al. |
| 9,532,572 B2 | 1/2017 | von Maltzahn et al. |
| 9,532,573 B2 | 1/2017 | von Maltzahn et al. |
| 9,545,111 B2 | 1/2017 | Sword |
| 9,622,485 B2 * | 4/2017 | von Maltzahn ........ A01N 63/10 |
| 9,652,840 B1 | 5/2017 | Shriver et al. |
| 9,687,001 B2 | 6/2017 | Vujanovic et al. |
| 9,756,865 B2 | 9/2017 | Sword |
| 10,058,101 B2 * | 8/2018 | von Maltzahn .......... A01C 1/06 |
| 10,076,120 B2 | 9/2018 | von Maltzahn et al. |
| 10,104,862 B2 | 10/2018 | Vujanovic et al. |
| 10,136,646 B2 | 11/2018 | Von Maltzahn et al. |
| 10,212,912 B2 | 2/2019 | Vujanovic et al. |
| 10,306,890 B2 | 6/2019 | Mitter et al. |
| 10,362,787 B2 | 7/2019 | Mitter et al. |
| 10,499,652 B2 * | 12/2019 | von Maltzahn ........ A01N 63/10 |
| 10,499,653 B2 * | 12/2019 | von Maltzahn .......... A01C 1/06 |
| 10,499,654 B2 * | 12/2019 | von Maltzahn .......... A01C 1/06 |
| 2002/0142917 A1 | 10/2002 | Triplett et al. |
| 2005/0070435 A1 | 3/2005 | Chopade et al. |
| 2005/0072047 A1 | 4/2005 | Conkling et al. |
| 2006/0046246 A1 | 3/2006 | Zeng et al. |
| 2006/0178269 A1 | 8/2006 | Medina-Vega |
| 2007/0028318 A1 | 2/2007 | Livore et al. |
| 2007/0055456 A1 | 3/2007 | Raftery et al. |
| 2007/0142226 A1 | 6/2007 | Franco |
| 2007/0292953 A1 | 12/2007 | Mankin et al. |
| 2008/0229441 A1 | 9/2008 | Young et al. |
| 2008/0289060 A1 | 11/2008 | De Beuckeleer et al. |
| 2009/0155214 A1 | 6/2009 | Isawa et al. |
| 2010/0064392 A1 | 3/2010 | Yang et al. |
| 2010/0095396 A1 | 4/2010 | Voeste et al. |
| 2010/0205690 A1 | 8/2010 | Blasing et al. |
| 2010/0227357 A1 | 9/2010 | Redman et al. |
| 2011/0182862 A1 | 7/2011 | Green et al. |
| 2012/0108431 A1 | 5/2012 | Williams et al. |
| 2012/0131696 A1 | 5/2012 | Aayal et al. |
| 2012/0144533 A1 | 6/2012 | Craven |
| 2012/0149571 A1 | 6/2012 | Kloepper et al. |
| 2012/0178624 A1 | 7/2012 | Kaminskyj et al. |
| 2012/0324599 A1 | 12/2012 | Kerns et al. |
| 2013/0031673 A1 | 1/2013 | Grandlic et al. |
| 2013/0071425 A1 | 3/2013 | Vidal et al. |
| 2013/0079225 A1 | 3/2013 | Smith et al. |
| 2013/0150240 A1 | 6/2013 | Newman et al. |
| 2013/0233501 A1 | 9/2013 | Van Zyl et al. |
| 2014/0020136 A1 | 1/2014 | Van Der Wolf et al. |
| 2014/0109249 A1 | 4/2014 | Turner et al. |
| 2014/0115731 A1 | 4/2014 | Turner et al. |
| 2014/0147425 A1 | 5/2014 | Henn et al. |
| 2014/0342905 A1 | 11/2014 | Bullis et al. |
| 2015/0020239 A1 | 1/2015 | von Maltzahn et al. |
| 2015/0033420 A1 | 1/2015 | Rodriguez et al. |
| 2015/0126365 A1 | 5/2015 | Sword |
| 2015/0230478 A1 | 8/2015 | Vujanovic et al. |
| 2015/0242970 A1 | 8/2015 | Avey et al. |
| 2015/0320050 A1 | 11/2015 | von Maltzahn et al. |
| 2015/0335029 A1 | 11/2015 | Mitter et al. |
| 2015/0366217 A1 | 12/2015 | Vujanovic et al. |
| 2015/0368607 A1 | 12/2015 | Arnold et al. |
| 2015/0370935 A1 | 12/2015 | Starr |
| 2015/0373993 A1 | 12/2015 | von Maltzahn et al. |
| 2016/0021891 A1 | 1/2016 | von Maltzahn et al. |
| 2016/0150796 A1 | 6/2016 | von Maltzahn et al. |
| 2016/0174570 A1 | 6/2016 | Vujanovic et al. |
| 2016/0192662 A1 | 7/2016 | Sword |
| 2016/0205947 A1 | 7/2016 | Sword |
| 2016/0235074 A1 | 8/2016 | von Maltzahn et al. |
| 2016/0255844 A1 | 9/2016 | Mitter et al. |
| 2016/0260021 A1 | 9/2016 | Marek |
| 2016/0286821 A1 | 10/2016 | Sword |
| 2016/0290918 A1 | 10/2016 | Xu et al. |
| 2016/0316760 A1 | 11/2016 | Ambrose et al. |
| 2016/0316763 A1 | 11/2016 | Sword |
| 2016/0330976 A1 | 11/2016 | Mitter et al. |
| 2016/0338360 A1 | 11/2016 | Mitter et al. |
| 2016/0366892 A1 | 12/2016 | Ambrose et al. |
| 2017/0020138 A1 | 1/2017 | Von Maltzahn et al. |
| 2017/0164619 A1 | 6/2017 | von Maltzahn et al. |
| 2017/0164620 A1 | 6/2017 | von Maltzahn et al. |
| 2017/0215358 A1 | 8/2017 | Franco et al. |
| 2017/0223967 A1 | 8/2017 | Mitter et al. |
| 2018/0020677 A1 | 1/2018 | Ambrose et al. |
| 2018/0092365 A1 | 4/2018 | Sword |
| 2018/0153174 A1 | 6/2018 | Riley et al. |
| 2018/0177196 A1 | 6/2018 | Sword |
| 2018/0213800 A1 | 8/2018 | Djonovic et al. |
| 2018/0249716 A1 | 9/2018 | Riley |
| 2018/0251776 A1 | 9/2018 | Riley |

FOREIGN PATENT DOCUMENTS

| | | |
|---|---|---|
| CA | 2562175 A1 | 4/2008 |
| CA | 2916678 A1 | 12/2014 |
| CA | 2960032 A1 | 3/2015 |
| CA | 2935218 A1 | 7/2015 |
| CA | 2953466 A1 | 12/2015 |
| CA | 2953697 A1 | 12/2015 |
| CN | 1604732 A | 4/2005 |
| CN | 1948459 A | 4/2007 |
| CN | 101311262 A | 11/2008 |
| CN | 101423810 A | 5/2009 |
| CN | 101570738 A | 11/2009 |
| CN | 101693881 A | 4/2010 |
| CN | 102010835 A | 4/2011 |
| CN | 102123596 A | 7/2011 |
| CN | 102168022 A | 8/2011 |
| CN | 102352327 A | 2/2012 |
| CN | 102533601 A | 7/2012 |
| CN | 103642725 A | 3/2014 |
| CN | 104250616 A | 12/2014 |
| CN | 104388356 A | 3/2015 |
| CN | 104560742 A | 4/2015 |
| EP | 0192342 A2 | 8/1986 |
| EP | 0223662 A1 | 5/1987 |
| EP | 0378000 A2 | 7/1990 |
| EP | 0494802 A1 | 7/1992 |
| EP | 0818135 A1 | 1/1998 |
| EP | 1621632 A1 | 2/2006 |
| EP | 1935245 A1 | 6/2008 |
| EP | 2676536 A1 | 12/2013 |
| JP | 2003300804 A | 10/2003 |
| JP | 2009/072168 A | 4/2009 |
| KR | 20050039979 | 5/2005 |
| KR | 20100114806 A | 10/2010 |
| KR | 101066283 | 9/2011 |
| KR | 101091151 B1 | 12/2011 |
| KR | 20130023491 A | 3/2013 |
| RU | 2043028 C1 | 9/1995 |
| WO | 1988/009114 | 1/1988 |
| WO | 1994/016076 | 7/1994 |
| WO | 2000/029607 A1 | 5/2000 |
| WO | 2001/083697 A2 | 11/2001 |

(56) References Cited

FOREIGN PATENT DOCUMENTS

| | | |
|---|---|---|
| WO | 2001/083818 A2 | 11/2001 |
| WO | 2002/065836 A2 | 8/2002 |
| WO | 2004/046357 A1 | 6/2004 |
| WO | 2005/003328 A1 | 1/2005 |
| WO | 2007/021200 A1 | 2/2007 |
| WO | 2007/107000 A1 | 9/2007 |
| WO | 2008/103422 A2 | 8/2008 |
| WO | 2009/012480 A2 | 1/2009 |
| WO | 2009/078710 A1 | 6/2009 |
| WO | 2009/126473 A1 | 10/2009 |
| WO | 2010/109436 A1 | 9/2010 |
| WO | 2010/115156 A2 | 10/2010 |
| WO | 2011/001127 A1 | 1/2011 |
| WO | 2011/011627 A1 | 1/2011 |
| WO | 2011/082455 A1 | 7/2011 |
| WO | 2011/112781 A2 | 9/2011 |
| WO | 2011/117351 A1 | 9/2011 |
| WO | 2012/034996 A1 | 3/2012 |
| WO | 2013/016361 A2 | 1/2013 |
| WO | 2013/029112 A1 | 3/2013 |
| WO | 2013/090628 A1 | 6/2013 |
| WO | 2013/122473 A1 | 8/2013 |
| WO | 2013/177615 A1 | 12/2013 |
| WO | 2013/190082 A1 | 12/2013 |
| WO | 2014/046553 A1 | 3/2014 |
| WO | 2014/082950 A1 | 6/2014 |
| WO | 2014/121366 A1 | 8/2014 |
| WO | 2014/206953 A1 | 12/2014 |
| WO | 2014/210372 A1 | 12/2014 |
| WO | 2015/035099 A1 | 3/2015 |
| WO | 2015/069938 A1 | 5/2015 |
| WO | 2015/100431 A2 | 7/2015 |
| WO | 2015/100432 A2 | 7/2015 |
| WO | 2015/192172 A1 | 12/2015 |
| WO | 2015/200852 A2 | 12/2015 |
| WO | 2015/200902 A2 | 12/2015 |
| WO | 2016/057991 A1 | 4/2016 |
| WO | 2016/090212 A1 | 6/2016 |
| WO | 2016/109758 A2 | 7/2016 |
| WO | 2016/179046 A1 | 11/2016 |
| WO | 2016/179047 A1 | 11/2016 |
| WO | 2016/200987 A1 | 12/2016 |
| WO | 2018102733 A1 | 6/2018 |
| WO | 2018160244 A1 | 9/2018 |
| WO | 2018160245 A1 | 9/2018 |

OTHER PUBLICATIONS

Tokala, R. T., et al., "Novel Plant-Microbe Rhizosphere Interaction Involving Streptomyces Lydicus WYEC108 and the Pea Plant (*Pisum sativum*)," Applied and Environmental Microbiology, May 2002, pp. 2161-2171, vol. 68, No. 5.

Trichoderma definition, 2016, 6 Pages, [online] [Retrieved on Sep. 16, 2016,] Retrieved from the Internet <URL: https://en.wikipedia.org/wiki/Trichoderma>.

Trotel-Aziz, P., et al., "Characterization of New Bacterial Biocontrol Agents *Acinetobacter, Bacillus, Pantoea* and *Pseudomonas* spp. Mediating Grapevine Resistance Against Botrytis cinerea," Environmental and Experimental Botany, 2008, pp. 21-32, vol. 64.

Truyens, S., et al., "Changes in the Population of Seed Bacteria of Transgenerationally Cd-Exposed *Arabidopsis thaliana*," Plant Biol., 2013, pp. 971-981, vol. 15.

Usadel, B., et al., "The Plant Transcriptome-From Integrating Observations to Models," Front Plant Sci., 2013, pp. 1-3, vol. 4., Article 48, 3 Pages.

Vacheron, J., et al., "Plant Growth-Promoting Rhizobacteria and Root System Functioning," Frontiers Plant Sci., 2013, vol. 4, Article 356, 19 Pages.

Valencia, C. U., et al., "Endophytic Establishment as an Unintended Consequence of Biocontrol with Fungal Entomopathogens," Power Point Presentation dated Jan. 7, 2013, 10 Pages.

Van Der Lelie, D., et al., "Poplar and its Bacterial Endophytes: Coexistence and Harmony," Critical Rev Plant Sci., 2009, pp. 346-358, vol. 28.

Verkley, G., et al., "Paraconiothyrium, a new genus to accommodate the mycoparasite *Coniothyrium minitans*, anamorphs of Paraphaeosphaeria, and four new species," Studies in Mycology, 2004,; pp. 323-335, vol. 50.

Vining K., et al., "Methylome Reorganization During in vitro Dedifferentiation and Regeneration of Populus trichocarpa," BMC Plant Biol., 2013, vol. 13, No. 92, 15 Pages.

Viruel, E., et al., "Pseudomonas thiveralensis Strain IEHa 16S Ribosomal RNA Gene, Partial Sequence," NCBI GenBankAccession No. GQ169380.1, Submitted May 15, 2009, 1 Page.

Visagie, C.M., et al., "Identification and nomenclature of the genus *Penicillium*," Studies in Mycology, Jun. 2014, pp. 343-371, vol. 78.

Waller, F., et al., "The Endophytic Fungus *Piriformospora indica* Reprograms Barley to Salt—Stress Tolerance, Disease Resistance, and Higher Yield," PNAS, 2005, pp. 13386-13391, vol. 102, No. 38.

Wang, B., et al., "Fungal endophytes of native *Gossypium* species in Australia," Mycological Research, 2007, pp. 347-354, vol. 111, No. 3.

Wang, K., et al., "Monitoring in Planta Bacterial Infection at Both Cellular and Whole-Plant Levels Using the Green Fluorescent Protein Variant GFPuv," New Phytol., 2007, pp. 212-223, vol. 174.

Wang, Q., et al., "Naive Bayesian Classifier for Rapid Assignment of rRNA Sequences into the New Bacterial Taxonomy," Appl. Environ. Microbiol., 2007, pp. 5261-5267, vol. 73, No. 16.

Waqas, M., et al., "Endophytic Fungi Produce Gibberellins and Indoleacetic Acid and Promotes Host-Plant Growth during Stress," Molecules, 2012, pp. 10754-10773, vol. 17.

Weindling, R., "Relation of dosage to control of cotton seedling diseases by seed treatment," Plant Disease Reporter, 1943, 27, pp. 68-70.

White, J. F., et al., "A Proposed Mechanism for Nitrogen Acquisition by Grass Seedlings Through Oxidation of Symbiotic Bacteria," Symbiosis, 2012, pp. 161-171, vol. 57.

Wiegand, I., et al., "Agar and Broth Dilution Methods to Determine the Minimal Inhibitory Concentration (MIC) of AntiMicrobiol Substances," Nature Protocols, 2008, pp. 163-175, vol. 3, No. 2.

Xu, M., et al., "Bacterial Community Compositions of Tomato (*Lycopersicum esculentum* Mill.) Seeds and Plant Growth Promoting Activity of ACC Deaminase Producing Bacillus subtilis (HYT-12-1) on Tomato Seedlings" World J Microbiol Biotechnol., 2014, pp. 835-845, vol. 30.

Xu, Y., et al., "Biosynthesis of the Cyclooligomer Despipeptide bassianolide, an Insecticidal Virulence Factor of Eleauveria bassiana," Fungal Genetics and Biology, 2009, pp. 353-364, vol. 46.

Yandigeri, M. S., et al., "Drought-tolerant endophytic actinobacteria promote growth of wheat (*Triticum aestivum*) under water stress conditions," Plant Growth Regulation, 2012, pp. 411-420, vol. 68.

Yezerski, A., et al., "The Effects of the Presence of Stored Product Pests on the Microfauna of a Flour Community," Journal of Applied Microbiology, 2005, pp. 507-515, vol. 98.

Zhang, J., et al. "Isolation and Characterization of Plant Growth-Promoting Rhizobacteria from Wheat Roots by Nheat Germ Agglutinin Labeled with Fluorescein Isothiocyanate", The Journal of Microbiology, Apr. 27, 2012, vol. 50, No. 2, pp. 191-198, GenBank Accession No. JN210900.

Zhao, J.H., et al., "Bioactive secondary metabolites from *Nigrospora* sp. LLGLM003, an endophytic fungus of the medicinal plant *Moringa oleifera* Lam." World Journal of Microbiology and Biotechnology, Kluwer Academic Publishers, Feb. 12, 2012, pp. 2107-2112, vol. 28, No. 5.

Zhou, W., et al., "Effects of the Fungal Endophyte *Paecilomyces* sp. in Cotton on the Roo-Knot Nematode Meloidogyne incognita," poster dated Jan. 7, 2013.

Zimmerman, N.B., et al., "Fungal Endophyte Communities Reflect Environmental Structuring Across a Hawaiian Landscape," Proc Natl Acad Sci USA, 2012, pp. 13022-13027, vol. 109, No. 32.

Zuniga, A., et al., "Quorum Sensing and Indole-3-Acetic Acid Degradation Play a Role in Colonization and Plant Growth Promotion of *Arabidopsis thaliana* by Burkholderia phytofirmans PsJN," Mol Plant Microbe Interact., 2013, pp. 546-553, vol. 26, No. 5.

(56) References Cited

OTHER PUBLICATIONS

Abello, J., et al., "Agrobacterium-mediated transformation of the endophytic fungus *Acremonium implicatum* associated with Brachiaria grasses", Mycological Research, pp. 407-413, vol. 112, Pt 3.

Antony-Badu, S., et al., "Multiple *Streptomyces* species with distinct secondary metabolomes have identical 16S rRNA gene sequences." Scientific Reports 7.1, Sep. 2017, No. 7, 11089, pp. 1-8.

Bandara, WM.M.S., et al., "Interactions among endophytic bacteria and fungi: effects and potentials" Journal of Biosciences, Dec. 2006, vol. 31, No. 5, pp. 645-650.

Bragantia, et al, "Identificaqao E Avaliaqao De Rizobacterias Isoladas De Raizes De Milho," Jan. 1, 2010, pp. 905-911, Retrieved from the Internet: URL:http://www.scielo.br/pdf/brag/v69n4/v69n4a17.pdf (With English Abstract).

De Medeiros, L., et al., "Evaluation of Herbicidal Potential of Depsides from *Cladosporium uredinicola* an Endophytic Fungus found in Guava Fruit," J. Braz. Chem. Soc., 2012, vol. 23, No. 8, p. 1551-1557.

Fox, G., et al., "How close is close: 16S rRNA sequence identity may not be sufficient to guarantee species identity." International Journal of Systematic and Evolutionary Microbiology 42.1, 1992, pp. 166-170.

NCBI, GenBankAccession No. XP_002568042, Aug. 14, 2009, 4 Pages, Berg, V.D., et al., "Genome sequencing and analysis of the filamentous fungus," Nat. Biotechnol. 26 (10), 1161-1168 (2008).

Goudjal, Y., et al., "Biocontrol of Rhizoctonia solani damping-off and promotion of tomato plant growth by endophytic actinomycetes isolated from native plants of Algerian Sahara", Microbiological Research, 2014, vol. 169, No. 1, pp. 59-65.

Guo, X., et al., "Red Soils Harbor Diverse Culturable Actinomycetes That are Promising Sources of Novel Secondary Metabolites", Applied and Environmental Microbiology, Feb. 27, 2015, vol. 81, No. 9, pp. 3086-3103.

Hjort, K., et al., "Chitinase genes revealed and compared in bacterial isolates, DNA extracts and a metagenomic library from a phytopathogen-suppressive soil", FEMS Microbiology Ecology, Feb. 2010, vol. 71, No. 2, pp. 197-207.

Kanbar, A., et al., "Relationship between Root and Yield Morphological Characters in Rainfed Low Land Rice (*Oryza sativa* L.)," Cereal Research Communications, 2009, vol. 37, No. 2, pp. 261-268.

Ogbo, F., et al., "Some Characteristics of a Plant Growth Promoting; iEnterobacter/isp. Isolated from the Roots of Maize", Advances in Microbiology, Jan. 1, 2012, vol. 02, No. 03, pp. 368-374.

Partida-Martinez, L.P., et al., "Endosymbiont-Dependent Host Reproduction Maintains Bacterial-Fungal Mutualism", Current Biology, May 1, 2007, vol. 17, No. 9, pp. 773-777.

"Sequence Alignment of JQ047949 with Instant SEQ ID No. 2," Search conducted on Jan. 2, 2019, 2 pages.

Sharma et al., "Detection and identification of bacteria intimately associated with fungi of the order Sebacinales", Cellular Microbiology, Aug. 5, 2008, pp. 2235-2246, vol. 10, No. 11.

Yashiro et al., "Effect of Streptomycin Treatment on Bacterial Community Structure in the Apple Phyllosphere," PLOS ONE, May 21 2012, vol. 7, No. 5, 10 pages.

Abdellatif, L., et al., "Characterization of virulence and PCR-DGGE profiles of Fusarium avenaceum from western Canadian Prairie Ecozone of Saskatchewan," Canadian Journal of Plant Pathology, 2010, pp. 468-480.

Abou-Shanab, R.A., et al: "Characterization of Ni-resistant bacteria in the rhizosphere of the hyperaccumulator Alyssum murale by 16S rRNA gene sequence analysis", World Journal of Microbiology and Biotechnology, vol. 26, No. 1, Aug. 15, 2009, pp. 101-108.

Amatuzzi, R.E, et al., "Universidade Federal Do Parana," Jan. 1, 2014, 52 Pages. (With English Abstract).

Aveskamp, M., et al., "DNA phylogeny reveals polyphyly of Phoma section Peyronellaea and multiple taxonomic novelties," Mycologia, 2009, vol. 101, No. 3, pp. 363-382.

Pedraza, R.O., et al., "Azospirillum inoculation and nitrogen fertilization effect on grain yield and on the diversity of endophytic bacteria in the phyllosphere of rice rainfed crop," European Journal of Soil Biology, 2009, pp. 36-43, vol. 45.

Welty, R.E., et al., "Influence of Moisture Content, Temperature, and Length of Storage onSeed Germination and Survival of Endophytic Fungi in Seeds of Tall Fescue and Perennial Ryegrass," Phytopathyol., 1987, pp. 893-900, vol. 77, No. 6.

Xue, Q.Y., et al., "Evaluation of the Strains of Acinetobacter and Enterobacter as potential Biocontrol Agents Against Ralstonia Wilt of Tomato," Biological Control, 2009, vol. 48, pp. 252-258.

Li, Q., "Agrobacterium tumefaciens Strain TA-AT-10 16S Ribosomal RNA Gene, Partial Sequence: GenBank: KF673157.1," Submitted Dec. 16, 2013.

Invitation to Pay Additional Fees, PCT Application No. PCT/US2015/038110, dated Sep. 22, 2015, 8 Pages.

NCBI GenBank: Accession No. XP55670271, "*Enterobacter* sp. MLB05 16S ribosomal RNA gene, partial sequence—Nucleotide", Jun. 9, 2012, 1 Page, can be retreived at URL:https://www.ncbi.nlm.nih.gov/nuccore/J Q765415.1/.

NCBI GenBank: Accession No. XP55670274, "*Enterobacter* sp. CR 6-3 16S ribosomal RNA gene, partial sequence—Nucleotide", Mar. 27, 2013, 1 Page, can be retreived at URL:https://www.ncbi.nlm.nih.gov/nuccore/K C355340.

NCBI GenBank: Accession No. XP55670279, "Uncultured bacterium clone bb2s4 16S ribosomal RNA gene, partial seque—Nucleotide", May 6, 2005, 1 Page, can be retreived at URL:https://www.ncbi.nlm.nih.gov/nuccore/D Q068880.

European Patent Office, Communication Pursuant to Article 94(3) EPC for European Patent Application No. EP 14777213.1, Jun. 18, 2018, 4 Pages.

PCT International Search Report and Written Opinion, Application No. PCT/AU2014/000360, dated Aug. 5, 2015, 12 Pages.

De Melo Pereira, G. V., et al. "A Multiphasic Approach for the Identification of Endophytic Bacterial in Strawberry Fruit and their Potential for Plant Growth Promotion," Microb. Ecology, 2012, pp. 405-417, vol. 63, No. 2.

Result 11 from a search in the GenEmbl database, GenEmbl Record No. EU 977189, Smith et al., "Bioactive endophytes warrant intensified exploration and conservation," PLoS ONE 3(8):E3052, 2008.

Result 3 from a search in the GenEmbl database, GenEmbl Record No. KF011597, Paenibacillus strain No. HA13, Park et al., "Isolation and characterization of humic substances-degrading bacteria from the subarctic Alaska grasslands," J Basic Microbiol, 2013.

PCT International Search Report and Written Opinion for PCT/AU2018/050387, dated Jul. 12, 2018, 8 pages. (originally cited as dated Apr. 27, 2018).

PCT International Search Report and Written Opinion for PCT/US2018/051467, dated Feb. 4, 2019, 22 pages.

Chaves, J., et al., "Identification and Phylogeny of Streptomyces Based on Gene Sequences", Research Journal of Microbiology, vol. 13, No. 1, Dec. 15, 2017, pp. 13-20, XP055675917.

Girard, G., et al., "A novel taxonomic marker that discriminates between morphologically complex actinomycetes", Open Biology, vol. 3, No. 10, Oct. 2013, p. 130073,XP055675916.

Guo, Y., et al. "A multi locus phylogeny of the Streptomyces griseus 16S rRNA gene Glade: use of multilocus sequence analysis for streptomycete systematics", International Journal of Systematic and Evolutionary Microbiology, vol. 58, No. 1, 2008, pp. 149-159, XP055675936.

PCT Invitation to Pay Additional Fees, PCT Application No. PCT/US2017/064292, dated Mar. 5, 2018, 15 Pages. (Attached document is dated Mar. 6, 2018 and is 16 pages).

PCT International Search Report and Written Opinion, PCT Application No. PCT/US2017/068255, dated Mar. 19, 2018, 14 Pages.

PCT International Search Report and Written Opinion PCT/AU2018/050387, dated Jul. 12, 2018, 8 pages. (Filing date is Apr. 27, 2018).

PCT International Search Report and Written Opinion for PCT/US2018/051467, dated Feb. 4, 2019, 22 pages. (Attached document is Invitation to Pay Additional Fees).

PCT International Search Report and Written Opinion for PCT/AU2018/050387, dated Jul. 12, 2018 (Filing date is Apr. 27, 2018).

PCT International Search Report and Written Opinion for PCT/US2017/064292, dated May 11, 2018, 20 Pages.

(56) References Cited

OTHER PUBLICATIONS

Bentley, S.D., et al, Complete genome sequence of the model actinomycete Streptomyces coelicolor A3(2), Nature. May 9, 2002;417(6885):141-7. (Year 2002).
Gabor, J., et al., "Mycorrhizal fungi effects on nutrient composition and yield of soybean seeds," Journal of Plant Nutrition, 20:4-5, 581-591, 1997.
Gopalakrishnan, S. et al., "Plant growth-promoting activities of Streptomyces spp. In sorghum and rice", SpringerPlus, 2/1/574, pp. 1-8, http://www.springerplus.com/content/2/1/574, 2013.
Groppe, K., et al., "Interaction between the endophytic fungus Epichloë bromicola and the grass Bromus erectus: affects of endophyte infection, fungal concentration and environment on grass growth and flowering," Mol Ecol., 8:1827-1835, 1999.
Hubbard, M., "Fungal Endophytes that Confer Heat and Drought Tolerance to Wheat," Doctoral dissertation, University of Saskatchewan, 2012.
Ikeda, H., et al., "Complete genome sequence and comparative analysis of the industrial microorganism Streptomyces avermitilis," Nat Biotechnol. May 2003;21 (5) :526-31. Epub Apr. 14, 2003. (Year 2003).
Lee, J. et al., "Streptomyces koyangensis sp. nov., a novel actinomycete that produces 4-phenyl-3-butenoic acid," Int J Syst Evol Microbial. Jan. 2005;55(Pt 1):257-62. (Year 2005).
Lind, A., et al., "Drivers of genetic diversity in secondary metabolic gene clusters within a fungal species", PLOS Biology, Nov. 17, 2017, 26 pages.
Pacovsky, R., "Carbohydrate, protein and amino acid status of Glycine-Glomus-Bradyrhizobium symbioses," Physiologia Pantarium; 75:346-354, 1989).
Sha, T. et al., "Genetic diversity of the endemic gourmet mushroom Thelephora ganbajun from southwestern China", Microbiology (2008), 154, 3460-3468.
Sugita, T. et al., "Intraspecies Diversity of Cryptococcus laurentii as Revealed by Sequences of Internal Transcribed Spacer Regions and 28S rRNA Gene and Taxonomic Position of C. laurentii Clinical Isolates", Journal of Clinical Microbiology, Apr. 2000, p. 1468-1471.
Wiebold, M., et al., "Agriculture Experiment Station, College of Agriculture, Food & Natural Resources, University of Missouri, Special Report 589, pp. 1-124)."
Le, X.H., et al., "Effects of endophytic Streptomyces on the lucerne (Medicago sativa L.) symbiosis at different levels of nitrogen," 17th Australian Nitrogen Fixation Conference 2014 Proceedings, Sep. 29, 2014, ed. Gupta, V.V.S.R., Unkovich, M. and Kaiser, B. N., ASNF, University of Adelaide, pp. 66-67.
Alvarez-Perez, S., et al., "Zooming-in on floral nectar: a first exploration of nectar-associated bacteria in wild plant communities," FEMS Microbiol. Ecol., 2012, vol. 80, No. 3, pp. 591-602.
NCBI GenBank: Accession No. JX880250.1, "Enterobacteriaceae bacterium Clero1 16S ribosomal RNA gene, partial sequence," NIH, Jun. 24, 2015, 2 Pages, can be retrieved at <URL:https://www.ncbi.nlm.nih.gov/nucleotide/JX880250.1?report=genbank&log$=nuclalign&blast_rank=80 &RID=KWUPBV08015>.
PCT International Search Report and Written Opinion, PCT Application No. PCT/US2015/038110, dated Dec. 11, 2015, 36 Pages.
Conn, V. M., "Effect of Microbial Inoculants on the Indigenous Actinobacterial Endophyte Population in the Roots of Wheats as Determined by Terminal Restriction Fragment Length Polymorphism," Applied and Environmental Microbiology, 2004, pp. 6407-6413, vol. 70, No. 11.
Darsonval, A., et al., "Adhesion and Fitness in the Bean Phyllosphere and Transmission to Seed of Xanthomonas fuscans subsp. fuscans," Molecular Plant-Microbe Interactions, 2009, pp. 747-757, vol. 22, No. 6.
Edgar, R. C., "Uparse: Highly Accurate OTU Sequences From Microbial Amplicon Reads," Nat. Methods, 2013, pp. 996-998, vol. 10, No. 10.

Gu, O., et al., "Glycomyces sambucus sp. nov., an endophytic actinomycete islolated from the stem of Sambucus adnata Wall," International Journal of Systematic and Evolutionary Microbiology, 2007, pp. 1995-1998, vol. 57.
Hardoim, P.R., et al., "Dynamics of Seed-Borne Rice Endophytes on Early Plant Growth Stages," PLoS ONE, 2012, vol. 7, No. 2, 13 Pages.
Kasana, R. C., et al., "A Rapid and Easy Method for the Detection of Microbial Cellulases on Agar Plates Using Gram's Iodine," Curr Microbial., 2008, pp. 503-507, vol. 57.
Lundberg, D.S., et al., "Defining the Core Arabidopsis thaliana Root Microbiome," Nature, 2012, pp. 86-90, vol. 488, No. 7409.
Hanshew, A., et al., "Characterization of Actinobacteria Associated with Three Ant-Plant Mutualisms", Microbiol Ecology, Ecology, Aug. 6, 2014, vol. 69, No. 1, pp. 192-203.
Langille, M.G.I. et al., "Predictive functional profiling of microbial communities using 16S rRNA marker; gene sequences," Nature Biotechnology, 2013, vol. 31, No. 9, pp. 814-821.
Li, M., et al., "ATP Modulates the Growth of Specific Microbial Strains", Current Microbiology, May 30, 2010, vol. 62, No. 1, pp. 84-89.
PCT Invitation to Pay Additional Fees, PCT Application No. PCT/US2017/064351, dated Feb. 9, 2018, 18 Pages.
PCT International Search Report and Written Opinion, PCT Application No. PCT/US2017/064351, dated Apr. 9, 2018, 25 Pages.
PCT Invitation to Pay Additional Fees, PCT Application No. PCT/US2017/064361, dated Mar. 7, 2018, 18 Pages.
PCT Invitation to Pay Additional Fees, PCT Application No. PCT/US2017/064292, dated Mar. 5, 2018, 15 Pages.
PCT International Search Report and Written Opinion, PCT Application No. PCT/USS2017/068255, dated Mar. 14, 2018, 14 Pages.
European Patent Office, Supplementary European Search Report for European Patent Application No. 15810847.2, Feb. 28, 2018, 19 Pages.
European Patent Office, Extended European Search Report, European Patent Application No. EP 15812324.0, dated Feb. 21, 2018, 23 Pages.
European Patent Office, Extended European Search Report, European Patent Application No. EP 15809264.3, dated Mar. 12, 2018, 14 Pages.
NCBI GenBank: CP000653.1 "Enterobacter sp. 638, complete genome" ASM1632v1, Apr. 18, 2007, 2 Pages, Can be retrieved at <URL:https://www.ncbi.nlm.nih.gov/assembly/GCA000016325.1 >.
NCBI GenBank: EBI accession No. EM STD:JQ759988, "Dothideomycetes sp. genotype 226 isolate FL0175 internal transcribed spacer 1, partial sequence; 5.85 ribosomal RNA gene and internal transcribed spacer 2, complete sequence; and 285 ribosomal RNA gene, partial sequence," May 17, 2012, 2 Pages.
GenBank: JN210900.1, "Enterobacter sp. WS05 16S ribosomal RNA gene, partial sequence," NCBI, Sep. 24, 2012, 1 Page, can be retrieved at <URL:https://www.ncbi.nlm.nih.gov/nuccore/jn210900>.
PCT International Search Report and Written Opinion for PCT/US2017/064361, dated May 11, 2018, 22 Pages.
PCT International Search Report and Written Opinion, PCT Application No. PCT/US2017/064292, dated May 11, 2018, 20 Pages.
European Patent Office, Extended European Search Report, European Patent Application No. EP 15876324.3, dated Jun. 12, 2018, 9 Pages.
Vujanovic, V., et al., "A comparative study of endophytic mycobiota in leaves of Acer saccharum in eastern North America," Mycological Progress, May 2002, pp. 147-154, vol. 1, Issue 2.
United States Patent Office, Non-Final Office Action, U.S. Appl. No. 14/766,065, dated Oct. 27, 2017, 11 Pages.
Cha, C., et al., "Production of Acyl-Homoserine Lactone Quorum-Sensing Signals by Gram-Negative Plant Associated Bacteria," Mol Plant Microbe Interact., 1998, pp. 1119-1129, vol. 11, No. 11.
Chernin, L. S., et al., "Chitinolytic Activity in Chromobacterium violaceum: Substrate Analysis and Regulation by Quorum Sensing," J Bacteriol., 1998, pp. 4435-4441, vol. 180, No. 17.
Hain, T., et al., "Chitinolytic transgenes from Streptomyces albidoflavus as phytochemicals defences against; herbivorous insects, use in

(56) References Cited

OTHER PUBLICATIONS transgenic plants and effect in plant development", International Journal of Systematic Bacteriology, Jan. 1997, vol. 47, No. 1, pp. 202-206.
Johnston-Monje, D., "Microbial Ecology of Endophytic Bacteria in *Zea* Species as Influenced by Plant Genotype, Seed Origin, and Soil Environment," Thesis, University of Guelph, 2011, 230 Pages.
Orakçi Ge et al, "Selection of antagonistic actinomycete isolates as biocontrol agents against root-rot fungi", Fresenius Environmental Bulletin, 2010, 19: 417-424 & GenBank Accession No. GQ475299, Oct. 5, 2009.
R Core Team, "R: A Language and Environment for Statistical Computing," R Foundation for Statistical Computing, Vienna, Austria, May 2013, ISBN: 3-900051-07-0. Available online at http://www.R-25project.org/, 3604 Pages.
NCBI, GenBankAccession No. KX641980.1, Jul. 29, 2017, Scott, M., et al., "*Dothideomycetes* sp. isolate FT14-6 internal transcribed spacer 1, partial sequence; 5.8S ribosomal RNA gene and internal transcribed spacer 2, complete sequence; and large subunit ribosomal RNA gene, partial sequence," 2 Pages, Can be retrieved at<URL:https://www.ncbi.nlm.nih.gov/nuccore/KX641980>.
Weaver, P.F., et al., "Characterization of Rhodopseudomonas capsulata," Arch Microbiol., 1975, pp. 207-216, vol. 105.
Redman, R. S., et al., "Thermotolerance Generated by Plant/Fungal Symbiosis," Science, Nov. 2002, vol. 298, 1 Page (with 4 pages of supplemental material).
You, Y., et al., "Analysis of Genomic Diversity of Endophytic Fungal Strains Isolated from the Roots of Suaeda aponica and S. maritima for the Restoration of Ecosystems in Buan Salt Marsh," Korean Journal of Microbiology and Biotechnology, 2012, pp. 287-295, vol. 40, No. 4. (with English Abstract).
Invitation to Pay Additional Fees, PCT Application No. PCT/CA2013/000091, dated Mar. 27, 2013, 2 Pages.
International Search Report and Written Opinion for PCT/EP2013/062976, dated Dec. 22, 2014, 9 Pages.
International Search Report and Written Opinion, Application No. PCT/US2014/054160, dated Dec. 9, 2014, 21 Pages.
Invitation to Pay Additional Fees, PCT Application No. PCT/US2014/064411, dated Feb. 5, 2015, 2 Pages.
International Search Report and Written Opinion, International Application No. PCT/US2014/064411, dated Mar. 27, 2015, 15 Pages.
International Search Report and Written Opinion, International Application No. PCT/US2014/072399, dated Jun. 26, 2015, 22 Pages.
Invitation to Pay Additional Fees, PCT Application No. PCT/US2014/072400, dated Apr. 16, 2015, 6 Pages.
International Search Report and Written Opinion, Application No. PCT/US2014/072400, dated Jul. 8, 2015, 38 Pages.
Abarenkov, K., et al., "PlutoF—A Web Based Workbench for Ecological and Taxonomic Research, with an Online Implementation for Fungal ITS Sequences," Evol Bioinform Online, 2010, pp. 189-196, vol. 6.
Castillo, D., et al., "Fungal Endophytes: Plant Protective Agents Against Herbivores," Power Point Presentation dated Aug. 4, 2013.
Hiatt, E.E., et al., "Tall Fescue Endophyte Detection: Commerical Immunoblot Test Kit Compared with Microscopic Analysis," Crop Science, 1999, pp. 796-799, vol. 39.
Johnston-Monje, D., et al., "Conservation and Diversity of Seed Associated Endophytes in *Zea* Across Boundaries of Evolution, Ethnography and Ecology," PLoS ONE, 2011, vol. 6, No. 6, 22 Pages.
PCT International Search Report and Written Opinion, Application No. PCT/AU2015/000360, dated Aug. 5, 2015, 12 Pages.
PCT Invitation to Pay Additional Fees, PCT Application No. PCT/US2015/038110, dated Sep. 22, 2015, 8 Pages.
PCT Invitation to Pay Additional Fees, PCT Application No. PCT/US2015/038187, dated Oct. 14, 2015, 5 Pages.
PCT International Search Report and Written Opinion, PCT Application No. PCT/US2015/038187, dated Jan. 22, 2016, 36 Pages.
PCT Invitation to Pay Additional Fees, PCT Application No. PCT/US2015/068206, dated Apr. 12, 2016, 5 Pages.
PCT International Search Report and Written Opinion, PCT Application No. PCT/US2015/068206, dated Jun. 27, 2016, 20 Pages.
PCT International Search Report and Written Opinion, PCT Application No. PCT/US2016/030292, dated Aug. 12, 2016, 20 Pages.
PCT International Preliminary Report on Patentability, PCT Application No. PCT/US2016/030292, dated Aug. 2, 2017, 23 Pages.
PCT International Search Report and Written Opinion, PCT Application No. PCT/US2016/030293, dated Aug. 11, 2016, 23 Pages.
PCT International Search Report and Written Opinion, PCT Application No. PCT/US2016/036504, dated Nov. 4, 2016, 18 Pages.
PCT International Search Report and Written Opinion, PCT Application No. PCT/US2016/039191, dated Nov. 29, 2016, 20 Pages.
PCT International Search Report and Written Opinion, PCT Application No. PCT/US2016/068144, dated May 18, 2017, 30 Pages.
Djordjevic, D., et al., "Microtiter Plate Assay for Assessment of Listeria monocytogenes Bioflim Formation," Annl Environ Microbiol., 2002, pp. 2950-2958, vol. 68, No. 6.
European Patent Office, Supplementary Partial European Search Report, European Patent Application No. 13874703.5, dated Jun. 21, 2016, 3 Pages.
European Patent Office, Supplementary European Search Report, European Patent Application No. 13874703.5, dated Oct. 21, 2016, 16 Pages.
European Patent Office, Communication Pursuant to Article 94(3) EPC for European Patent Application No. 13874703.5, dated Jan. 5, 2018, 4 Pages.
European Patent Office, Supplementary European Search Report, European Patent Application No. 14860187.5, dated May 24, 2017, 9 Pages.
European Patent Office, Supplementary European Search Report, European Patent Application No. 14874589.6, dated Jul. 11, 2017, 9 Pages.
European Patent Office, Communication Pursuant to Article 94(3) Epc for European Patent Application No. EP 14748326.7, dated Feb. 15, 2018, 7 Pages.
European Patent Office, Examination Report, European Patent Application No. 14748326.7, dated Jul. 19, 2017, 4 Pages.
European Patent Office, Examination Report for European Patent Application No. EP 14777213.1, dated Oct. 20, 2017, 12 Pages.
European Patent Office, Supplementary European Search Report, European Patent Application No. EP 15809264.3, dated Dec. 4, 2017, 16 Pages.
European Patent Office, Communication Pursuant to Article 94(3) EPC for European Patent Application No. 15810847.2, dated Nov. 17, 2017, 17 Pages.
European Patent Office, Supplementary European Search Report, European Patent Application No. EP 15812324.0, dated Nov. 2, 2017, 19 Pages.
United States Patent Office, Non-Final Office Action, U.S. Appl. No. 15/436,592, dated Aug. 30, 2017, 17 Pages.
United States Patent Office, Non-Final Office Action, U.S. Appl. No. 15/436,609, dated Aug. 30, 2017, 21 Pages.
Abarenkov, K., et al., "The UNITE Database for Molecular Identification of Fungi—Recent Updates and Future Perspectives," New Phvtol., 2010, pp. 281-285, vol. 186.
Abdellatif, L., et al., "Endophytic hyphal compartmentalization is required for successful symbiotic Ascomycota association with root cells," Mycological Research, 2009, pp. 782-791, vol. 113.
Abdou, R., et al., "Botryorhodines A-D, antifungal and cytotoxic depsidones from Botryosphaeria rhodina, an endophyte of the medicinal plant *Bidens pilosa*," Phytochemistry, 2010, vol. 71, pp. 110-116.
Adhikari, M., et al., "A New Record of Pseudeurotium bakeri from Crop Field Soil in Korea," The Korean Journal of Mycology, 2016, pp. 145-149, vol. 44.
Ahmad, F., et al., "Screening of Free-Living Rhizospheric Bacteria for Their Multiple Plant Growth Promotingq Activities," Microbiol Res., 2008, pp. 173-181, vol. 163.
Amann, R., et al., "The Identification of Microorganisms by Fluorescence in Situ Hybridisation," Curr Opin Biotechnol., 2001, pp. 231-236, vol. 12.

(56) References Cited

OTHER PUBLICATIONS

Apel K. et al., "Reactive Oxygen Species: Metabolism, Oxidative Stress, and Signal Transduction," Annu Rev Plant Biol., 2004, pp. 373-399, vol. 55.
Arendt, K. R., et al., "Isolation of endohyphal bacteria from foliar Ascomycota and in vitro establishment of their symbiotic associations," Appl. Environ. Microbiol., 2016, pp. 2943-2949, vol. 82, No. 10.
Ashrafuzzaman, M., et al., "Efficiency of plant growth-promoting rhizobacteria (PGPR) for the enhancement of rice growth," African Journal of Biotechnology, 2009, pp. 1247-1252, vol. 8, No. 7.
Bacon, C. W, et al., "Isolation, in Planta Detection, and Uses of Endophytic Bacteria for Plant Protection," Manual of Environmental Microbiology, 2007, pp. 638-647.
Baker, K. F., et al., "Dynamics of Seed Transmission of Plant Pathogens," Annu Rev. Phytopathol., 1966, pp. 311-334, vol. 4.
Baltruschat, H., et al., "Salt tolerance of barley induced by the root endophyte *Piriformospora indica* is associated with a strong increase in antioxidants," New Phytologist., 2008, pp. 501-510, vol. 180.
Bensch, K., et al., "Species and ecological diversity within the Cladosporium cladosporioides complex (Davidiellaceae, Capnodiales)," Studies in Mycology, 2010, pp. 1-94, vol. 67.
Block, C. C., et al., "Seed Transmission of Pantoea stewartii in Field and Sweet Corn," Plant Disease, 1998, pp. 775-780, vol. 82.
Brinkmeyer, R., et al., "Uncultured Bacterium Clone ARKMP-100 16S Ribosomal RNA Gene, Partial Sequence," NCBI GenBank Accession No. AF468334, Submitted Jan. 14, 2002.
Brodie, E.L., et al., "Uncultured Bacterium Clone BANW722 16S Ribosomal RNA Gene, Partial Sequence," NCBI GenBank Accession No. DQ264636, Submitted Oct. 25, 2005, 1 Page.
Bulgarelli, D., et al., "Structure and Functions of the Bacterial Microbiota of Plants," Annu Rev Plant Biol., 2013, pp. 807-838, vol. 64.
Büttner, D., et al., "Regulation and secretion of Xanthomonas virulence factors," FEMS Microbiology Reviews, 2010, pp. 107-133, vol. 34, No. 2.
Caporaso, J.G., et al., "Ultra-High-Throughput Microbiol Community Analysis on the Illumina HiSeq and MiSeq Platforms," ISME J., 2012, pp. 1621-1624, vol. 6.
Castillo, D., et al., "Fungal Entomopathogenic Endophytes: Negative Effects on Cotton Aphid Reproduction in Greenhouse and Field Conditions," Power Point Presentation dated Mar. 23, 2013, 21 Pages.
Cavalier-Smith, T., "A Revised Six-Kingdom System of Life," Biol Rev Camb Philos Soc., 1998, pp. 203-266, vol. 73.
Chagas, F., et al., "A Mixed Culture of Endophytic Fungi Increases Production of Antifungal Polyketides," J. Chem Ecol., Oct. 2013, pp. 1335-1342, vol. 39.
Clark, E. M., et al., "Improved Histochemical Techniques for the Detection of Acremonium coenophilum in Tall Fescue and Methods of in vitro Culture of the Fungus," J Microbiol Methods, 1983, pp. 149-155, vol. 1.
Clarridge, J., "Impact of 16S rRNA Gene Sequence Analysis for Identification of Bacteria on Clinical Microbiology and Infectious Diseases," Clinical Microbiology Reviews, Oct. 2004, pp. 840-862, vol. 17, No. 4.
Lopez-Lopez, A., et al., "Phaseolus vulgaris Seed-Borne Endophytic Community with Novel Bacterial Species such as *Rhizobium endophyticum* sp. nov.," Systematic Appl Microbiol., 2010, pp. 322-327, vol. 33.
Lorck, H., "Production of Hydrocyanic Acid by Bacteria," Physiol Plant, 1948, pp. 142-146, vol. 1.
Lugtenberg, B., et al., "Plant-Growth-Promoting Rhizobacteria," Ann. Rev. Microbiol., 2009, pp. 541-556, vol. 33.
Lundberg, D.S., et al., "Practical Innovations for High-Throughput Amplicon Sequencing," Nat Methods, 2013, pp. 999-1002, vol. 10, No. 10.
Ma, Y., et al., "Plant Growth Promoting Rhizobacteria and Endophytes Accelerate Phytoremediation of Metalliferous Soils," Biotechnology Advances, 2011, pp. 248-258, vol. 29.
Madi, L. et al., "Aggregation in Azospirillum brasilense Cd: Conditions and Factors Involved in Cell-to-Cell Adhesion," Plant Soil, 1989, pp. 89-98, vol. 115.
Mannisto, M.K., et al., "Characterization of Psychrotolerant Heterotrophic Bacteria From Finnish Lapland," Syst Appl Microbiol., 2006, pp. 229-243, vol. 29.
Mano, H., et al., "Culturable Surface and Endophytic Bacterial Flora of the Maturing Seeds of Rice Plants (*Oryza saliva*) Cultivated in a Paddy Field," Microbes Environ., 2006, vol. 21, No. 2.
Manter, D. K., et al., "Use of the ITS Primers, ITSIF and ITS4, to Characterize Fungal Abundance and Diversity in Mixed-Template Samples by qPCR and Length Heterogeneity Analysis," J Microbiol Methods, 2007, pp. 7-14, vol. 71.
Mao, W., et al., "Seed Treatment with a Fungal or a Bacterial Antagonist for Reducing Corn Damping-off Caused by Species of *Pythium* and *Fusarium*," Plant Disease, 1997, pp. 450-454, vol. 81, No. 5.
Marasco, R., et al., "A Drought Resistance-Promoting Microbiome is Selected by Root System Under Desert Farming," PLoS ONE, 2012, vol. 7, No. 10, 14 Pages.
Marquez, L. M., et al., "A Virus in a Fungus in a Plant: Three-Way Symbiosis Required for Thermal Tolerance," Science, 2007, pp. 513-515, vol. 315.
Mastretta, C., et al., "Endophytic Bacteria from Seeds of Nicotiana Tabacum Can Reduce Cadmium Phytotoxicity," Intl J Phytoremediation, 2009, pp. 251-267, vol. 11.
Mateos, P. F., et al. "Cell-Associated Pectinolytic and Cellulolytic Enzymes in Rhizobium leguminosarum biovartnfolii," Appl Environ Microbiol., 1992, pp. 816-1822, vol. 58, No. 6.
McDonald, D., et al., "An Improved Greengenes Taxonomy with Explicit Ranks for Ecological and Evolutionary Analyses of Bacteria and Archaea," ISME J., 2012, pp. 610-618, vol. 6.
McGuire, K.L., et al., "Digging the New York City Skyline: Soil Fungal Communities in Green Roofs and City Parks," PloS One, 2013, vol. 8, No. 3, 13 Pages.
Medina, P., et al., "Rapid Identification of Gelatin and Casein Hydrolysis Using TCA," J Microbiol Methods, 2007, pp. 391-393, vol. 69.
Mehnaz, S., et al., "Growth Promoting Effects of Corn (*Zea mays*) Bacterial Isolates Under Greenhouse and Field Conditions," Soil Biology and Biochemistry, 2010, pp. 1848-1856, vol. 42.
Mehnaz, S., et al., "Isolation and 16S rRNA sequence analysis of the beneficial bacteria from the rhizosphere of rice," Canada Journal of Microbiology, 2001, pp. 110-117, vol. 47, No. 2.
Mei, C., et al., "The Use of Beneficial Microbial Endophytes for Plant Biomass and Stress Tolerance Improvement," Recent Patents on Biotechnology, 2010, pp. 81-95, vol. 4.
Michel, B. E., et al., "The Osmotic Potential of Polyethylene Glycol 6000," Plant Physiol., 1973, pp. 914-916, vol. 51.
Misk, A., et al., "Biocontrol of chickpea root rot using endophytic actinobacteria", Biocontrol, vol. 56, No. 5, Mar. 12, 2011, pp. 811-822, XP036215297.
Moe, L. A., "Amino Acids in the Rhizosphere: From Plants to Microbes," American Journal of Botany, 2013, pp. 1692-1705, vol. 100, No. 9.
Mohiddin, F. A., et al., "Tolerance of Fungal and Bacterial Biocontrol Agents to Six Pesticides Commonly Used in the control of Soil Borne Plant Pathogens," African Journal of Agricultural Research, 2013, pp. 5331-5334, vol. 8, No. 43.
Mousa, W. K., et al., "The Diversity of Anti-Microbial Secondary Metabolites Produced by Fungal Endophytes: An Interdisciplinary Perspective," Front Microbiol., 2013, vol. 4, No. 65, 18 Pages.
Mundt, J.O., et al., "Bacteria Within Ovules and Seeds," Appl Environ Microbiol., 1976, pp. 694-698, vol. 32, No. 5.
Naik, B. S., et al., "Study on the diversity of endophytic communities from rice (*Oryza sativa* L.) and their antagonistic activities in vitro," Microbiological Research, 2009, pp. 290-296, vol. 164.
Naveed, M., "Maize Endophytes—Diversity, Functionality and Application Potential," University of Natural Resources and Life Sciences, 2013, pp. 1-266 and 81-87; Tables 1-3; Figure 2.
Nejad, P. et al., "Endophytic Bacteria Induce Growth Promotion and Wilt Disease Suppression in Oilseed Rape and Tomato," Biological Control, 2000, pp. 208-215, vol. 18.

(56) References Cited

OTHER PUBLICATIONS

Neslon, E.B., "Microbial Dynamics and Interactions in the Spermosphere," Ann. Rev. Phytopathol., 2004, pp. 271-309, vol. 42.
Nikolcheva, L.G., et al., "Taxon-Specific Fungal Primers Reveal Unexpectedly High Diversity During Leaf Decomposition in a Stream," Mycological Progress, 2004, pp. 41-49, vol. 3, No. 1.
Nimnoi, P., et al., "Co-Inoculation of Soybean (*Glycin max*) wtth Actinomycetes and Bradyrhizobium Japonicum Enhances Plant Growth, Nitrogenase Activity and Plant Nutrition," Journal of Plant Nutrition, 2014, pp. 432-446, vol. 37.
Nishijima, K.A., et al., "Demonstrating Pathogenicity of Enterobacter cloacae on Macadamia and Identifying Associated Volatiles of Gray Kernel of Macadamia in Hawaii," Plant Disease, Oct. 2007, vol. 91, No. 10, pp. 1221-1228.
Normander, B., et al., "Bacterial Origin and Community Composition in the Barley Phytosphere as a Function of Habitat and Presowing Conditions," Appl Environ Microbiol., Oct. 2000, pp. 4372-4377, vol. 66, No. 10.
Okunishi, S., et al., "Bacterial Flora of Endophytes in the Maturing Seeds of Cultivated Rice (*Oryza sativa*)," Microbes and Environment, 2005, pp. 168-177, vol. 20, No. 3.
Op De Beeck, M., et al., "Comparison and Validation of Some ITS Primer Pairs Useful for Fungal Metabarcoding Studies," PLOS ONE, Jun. 2014, vol. 9, Issue 6, e97629, pp. 1-11.
Orole, O. O., et al., "Bacterial and fungal endophytes associated with grains and roots of maize," Journal of Ecology and the Natural Environment, 2011, pp. 298-303, vol. 3, No. 9.
Partida-Martinez, L.P., et al., "The Microbe-Free Plant: Fact or Artifact?" Front Plant Sci., 2011, vol. 2, No. 100, 16 Pages.
Pearson, W.R., et al., "Rapid and Sensitive Sequence Comparison With FASTP and FASTA," Methods Enzymol., 2011, pp. 63-98, vol. 183.
Perez-Fernandez, M.A., et al., "Simulation of Germination of Pioneer Species Along an Experimental Drought Gradient," J Environ Biol., 2006, pp. 669-685, vol. 27, No. 4.
Perez-Miranda, S., et al., "O-CAS, A Fast and Universal Method for Siderophore Detection," J Microbiol Methods, 2007, pp. 127-131, vol. 70.
Petti, C. A., "Detection and Identification of Microorganisms by Gene Amplification and Sequencing," Clinical Infectious Diseases, 2007, pp. 1108-1114, vol. 44.
Phalip, V. et al., "A Method for Screening Diacetyl and Acetoin-Producing Bacteria on Agar Plates," J Basic Microbiol., 1994, pp. 277-280, vol. 34.
Philippot, L., et al., "Going Back to the Roots: The Microbial Ecology of the Rhizosphere," Nat Rev Microbiol., Nov. 2013, pp. 789-799, vol. 11.
Philrice Batac, Philippine Rice R&D Highlights, 2012, Area-Based R&D Projects, [online][Retrieved Aug. 11, 2016] Retrieved from the Internet URL:http://www.philrice.gov.ph/2012-rd-highlights/, 52 Pages.
Pillay, V. K., et al., "Inoculum Density, Temperature, and Genotype Effects on in vitro Growth Promotion and Epiphytic and Endophytic Colonization of Tomato (*Lycopersicon esculentum* L.) Seedlings Inoculated with a Pseudomonad Bacterium," Can J Microbiol., 1997, pp. 354-361, vol. 43.
Powell, W. A., et al., "Evidence of Endophytic Beauveria Bassiana in Seed-Treated Tomato Plants Acting as a Systemic Entomopathogen to Larval Helicoverpa zea (Lepidoptera: Noctuidae)," J. Entomol. Sci., 2009, pp. 391-396, vol. 44, No. 4.
Quadt-Hallmann, A., et al., "Bacterial Endophytes in Cotton: Mechanisms of Entering the Plant," Can J Microbiol., 1997, pp. 577-582, vol. 43.
Rasmussen, S., et al., "Grass-endophyte interactions: a note on the role of monosaccharide transport in the Neotyphodium lolii-Lolium perenne symbiosis," New Phytologist, 2012, pp. 7-12, vol. 196.
Ravel, C., et al., "Beneficial effects of Neotyphodium lolii on the growth and the water status in perennial ryegrass cultivated under nitrogen deficiency or drought stress," Agronomie, 1997, pp. 173-181, vol. 17.
Clay, K., "Effects of fungal endophytes on the seed and seedling biology of Lolium perenne and Festuca arundinacea," Oecologia, 1987, pp. 358-362, vol. 73.
Clough, S. J., et al., "Floral Dip: A Simplified Method for Agrobacterium-mediated Transformation of *Arabidopsis thaliana*," Plant J., 1998, pp. 735-743, vol. 16, No. 6.
Compant, S., et al., "Endophytes of Grapevines Flowers, Berries, and Seeds: Identification of Cultivable Bacteria, Comparison with Other Plant Parts, and Visualization of Niches of Colonization," Microbial Ecology, 2011, pp. 188-197, vol. 62.
Cottyn, B., et al., "Phenotypic and genetic diversity of rice seed-associated bacteria and their role in pathogenicity and biological control," Journal of Applied Microbiology, 2009, pp. 885-897, vol. 107.
Cox, C. D., "Deferration of Laboratory Media and Assays for Ferric and Ferrous Ions," Methods Enzymol., 1994, pp. 315-329, vol. 235.
Craine, J. M., et al., "Global Diversity of Drought Tolerance and Grassland Climate-Change Resilience," Nature Climate Change, 2013, pp. 63-67, vol. 3.
Dalal, J.M., et al., "Utilization of Endophytic Microbes for Induction of Systemic Resistance (ISR) in Soybean (*Glycine max* (L) Merril) Against Challenge Inoculation with R. solani," Journal of Applied Science and Research, 2014, pp. 10-84, vol. 2, No. 5.
Danhorn, T., et al., "Biofilm Formation by Plant-Associated Bacteria," Annu Rev Microbial., 2007, pp. 401-422, vol. 61.
Daniels, R., et al., "Quorum Signal Molecules as Biosurfactants Affecting Swarming in Rhizobium etli," PNAS, 2006, pp. 14965-14970, vol. 103, No. 40.
Darsonval, A., et al., "The Type III Secretion System of *Xanthomonas fuscans* subsp. *fuscans* is involved in the Phyllosphere Colonization Process and in Transmission to Seeds of Susceptible Beans," Applied and Environmental Microbiology, 2008, pp. 2669-2678, vol. 74, No. 9.
DBGET, "Orthology: K14454," 2005, 2 pages, can be retrieved at <URL:http://www.genome.jp/dbget-bin/wwwbget?ko:K14454>.
De Freitas, J. R., et al., "Phosphate-Solubilizing Rhizobacteria Enhance the Growth and Yield but not Phosphorus Uptake of Canola (*Brassica napus* L.)," Biol Fertil Soils, 1997, pp. 358-364, vol. 24.
De Lima Favaro, L. C., et al., "Epicoccum nigrum P16, a Sugarcane Endophyte, Produces Antifungal Compounds and Induces Root Growth," PLoS One, 2012, pp. 1-10, vol. 7, No. 6.
De Souza, J. J., et al., "Terpenoids from Endophytic Fungi," Molecules, 2011, pp. 10604-10618, vol. 16, No. 12.
Dennis, C., et al., "Antagonistic Properties of Species Groups of Trichoderma," Trans Brit Mycol Soc, 1971, pp. 25-39, vol. 57, No. 1.
Desiro, A., et al., "Detection of a novel intracellular microbiome hosted in arbuscular mycorrhizal fungi," ISME Journal, 2014, pp. 257-270, vol. 8.
Don, R.H., et al., "Properties of Six Pesticide Degradation Plasmids Isolated From Alcaligenes Paradoxus and Alcaligenes eutrophus," J Bacteriol., 1981, pp. 681-686, vol. 145, No. 2.
Dunbar, J, et al., "Uncultured Bacterium Clone NT42a2_20488 16S Ribosomal RNA Gene, Partial Sequence," NCBI GenBank Accession No. JQ378705. Submitted Nov. 8, 2012, 2 Pages.
Eberhard, A., et al., "Structural Identification of Autoinducer of Photobacterium fischeri Luciferase," Biochem., 1981, pp. 2444-2449, vol. 20.
Edgar, R. C., "Search and Clustering Orders of Magnitude Faster than BLAST," Bioinformatics, 2010, pp. 2460-2461, vol. 26, No. 19.
Ek-Ramos, M. J., "Ecology, Distribution and Benefits of Fungal Endophytes Isolated from Cultivated Cotton (*Gossypium hirsutum*) in Texas," Power Point Presentation dated Nov. 7, 2012, 27 Pages.
Ek-Ramos, M. J., et al., "Spatial and Temporal Variation in Fungal Endophyte Communities Isolated from Cultivated Cotton (*Gossypium hirsutum*)," PLoS ONE, 2013, vol. 8, No. 6, 13 Pages, e66049.
Ek-Ramos, M. J., et al., "Spatial and Temporal Variation in Fungal Endophyte Communities Isolated from Cultivated Cotton (*Gossypium hirsutum*)," Power Point Presentation dated Jan. 7, 2013.

(56) References Cited

OTHER PUBLICATIONS

El-Sfianshoury, A. R., "Growth Promotion of Wheat Seedlings by Streptomyces atroolivaceus," Journal of Agronomy and Crop Science, 1989, pp. 109-114, vol. 163.
Emerson, D., et al., "Identifying and Characterizing Bacteria in an Era of Genomics and Proteomics," BioScience, 2008, pp. 925-936, vol. 58, No. 10.
Endre, G., et al., "A Receptor Kinase Gene Regulating Symbiotic Nodule Development," Nature, 2002, pp. 962-966, vol. 417.
Faria, D. c., et al. "Endophytic Bacteria Isolated from Orchid and Their Potential to Promote Plant Growth," World J Microbiol Biotechnol., 2013, pp. 217-221, vol. 29.
Ferrando, L., et al., "Molecular and Culture-Dependent Analyses Revealed Similarities in the Endophytic Bacterial Community Composition of Leaves from Three Rice (*Oryza sativa*) Varieties," FEMS Microbiol Ecol., 2012, pp. 396-708, vol. 80.
Fiehn, 0., et al., "Metabolite Profiling for Plant Functional Genomics," Nature BiotechnoL, 2000, pp. 1157-1161, vol. 8.
Fierer, N., et al., "Cross-Biome Metagenomic Analyses of Soil Microbiol Communities and Their Functional Attributes," Proc Natl Acad Sci USA, 2012, pp. 21390-21395, vol. 109, No. 52.
Fincher, G. B., "Molecular and Cellular Biology Associated with Endosperm Mobilization in Germinating Cereal Grains," Annu Rev Plant Physiol Plant Mol Biol., 1989, pp. 305-346, vol. 40.
Fisher, P. J., et al., "Fungal saprobes and pathogens as endophytes of rice (*Oryza sativa* L.)," New Phytol., 1992, pp. 137-143, vol. 120.
Fisher, P.R., et al., "Isolation and Characterization of the Pesticide-Degrading Plasmid pJP1 from Alcaligenes paradoxus," J Bacterial., 1978, pp. 798-804, vol. 135, No. 3.
Franco, C., et al., "Actinobacterial Endophytes for Improved Crop Performance," Australasian Plant Pathology, 2007, pp. 524-531, vol. 36.
Fulthorpe, R. R., et al., "Distantly Sampled Soils Carry Few Species in Common," ISME J., 2008, pp. 901-910, vol. 2.
Gantner, S., et al., "Novel Primers for 16S rRNA-based Archaeal Community Analyses in Environmental Samples," J Microbiol Methods, 2011, pp. 12-18, vol. 84.
Gao, Z., et al., "Quantitation of Major Human Cutaneous Bacterial and Fungal Populations," J Clin Microbiol., 2010, pp. 3575-3581, vol. 48, No. 10.
Garazzino, S., et al., "Osteomyelitis Caused by Enterobacter cancerogenus Infection following a Traumatic Injury: Case Report and Review of the Literature," J Clin Microbiol., Mar. 2005, vol. 43, No. 3, pp. 1459-1461.
Gasser, I., et al., "Ecology and Characterization of Polyhydroxyalkanoate-Producing Microorganisms on and in Plants," FEMS Microbiol Ecol., 2010, pp. 142-150, vol. 70.
Gavrish, E, et al., "*Lentzea* sp. MS6 16S Ribosomal RNA Gene, Partial Sequence," NCBI GenBank Accession No. EF599958. Submitted May 9, 2007, 1 Page.
Gebhardt, J., et al., "Characterization of a single soybean cDNA encoding cytosolic and glyoxysomal isozymes of aspartate aminostransferase," Plant Molecular Biology, 1998, pp. 99-108, vol. 37.
GenBank: AF034210.1 "Glycine max aspartate aminotransferase glyoxysomal isozyme AAT1 precursor and aspartate aminotransferase cytosolic isozyme AAT2 (AAT) mRNA, complete eds," NCBI, May 26, 1998, 2 Pages, can be retrieved at <URL:https://www.ncbi.nlm.nih.gov/nuccore/AF034210>.
GenBank: NP_001237541.1, "aspartate aminotransferase glyoxysomal isozyme AAT1 precursor [*Glycine max*]," NCBI, Oct. 29, 2016, 2 Pages, can be retrieved at <URL:https://www.ncbi.nlm.nih.gov/protein/NP_001237541.1 >.
GenEmbl Database, GenEmbl Record No. KF673660, Sandberg, et al., "Fungal endophytes of aquatic macrophytes: diverse host-generalists characterized by tissue preferences and geographic structure," 2013, 35 Pages.
GenEmbl Database, GenEmbl Record No. KP991588, Huang, et al., "Pervasive effects of wildfire on foliar endophyte communities in montane forest trees," Mar. 2015, 35 Pages.
GenEmbl Database, GenEmbl Record No. JN872548, 38 Pages, Alvarez-Perez, S., et al., "Zooming-in on floral nectar: a first exploration of nectar-associated bacteria in wild plant communities," FEMS Microbiol. Ecol., 2012, vol. 30, No. 3, pp. 591-602.
GenEmbl database, GenEmbl Record No. EU 977189, Jan. 21, 2009, 4 pages, Smith, S.A., et al., "Bioactive endophytes warrant intensified exploration and conservation," PloS ONE 3(8):E3052, 2008.
GenEmbl database, GenEmbl Record No. KF011597, Paenibacillus strain No. HA 13, Aug. 26, 2013, 5 Pages, Park, H.J., et al., "Isolation and characterization of humic substances-degrading bacteria from the subarctic Alaska grasslands," J Basic Microbiol, 2013.
Database Geneseq Database accession No. BAP97938 "Pantoea dispersa strain KACC91642P 16S rDNA sequence, SEQ ID 1." Aug. 15, 2013, 1 Page.
Gilmour, S. J., et al., "Overexpression of the *Arabidopsis* CBF3 Transcriptional Activator Mimics Multiple Biochemical Changes Associated with Cold Acclimation," Plant Physiol., 2000, pp. 1854-1865, vol. 124.
Azcon, R., et al., "Selective interactions between different species of mycorrhizal fungi and Rhizobium meliloti strains, and their effects on growth, N2- fixation (15N) and nutrition of *Medicago sativa* L.," New Phytol., 1991, vol. 117, pp. 399-404.
Bethlenfalvay, G., et al., "Mycorrhizal fungi effects on nutrient composition and yield of soybean seeds", Journal of Plant Nutrition, vol. 20, pp. 4-5, Apr. 1, 1997, pp. 581-591.
Compant, S., et al., "Endophytic colonization of *Vitis vinfera* L. by Burkholderia phytofirmans strain PsJN: from the rhizosphere to inflorescence tissues," FEMS Microbiol Ecol, 2008, pp. 84-93, vol. 63.
NCBI GenBank: CP000653.1 "*Enterobacter* sp. 638, complete genome" Jan. 28, 2014, 5 Pages, Can be retrieved at<URL:https://www.ncbi.nlm.nih.gov/nuccore/CP000653.1>.
NCBI GenBank: EU340965.1 "*Enterobacter* sp. 638 16S ribosomal RNA gene, partial sequence" Jan. 30, 2009, 1 Page, Can be retrieved at <URL:https://www.ncbi.nlm.nih.gov/nuccore/EU340965.1>.
NCBI GenBank: EBI accession No. EM STD:GU055658, "Uncultured Periconia clone NG R 806 18S ribosomal RNA gene, partial sequence; internal transcribed spacer 1, 5.8S ribosomal RNA gene, and internal transcribed spacer 2, complete sequence; and 28S ribosomal RNA gene, partial sequence," Oct. 27, 2009, 2 Pages.
Database EMBL [Online] Oct. 1, 2001, 2 Pages, "Setosphaeria monoceras 28S ribosomal RNA gene, partial sequence," XP002777918, retrieved from EBI accession No. EM_STD:AY016368 Database accession; No. AY016368 sequence.
Hamayun, M., et al., "Cladosporium sphaerospermum as a new plant growth-promoting endophyte from the roots of *Glycine max* (L.) Merr," World Journal of Microbiology and Biotechnology, Kluwer Academic Jublishers, DO, vol. 25, No. 4, Feb. 15, 2009 (Feb. 15, 2009), pp. 627-632.
Hoffman, M., et al., "Diverse Bacteria Inhabit Living Hyphae of Phylogenetically Diverse Fungal Endophytes," Applied and Environmental Microbiology, Jun. 2010, p. 4063-4075, vol. 76, No. 12.
Hoffman, M., et al., "Endohyphal Bacterium Enhances Production of Indole-3-Acetic Acid by a Foliar Fungal Endophyte," PLOS One, Sep. 24, 2013, pp. 1-8, vol. 8, Issue 9, e73132.
Hubbard, M., et al., 2011. "Agricultural Potential of Fungal Endophytes of Grasses, Cereals and Wheat," In: Wheat: Genetics, Crops and Food Production. Nova Science Publishers Hauppauge, pp. 333-345.
Impullitti, A.E., et al., "Fungal endophyte diversity in soybean", Journal of Applied Microbiolog, vol. 114, No. 5, May 1, 2013, pp. 1500-1506.
Jung, C., et al., "The Effects of Endohyphal Bacteria on Anti-Cancer and Anti-Malaria Metabolites of Endophytic Fungi," Honors Thesis, University of Arizona, May 2012, 15 Pages.
Kim, M., et al., "Towards a taxonomic coherence between average nucleotide identity and 16S rRNA gene sequence similarity for species demarcation of prokaryotes", Int J Systematic Evolutionary Microbiol., 2014, vol. 64, pp. 346-351.

(56) References Cited

OTHER PUBLICATIONS

Klaubauf S. et al., "Molecular diversity of fungal conmunities in agricultural soils from Lower Austria," Fungal Diversity, Aug. 13, 2010, pp. 65-75, vol. 44, No. 1.

Knapp, D., et al., "Inter- and intraspecific functional diversity of fungal root endophytes of semiarid sandy grasslands," Acta Microbiologica et Immunologica Hungarica, Nov. 2017, vol. 64, Issue Supplement 1, pp. 1-101.

Kumar, A., et al., "Bio-control potential of Cladosporium sp. (MCPL-461), against a noxious weed Parthenium hysterophorus L.," J. Environ Biol., Mar. 2009, pp. 307-312, vol. 30, Issue 2.

Kusari, S., et al. "Chemical ecology of endophytic fungi: origins of secondary metabolites," Cell Press, Chem & Biol, vol. 19, pp. 792-798, 2012.

Liu Y. et al., "Phylogenetic relationships among ascomycetes: evidence from an RNA polymerase II subunit," Mol. Biol. Evol. 1999. vol. 16, No. 12, pp. 1799-1808.

Mandyam, K., et al., "Mutualism-parasitism paradigm synthesized from results of root-endophyte models", Frontiers in Microbiology, vol. 5, Jan. 12, 2015, pp. 1-14.

Miyoshi-Akiyama, T., et al., "Multilocus Sequence Typing (MLST) for Characterization of Enterobacter cloacae," PLoS ONE, 2013, vol. 8, No. 6, 10 Pages, e66358.

Nassar, A., et al., "Promotion of plant growth by an auxin-producing isolate of the yeast Williopsis satumus endophytic in maize (Zea mays L) roots", Biology and Fertility of Soils; Cooperating Journal of International Society of Soil Science, Springer, Berlin, DE, vol. 42, No. 2, Nov. 1, 2005, pp. 97-108.

O'Hanlon, K., et al., "Exploring the potential of symbiotic fungal endophytes in cereal disease suppression", Biological Control, vol. 63, No. 2, Sep. 5, 2012, pp. 69-78.

Rae, R., et al., "A subset of naturally isolated Bacillus strains show extreme virulence to the free-living nematodes Caenorhabditis elegans and Pristionchus pacificus", Environmental Microbiology, vol. 12, No. 11, 2010, pp. 3007-3021.

Riess, K., et al., "High genetic diversity at the regional scale and possible speciation in Sebacina epigaea and S. incrustans," BMC Evolutionary Biology, 2013, vol. 13, No. 102, 17 Pages.

Samways, M.J., et al., "Assessment of the Fungus Cladosporium oxyspoum (BERK. and CURT.) As a Potential BioControl Agent Against Certain Homoptera," Elsevier Science Publishers B.V., Jan. 1, 1986, pp. 231-239.

Sarkar, S., et al., "New report of additional enterobacterial species causing wilt in West Bengal, India," Canadian Journal of Microbiology, 2015, vol. 61, No. 7, pp. 477-486.

Saunders, M., et al., "Host-Synthesized Secondary Compounds Influence the In Vitro Interactions between Fungal Endophytes of Maize", Applied and Environmental Microbiology, Nov. 9, 2007, pp. 136-142, vol. 14, No. 1.

Schneider, C., et al., "Endophytes for plant protection: the state of the art Proceedings," DPG Spectrum Phytomedizin, Proceedings of the 5th International Symposium on Plant Protection and Plant Health in Europe, May 26-29, 2013, 347 Pages.

Shiraishi, A., et al., "Nodulation in black locust by the ammaproteobacteria Pseudomonas sp. and the Betaproteobacteria Burkholderia sp", Systematic and Applied Microbiology, vol. 33, No. 5, Aug. 2010, pp. 269-274.

Simola, L., et al., "The Effect of Some Protein and Non-Protein Amino Acids on the Growth of Cladosporium herbarum and Trichotheeium roseum," Effect of Amino Acids on Fungi, Physiologia Plantarum, 1979, vol. 46, pp. 381-387.

Stielow, J.B., et al., "One fungus, which genes? Development and assessment of universal primers for potential secondary fungal DNA barcodes," Persoonia: Molecular Phylogeny and Evolution of Fungi, 2015, vol. 35, pp. 242-263.

U'Ren, J.M., et al., "Host and geographic structure of endophytic and endolichenic fungi at the continental scale," American Journal of Botany, May 1, 2012, pp. 898-914, vol. 99, No. 5.

Valencia, E., et al., "Mini-review: Brazilian fungi diversity for biomass degradation," Fungal Genetics and Biology, 2013, pp. 9-18, vol. 60.

Vujanovic, V., et al., "Viability Testing of Orchid Seed and the Promotion of Colouration and Germination," Annals of Botany, Mar. 17, 2000, pp. 79-86, vol. 86.

Vujanovic, V., et al., "Endophytic hyphal compartmentalization is required for successful mycobiont-wheat interaction as revealed by confocal laser microscopy," The proceedings of the Soils and Crops conference in Saskatoon (2008) published 2009, 7 Pages.

Vujanovic, V., et al.,"Orchid seed viability testing by fungal bioassays and molecular phylogeny," Floriculture, ornamental and plant biotechnology, 2006, vol. 63, pp. 563-569.

Vujanovic, V., et al., "Mycovitality—a new concept of plant biotechnology," Canadian Journal Plant Pathol. 2007, vol. 29, p. 451.

Vujanovic, V., et al., "19th International Conference on Arabidopsis. Research Proceedings—ICAR13," Jul. 23-27, 2008, 264 Pages, Montreal, QC, Canada.

Vujanovic, V., et al., "Mycovitality and mycoheterotrophy: where lies dormancy in terrestrial orchid and plants with minute seeds?" Symbiosis, 2007, vol. 44, pp. 93-99.

Vujanovic, V., et al., "Seed endosymbiosis: a vital relationship in providing prenatal care to plants," Can. J. Plant Sci., NRC Research Press, Feb. 6, 2017, pp. 972-981, vol. 97.

Vujanovic, V., et al: "Fungal communities associated with durum wheat production system: A characterization by growth stage, plant organ and preceding crop", Crop Protection, Elsevier Science, GB, vol. 37, Feb. 19, 2012, pp. 26-34.

Yennamalli, R., et al., "Endoglucanases: insights into thermostability for biofuel applications", Biotech Biofuels, 2013, vol. 6, Issue 136, pp. 1-9.

Youssef, Y.A., et al., "Production of Plant Growth Substances by Rhizosphere Myoflora of Broad Bean and Cotton," Biologia Plantarum, 1975, pp. 175-181, vol. 17, No. 3.

Zhang, Y., et al., "BcGsl, a glycoprotein from Botrytis cinerea, elicits defence response and improves disease resistance in host plants. Biochemical and biophysical research communications," Biochemical and Biophysical Research Communications, 2015, vol. 457, No. 4, pp. 627-634.

Zhang, W., et al., Host range of Exserohilum monoceras, a potential bioherbicide for the control of Echinochloa species, Canadian Journal of Botany/ Journal Canadien De Botan, National Research Council, Ottawa, CA, vol. 75, Jan. 1, 1997, pp. 685-692.

Zhu et al., "Helminthosporium velutinum and H. aquaticum sp. nov. from aquatic habitats in Yunnan Province, China." Phytotaxa, 2016, vol. 253, No. 3, pp. 179-190.

Amatuzzi, R.E, et al., "Potential of endophytic fungi as biocontrol agents of Duponchelia fovealis (Zeller) (Lepidoptera:Crambidae)," Brazilian Journal of Biology, Nov. 9, 2017, 7 Pages.

Artursson, V., et al., "Interactions between arbuscular mycorrhizal fungi and bacteria and their potential for stimulating plant growth", Environmental Microbiology, vol. 8, No. 1, Jan. 1, 2006, pp. 1-10.

Bing, La, et al., "Suppression of Ostrinia nubilalis (Hübner) (Lepidoptera: Pyralidae) by endophytic Beauveria bassiana (Balsamo) Vuillemin", Environmental Entomol, Entomological Society of America, College Park, MD, US, vol. 20, Jan. 1, 1991, pp. 1207-1211.

PCT International Search Report and Written Opinion for PCT/AU2018/050387, dated Jul. 12, 2018, 8 pages.

PCT International Search Report and Written Opinionfor PCT/US2018/051467, dated Mar. 25, 2019 26 pages.

Al-Askar AA, "Microbiological studies on the in vitro inhibitory effect of Streptomyces collinus albescens against some phytopathogenic fungi", African Journal of Microbiology Research, 2012, 6: 3277-3283 & GenBank Accession No. AB184101, May 20, 2008.

Ardakani, M.R. et al., "Absorption of N, P, K thorugh triple inoculation of wheat (Triticum aestivum L.) by Azospirillurn brasilense, Streptomyces sp., Glomus intraradices and manure application," Physiol Mol Biol Plants, 2011, vol. 17, No. 2, pp. 181-192.

Barnett, S., et al., "Selection of microbes for control of Rhizoctonia root rot on wheat using a high throughput pathosystem", Biological Control, Jul. 6, 2017, 113: 45-57.

(56) References Cited

OTHER PUBLICATIONS

Bashan, Yoav Ed, et al., "Inoculants of plant growth-promoting bacteria for use in agriculture," Biotechnology Advances, Elsevier Publishing, Barking, GB, vol. 16, No. 4, Jul. 1, 1998, pp. 729-770, XP004123985.
Bashan, Yoav E., et al., "Alginate Beads as Synthetic Inoculant Carriers for Slow Release of Bacteria that Affect Plant Growth," Applied and Environmental Microbiology, pp. 1089-1098, May 1986.
Chenhua Li, et al., "Change in deep soil microbial communities due to long-term fertilization," Soil Biology and Biochemistry, vol. 75, Mar. 5, 2014, pp. 264-272, XP055530941.
Cheow, W.S., et al., "Biofilm-like Lactobacillus rhamnosus Probiotices Encapsulated in Algiinate and Carrageenan Microcapsules Exhibiting Enhanced Thermotolerance and Freeze-drying Resistance," Biomacromolecules 2013, vol. 14(9):3214-3222.
De Santi, M. et al., "A combined morphologic and molecular approach for characterizing fungal microflora from a traditional Italian cheese (Fossa cheese)," Inter. Dairy J., 2010, vol. 10, No. 7, pp. 465-471.
Fatima Z et al, "Antifungal activity of plant growth-promoting rhizobacteria isolates against Rhizoctonia solani in wheat", African Journal of Biotechnology, 2009, 8: 219-225.
GenBank Accession No. KY643705, Feb. 27, 2017.
GenBank Accession No. KF951483, Jan. 5, 2014.
GenBank Accession No. KJ152029, May 6, 2015.
GenBank Accession No. KJ162248, Apr. 8, 2014.
Govindarajan, M. et al., "Effects of the Inoculation of Burkholderia vietnamensis and Related Endophytic Diaztrophic Bacteria on Grain Yield of Rice", Microbiol Ecology, Apr. 4, 2007, 17 Pages.
Iverson, C., et al, "The taxonomy of Enterobacter sakazakii: proposal of a new genus *Cronobacter* gen. nov. and descriptions of *Cronobacter sakazakii* comb. nov. *Cronobacter sakazakii* subsp. *sakazakii*, comb. nov., *Cronobacter sakazakii* subsp. *malonaticus* subsp. nov., *Cronobacter turicensis* sp. nov., *Cronobacter muytjensii* sp. nov., *Cronobacter dublinensis* sp. nov. and *Cronobacter* genomospecies I", BMC Evolutionary Biology 2007, Apr. 17, 2017, 11 pages.
Joe, M.M. et al., "Development of alginate-based aggregate inoculants of *Methylobacterium* sp. and Azospirillum brasilense tested under in vitro conditions to promote plant growth," Journal of Applied Microbiology 2013, 116 (2):408-423, XP055225426, Nov. 22, 2013.
Manoharan, M. J. et. Al., "Survival of flocculated cells in alginate and its inoculatin effect on growth and yield of maize under water deficit conditions," EP J of Soil Biology, Gauthier-Villars, Montrouge, FR, vol. 50, Mar. 7, 2012, pp. 198-206, XP028421147.
Murali, Gopal, et al., "Microbiome Selection Could Spur Next-Generation Plant Breeding Strategies," Frontiers in Microbiology, vol. 7, Dec. 7, 2016, XP055531064.
United States Patent Office, Non-Final Office Action, U.S. Appl. No. 14/964,429, dated Aug. 9, 2016, 6 Pages.
United States Patent Office, Final Office Action, U.S. Appl. No. 14/964,429, dated May 31, 2017, 9 Pages.
United States Patent Office, Non-Final Office Action, U.S. Appl. No. 15/212,038, dated Sep. 21, 2016, 10 Pages.
United States Patent Office, Non-Final Office Action, U.S. Appl. No. 15/063,350, dated Nov. 10, 2016, 18 Pages.
United States Patent Office, Final Office Action, U.S. Appl. No. 14/614,193, dated Dec. 22, 2016, 13 Pages.
United States Patent Office, Final Office Action, U.S. Appl. No. 14/614,193, dated Jul. 18, 2017, 14 Pages.
United States Patent Office, Final Office Action, U.S. Appl. No. 14/614,193, dated May 3, 2018, 10 Pages.
United States Patent Office, Non-Final Office Action, U.S. Appl. No. 15/107,973, dated Apr. 10, 2017, 39 Pages.
United States Patent Office, Final Office Action, U.S. Appl. No. 15/107,973, dated Jan. 26, 2018, 20 Pages.
United States Patent Office, Final Office Action, U.S. Appl. No. 14/410,537, dated May 5, 2017, 9 Pages.
United States Patent Office, Non-Final Office Action, U.S. Appl. No. 15/034,862, dated May 19, 2017, 8 Pages.
United States Patent Office, Final Office Action, U.S. Appl. No. 15/034,862, dated Jan. 12, 2018, 14 Pages.
United States Patent Office, Non-Final Office Action, U.S. Appl. No. 14/916,514, dated Sep. 20, 2017, 31 Pages.
United States Patent Office, Non-Final Office Action, U.S. Appl. No. 15/143,398, dated Sep. 22, 2017, 17 Pages.
United States Patent Office, Non-Final Office Action, U.S. Appl. No. 15/143,394, dated Sep. 25, 2017, 15 Pages.
United States Patent Office, Non-Final Office Action, U.S. Appl. No. 15/107,965, dated Jun. 21, 2018, 27 Pages.
Wang, L. et al. Application of Bioorganic Fertilizer Significantly Increased Apple Yields and Shaped Bacterial Community Structure in Orchard Soil.
Whelehan, et al., "Microencapsulation using vibrating technology," Journal of Microencapsulation 2011, vol. 28(8), pp. 669-688.
Zhao, Jun, et al., "Effects of organic-inorganic compound fertilizer with reduced chemical fertilizer application on crop yields, soil biological activity and bacterial community structure in a rice-wheat cropping system," Applied Soil Ecology, vol. 99, Nov. 28, 2015, pp. 1-12, XP055530937.
PCT Invitation to Pay Additional Fees, PCT Application No. PCT/CA2013/000091, dated Mar. 27, 2013, 2 Pages.
PCT International Search Report and Written Opinion for PCT/CA2013/000091, dated Sep. 20, 2013, 17 Pages.
PCT International Search Report and Written Opinion for PCT/EP2013/062976, dated Dec. 22, 2014, 9 Pages.
PCT International Search Report, Application No. PCT/US2014/044427, dated Dec. 3, 2014, 9 Pages.
PCT International Search Report and Written Opinion, Application No. PCT/US2014/054160, dated Dec. 9, 2014, 21 Pages.
PCT Invitation to Pay Additional Fees, PCT Application No. PCT/US2014/064411, dated Feb. 5, 2015, 2 Pages.
PCT International Search Report and Written Opinion, International Application No. PCT/US2014/064411, dated Mar. 27, 2015, 15 Pages.
PCT Invitation to Pay Additional Fees, PCT Application No. PCT/US2014/072399, dated Apr. 14, 2015, 2 Pages.
PCT International Search Report and Written Opinion, International Application No. PCT/US2014/072399, dated Jun. 26, 2015, 22 Pages.
PCT Invitation to Pay Additional Fees, PCT Application No. PCT/US2014/072400, dated Apr. 16, 2015, 6 Pages.
PCT International Search Report and Written Opinion, Application No. PCT/US2014/072400, dated Jul. 8, 2015, 38 Pages.
Giraldo, A., et al., "Phylogeny of Sarocladium (Hypocreales)," Persoonia, 2015, pp. 10-24, vol. 34.
Gitaitis, R., et al., "The Epidemiology and Management of Seedbome Bacterial Diseases," Annu Rev Phytopathol., 2007, pp. 371-397, vol. 45.
Grondona, I., et al., "TUSAL®, a commercial biocontrol formulation based on Trichoderma," Bulletin OILB/SROP, 2004, pp. 285-288, vol. 27, No. 8.
Haake, V., et al., "Transcription Factor CBF4 is a Regulator of Drought Adaptation in *Arabidopsis*," Plant Physiol., 2002, pp. 639-648, vol. 130.
Haas, D., et al., "R Factor Variants with Enhanced Sex Factor Activity in Pseudomonas aeruginosa," Mol Gen Genet., 1976, pp. 243-251, vol. 144.
Hahm, M-S., et al., "Biological Control and Plant Growth Promoting Capacity of Rhizobacteria and Pepper Under Greenhouse and Field Conditions," The Journal of Microbiology, The Microbiological Society of Korea, Heidelberg, Jun. 30, 2012, pp. 380-385, vol. 50, No. 3.
Hallman, J., et al., "Bacterial Endophytes in Agricultural Crops," Canadian J Microbiol., 1997, pp. 895-914, vol. 43.
Hanson, L.E., "Reduction of Verticillium Wilt Symptoms in Cotton Following Seed Treatment with Trichoderma virens," The Journal of Cotton Science, 2000, pp. 224-231, vol. 4, No. 4.
Hanson, LE., "Reduction of Verticillium Wilt Symptoms in Cotton Following Seed Treatment with Trichoderma virens," Proceedings Beltwide Cotton Conferences, 2000, vol. 1. (Abstract), 1 Page.

(56) References Cited

OTHER PUBLICATIONS

Hardegree, S. P. et al., "Effect of Polyethylene Glycol Exclusion on the Water Potential of Solution-Saturated Filter Paper," Plant Physiol., 1990, pp. 462-466, vol. 92.

Hardoim, P. R., et al., "Assessment of Rice Root Endophytes and Their Potential for Plant Growth Promotion," In: Hardoim, P.R., Bacterial Endophytes of Rice—Their Diversity, Characteristics and Perspectives, Groningen, 2011, pp. 77-100.

Harman, G.E., et al., "Symposium: biocontrol and biotechnological methods for controlling cotton pests," Proceedings of the Beltwide Cotton Production Research Conf., 1989, Memphis, Tennessee, USA, pp. 15-20. (Abstract).

Hepler, P. K., et al., "Polarized Cell Growth in Higher Plants," Annu Rev Cell Dev Biol., 2001, pp. 159-187, vol. 17.

Hibbett, D.S., et al., "A Higher-Level Phylogenetic Classification of the Fungi," Mycol Res., 2007, pp. 509-547, vol. 111.

Hill, N. S., et al., "Endophyte Survival during Seed Storage: Endophyte-Host Interactions and Heritability," Crop Sci., 2009, pp. 1425-1430, vol. 49.

Hill N. S., et al., "Endophyte Survival during Seed Storage: Endophyte-Host Interactions and Heritability," PowerPoint, Dept. Crop Soil Sciences, University of Georgia, Nov. 16, 2012, 3 Pages.

Hinton, D. M., et al., "Enterobacter cloacae is an endophytic symbiont of corn," Mycopathologia, 1995, pp. 117-125, vol. 129.

Howell, C.R., et al., "Induction of Terpenoid Synthesis in Cotton Roots and Control of Rhizoctonia solani by Seed Treatment with Trichoderma virens," Phytopathology, 2000, pp. 248-252, vol. 90, No. 3.

Hubbard, M., et al., "Fungal Endophytes Improve Wheat Seed Germination Under Heat and Drought Stress," Botany, 2012, pp. 137-149, vol. 90.

Humann, J., et al., "Complete genome of the onion pathogen Enterobacter cloacae EcWSU1 ," Standard in Genomic Sciences, Dec. 31, 2011, vol. 5, No. 3, pp. 279-286.

Hung, P.Q., et al., "Isolation and Characterization of Endophytic Bacteria in Soybean (*Glycine* Sp.)," Omonrice, 2004, pp. 92-101, vol. 12.

Idris, A., et al., "Efficacy of Rhizobacteria for Growth Promotion in Sorghum Under Greenhouse Conditions and Selected Modes of Action Studies," J Agr Sci., 2009, pp. 17-30, vol. 147.

Ikeda, S., et al., "The Genotype of the Calcium/Calmodulin-Dependent Protein Kinase Gene (CCaMK) Determines Bacterial Community Diversity in Rice Roots Under Paddy and Upland Field Conditions," Applied and Environmental Microbiology, 2011, pp. 4399-4405, vol. 77, No. 13.

Imoto, K, et al., "Comprehensive Approach to Genes Involved in Cell Wall Modifications in *Arabidopsis thaliana*," Plant Mol Biol., 2005, pp. 177-192, vol. 58.

Jalgaonwala, R., et al., "A Review on Microbiol Endophytes from Plants: A Treasure Search for Biologically Active Metabolites," Global Journal of Research on Medicinal Plants & Indigenous Medicine, 2014, pp. 263-277, vol. 3, No. 6.

Janda, J.M., et al., "16S rRNA Gene Sequencing for Bacterial Identification in the Diagnostic Laboratory: Pluses, Perils, and Pitfalls," Journal of Clinical Microbiology, 2007, pp. 2761-2764, vol. 45, No. 9.

Johnston-Monje, D., et al., "Plant and Endophyte Relationships: Nutrient Management," Comprehensive Biotechnol., 2011, pp. 713-727, vol. 4.

Jones, K.L., "Fresh Isolates of Actinomycetes in which the Presence of Sporogenous Aerial Mycelia is a Fluctuating Characteristic," J Bacteriol., 1949, pp. 141-145, vol. 57, No. 2.

Kaga, H., et al., "Rice Seeds as Sources of Endophytic Bacteria," Microbes Environ., 2009, pp. 154-162, vol. 24, No. 2.

Kalns, L., et al., "The Effects of Cotton Fungal Endophytes in the Field on Arthropod Community Structure," Power Joint Presentation dated Jan. 7, 2013, 17 Pages.

Kang, B. H., et al., "Members of the *Arabidopsis* Dynamin-Like Gene Family, ADL1, are Essential for Plant Cytokinesis and Polarized Cell Growth," Plant Cell, 2003, pp. 899-913, vol. 15.

Khan, A.L., et al., "Salinity Stress Resistance Offered by Endophytic Fungal Interaction Between Penicillium minioluteum LHL09 and *Glycine max*. L," J. Microbiol. Biotechnol., 2011, pp. 893-902, vol. 21, No. 9.

Kruger, M., et al., "DNA-Based Species Level Detection of Glomeromycota: One PCR Primer Set for All Arbuscular Mycorrhizal Fungi," New Phytol., 2009, pp. 212-223, vol. 183.

Kuklinsky-Sobral, J., et al., "Isolation and Characterization of Endophytic Bacteria from Soybean (*Glycine max*) Grown in Soil Treated with Glyphosate Herbicide," Plant and Soil, 2005, pp. 91-99, vol. 273.

Kuklinsky-Sobral, J., et al., "Isolation and characterization of soybean-associated bacteria and their potential for plant growth promotion," Environmental Microbiology, 2004, pp. 1244-1251, vol. 6, No. 12.

Kumar, S. et al., "MEGA7: Molecular Evolutionary Genetics Analysis version 7.0 for bigger datasets," Molecular Biology and Evolution, Mar. 22, 2016, vol. 33, pp. 1870-1874.

Labeda, D.P., et al., "Phylogenetic study of the species within the family Streptomycetaceae," Antonie van Leeuwenhoek, 2012, vol. 101, pp. 73-104, Springer.

Lanver, D., et al., "Shot and Msb2-Related Proteins Regulate Appressorium Development in the Smut Fungus *Ustilago aydis*," Plant Cell, 2010, pp. 2085-2101, vol. 22.

Laus, M. C., et al., "Role of Cellulose Fibrils and Exopolysaccharides of Rhizobium leguminosarum in Attachment to and Infection of Vicia sativa Root Hairs," Mol Plant Microbe Interact., 2005, pp. 533-538, vol. 18, No. 6.

Le, X.H., et al., "Isolation and characterisation of endophytic actinobacteria and their effect on the early growth and nodulation of lucerne (*Medicago sativa* L.)," 17th Australian Nitrogen Fixation Conference 2014 Proceedings, Sep. 29, 2014, ed. Gupta, V.V.S.R., Unkovich, M. and Kaiser, B. N., ASNF, University of Adelaide, pp. 134-136.

Lehman, S.G., "Treat Cotton Seed," Review of Applied Mycology, 1945, 24, 369, 16 Pages.

Lehman, S.G., "Treat Cotton Seed," Research and Farming III, Progr. Rept., 1945, 3, 5, 16 Pages.

Leonard., C.A., et al., "Random Mutagenesis of the Aspergillus oryzae Genome Results in Fungal Antibacterial Activity," Int J Microbiot, 2013, vol. 2013, Article ID 901697, 6 Pages.

Li, H.M., et al., "Expression of a Novel Chitinase by the Fungal Endophyte in Poa ampla," Mycologia, 2004, pp. 526-536, vol. 96, No. 3.

Li, H., et al., "Endophytes and their role in phytoremediation," Fungal Diversity, 2012, pp. 11-18, vol. 54.

Liu, M., et al., "A Novel Screening Method for Isolating Exopolysaccharide-Deficient Mutants," Appl Environ Microbiol., 1998, pp. 4600-4602, vol. 64, No. 11.

Liu, Y., et al., "Investigation on Diversity and Population Succession Dynamics of Endophytic Bacteria from Seeds of Maize (*Zea mays* L., Nongda108) at Different Growth Stages," Ann Microbiol., 2013, pp. 71-79, vol. 63.

Liu, D., et al., "Osmotin Overexpression in Potato Delays Development of Disease Symptoms," Proc Natl Acad Sci USA, 1994, pp. 1888-1892, vol. 91.

Liu, Y., et al., "Study on Diversity of Endophytic Bacterial Communities in Seeds of Hybrid Maize and their Parental Lines," Arch Microbiol., 2012, pp. 1001-1012, vol. 194.

Long, H. H., et al., "The Structure of the Culturable Root Bacterial Endophyte Community of Nicotiana attenuata is Organized by Soil Composition and Host Plant Ethylene Production and Perception," New Phytol., 2010, pp. 554-567, vol. 185.

Reiter, B., et al., "Response of Endophytic Bacterial Communities in Potato Plants to Infection with *Erwinia carotovora* subsp. *atroseptica*," Appl Environ Microbiol., 2001, pp. 2261-2268, vol. 68, No. 5.

Ren, Y., et al., "Complete Genome Sequence of *Enterobacter cloacae* subsp. *cloacae* Type Strain ATCC 13047," J. Bacteriol. May 2010, vol. 192, No. 9, pp. 2463-2464.

Riken, GI No. GMFL01-01-D03, 2 Pages, [online] [Retrieved on Dec. 18, 2017] Retrieved from the internet <URL:http://spectra.psc.riken.jp/menta.cgi/rsoy/datail?id=GMFL01-01-D03>.

(56) References Cited

OTHER PUBLICATIONS

Rodriguez, H., et al., "Expression of a Mineral Phosphate Solubilizing Gene From Erwinia herbicola in Two Rhizobacterial Strains," J Biotechnol., 2001, pp. 155-161, vol. 84.
Rodriguez, R.J., et al., "Stress Tolerance in Plants via Habitat-Adapted Symbiosis," ISME J., 2008, pp. 404-416, vol. 2.
Rodriguez-Navarro, D., et al., "Soybean Interactions with Soil Microbes, Agronomical and Molecular Aspects," Agronomy for Sustainable Development, 2011, pp. 173-190, vol. 31, No. 1.
Roessner, U., et al., "Metabolic Profiling Allows Comprehensive Phenotyping of Genetically or Environmentally Modified Plant Systems," Plant Cell, 2001, pp. 11-29, vol. 13.
Rosado, A. S., et al., "Phenotypic and Genetic Diversity of Paenibacillus azotofixans Strains Isolated from the Rhizoplane or Rhizosphere Soil of Different Grasses," J App Microbiol., 1998, pp. 216-226, vol. 84.
Rosenblueth, A., et al., "Seed Bacterial Endophytes: Common Genera, Seed-to-Seed Variability and Their Possible Role in Plants," Acta Hort., 2012, pp. 39-48, vol. 938.
Rosenblueth, M., et al., "Bacterial Endophytes and Their Interactions With Host," Molecular Plant-Microbe Interactions, 2006, pp. 827-837, vol. 19, No. 8.
Ross, P.L., et al., "Multiplexed Protein Quantitation in *Saccharomyces cerevisiae* Using Amine-Reactive Isobaric Tagging Reagents," Mol Cell Proteomics, 2004, pp. 1154-1169, vol. 3, No. 12.
Saleem, M., et al., "Perspective of Plant Growth Promoting Rhizobacteria (PGPR) Containing ACC Deaminase in Stress Agriculture," J Ind Microbiol Biotechnol., Oct. 2007, pp. 635-648, vol. 34.
Samac, D.A., et al., "Recent Advances in Legume-Microbe Interactions: Recognition, Defense Response, and Symbiosis from a Genomic Perspective," Plant Physiol., 2007, pp. 582-587, vol. 144.
Sardi, P, et al., "Isolation of Endophytic Streptomyces Strains from Surface Sterilized Roots," Applied and Environmental Microbiology, 1992, pp. 2691-2693, vol. 58, No. 8.
Sarwar, M., et al., "Tryptophan Dependent Biosynthesis of Auxins in Soil," Plant Soil, 1992, pp. 207-215, vol. 147.
Schmieder, R., et al., "Quality Control and Preprocessing of Metagenomic Datasets," Bioinformatics, 2011, pp. 863-864, vol. 27, No. 6.
Schoch, C. L., et al., "Nuclear Ribosomal Internal Transcribed Spacer (ITS) Region as a Universal DNA Barcode Marker for Fungi," Proc Natl Acad Sci USA, 2012, pp. 6241-6246, vol. 109, No. 16.
Schwyn, B. et al., "Universal Chemical Assay for the Detection and Determination of Siderophores," Analytical Biochemistry, 1987, pp. 47-56, vol. 160.
Senthilkumar, M., et al., "Biocontrol Potential of Soybean Bacterial Endophytes Against Charcoal Rot Fungus, *Rhizoctonia batatiola*," Current Microbiology, 2009, vol. 58, pp. 288-293.
Sessitsch, A., et al., "*Burkholderia phytofirmans* sp. Nov., a novel plant-associated bacterium with plant-beneficial properties," International Journal of Systematic and Evoluntary Microbiology, 2005, pp. 1187-1192, vol. 55.
Shapiro-Ilan, D.I., et al., "The Potential for Enhanced Fungicide Resistance in Beauveria Bassiana Through Strain Discovery and Artificial Selection," Journal of Invertebrate Pathology, 2002, pp. 86-93, vol. 81.
Shankar, M., et al., "Root colonization of a rice growth promoting strain of Enterobacter cloacae," Journal of Basic Microbiology, 2011, pp. 523-530, vol. 51.
Singh, A K., et al., "Uncultured *Actinomyces* sp. Clone EMLACT 80 IV (New) 16S Ribosomal RNA Gene, Partial Sequence," NCBI GenBank Accession No. JQ285908. Submtted Dec. 13, 2011, 1 page.
Soares, M. M. C. N., et al., "Screening of Bacterial Strains for Pectinolytic Activity: Characterization of the Polygalacturonase Produced by *Bacillus* Sp," Revista de Microbiolgia, 1999, pp. 299-303, vol. 30.
Soe, K.M., et al., "Effects of endophytic actinomycetes and Bradyrhizobium japonicum strains on growth, nodulation, nitrogen fixation and seed weight of different soybean varieties," Soil Science and Plant Nutrition, 2012, pp. 319-325, vol. 58, No. 3.
Soe, K.M., et al., "Low-Density Co-Inoculation of Myanmar Bradyrhizobium yuanmingense MAS34 and Streptomyces griseoflavus P4 to Enhance Symbiosis and Seed Yield in Soybean Varieties," American Journal of Plant Sciences, 2013, pp. 1879-1892, vol. 4.
Sogonov, M.V., et al., "The hyphomycete *Teberdinia hygrophila* gen. nov., sp. nov. and related anamorphs of *Pseudeurotium* species," Mycologia, May 2005, pp. 695-709, vol. 97, No. 3.
Song, M., et al., "Effects of Neotyphodium Endophyte on Genmination of Hordeum brevisubulatum under Temperature and Water Stress Conditions," Acta Agrestia Sinica, 2010, pp. 834-837, vol. 18, No. 6. (English Abstract).
Souleimanov, A., et al., "The Major Nod Factor of Bradyrhizobium japonicum Promotes Early Growth of Soybean and Corn," J. Exp. Bot., 2002, pp. 1929-1934, vol. 53, No. 376.
Spiekermann, P., et al., "A Sensitive, Viable-Colony Staining Method Using Nile Red for Direct Screening of Bacteria that Accumulate Polyhydroxyalkanoic Acids and Other Lipid Storage Compounds," Arch Microbiol., 1999, pp. 73-80, vol. 171.
Staudt, A. K., et al., "Variations in Exopolysaccharide Production by Rhizobium tropici," Arch Microbiol., 2012, pp. 197-206, vol. 194.
Strobel, G. A., "Endophytes as Sources of Bioactive Products," Microbes and Infection, 2003, pp. 535-544, vol. 5.
Sturz, A. V., et al., "Weeds as a Source of Plant Growth Promoting Rhizobacteria in Agricultural Soils," Can J Microbiol., 2001, pp. 1013-1024, vol. 47, No. 11.
Burette, M.A., et al. "Bacterial Endophytes in Processing Carrots (*Daucus carota* L. var. *sativus*): Their Localization, Population Density, Biodiversity and Their Effects on Plant Growth," Plant and Soil, 2003, pp. 381-390, vol. 253, No. 2.
Suto, M., et al., "Endophytes as Producers of Xylanase," J Biosci Bioeng., 2002, pp. 88-90, vol. 93, No. 1.
Sword, G., "Manipulating Fungal Endophytes to Protect Plants from Insects and Nematodes," Power Point Presentation dated Aug. 7, 2013, 48 Pages.
Sword, G., et al., "Manipulating Fungal Endophytes for the Protection of Cotton in the Field," Power Point Presentation dated Jan. 7, 2013.
Sword, G., et al., "Field Trials of Potentially Beneficial Fungal Endophytes in Cotton," Power Point Presentation dated Jan. 7, 2013, 17 Pages.
Sword, G., "Fungal Endophytes to Protect Cotton from Insects and Nematodes," Power Point Presentation dated Dec. 7, 2012, 20 Pages.
Sword, G., "Natural Enemies—The Forgotten Basis of IPM?," Power Point Presentation dated Sep. 6, 2013, 33 Pages.
Taghavi, S., et al., "Genome Survey and Characterization of Endophytic Bacteria Exhibiting a Beneficial Effect on Growth and Development of Poplar Trees," Applied and Environmental Microbiology, 2009, pp. 748-757, vol. 75, No. 3.
Taghavi, S., et al., "Genome Sequence of the Plant Growth promoting Endophytic Bacterium *Enterobacter* sp. 638", PLoS Genet., May 2010, vol. 6, Issue 5, e1000943, pp. 1-15.
Tamura, K, et al., "Estimation of the number of nucleotide substitutions in the control region of mitochondrial DNA in humans and chimpanzees," Molecular Biology and Evolution, 1993, vol. 10, No. 3, pp. 512-526.
Taylor, A.G., et al., "Concepts and Technologies of Selected Seed Treatments," Annu. Rev. Phytopathol., 1990, pp. 321-339, vol. 28.
Teather, R. M., et al., "Use of Congo Red-Polysaccharide Interactions in Enumeration and Characterization of Cellulolytic Bacteria from the Bovine Rumen," Appl Environ Microbiol., 1982, pp. 777-780, vol. 43, No. 4.
Thakur, A., et al., "Detrimental effects of endophytic fungus *Nigrospora* sp. on survival and development of Spodoptera litura," Biocontrol Science and Technology, Feb. 1, 2012, pp. 151-161, vol. 22, No. 2.
Thakur, A., et al., "Enhanced Resistance to Spodoptera litura in Endophyte Infected Cauliflower Plants," Environmental Entomology, Apr. 1, 2013, pp. 240-246, vol. 42, No. 2.

(56) References Cited

OTHER PUBLICATIONS

Thakur, A., et al., "Suppression of Cellular Immune Response in Spodoptera litura (Lepidoptera: Noctuidae) Larvae by Endophytic Fungi *Nigrospora oryzae* and *Cladosporium uredinicola*,", Annals of the Entomological Society of America, May 1, 2014, pp. 674-679, vol. 107, No. 3.

Theis, K. R., et al., "Uncultured Bacterium Clone GM2GI8201A64RC 16S Ribosomal RNA Gene, Partial Sequence," NCBI GenBank Accession No. JX051943, Submitted May 14, 2012, 1 Page.

Thomas, L., et al., "Development of Resistance to Chlorhexidine Diacetate in Pseudomonas aeruginosa and the Effect of a "Residual" Concentration," J Hosp Infect., 2000, pp. 297-303, vol. 46.

Soe, K.M, et al, "Evaluation of effective Myanmar Bradyrhizobium strains isolated from Myanmar soybean and effects of coinoculation with Streptomyces griseoglavus P4 for nitrogen fixation", Soil science and plant nutrition 59.3 (2013): 361-370 (Year: 2013).

Ngom, A et al., "A novel symbiotic nitrogen-fixing member of the Ochrobactrum clade isolated from root nodues of Acacia mangium". J. Gen. Appl. Microbiol. (2004) 50: 17-27.

Trujillo, M.E. et al., "Nodulation of Lupinus albus by strins of *Ochrobactrum lupini* sp. nov." Appl. Environ Microbial Mar. 2005; 71(3): 1318-1327.

Bal, H.B et al., "Isolation of ACC deaminase producting PGPR from rice rhizosphere and evaluating their plant growth promoting activity under salt stress". Plant Soil (2013) 366: 93-105 doi: 10/1007/s11104-012-1402-5.

Chakraborty et al., "Evaluation of Ochrobactrum anthropi TRS-2 and its talcbased formulation for enhancement of growth of tea plants and management of brown root rot disease." Journal of Applied Microbiology, 2009, 107 (2):625-634 DOI:10.1111/j.1365-2672.2009.04242.x <https://doi.org/10.1111/j.1365-2672.2009.04242.x.

Sulistiyani, et al., "Population and Diversity of Endophytic Bacteria Associated with Medicinal Plan Curumma zedoaria ", Microbiology Indonesia 8.2 (2014):4.

Bevivino, A., et al., "Characerization of free-living maize rhizosphere populatin of Burkholderia cepacia: effect of seed treatment on disease suppresssion and growth promotion of maize", FEMS Microbiology Ecology 27 (1998) 225-237.

Ciccillo, F., et al., Effects of two different application methods of Burkholderia ambifaria MCI 7 on plant growth and rhizospheric bacterial diversity.

Estrada, P., et al., "A N2-fixing endophytic *Burkholderia* sp. associated with maize plants culitvated in Mexico", Canadian Journal of Microbiology (2002), vol. 48(4), pp. 528-536.

Sharma, V.K., et al., "Enhancement of verticillium wilt resistance in tomato transplants by in vitro co-culture of seedlings with a plant growth promoting rhizobacterium (*Pseudomonas* sp. strain PsJN)", Canadian Journal of Microbiology (1998), vol. 44(6), pp. 285-294.

Grady, E., et al., "Current knowledge and perspectives of Paenibacillus: a review" Microb Cell Fact (2016) 15:203.

Li, J. et al. "Antitumour and antimicrobial activities of endophytic stretomycetes from pharmaceutical plants in rainforest", Lett Appl Microbiol. Dec. 2008; 47(6): 574-80. (Year: 2008).

Hamayun, M., et al., "Gibberellin production and plant growth promotion from pure cultures of *Cladosporium* sp. MH-6 isolated from cucumber (*Cucumis sativus* L.)", Mycologia, 102 (5), 2010, pp. 989-995.

Shupeng, T., et al. "Advances in Study of Interactions between Mycorrhizal Fungi and Bacteria", Journal of Qingdao Agricultural University (Natural Science Edition), vol. 30, Issue 4, pp. 240-246, Dec. 31, 2013.

Kim, S., et al., "Physiological and proteomic analyses of Korean F1 maize (*Zea mays* L.) hybrids under water-deficit stress during flowering", Appl. Biol. Chem. (2019) 62:32.

Halligan, B., et al., "Cloning of the murine cDNA encoding VDJP, a protein homologous to the large subunit of replication factor C and bacterial DNA ligases", Gene (1995) 217-222.

Arend, J., et al., "Hydroquinone: O-glucosytransferase from cultivated Rauvolfia cells: enrichment and partial amino acid sequences", Phytochemistry (2000) 53:187-193.

Enchev, R., et al., "Protein neddylation: beyond cullin-RING ligases", (Nature Reviews: Molecular Cell Biology (2015) 16:30-44.

Bais, H., et al., "The Role of Root Exudates in Rhizosphere Interactions with Plants and Other Organisms", Annual Review. Plant Biol. (2006) 57:233-266.

Goepfert, S., et al., "Molecular Identification and Characterization of the *Arabidopsis* D3,5, D2,4-Dienoyl-Coenzyme A Isomerase, a Peroxisomal Enzyme Participating in the b-Oxidation Cycle of Unsaturated Fatty Acids1", Plant Physiology (2005) 138:1947-1956.

Thomas, P., et al: "Endophytic Bacteria Associated with Growing Shoot Tips of Banana (*Musa* sp.) cv. Grand Naine and the Affinity of Endophytes to the Host", Microbial Ecology, Springer-Verlag, NE, vol. 58, No. 4, Jul. 25, 2009 (Jul. 25, 2009), pp. 952-964, XP019757395, ISSN: 1432-184X, DOI: 10.1007 /S00248-009-9559-Z.

Database Geneseq [Online] Sep. 30, 2010 (Sep. 30, 2010), "Cellulomonas fermentans 16s rRNA gene SEQ ID:39.", retrieved from EBI accession No. GSN:AWL84299 Database accession No. AWL84299; & JP 2009 072168 A (Univ of Occupational & Environ) Apr. 9, 2009 (Apr. 9, 2009).

European Patent Office, Partial European Search Report, European Patent Application No. 20171870.7, dated Nov. 20, 2020, 18 Pages.

European Patent Office, European Search Report, European Patent Application No. 20171870.7, dated Mar. 1, 2021, 15 Pages.

GenBank Accession NR_041978, dated Aug. 8, 2011. (Year: 2011).

GenBank Accession AF394537, dated Jul. 2, 2002. (Year: 2002).

Andreolli, M., et al., "Endophytic Burkholderia fungorum DBT1 can improve phytoremediation efficiency of polycyclic aromatic hyrocarbons", Chemosphere, Pergamon Press, Oxford, GB, vol. 92, No. 6, May 21, 2013, pp. 688-694.

Extended European Search Report for EP 20202875.9, dated Apr. 19, 2021, 16 Pages.

Douglas, G., et al., "PICRUSt2 for prediction of metagenome functions", Nature Biotechnology, vol. 38, No. 6, Jun. 1, 2020, pp. 685-688.

\* cited by examiner

METHODS OF USE OF SEED-ORIGIN ENDOPHYTE POPULATIONS

CROSS-REFERENCE TO RELATED APPLICATIONS

This application is a continuation of U.S. application Ser. No. 16/024,029, filed Jun. 29, 2018, allowed, which is a continuation of U.S. application Ser. No. 15/436,592, filed Feb. 17, 2017, now U.S. Pat. No. 10,058,101, issued Aug. 28, 2018, which is a continuation of U.S. application Ser. No. 15/145,687, filed May 3, 2016, now U.S. Pat. No. 9,622,485, issued Apr. 18, 2017, which is a continuation of U.S. application Ser. No. 15/017,531, filed Feb. 5, 2016, now U.S. Pat. No. 9,532,573, issued Jan. 3, 2017, which is a continuation of U.S. application Ser. No. 14/704,891, filed May 5, 2015, now U.S. Pat. No. 9,288,995, issued Mar. 22, 2016, which is a continuation of U.S. application Ser. No. 14/316,469, filed Jun. 26, 2014, now U.S. Pat. No. 9,113,636, issued Aug. 25, 2015, which claims priority to Provisional Application No. 61/957,255, filed Jun. 26, 2013; Provisional Application No. 61/959,859, filed Sep. 4, 2013; Provisional Application No. 61/959,847, filed Sep. 4, 2013; Provisional Application No. 61/959,858, filed Sep. 4, 2013; Provisional Application No. 61/959,854, filed Sep. 4, 2013; Provisional Application No. 61/959,861, filed Sep. 4, 2013; Provisional Application No. 61/959,870, filed Sep. 4, 2013; and Provisional Application No. 61/935,761, filed Feb. 4, 2014, the disclosures of which are incorporated by reference in their entirety.

SEQUENCE LISTING

The instant application contains a Sequence Listing which has been submitted electronically in ASCII format and is hereby incorporated by reference in its entirety. Said ASCII copy, created on Oct. 18, 2019, is named IAI001C12_Sequence_Listing.txt, includes 1470 sequences, and is 1,952,080 bytes in size.

TECHNICAL FIELD

This application relates to methods and materials for providing a benefit to a seed or seedling of an agricultural plant such as an agricultural grass plant, particularly a cereal, or an agricultural plant such as an agricultural grass plant derived from the seed or seedling. For example, this application provides purified bacterial populations that include novel seed-origin bacterial endophytes, and synthetic combinations of seeds and/or seedlings with heterologous seed-derived bacterial endophytes. Such seed-origin bacterial endophytes can provide beneficial properties to the seed, seedling, or the agricultural plant derived from the seed or seedling, including metabolism, transcription, proteome alterations, morphology, and the resilience to a variety of environmental stresses, and combination of such properties.

BACKGROUND

Economically-, environmentally-, and socially-sustainable approaches to agriculture and food production are required to meet the needs of a growing global population. By 2050 the United Nations' Food and Agriculture Organization projects that total food production must increase by 70% to meet the needs of the growing population, a challenge that is exacerbated by numerous factors, including diminishing freshwater resources, increasing competition for arable land, rising energy prices, increasing input costs, and the likely need for crops to adapt to the pressures of a drier, hotter, and more extreme global climate. The need to grow nearly twice as much food with less water in more arid climates is driving a critical need for innovations in crop water use efficiency and temperature tolerance.

Today, crop performance is optimized primarily via technologies directed towards the interplay between crop genotype (e.g., plant breeding, genetically-modified (GM) crops) and its surrounding environment (e.g., fertilizer, synthetic herbicides, pesticides). While these paradigms have assisted in doubling global food production in the past fifty years, yield growth rates have stalled in many major crops, and shifts in the climate have been linked to production instability and declines in important crops such as wheat, driving an urgent need for novel solutions to crop yield improvement. In addition to their long development and regulatory timelines, public fears of GM-crops and synthetic chemicals has challenged their use in many key crops and countries, resulting in a complete lack of acceptance for GM traits in wheat and the exclusion of GM crops and many synthetic chemistries from European markets. Thus, there is a significant need for innovative, effective, environmentally-sustainable, and publically-acceptable approaches to improving the yield and resilience of crops to severe drought and heat stresses.

Improvement of crop resilience to heat and drought stress has proven challenging for conventional genetic and chemical paradigms for crop improvement. This challenge is in part due to the complex, network-level changes that arise during exposure to these stresses. For example, plants under such stress can succumb to a variety of physiological and developmental damages, including dehydration, elevated reactive oxygen species, impairment of photosynthetic carbon assimilation, inhibition of translocation of assimilates, increased respiration, reduced organ size due to a decrease in the duration of developmental phases, disruption of seed development, and a reduction in fertility.

Like humans, who utilize a complement of beneficial microbial symbionts, plants have been purported to derive a benefit from the vast array of bacteria and fungi that live both within and around their tissues in order to support the plant's health and growth. As described in detail herein, endophytes are fungal or bacterial organisms that live within plants. Bacterial endophytes, such as Firmicutes, Actinobacteria, Proteobacteria, Bacteroidetes, and Verrucomicrobia, appear to inhabit various host plant tissues and have been isolated from plant leaves, stems, and roots.

To date, a small number of these symbiotic endophyte-host relationships have been analyzed in limited studies to provide fitness benefits to model host plants within controlled laboratory settings, such as enhancement of biomass production (i.e., yield) and nutrition, increased tolerance to stress such as drought and pests. Yet, such endophytes have been demonstrated to be ineffective or of limited efficacy in conferring benefits to a variety of agriculturally-important plants such as modern cereals; as such, they do not adequately address the need to provide improved yield and tolerance to environmental stresses present in many agricultural situations for such crops, particularly drought and heat.

Thus, there is a need for compositions and methods of providing cereal crops with improved yield and resistance to various environmental stresses. Provided herein are novel compositions of symbionts, bacterial and fungal endophytes, as well as novel symbiont-plant compositions, created based on the analysis of the key properties that enhance the utility and commercialization of an endophytic composition.

SUMMARY

The present invention is based, in part, on the surprising discovery that endophytic microbes can be found in dry mature seeds of plants. The inventors have isolated and extensively characterized a large number of bacterial and fungal endophytes of seed-origin that are able to colonize agricultural grass plants and to provide beneficial traits to these plants. As such, provided herein are purified bacterial and fungal populations that contain one or more populations of seed-origin endophytes, particularly bacterial endophytes (herein referred to as seed-original bacterial endophytes), compositions (e.g., agricultural formulations and articles of manufacture) that include such purified bacterial populations, as well as synthetic combinations of such purified bacterial populations in association with seeds or seedlings of an agricultural cereal plant and other agricultural products, including seeds. In addition, provided herein are methods of using such seed-origin bacterial endophytes to prepare synthetic combinations, agricultural formulations, articles of manufacture, or other agricultural products, and to provide benefits to agricultural cereal plants. Seed-derived endophytes can confer significant advantages to cereal crops, spanning growth under normal and stressed conditions, altered expression of key plant hormones, altered expression of key transcripts in the plant, and other desirable features.

As described herein, beneficial microbes can be robustly derived from agricultural seeds, cultured, administered heterologously to agricultural cereal seeds or seedlings, and colonize the resulting plant tissues with high efficiency to confer multiple beneficial properties, that are durably retained in the plants and their progeny. This is surprising given the historical observed variability in microbe isolation from healthy seeds and the previous observations of inefficient seed pathogen colonization of a plant host's tissues. Further, the ability of heterologously disposed seed-origin bacterial endophytes to colonize seeds and seedlings from the exterior surface of seeds is surprising given that such endophytes can be isolated from within internal seed tissues and therefore may not natively need the capacity to penetrate and invade into internal host tissues in their natural state.

Seed-origin bacterial endophytes are heterologously disposed onto seedlings of a distinct cultivar, species, or cereal crop type and confer benefits to those new recipients. For example, seed-origin bacterial endophytes from corn cultivars are heterologously provided to wheat cultivars to confer a benefit. This is surprising given the prior observations of distinct microbiome preferences in distinct plant and mammalian hosts and, in particular, the likelihood that microbes derived from seeds may have been co-evolved to be specialized to a particular host.

In one aspect, the invention features a method for treating seeds. The method includes contacting the surface of a plurality of Gramineae agricultural plant seeds with a formulation comprising a purified bacterial population at a concentration of at least about $10^2$ CFU/ml in a liquid formulation or about $10^2$ CFU/gm in a non-liquid formulation, where at least 10% of the CFUs present in the formulation comprise a preferred seed-origin bacterial endophyte, which exhibits: production of an auxin, nitrogen fixation, production of an antimicrobial, production of a siderophore, mineral phosphate solubilization, production of a cellulase, production of a chitinase, production of a xylanase, or production of acetoin, wherein the seed-origin bacterial endophyte is present in the formulation in an amount capable of providing a benefit to the plant seeds or to agricultural plants derived from the plant seeds; and packaging the contacted seeds in a container. The method can further include drying the contacted seed. The contacting can include spraying, immersing, coating, encapsulating, or dusting the seeds or seedlings with the formulation.

The invention also features a method for treating seedlings. The method includes contacting foliage or the rhizosphere of a plurality of Gramineae agricultural plant seedlings with a formulation comprising a purified bacterial population at a concentration of at least about $10^2$ CFU ail in a liquid formulation or about $10^2$ CFU/g in a non-liquid formulation, wherein at least 10% of the CFUs present in the formulation comprise a seed-origin bacterial endophyte exhibiting production of an auxin, nitrogen fixation, production of an antimicrobial compound, production of a siderophore, mineral phosphate solubilization, production of a cellulase, production of a chitinase, production of a xylanase, or production of acetoin, and wherein the seed-origin bacterial endophyte is present in the formulation in an amount capable of providing a benefit to the seedlings or to agricultural plants derived from the seedlings; and growing the contacted seedlings. The contacting can include spraying, immersing, coating, encapsulating, or dusting the seeds or seedlings with the formulation.

In another aspect, a method for modulating a Gramineae plant trait is featured. The method includes applying to vegetation (e.g., corn, wheat, rice, or barley seedlings) or an area adjacent the vegetation, a formulation that includes a purified bacterial population at a concentration of at least about $10^2$ CFU/ml in a liquid formulation or about $10^2$ CFU/g in a non-liquid formulation, at least 10% of the CFUs present in the formulation comprising a seed-origin bacterial endophyte exhibiting: production of an auxin, nitrogen fixation, production of an antimicrobial compound, production of a siderophore, mineral phosphate solubilization, production of a cellulase, production of a chitinase, production of a xylanase, or production of acetoin, and combinations of two or more thereof, wherein the formulation is capable of providing a benefit to the vegetation, or to a crop produced from the vegetation.

A method for modulating a Gramineae plant trait is featured that includes applying a formulation to soil, the formulation comprising a purified bacterial population at a concentration of at least about $10^2$ CFU/g, at least 10% of the CFUs present in the formulation comprising a seed-origin bacterial endophyte exhibiting: production of an auxin, nitrogen fixation, production of an antimicrobial compound, production of a siderophore, mineral phosphate solubilization, production of a cellulase, production of a chitinase, production of a xylanase, or production of acetoin, and combinations of two or more thereof, wherein the formulation is capable of providing a benefit to seeds planted within the soil, or to a crop produced from plants grown in the soil.

A method of making an article of manufacture also is featured. The method includes applying an agricultural formulation to Gramineae plant seeds, the formulation including a purified bacterial population and an agriculturally acceptable carrier, the bacterial population consisting essentially of a seed-origin bacterial endophyte that exhibits: production of an auxin, nitrogen fixation, production of an antimicrobial, production of a siderophore, mineral phosphate solubilization, production of a cellulase, production of a chitinase, production of a xylanase, or production of acetoin, or combinations of two or more thereof; and packaging the coated seeds in packaging material.

The invention also features a method of identifying a modulator of a plant trait. The method includes applying a bacterial population to seeds of an agricultural plant, the population comprising bacteria of one or more species of seed-origin bacterial endophytes; measuring a trait in seedlings or plants derived from the seeds, the trait selected from the group consisting of root biomass, root length, height, shoot length, leaf number, water use efficiency, overall biomass, grain yield, photosynthesis rate, tolerance to drought, heat tolerance, salt tolerance, resistance to nematode stress, resistance to a fungal pathogen, resistance to a bacterial pathogen, resistance to a viral pathogen, the level of a metabolite, and proteome expression; and identifying at least one of the traits for which the bacterial population results in a modulation of the trait, relative to reference seedlings or plants.

In another aspect, a method of identifying a modulator of a plant trait is featured. The method includes applying a bacterial population to seedlings of an agricultural plant, the population comprising bacteria of one or more species of seed-origin bacterial endophytes; measuring a trait in the seedlings or in plants derived from the seedlings, the trait selected from the group consisting of root biomass, root length, height, shoot length, leaf number, water use efficiency, overall biomass, grain yield, photosynthesis rate, tolerance to drought, heat tolerance, salt tolerance, resistance to nematode stress, resistance to a fungal pathogen, resistance to a bacterial pathogen, resistance to a viral pathogen; the level of a metabolite, and proteome expression; and identifying at least one of the traits for which the bacterial population results in a modulation of the trait, relative to reference seedlings or plants. The modulation can be an increase in root biomass, an increase in root length, an increase in height, an increase in shoot length, an increase in leaf number, an increase in water use efficiency, an increase in overall biomass, an increase in grain yield, an increase in photosynthesis rate, an increase in tolerance to drought, an increase in heat tolerance, an increase in salt tolerance, an increase in resistance to nematode stress, an increase in resistance to a fungal pathogen, an increase in resistance to a bacterial pathogen, an increase in resistance to a viral pathogen, a detectable modulation in the level of a metabolite, or a detectable modulation in the proteome.

This invention also features a method for treating a cereal seed or seedling. The method includes contacting the exterior surface of a cereal seed or seedling with a formulation comprising a purified bacterial population, the purified bacterial population comprising at a level of at least 10% of the CFUs present in the formulation a seed-origin bacterial endophyte capable of at least one of: production of an auxin, nitrogen fixation, production of an antimicrobial, production of a siderophore, mineral phosphate solubilization, production of a cellulase, production of a chitinase, production of a xylanase, or acetoin production, or a combination of two or more, under conditions such that the formulation becomes disposed upon an exterior surface of the cereal seed or seedling in a manner effective for the seed-origin bacterial endophyte to provide a benefit to the cereal seed or seedling or to a cereal agricultural plant derived from the seed or seedling, and wherein the seed-origin bacterial endophyte is capable of host colonization and/or replication within a tissue of the cereal agricultural plant; and packaging the contacted cereal seed or seedling in a container. In embodiments in which the cereal seed is contacted, the method further can include drying the contacted cereal seed. In embodiments in which the cereal seed is contacted, the seed-origin bacterial endophyte can be present at a concentration of at least 1 CFU/seed on the surface of the contacted cereal seed. Contacting can include spraying, immersing, coating, dusting, or dipping the cereal seed or seedling with the formulation. The seed-origin bacterial endophyte can be obtained or obtainable from an interior seed compartment, e.g., the seed-origin bacterial endophyte can be obtained or obtainable from an interior seed compartment of a heterologous seed or seedling to the contacted cereal seed or seedling, or can be obtained or obtainable from an exterior surface of a heterologous seed or seedling to the contacted cereal seed or seedling. The seed-origin bacterial endophyte can be heterologous to the microbial population within the contacted cereal seed or seedling. The seed-origin bacterial endophyte can be obtained or obtainable from the interior seed compartment of a different cultivar, variety or crop as compared to the seed or seedling. The seed-origin bacterial endophyte can be obtained or obtainable from an exterior surface of a different cultivar, variety or crop as compared to the seed or seedling. The benefit can be heritable by progeny of the agricultural cereal plant derived from the contacted cereal seed or seedling. The seed-origin bacterial endophyte can include a 16S nucleic acid sequence at least 97% identical to a 16S nucleic acid sequence of a bacterial endophyte set forth in Table 1. The seed-origin bacterial endophyte can be obtained or obtainable from the seed of a rice, maize, wheat, or barley plant. The seed-origin bacterial endophyte can be capable of at least two of: production of an auxin, nitrogen fixation, production of an antimicrobial, production of a siderophore, mineral phosphate solubilization, production of a cellulase, production of a chitinase, production of a xylanase, and acetoin production.

A method for improving a plant trait in a cereal agricultural plant grown in a soil region also is featured. The method includes contacting at least a portion of the soil region with a formulation comprising a purified bacterial population, the purified bacterial population comprising at a level of at least 10% of the CFUs present in the formulation a seed-origin bacterial endophyte capable of at least one of: production of an auxin, nitrogen fixation, production of an antimicrobial, production of a siderophore, mineral phosphate solubilization, production of a cellulase, production of a chitinase, production of a xylanase, and acetoin production, or a combination of two or more, under conditions such that the seed-origin bacterial endophyte is capable of providing a benefit to a cereal seed or seedling planted within the soil region, or to an agricultural cereal plant derived from the cereal seed or seedling. The method can include planting a cereal seed or seedling in the soil region. The seed-origin bacterial endophyte can be obtained or obtainable from an interior seed compartment, e.g., the seed-origin bacterial endophyte can be obtained or obtainable from an interior seed compartment of a heterologous seed or seedling to the contacted cereal seed or seedling, or can be obtained or obtainable from an exterior surface of a heterologous seed or seedling to the contacted cereal seed or seedling. The seed-origin bacterial endophyte can be exogenous to the microbial population within the contacted cereal seed or seedling.

The invention also features a method for planting a field region with an agricultural cereal crop. The method includes obtaining a container comprising at least 10 synthetic combinations, wherein each synthetic combination comprises a purified bacterial population in association with a cereal seed or seedling, wherein the purified bacterial population comprises a seed-origin bacterial endophyte capable of at least one of: production of an auxin, nitrogen fixation, production of an antimicrobial, production of a siderophore, mineral phosphate solubilization, production of a cellulase, production of a chitinase, production of a xylanase, or acetoin production, or combinations of two or more thereof, and wherein the seed-origin bacterial endophyte is present in an amount effective to provide a benefit to the cereal seed or seedling or the agricultural cereal plant derived from the cereal seed or seedling; and distributing the synthetic combinations from the container in the field region. In any of the methods, the seed-origin bacterial endophyte can be obtained or obtainable from an interior seed compartment, e.g., the seed-origin bacterial endophyte can be obtained or obtainable from an interior seed compartment of a heterologous seed or seedling to the contacted cereal seed or seedling, or can be obtained or obtainable from an exterior surface of a heterologous seed or seedling to the contacted cereal seed or seedling. The seed-origin bacterial endophyte can be exogenous to the microbial population within the contacted cereal seed or seedling.

In any of the methods, the seed-origin bacterial endophyte can be present at a concentration of at least $10^2$ CFU/seed on the surface of the seeds after contacting.

In any of the methods, the seed-origin bacterial endophyte can be obtained from an interior seed compartment (e.g., cotyledon, plumule, embryo, or endosperm).

In any of the methods, the seed-origin bacterial endophyte can be obtained from a plant species other than the seeds with which the formulation is contacted.

In any of the methods, the seed-origin bacterial endophyte can be obtained from a plant cultivar different from the cultivar of the seeds with which the formulation is contacted.

In any of the methods, the seed-origin bacterial endophyte can be obtained from a surface sterilized seed.

In any of the methods, the benefit can be maternally inherited by progeny of the contacted plant seeds.

In any of the methods, the seed-origin bacterial endophyte can include a 16S nucleic acid sequence having at least 97% sequence identity to a 16S nucleic acid sequence of a bacterial endophyte selected from a genus provided in Table 1 or a family provided in Table 2.

In any of the methods, the seed-origin bacterial endophyte can include a 16S nucleic acid sequence that is less than 97% identical to any 16S nucleic acid sequence shown in Table 1.

In any of the methods, the bacterial population can include a first seed-origin bacterial endophyte having a first 16S nucleic acid sequence and a second seed-origin bacterial endophyte having a second 16S nucleic acid sequence, wherein the first and the second 16S nucleic acid sequences are less than 97% identical.

In any of the methods, the bacterial population can include two or more families of seed-origin bacterial endophytes.

In any of the methods, the bacterial population can include two or more species of seed-origin bacterial endophytes.

In any of the methods, the seed-origin bacterial endophyte can be a non-*Bacillus* species and/or a non-*Pseudomonas* species.

In any of the methods, the seed-origin bacterial endophyte can be obtained from a rice, maize, wheat, or barley seed.

In any of the methods, the seed-origin bacterial endophyte can exhibit at least two of: production of an auxin, nitrogen fixation, production of an antimicrobial, production of a siderophore, mineral phosphate solubilization, production of a cellulase, production of a chitinase, production of a xylanase, or production of acetoin, or combinations thereof.

In any of the methods, the benefit can be selected from the group consisting of: increased root biomass, increased root length, increased height, increased shoot length, increased leaf number, increased water use efficiency, increased overall biomass, increase grain yield, increased photosynthesis rate, increased tolerance to drought, increased heat tolerance, increased salt tolerance, increased resistance to nematode stress, increased resistance to a fungal pathogen, increased resistance to a bacterial pathogen, increased resistance to a viral pathogen, a detectable modulation in the level of a metabolite, and a detectable modulation in the proteome, relative to reference seeds or agricultural plants derived from reference seeds. The benefit can include a combination of at least two of such benefits.

In another aspect, the invention features a synthetic combination that includes a purified bacterial population in association with a plurality of seeds or seedlings of a Gramineae agricultural plant, wherein the purified bacterial population comprises a seed-origin bacterial endophyte capable of at least one of: production of an auxin, nitrogen fixation, production of an antimicrobial, production of a siderophore, mineral phosphate solubilization, production of a cellulase, production of a chitinase, production of a xylanase, or production of acetoin, or a combination of two or more thereof, and wherein the seed-origin bacterial endophyte is present in the synthetic combination in an amount effective to provide a benefit to the seeds or seedlings or the plants derived from the seeds or seedlings. For example, the effective amount can be $1 \times 10^3$ CFU/per seed or from about $1 \times 10^2$ CFU/seed to about $1 \times 10^8$ CFU/seed. The benefit can be heritable by progeny of plants derived from the seeds or seedlings. The benefit can be selected from the group consisting of increased root biomass, increased root length, increased height, increased shoot length, increased leaf number, increased water use efficiency, increased overall biomass, increase grain yield, increased photosynthesis rate, increased tolerance to drought, increased heat tolerance, increased salt tolerance, increased resistance to nematode stress, increased resistance to a fungal pathogen, increased resistance to a bacterial pathogen, increased resistance to a viral pathogen, a detectable modulation in the level of a metabolite, and a detectable modulation in the proteome relative to a reference plant, and combinations of two or more thereof. The synthetic combination further can include one or more additional seed-origin bacterial endophyte species.

The synthetic combination can include seeds and the seed-origin bacterial endophyte can be associated with the seeds as a coating on the surface of the seeds (e.g., a substantially uniform coating on the seeds). The synthetic combination can include seedlings and the seed-origin bacterial endophyte can be contacted with the seedlings as a spray applied to one or more leaves and/or one or more roots of the seedlings.

The synthetic combination can be disposed within a packaging material selected from a bag, box, bin, envelope, carton, or container. The synthetic combination can include 1000 seed weight amount of seeds, wherein the packaging material optionally comprises a desiccant, and wherein the synthetic combination optionally comprises an anti-fungal agent. The purified bacterial population can be localized on the surface of the seeds or seedlings. The seed-origin bacterial endophyte can be obtained from an interior seed compartment.

In another aspect, the invention features an agricultural product that includes a 1000 seed weight amount of a synthetic combination produced by the step of contacting a plurality of Gramineae agricultural plant seeds with a liquid formulation comprising a bacterial population at a concentration of at least 1 CFU per agricultural plant seed, wherein at least 10% of the CFUs present in the formulation are one or more seed-origin bacterial endophytes, under conditions such that the formulation is associated with the surface of the seeds in a manner effective for the seed-origin bacterial endophytes to confer a benefit to the seeds or to a crop comprising a plurality of agricultural plants produced from the seeds. The seed-origin bacterial endophytes can be present in a concentration of from about $10^2$ to about $10^5$ CFU/ml or from about $10^5$ to about $10^8$ CFU/seed. The formulation can be a liquid and the bacterial concentration can be from about $10^3$ to about $10^{11}$ CFU/ml. The formulation can be a gel or powder and the bacterial concentration can be from about $10^3$ to about $10^{11}$ CFU/gm.

The invention also features an agricultural formulation that includes a purified bacterial population and an agriculturally acceptable carrier, the bacterial population consisting essentially of a seed-origin bacterial endophyte that exhibits: production of an auxin, nitrogen fixation, production of an antimicrobial, production of a siderophore, mineral phosphate solubilization, production of a cellulase, production of a chitinase, production of a xylanase, or production of acetoin, or combinations of two or more thereof, where the seed-origin bacterial endophyte present in an amount effective to confer a benefit to a Gramineae agricultural plant seed to which the formulation is applied or to an agricultural plant seedling to which the formulation is applied. The seed-origin bacterial endophyte can be obtained from a surface sterilized seed, from the surface of a seedling, or an unsterilized seed.

In yet another aspect, the invention features an article of manufacture that includes packaging material; Gramineae plant seeds within the packaging material, and at least one species of seed-origin bacterial endophyte associated with the seeds. The article can include two or more species of seed-origin bacterial endophytes.

A synthetic combination also is featured that includes a purified bacterial population in association with a seed or seedling of a cereal agricultural plant, wherein the purified bacterial population comprises a seed-origin bacterial endophyte capable of at least one of: production of an auxin, nitrogen fixation, production of an antimicrobial, production of a siderophore, mineral phosphate solubilization, production of a cellulase, production of a chitinase, production of a xylanase, and acetoin production, or a combination of two or more thereof, wherein the seed-origin bacterial endophyte is present in the synthetic combination in an amount effective to provide a benefit to the seed or seedling or the cereal agricultural plant derived from the seed or seedling. The synthetic combination can be disposed within a package and is shelf stable. The purified bacterial population can be localized on the surface of the seed or seedling. The seed-origin bacterial endophyte can be present at a concentration of at least 1 CFU/seed on the surface of a seed. The seed-origin bacterial endophyte can be obtained or can be obtainable from an interior seed compartment. The seed-origin bacterial endophyte can be obtained or can be obtainable from an interior seed compartment of a heterologous seed or seedling. The seed-origin bacterial endophyte can be obtained or can be obtainable from an exterior surface of a heterologous seed or seedling. The seed-origin bacterial endophyte can be exogenous to the microbial population within the seed or seedling. The benefit can be heritable by progeny of the agricultural plant. The benefit can include at least two benefits, wherein the synthetic combination comprises two or more seed-origin bacterial endophyte.

In another aspect, the invention features a synthetic combination of a purified bacterial population in association with a seed or seedling of a cereal agricultural plant, wherein the synthetic combination is produced by the step of contacting the seed or seedling with a formulation comprising a purified bacterial population, wherein the purified bacterial population comprises an effective amount of a seed-origin bacterial endophyte capable of conferring a benefit on the contacted seed or seedling or cereal agricultural plant derived from the seed or seedling, the benefit selected from the group consisting of: increased root biomass, increased root length, increased height, increased shoot length, increased leaf number, increased water use efficiency, increased overall biomass, increase grain yield, increased photosynthesis rate, increased tolerance to drought, increased heat tolerance, increased salt tolerance, increased resistance to nematode stress, increased resistance to a fungal pathogen, increased resistance to a bacterial pathogen, increased resistance to a viral pathogen, a detectable modulation in the level of a metabolite, and a detectable modulation in the proteome relative to a reference plant, under conditions such that the formulation becomes disposed upon an exterior surface of the seed or seedling in a manner effective for the seed-origin bacterial endophyte to provide the benefit to the seed or seedling or to the cereal agricultural plant derived from the seed or seedling, and wherein the seed-origin bacterial endophyte is capable of host colonization and/or replication within a tissue of the cereal agricultural plant.

In yet another aspect, the invention features an agricultural formulation comprising a purified bacterial population consisting essentially of a seed-origin bacterial endophyte capable of conferring on a seed, seedling, or agricultural plant a benefit selected from: increased tolerance to drought, increased heat tolerance, and increased salt tolerance, wherein the seed-origin bacterial endophyte is present in an amount effective to provide the benefit to a seed or seedling to which the formulation is administered or to an agricultural plant derived from the seed or seedling to which the formulation is administered, and an agriculturally acceptable carrier. The seed-origin bacterial endophyte is obtained or obtainable from an interior seed compartment. The seed-origin bacterial endophyte can be obtained or obtainable from an exterior surface of a seed. The seed-origin bacterial endophyte can be heterologous to the microbial population within the contacted cereal seed or seedling. The seed-origin bacterial endophyte can be obtained or obtainable from the interior seed compartment of a different cultivar, variety or crop as compared to the seed or seedling. The seed-origin bacterial endophyte can be obtained or obtainable from an exterior surface of a different cultivar, variety or crop as compared to the seed or seedling. The seed-origin bacterial endophyte is capable of: production of an auxin, nitrogen fixation, production of an antimicrobial, production of a siderophore, mineral phosphate solubilization, production of a cellulase, production of a chitinase, production of a xylanase, or acetoin production, or a combination of two or more thereof. The seed-origin bacterial endophyte can be capable of generating a bacterial network in the agricultural plant derived from the seed or seedling or in the seed or seedling to which the formulation is administered, or in the surrounding environment of the plant, seed, or seedling, and wherein the bacterial network is capable of causing a detectable modulation in the level of a metabolite in the seed, seedling, or plant or a detectable modulation in the proteome of the agricultural plant derived from the seed or seedling. The purified bacterial population can consist essentially of two seed-origin bacterial endophytes.

In any of the methods, synthetic combinations, agricultural products, agricultural formulations, or articles of manufacture, the purified bacterial population can consist essentially of two or more species of seed-origin bacterial endophytes. The purified bacterial population can consist essentially of seed-origin bacterial endophytes having a 16S nucleic acid sequence at least 97% identical to a bacterial endophyte selected from a genus shown in Table 1 or from a family shown in Table 2. The purified bacterial population can consist essentially of a synergistic combination of two seed-origin bacterial endophytes. The bacterial population can be shelf-stable. The benefit can be selected from the group consisting of: increased root biomass, increased root length, increased height, increased shoot length, increased leaf number, increased water use efficiency, increased overall biomass, increase grain yield, increased photosynthesis rate, increased tolerance to drought, increased heat tolerance, increased salt tolerance, increased resistance to nematode stress, increased resistance to a fungal pathogen, increased resistance to a bacterial pathogen, increased resistance to a viral pathogen, a detectable modulation in the level of a metabolite, and a detectable modulation in the proteome relative to a reference plant, or a combination of two or more thereof.

In any of the methods, synthetic combinations, agricultural products, agricultural formulations, or articles of manufacture, the seed-origin bacterial endophyte can be a non-spore forming bacterial species. The seed-origin bacterial endophyte can exhibit: production of auxin, production of an antimicrobial, production of a siderophore, production of a cellulase, production of a chitinase, production of a xylanase, or production of acetoin, or combinations thereof. The seed-origin bacterial endophyte can exhibit: production of auxin production of a siderophore, mineral phosphate solubilization, production of a cellulase, production of a chitinase, production of a xylanase, or production of acetoin, but does not increase nitrogen fixation relative to a reference plant. The seed-origin bacterial endophyte can be shelf-stable. The seed-origin bacterial endophyte can be a non-*Bacillus* species and/or a non-*Pseudomonas* species.

In any of the methods, synthetic combinations, agricultural products, agricultural formulations, or articles of manufacture, the seed-origin bacterial endophyte can be obtained from a plant species other than the seeds or seedlings of the synthetic combination. The seed-origin bacterial endophyte can be obtained from a plant cultivar different from the cultivar of the seeds or seedlings of the synthetic combination. The seed-origin bacterial endophyte can be obtained from a plant cultivar that is the same as the cultivar of the seeds or seedlings of the synthetic combination. The seed-origin bacterial endophyte can be obtained from an exterior surface of a heterologous seed or seedling.

In any of the methods, synthetic combinations, agricultural products, agricultural formulations, or articles of manufacture, the bacterial population can include a seed-origin bacterial endophyte having a 16S nucleic acid sequence that is less than 97% identical to any 16S nucleic acid sequence shown in Table 1. The bacterial population can include a seed-origin bacterial endophyte having a 16S nucleic acid sequence that is at least 97% identical to a 16S nucleic acid sequence shown in Table 1. The bacterial population can include two or more families of seed-origin bacterial endophytes. The bacterial population can include a first seed-origin bacterial endophyte having a first 16S nucleic acid sequence and a second seed-origin bacterial endophyte having a second 16S nucleic acid sequence, wherein the first and the second 16S nucleic acid sequences are less than 97% identical.

In any of the methods, synthetic combinations, agricultural products, agricultural formulations, or articles of manufacture, the bacterial population can include a first seed-origin bacterial endophyte and a second seed-origin bacterial endophyte, wherein the first and second seed-origin bacterial endophytes are independently capable of at least one of production of an auxin, nitrogen fixation, production of an antimicrobial, production of a siderophore, mineral phosphate solubilization, production of a cellulase, production of a chitinase, production of a xylanase, or production of acetoin, or a combination of two or more thereof.

In any of the methods, synthetic combinations, agricultural products, agricultural formulations, or articles of manufacture, the bacterial population can include a first seed-origin bacterial endophyte and a second seed-origin bacterial endophyte, wherein the first and second seed-origin bacterial endophytes are capable of synergistically increasing at least one of: production of an auxin, nitrogen fixation, production of an antimicrobial, production of a siderophore, mineral phosphate solubilization, production of a cellulase, production of a chitinase, production of a xylanase, or production of acetoin, or a combination of two or more thereof, in an amount effective to increase tolerance to drought relative to a reference plant.

In any of the methods, synthetic combinations, agricultural products, agricultural formulations, or articles of manufacture, the bacterial population can include a first seed-origin bacterial endophyte and a second seed-origin bacterial endophyte, wherein the first and second seed-origin bacterial endophytes are obtained from the same cultivar. The bacterial population can include a first seed-origin bacterial endophyte and a second seed-origin bacterial endophyte, wherein the first and second seed-origin bacterial endophytes are obtained from different cultivars of the same agricultural plant.

In any of the methods, synthetic combinations, agricultural products, agricultural formulations, or articles of manufacture, the bacterial population can include a first seed-origin bacterial endophyte and a second seed-origin bacterial endophyte, wherein the first seed-origin bacterial endophyte is capable of colonizing a first agricultural plant tissue and wherein the second seed-origin bacterial endophyte is capable of colonizing a second agricultural plant tissue not identical to the first agricultural plant tissue.

In any of the methods, synthetic combinations, agricultural products, agricultural formulations, or articles of manufacture, the seed-origin bacterial endophyte can be obtained or can be obtainable from a barley, rice, maize, or wheat seed. For example, the seed-origin bacterial endophyte can be obtained or can be obtainable from an interior compartment of a corn, wheat, or barley seed. The seed-origin bacterial endophyte can be a non-spore forming bacterial species. The seed-origin bacterial endophyte can be a non-*Bacillus* species and/or a non-*Pseudomonas* species.

In any of the methods, the synthetic combinations, agricultural products, agricultural formulations, or articles of manufacture, the seed-origin bacterial endophyte can exhibit production of auxin, production of an antimicrobial, production of a siderophore, production of a cellulase, production of a chitinase, production of a xylanase, or production of acetoin, or combinations of two or more thereof. The seed-origin bacterial endophyte can be shelf-stable.

In any of the methods, synthetic combinations, agricultural products, agricultural formulations, or articles of manufacture, the seed-origin bacterial endophyte can exhibit production of auxin, production of a siderophore, mineral phosphate solubilization, production of a cellulase, production of a chitinase, production of a xylanase, or production of acetoin, or combinations of two or more thereof, but does not increase nitrogen fixation relative to a reference plant.

In any of the methods, synthetic combinations, agricultural products, agricultural formulations, or articles of manufacture, the bacterial population can include two or more families of seed-origin bacterial endophytes or two or more seed-origin bacterial endophyte species.

In any of the methods, synthetic combinations, agricultural products, agricultural formulations, or articles of manufacture, the seed-origin bacterial endophyte can be a non-*Bacillus* species and/or a non-*Pseudomonas* species.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims. The word "comprising" in the claims may be replaced by "consisting essentially of" or with "consisting of," according to standard practice in patent law.

DEFINITIONS

Figure 1A:
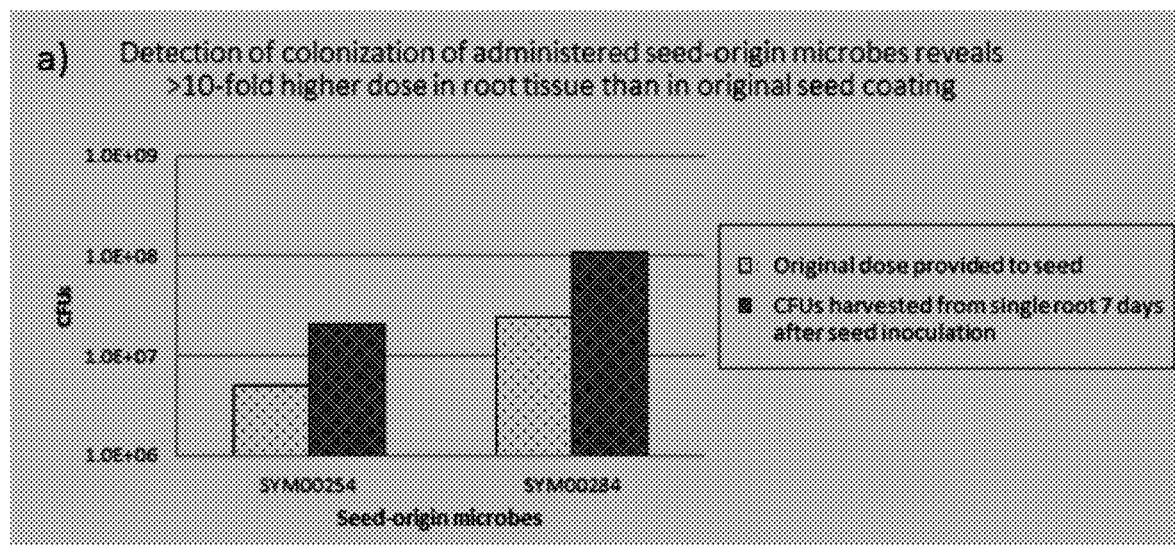
FIG. 1A is a graph of seed-origin microbes SYM00254 and SYM00284 were coated on the outside of surface sterilized corn seeds, planted in axenic conditions and incubated for 7 days to germinate. The dose delivered to the seed surface was quantified by serial dilution and plating of liquid inoculum, while the microbial population colonizing roots after 7 days of incubation was quantified by macerating roots, serial dilution, plating and colony counting to obtain CFUs per root.

An "endophyte" or "endophytic microbe" is an organism that lives within a plant or is otherwise associated therewith. Endophytes can occupy the intracellular or extracellular spaces of plant tissue, including the leaves, stems, flowers, fruits, seeds, or roots. An endophyte can be either a bacterial or a fungal organism that can confer a beneficial property to a plant such as an increase in yield, biomass, resistance, or fitness in its host plant. As used herein, the term "microbe" is sometimes used to describe an endophyte.

In some embodiments, a bacterial endophyte is a seed-origin bacterial endophyte. As used herein, a "seed-origin bacterial endophyte" refers to a population of bacteria associated with or derived from the seed of a grass plant. For example, a seed-origin bacterial endophyte can be found in mature, dry, undamaged (e.g., no cracks, visible fungal infection, or prematurely germinated) seeds. The bacteria can be associated with or derived from the surface of the seed; alternatively, or in addition, it can be associated with or derived from the interior seed compartment (e.g., of a surface-sterilized seed). In some cases, a seed-origin bacterial endophyte is capable of replicating within the plant tissue, for example, the interior of the seed. Also, in some cases, the seed-origin bacterial endophyte is capable of surviving desiccation.

Seed-origin means that the bacterial entity is obtained directly or indirectly from the seed surface or seed interior compartment or is obtainable from a seed surface or seed interior compartment. For example, a seed-origin bacterial entity can be obtained directly or indirectly from a seed surface or seed interior compartment when it is isolated, or isolated and purified, from a seed preparation; in some cases, the seed-origin bacterial entity which has been isolated, or isolated and purified, may be cultured under appropriate conditions to produce a purified bacterial population consisting essentially of a seed-origin bacterial endophyte. A seed-origin bacterial endophyte can be considered to be obtainable from a seed surface or seed interior compartment if the bacteria can be detected on or in, or isolated from, a seed surface or seed interior compartment of a plant.

The compositions provided herein are preferably stable. The seed-origin bacterial endophyte is optionally shelf stable, where at least 10% of the CFUs are viable after storage in desiccated form (i.e., moisture content of 30% or less) for 1, 2, 3, 4, 5, 6, 7, 8, 9, 10 or greater than 10 weeks at 4° C. or at room temperature. Optionally, a shelf stable formulation is in a dry formulation, a powder formulation, or a lyophilized formulation. In some embodiments, the formulation is formulated to provide stability for the population of bacterial endophytes. In one embodiment, the formulation is substantially stable at temperatures between about 0° C. and about 50° C. for at least about 1, 2, 3, 4, 5, or 6 days, or 1, 2, 3 or 4 weeks, or 1, 2, 3, 4, 5, 6, 7, 8, 9, 10, 11 or 12 months, or one or more years. In another embodiment, the formulation is substantially stable at temperatures between about 4° C. and about 37° C. for at least about 5, 10, 15, 20, 25, 30 or greater than 30 days.

An agricultural plant can be a monocotyledonous (i.e., an "agricultural grass plant") or a dicotyledonous plant typically used in agriculture. An agricultural grass plant includes, but is not limited to, maize (*Zea mays*), common wheat (*Triticum aestivum*), spelt (*Triticum spelta*), einkorn wheat (*Triticum monococcum*), emmer wheat (*Triticum dicoccum*), durum wheat (*Triticum durum*), Asian rice (*Oryza sativa*), African rice (*Oryza glabaerreima*), wild rice (*Zizania aquatica, Zizania latifolia, Zizania palustris, Zizania texana*), barley (*Hordeum vulgare*), Sorghum (*Sorghum bicolor*), Finger millet (*Eleusine coracana*), Proso millet (*Panicum miliaceum*), Pearl millet (*Pennisetum glaucum*), Foxtail millet (*Setaria italic*), Oat (*Avena sativa*), Triticale (*Triticosecale*), rye (*Secale* cereal), Russian wild rye (*Psathyrostachys juncea*), bamboo (*Bambuseae*), or sugarcane (e.g., *Saccharum arundinaceum, Saccharum barberi, Saccharum bengalense, Saccharum edule, Saccharum munja, Saccharum officinarum, Saccharum procerum, Saccharum ravennae, Saccharum robustum, Saccharum sinense*, or *Saccharum spontaneum*).

A "host plant" includes any plant, particularly an agricultural plant, which an endophytic microbe such as a seed-origin bacterial endophyte can colonize. As used herein, a microbe is said to "colonize" a plant or seed when it can be stably detected within the plant or seed over a period time, such as one or more days, weeks, months or years; in other words, a colonizing microbe is not transiently associated with the plant or seed. A preferred host plant is a cereal plant.

As used herein, a "reference agricultural plant" is an agricultural plant of the same species, strain, or cultivar to which a treatment, formulation, composition or endophyte preparation as described herein is not administered/contacted. Exemplary reference agricultural plants are cereals. A reference agricultural plant, therefore, is identical to the treated plant with the exception of the presence of the endophyte and can serve as a control for detecting the effects of the endophyte that is conferred to the plant.

"Biomass" means the total mass or weight (fresh or dry), at a given time, of a plant tissue, plant tissues, an entire plant, or population of plants. Biomass is usually given as weight per unit area. The term may also refer to all the plants or species in the community (community biomass).

A "bacterial network" means a plurality of endophyte entities (e.g., bacteria, fungi, or combinations thereof) co-localized in an environment, such as on or within a cereal agricultural plant. Preferably, a bacterial network includes two or more types of endophyte entities that synergistically interact, such synergistic endophytic populations capable of providing a benefit to the agricultural seed, seedling, or plant derived thereby.

An "increased yield" can refer to any increase in biomass or seed or fruit weight, seed size, seed number per plant, seed number per unit area, bushels per acre, tons per acre, kilo per hectare, or carbohydrate yield. Typically, the particular characteristic is designated when referring to increased yield, e.g., increased grain yield or increased seed size.

A "transgenic plant" includes a plant or progeny plant of any subsequent generation derived therefrom, wherein the DNA of the plant or progeny thereof contains an exogenous DNA not naturally present in a non-transgenic plant of the same strain. The transgenic plant may additionally contain sequences that are native to the plant being transformed, but wherein the "exogenous" gene has been altered in order to alter the level or pattern of expression of the gene, for example, by use of one or more heterologous regulatory or other elements.

The terms "pathogen" and "pathogenic" in reference to a bacterium includes any such organism that is capable of causing or affecting a disease, disorder or condition of a host containing the organism.

A "spore" or a population of "spores" refers to bacteria that are generally viable, more resistant to environmental influences such as heat and bacteriocidal agents than vegetative forms of the same bacteria, and typically capable of germination and out-growth. Bacteria that are "capable of forming spores" are those bacteria containing the genes and other necessary abilities to produce spores under suitable environmental conditions.

As used herein, an "agricultural seed" is a seed used to grow a plant typically used in agriculture (an "agricultural plant"). The seed may be of a monocot or dicot plant, and may be planted for the production of an agricultural product, for example grain, food, fiber, etc. As used herein, an agricultural seed is a seed that is prepared for planting, for example, in farms for growing.

In some cases, the present invention contemplates the use of microbes that are "compatible" with agricultural chemicals, for example, a fungicide, an anti-bacterial compound, or any other agent widely used in agricultural which has the effect of killing or otherwise interfering with optimal growth of microbes. As used herein, a microbe is "compatible" with an agricultural chemical when the microbe is modified, such as by genetic modification, e.g., contains a transgene that confers resistance to an herbicide, or is adapted to grow in, or otherwise survive, the concentration of the agricultural chemical used in agriculture. For example, a microbe disposed on the surface of a seed is compatible with the fungicide metalaxyl if it is able to survive the concentrations that are applied on the seed surface.

In some embodiments, an agriculturally compatible carrier can be used to formulate an agricultural formulation or other composition that includes a purified bacterial preparation. As used herein an "agriculturally compatible carrier" refers to any material, other than water, which can be added to a seed or a seedling without causing or having an adverse effect on the seed (e.g., reducing seed germination) or the plant that grows from the seed, or the like.

As used herein, a "portion" of a plant refers to any part of the plant, and can include distinct tissues and/or organs, and is used interchangeably with the term "tissue" throughout.

A "population" of plants, as used herein, can refer to a plurality of plants that were subjected to the same inoculation methods described herein, or a plurality of plants that are progeny of a plant or group of plants that were subjected to the inoculation methods. In addition, a population of plants can be a group of plants that are grown from coated seeds. The plants within a population will typically be of the same species, and will also typically share a common genetic derivation.

A "reference environment" refers to the environment, treatment or condition of the plant in which a measurement is made. For example, production of a compound in a plant associated with a purified bacterial population (e.g., a seed-origin bacterial endophyte) can be measured in a reference environment of drought stress, and compared with the levels of the compound in a reference agricultural plant under the same conditions of drought stress. Alternatively, the levels of a compound in plant associated with a purified bacterial population (e.g., a seed-origin bacterial endophyte) and reference agricultural plant can be measured under identical conditions of no stress.

As used herein, a nucleic acid has "homology" or is "homologous" to a second nucleic acid if the nucleic acid sequence has a similar sequence to the second nucleic acid sequence. The terms "identity," "percent sequence identity" or "identical" in the context of nucleic acid sequences refer to the residues in the two sequences that are the same when aligned for maximum correspondence. There are a number of different algorithms known in the art that can be used to measure nucleotide sequence identity. For instance, polynucleotide sequences can be compared using FASTA, Gap or Bestfit, which are programs in Wisconsin Package Version 10.0, Genetics Computer Group (GCG), Madison, Wis. FASTA provides alignments and percent sequence identity of the regions of the best overlap between the query and search sequences. Pearson, Methods Enzymol. 183:63-98 (1990). The term "substantial homology" or "substantial similarity," when referring to a nucleic acid or fragment thereof, indicates that, when optimally aligned with appropriate nucleotide insertions or deletions with another nucleic acid (or its complementary strand), there is nucleotide sequence identity in at least about 76%, 80%, 85%, or at least about 90%, or at least about 95%, 96%, 97%, 98% 99%, 99.5% or 100% of the nucleotide bases, as measured by any well-known algorithm of sequence identity, such as FASTA, BLAST or Gap, as discussed above.

As used herein, the terms "operational taxon unit," "OTU," "taxon," "hierarchical cluster," and "cluster" are used interchangeably. An operational taxon unit (OTU) refers to a group of one or more organisms that comprises a node in a clustering tree. The level of a cluster is determined by its hierarchical order. In one embodiment, an OTU is a group tentatively assumed to be a valid taxon for purposes of phylogenetic analysis. In another embodiment, an OTU is any of the extant taxonomic units under study. In yet another embodiment, an OTU is given a name and a rank. For example, an OTU can represent a domain, a sub-domain, a kingdom, a sub-kingdom, a phylum, a sub-phylum, a class, a sub-class, an order, a sub-order, a family, a subfamily, a genus, a subgenus, or a species. In some embodiments, OTUs can represent one or more organisms from the kingdoms eubacteria, protista, or fungi at any level of a hierarchal order. In some embodiments, an OTU represents a prokaryotic or fungal order.

As used herein, a "colony-forming unit" ("CFU") is used as a measure of viable microorganisms in a sample. A CFU is an individual viable cell capable of forming on a solid medium a visible colony whose individual cells are derived by cell division from one parental cell.

DETAILED DESCRIPTION

As demonstrated herein, agricultural plants, in particular cereals, appear to associate with symbiotic microorganisms termed endophytes, particularly bacteria and fungi, that may have been important during evolution and may contribute to plant survival and performance. However, modern agricultural processes may have perturbed this relationship, resulting in increased crop losses, diminished stress resilience, biodiversity losses, and increasing dependence on external chemicals, fertilizers, and other unsustainable agricultural practices. There is a need for novel methods for generating plants with novel microbiome properties that can sustainably increase yield, stress resilience, and decrease fertilizer and chemical use.

Currently, the generally accepted view of plant endophytic communities focuses on their homologous derivation, predominantly from the soil communities in which the plants are grown (Hallman, J., et al., (1997) Canadian Journal of Microbiology. 43 (10): 895-914). Upon observing taxonomic overlap between the endophytic and soil microbiota in *A. thaliana*, it was stated, "Our rigorous definition of an endophytic compartment microbiome should facilitate controlled dissection of plant—microbe interactions derived from complex soil communities" (Lundberg et al., (2012) Nature. 488, 86-90). There is strong support in the art for soil representing the repository from which plant endophytes are derived. New Phytologist (2010) 185: 554-567. Notable plant-microbe interactions such as mycorrhyzal fungi and bacterial *rhizobia* fit the paradigm of soil-based colonization of plant hosts and appear to primarily establish themselves independently of seed. As a result of focusing attention on the derivation of endophytes from the soil in which the target agricultural plant is currently growing, there has been an inability to achieve commercially significant improvements in plant yields and other plant characteristics such as increased root biomass, increased root length, increased height, increased shoot length, increased leaf number, increased water use efficiency, increased overall biomass, increase grain yield, increased photosynthesis rate, increased tolerance to drought, increased heat tolerance, increased salt tolerance, increased resistance to nematode stress, increased resistance to a fungal pathogen, increased resistance to a bacterial pathogen, increased resistance to a viral pathogen, a detectable modulation in the level of a metabolite, and a detectable modulation in the proteome relative to a reference plant.

In part, the present invention describes preparations of novel seed-derived endophytes, and the creation of synthetic combinations of cereal seeds and/or seedlings with heterologous seed-derived endophytes and formulations containing the synthetic combinations, as well as the recognition that such synthetic combinations display a diversity of beneficial properties present in the agricultural plants and the associated endophyte populations newly created by the present inventors. Such beneficial properties include metabolism, transcription, proteome alterations, morphology, and the resilience to a variety of environmental stresses, and the combination of a plurality of such properties.

Little attention has been provided in the art to understand the role of seeds as reservoirs for microbes that can efficiently populate the endosphere of cereal plants. While the concept that seeds may harbor plant pathogens was promoted by Baker and Smith (Annu Rev Phytopathol 14: 311-334 (1966)), and the understanding that bacterial and fungal pathogens are known to be able to infect seed, the ability to harness endophytes derived from a broad spectrum of seeds to heterologously confer single or multiple advantages to cereal crops was previously unrecognized. As the presence of detectable pathogens in a seed lot can necessitate destruction of vast numbers of agricultural germplasm (Gitaitis, R. and Walcott, R. (2007) Annu. Rev. Phytopathol. 45:371-97), safety concerns have surrounded the consideration of seed-associated microbes or non-soil endophytes. Moreover, when seed pathogens are detected, their transfer to the growing plant can be highly inefficient. For example, a study of seed-based transmission of the seed pathogen, *Pantoea stewartii*, found that seed produced from a population of pathogen-infected plants gave rise to infected seedlings in only 0.0029% of cases (1 of 34,924 plants) and artificially infected kernels only gave rise to infected seedlings in 0.022% of cases (Block, C. C., el al., (1998). Plant disease. 82(7). 775-780). Thus, the efficiency with which plants introduce microbes into their seeds, and with which microbes within seeds propagate within the resulting plant tissues, has been previously thought to be low and often substantially variable. Thus, the potential for microbial content within cereal seeds to populate the resulting plant has been unclear.

The potential for agricultural cereal seeds to serve as reservoirs for non-pathogenic microbes also remains controversial (Hallman, J., et al., (1997) Canadian Journal of Microbiology. 43 (10): 895-914). Sato, et al., did not detect any bacteria inside rice seeds ((2003) In. Morishima, H. (ed.) The Natural History of Wild Rice—Evolution Ecology of Crop. p. 91-106) and Mundt and Hinkle only obtained endophytes from seed samples where seed coats had been broken or fractured in 29 kinds of plant seed (Appl Environ Microbiol. (1976) 32(5):694-8). Another group detected simply bacterial populations inside rice seeds ranging in population size from $10^2$ to $10^6$ CFU/g fresh weight (Okunishi, S., et al., (2005) Microbes and Environment. 20:168-177). Rosenblueth et al described seeds to harbor very simple microbial communities with significant variability of the microbial communities between individual maize seeds, including substantial variability between seeds taken from the same cobb (Rosenblueth, M. et al, Seed Bacterial Endophytes: Common Genera, Seed-to-Seed Variability and Their Possible Role in Plants; Proc. XXVIIIth IHC-IS on Envtl., Edaphic & Gen. Factors; Affecting Plants, Seeds and Turfgrass; Eds.: G. E. Welbaum et al. Acta Hort. 938, ISHS 2012).

These findings demonstrate limitations recognized in the art regarding the attempted use of endophytes derived from seeds; i.e., maize seeds appear to contain limited taxonomic diversity, and that the microbiota of individual seeds produced by plants is often distinct, indicating that there may not be single seed-derived symbionts capable of providing benefits across a large population of agricultural plants and in specific, the utilization of endophytes on seed. For example, characterization of ~15 pooled seeds from within various cultivars from the genus *Zea* showed that populations of maize seeds tend to harbor a very limited number of taxa that appear to be conserved across modern and ancestral variants, and that the maize seed content of such taxa is low and substantially variable. It is unclear whether the presence of such limited taxa resulted from common storage conditions, environmental contamination, or a potential vertical transmission of microbes via seeds, and also uncertain was the applicability of such limited taxa in increasing agricultural yield. Notably, 99% of these strains were shown to provide detrimental or to lack beneficial effects on agricultural plants, e.g., when tested in a potato growth assay (i.e., a non-cereal crop) (Johnston-Monje D, Raizada M N (2011) Conservation and Diversity of Seed Associated Endophytes in *Zea* across Boundaries of Evolution, Ethnography and Ecology. PLoS ONE 6(6): e20396. doi:10.1371/journal-.pone.0020396). Further, some of the microbes isolated bear close evolutionary relation to plant pathogens, making it possible that such microbes represent a latent reservoir of pathogens, rather than potentially beneficial constituents.

Surprisingly, it was discovered here that seed-derived endophytes can confer significant advantages to cereal crops, spanning growth under normal and stressed conditions, altered expression of key plant hormones, altered expression of key transcripts in the plant, and other desirable features. Provided are novel compositions, methods, and products related our invention's ability to overcome the limitations of the prior art in order to provide reliable increases in cereal yield, biomass, germination, vigor, stress resilience, and other properties to agricultural crops.

The invention described herein is surprising for multiple reasons based on the previous demonstrations in the art. Notably, there is a lack of clarity related to whether endophytes are associated with healthy cereal seeds, whether microbes isolated from cereal seeds could efficiently colonize the cereal host if disposed on the exterior of a seed or seedling, and whether such microbes would confer a beneficial or detrimental effects on cereal hosts. It is further unclear whether the heterologous application of such microbes to distinct cereal seeds from which they were derived could provide beneficial effects.

As described herein, beneficial microbes can be robustly derived from agricultural seeds, optionally cultured, administered heterologously to agricultural cereal seeds or seedlings, and colonize the resulting plant tissues with high efficiency to confer multiple beneficial properties. This is surprising given the variability observed in the art in microbe isolation from healthy seeds and the previous observations of inefficient seed pathogen colonization of plant host's tissues. Further, the ability of heterologously disposed seed-derived endophytes to colonize seeds and seedlings from the exterior of seeds is surprising, given that such endophytes can be isolated from within internal seed tissues and therefore do not natively need the capacity to externally penetrate and invade into host tissues.

Prior characterization of microbial content of seeds has indicated that microbial concentrations in seeds can be variable and are generally very low (i.e., less than 10, 100, $10^3$, $10^4$, $10^5$ CFUs/seed). As such, it was unclear whether altered or increased concentrations of microbes associated with seeds could be beneficial. We find that microbes can confer beneficial properties across a range of concentrations.

We find that seed-derived endophytes can be heterologously disposed onto seedlings of a distinct cultivar, species, or cereal crop type and confer benefits to those new recipients. For example, seed-derived endophytes from corn cultivars are heterologously provided to wheat cultivars to confer a benefit. This is surprising given the observations of distinct microbiome preferences in distinct plant and mammalian hosts and, in particular, the likelihood that microbes derived from seeds have been co-evolved to be specialized to a particular host.

We further find that combinations of heterologously disposed seed-derived endophytes confer additive advantages to plants, including multiple functional properties and resulting in seed, seedling, and plant hosts that display single or multiple improved agronomic properties.

In general, this application provides methods and materials for providing a benefit to a seed or seedling of an agricultural grass plant using purified bacterial populations that include novel seed-origin endophytes that are unique in that they have been isolated from seeds of grass plants. Such seed-origin bacterial endophytes can provide beneficial properties to the seed, seedling, or the agricultural grass plant derived from the seed or seedling, including benefits to metabolism, transcription, proteome alterations, morphology, and the resilience to a variety of environmental stresses, and combinations of such properties.

As described herein, synthetic combinations that include a host plant such as an agricultural grass plant associated with a purified bacterial population that contains an endophyte, e.g., a seed-origin bacterial endophyte can be used to provide the benefit to a seed, seedling, or agricultural plant derived from the seed or seedling. The synthetic combination may be produced, for example, by inoculation, application to foliage (e.g., by spraying) or to seeds (e.g., coating of seeds), grafting, root dips, soil drenches, or infection of a host plant, host plant tissues, or a seed, or combinations thereof, as described herein. In any of the methods, any of such techniques can be used to make synthetic combinations. Inoculation, application to foliage or seeds, or infection can be particularly useful.

In some embodiments, the invention uses microbes that are heterologous to a seed or plant in making synthetic combinations or agricultural formulations. A microbe is considered heterologous to the seed or plant if the seed or seedling that is unmodified (e.g., a seed or seedling that is not treated with a bacterial endophyte population described herein) does not contain detectable levels of the microbe. For example, the invention contemplates the synthetic combinations of seeds or seedlings of agricultural plants (e.g., agricultural grass plants) and an endophytic microbe population (e.g., a seed-origin bacterial endophyte), in which the microbe population is "heterologously disposed" on the exterior surface of or within a tissue of the agricultural seed or seedling in an amount effective to colonize the plant. A microbe is considered "heterologously disposed" on the surface or within a plant (or tissue) when the microbe is applied or disposed on the plant in a number that is not found on that plant before application of the microbe. For example, a bacterial endophytic population that is disposed on an exterior surface or within the seed can be an endophytic bacterium that may be associated with the mature plant, but is not found on the surface of or within the seed. As such, a microbe is deemed heterologously disposed when applied on the plant that either does not naturally have the microbe on its surface or within the particular tissue to which the microbe is disposed, or does not naturally have the microbe on its surface or within the particular tissue in the number that is being applied. Indeed, several of the endophytic microbes described herein have not been detected, for example, in any of the corn seeds sampled, as determined by highly sensitive methods.

In some embodiments, a microbe can be "endogenous" to a seed or plant. As used herein, a microbe is considered "endogenous" to a plant or seed, if the microbe is derived from, or is otherwise found in, the seed or the plant, or any plant or seed of the same species. In embodiments in which an endogenous microbe is applied, the endogenous microbe is applied in an amount that differs from the levels typically found in the plant.

Seed-Origin Bacterial Endophytes

In some embodiments, this application relates to purified bacterial populations that contain seed-origin bacterial endophytes from, for example, maize, wheat, rice, or barley, compositions such as agricultural formulations or articles of manufacture that include such purified bacterial populations, as well as methods of using such bacterial populations to make synthetic combinations or agricultural products. A seed-origin bacterial endophyte used in a composition or used to make a synthetic composition can be obtained from the same cultivar or species of agricultural plant to which the composition is being applied or can be obtained from a different cultivar or species of agricultural plant.

Many bacterial species are sensitive to conditions of drying and desiccation. Surprisingly, the bacterial endophytes described herein have been isolated from mature, dry seeds of grass plants, including maize, rice, and wheat seeds. The recovery of viable bacterial endophytes from these mature dry seeds demonstrates that, unlike most other bacteria, these seed-origin bacterial endophytes are capable of surviving conditions of desiccation. Therefore, in one embodiment, the purified bacterial population containing seed-origin bacterial endophytes is desiccation tolerant. For example, a substantial portion of the population (e.g., at least 5, 10, 15, 20, 25, 30, 35, 40, 45, 50, 55, 60, 65, 70, 75, 80, 85, 90, 95, 96, 97, 98, 99 or greater than 99%) of the seed-origin bacterial endophytes can survive in moisture content levels of 30% or less, for example, 25% or less, 20% or less, 15% or less, 12% or less, 10% or less, or 8% or less, for a period of at least 1 day, for example, at least 3 days, at least 5 days, at least 7 days, at least 10 days, at least 14 days, at least 21 days, at least 30 days, at least 45 days, at least 60 days, or more, within the seeds of a grass plant that are stored at between 1° C. and 35° C.

In another embodiment, the seed-origin bacterial endophyte is capable of forming spores. In still another embodiment, at least 1% of the population of the seed-origin bacterial endophyte, for example, at least 5%, at least 10%, at least 20%, at least 30%, at least 40%, at least 50%, at least 75%, at least 80%, at least 90%, or at least 95% or more, is used in spore form.

In some embodiments, the seed-origin bacterial endophyte can be cultured on a culture medium or can be adapted to culture on a culture medium.

In some embodiments, a purified bacterial population is used that includes two or more (e.g., 3, 4, 5, 6, 7, 8, 9, 10, 15, 20, 25 or greater than 25) different seed-origin bacterial endophytes, e.g., obtained from different families or different genera of bacteria, or from the same genera but different species of bacteria. The different seed-origin bacterial endophytes can be obtained from the same cultivar of agricultural plant (e.g., the same maize, wheat, rice, or barley plant), different cultivars of the same agricultural plant (e.g., two or more cultivars of maize, two or more cultivars of wheat, two or more cultivars of rice, or two or more cultivars of barley), or different species of the same type of agricultural plant (e.g., two or more different species of maize, two or more different species of wheat, two or more different species of rice, or two or more different species of barley). In embodiments in which two or more seed-origin bacterial endophytes are used, each of the seed-origin bacterial endophytes can have different properties or activities, e.g., produce different metabolites, produce different enzymes such as different hydrolytic enzymes, confer different beneficial traits, or colonize different parts of a plant (e.g., leaves, stems, flowers, fruits, seeds, or roots). For example, one seed-origin bacterial endophyte can colonize a first and a second seed-origin bacterial endophyte can colonize a tissue that differs from the first tissue. Combinations of bacterial endophytes are discussed in detail below.

In one embodiment, the endophyte is an endophytic microbe isolated from a different plant than the inoculated plant. For example, in one embodiment, the endophyte is an endophyte isolated from a different plant of the same species as the inoculated plant. In some cases, the endophyte is isolated from a species related to the inoculated plant.

The breeding of plants for agriculture, as well as cultural practices used to combat microbial pathogens, may have resulted in the loss in modern cultivars of the endophytes present in their wild ancestors, or such practices may have inadvertently promoted other novel or rare plant-endophyte interactions, or otherwise altered the microbial population. We hypothesized that an altered diversity and titer of endophytes in the ancestor could correlate with an altered range of physiological responses derived from the symbiosis that allow the plant to better adapt to the environment and tolerate stress. In order to survey plant groups for potentially useful endophytes, seeds of their wild ancestors, wild relatives, primitive landraces, modern landraces, modern breeding lines, and elite modern agronomic varieties are screened for microbial endophytes by culture and culture independent methods as described herein.

In some cases, plants are inoculated with endophytes that are heterologous to the seed of the inoculated plant. In one embodiment, the endophyte is derived from a plant of another species. For example, an endophyte that is normally found in dicots is applied to a monocot plant (e.g., inoculating corn with a soy bean-derived endophyte), or vice versa. In other cases, the endophyte to be inoculated onto a plant is derived from a related species of the plant that is being inoculated. In one embodiment, the endophyte is derived from a related taxon, for example, from a related species. The plant of another species can be an agricultural plant. For example, an endophyte derived from *Hordeum irregulare* can be used to inoculate a *Hordeum vulgare* L., plant. Alternatively, it is derived from a 'wild' plant (i.e., a non-agricultural plant). For example, endophytes normally associated with the wild cotton *Gossypium klotzschianum* are useful to inoculate commercial varieties of *Gossypium hirsutum* plants. As an alternative example of deriving an endophyte from a 'wild' plant, endophytic bacteria isolated from the South East Asian jungle orchid, *Cymbidium eburneum*, can be isolated and testing for their capacity to benefit seedling development and survival of agricultural crops such as wheat, maize, soy and others (Facia, D. C., et al., (2013) *World Journal of Microbiology and Biotechnology*. 29(2). pp. 217-221). In other cases, the endophyte can be isolated from an ancestral species of the inoculated plant. For example, an endophyte derived from *Zea diploperennis* can be used to inoculate a commercial variety of modern corn, or *Zea mays*.

In some embodiments, a purified bacterial populations contains seed-origin bacterial endophytes from one or more (e.g., two, three, four, five, six, seven, eight, nine, 10, or more families selected from the group consisting of Acidithiobacillaceae, Actinosynnemataceae, Aerococcaceae, Aeromonadaceae, Alcaligenaceae, Alteromonadaceae, Bacillaceae, Bdellovibrionaceae, Bradyrhizobiaceae, Brucellaceae, Burkholderiaceae, Carnobacteriaceae, Caulobacteraceae, Cellulomonadaceae, Chitinophagaceae, Chromatiaceae, Clostridiaceae, Comamonadaceae, Coriobacteriaceae, Corynebacteriaceae, Deinococcaceae, Ectothiorhodospiraceae, Enterobacteriaceae, Flavobacteriaceae, Halomonadaceae, Hyphomicrobiaceae, Lachnospiraceae, Lactobacillaceae, Methylobacteriaceae, Microbacteriaceae, Micrococcaceae, Moraxellaceae, Mycobacteriaceae, Neisseriaceae, Nocardiaceae, Oxalobacteraceae, Paenibacillaceae, Planococcaceae, Propionibacteriaceae, Pseudonocardiaceae, Rhizobiaceae, Rhodospirillaceae, Sphingobacteriaceae, Sphingomonadaceae, Streptomycetaceae, Tissierellaceae, Weeksellaceae, Xanthobacteraceae, and Xanthomonadaceae.

In one embodiment, the purified bacterial population includes seed-origin bacterial endophytes is from one or more families selected from the group consisting of Xanthomonadaceae, Sphingomonadaceae, Weeksellaceae, Microbacteriaceae, Micrococcaceae, Methylobacteriaceae, Xanthomonadaceae, Rhizobiaceae, Paenibacillaceae, Staphylococcaceae, Enterobacteriaceae, Pseudomonadaceae, and Bacillaceae.

In some embodiments, the purified bacterial population includes seed-origin bacterial endophytes from one or more (e.g., two, three, four, five, six, seven, eight, nine, 10, or more) of the generas selected from the group consisting of *Achromobacter, Acidithiobacillus, Acidovorax, Acidovoraz, Acinetobacter, Aerococcus, Aeromonas, Agromyces, Ancylobacter, Arthrobacter, Azospirillum, Bacillus, Bdellovibrio, Bosea, Bradyrhizobium, Brevibacillus, Brevundimonas, Burkholderia, Cellulomonas, Cellvibrio, Chryseobacterium, Citrobacter, Clostridium, Corynebacterium, Cupriavidus, Curtobacterium, Curvibacter, Deinococcus, Desemzia, Devosia, Dokdonella, Dyella, Enhydrobacter, Enterobacter, Enterococcus, Erwinia, Escherichia, Finegoldia, Flavisolibacter, Flavobacterium, Frigoribacterium, Hafnia, Halomonas, Herbaspirillum, Klebsiella, Kocuria, Lactobacillus, Leclercia, Lentzea, Luteibacter, Luteimonas, Massilia,*

Methylobacterium, Microbacterium, Micrococcus, Microvirga, Mycobacterium, Neisseria, Nocardia, Oceanibaculum, Ochrobactrum, Oxalophagus, Paenibacillus, Panteoa, Pantoea, Plantibacter, Propionibacterium, Propioniciclava, Pseudomonas, Pseudonocardia, Pseudoxanthomonas, Psychrobacter, Rheinheimera, Rhizobium, Rhodococcus, Roseateles, Ruminococcus, Sediminibacillus, Sediminibacterium, Serratia, Shigella, Shinella, Sphingobacterium, Sphingomonas, Sphingopyxis, Sphingosinicella, Staphylococcus, Stenotrophomonas, Strenotrophomonas, Streptomyces, Tatumella, Tepidimonas, Thermomonas, Thiobacillus, Uncultured bacterium, Variovorax, and Xanthomonas.

In some embodiments, the purified bacterial population does not include at least one of *Acetobacter* sp., *Acidovorax facilis*, *Azospirillum brasilense*, *Azospirillum hpoferum*, *Azospirillum* sp., *Azotobacter* sp., *Azotobacter vinelandii*, *Bacillus amyloliquefaciens* FZB42, *Bacillus amyloliquefaciens* strain D747, *Bacillus amyloliquefaciens* TJI000, *Bacillus amyloliquefaciens* TM45, *Bacillus chitinosporus*, *Bacillus firmus*, *Bacillus firmus* NCIM 2637, *Bacillus firmus* 1-1582, *Bacillus laterosporus*, *Bacillus licheniformis*, *Bacillus lichenformus*, *Bacillus marinus*, *Bacillus megaterium*, *Bacillus megaterium* var. *phosphaticum*, *Bacillus megatherium*, *Bacillus oleronius*, *Bacillus pumilus*, *Bacillus pumilus* QST 2808, *Bacillus* sp., *Bacillus subtilis*, *Bacillus subtilis* FZB24, *Bacillus subtilis* MBI 600, *Bacillus subtilis* BSF4, *Bacillus subtilis* MB1600, *Bacillus subtilis* QST 713, *Bacillus thuringensis* var *Kurstaki* (NCIM 2514), *Bacillus thuringiensis aizawai*, *Bacillus thuringiensis kurstaki*, *Bacillus thuringiensis kurstaki* strain EG7841, *Bacillus thuringiensis kurstaki* strain SA-11, *Bacillus thuringiensis* subsp. *kurstaki* ABTS-351, *Bacillus thuringiensis* SV *kurstaki* EG 2348, *Bacillus thuringiensis* var *Israelensis*, *Bacillus thuringiensis*, *Kurstaki* variety, serotype 3A 3B, *Bacillus thuringiensis*, subsp. *aizawai*, Strain ABTS-1857, *Bacillus thuringiensis*, subsp. *israelensis*, strain AM 65-52, *Chromobacterium subtsugae* strain PRAA4-1, *Delftia acidovorans*, *Frateuria aurantia*, *Lactobacillus casei*, *Lactobacillus delbrueckii*, *Lactobacillus fermentum*, *Lactobacillus helveticus*, *Lactobacillus plantarum*, *Lactococcus lactus*, *Methylobacterium mesophilicum*, *Methylobacterium organophilum*, *Methylobacterium extorquens*, *Paenibacillus polymyxa*, *Pasteuria* spp., *Pseudomonas* spp., *Pseudomonas fluorescens*, *Rhizobium* sp., *Rhodococcus rhodochrous*, *Rhodopseudomonas palustris*, *Streptomyces lydicus* WYEC 108, *Streptomyces* ray, or *Thiobacillus thiooxidans*.

In some embodiments, the purified fungal population does not include at least one of *Acremonium* butyri, *Ampelomyces quisqualis*, *Ampelomyces quisqualis* (DSM 2222), *Ampelomyces quisqualis* M-10, *Arthrobotrys oligospora*, *Aspergillus oryzae*, *Beauvaria bassiana* strain ATCC 74040, *Beauveria bassiana*, *Beauveria bassiana* (NCIM 1216 ATCC 26851), *Beauveria bassiana* strain GHA, *Beauveria bassiana* strain GHA 1991, *Candida utilis*, *Chaetomium cupreum* (CABI 353812), *Chaetomium globosum*, *Clonostachys rosea* 88-710, *Fusarium oxysporum* IF23, *Fusarium proliferatum* (NCIM 1101), *Gliocladium*, *Gliocladium catenulatum* strain J1446, *Gliocladium vixens* GL-21, *Glomus fasciculatum*, *Glomus intraradices*, *Hirsutella rhossiliensis*, *Isaria fumosorosea* Apopka Strain 97, *Metarhizium anisopliae*, *Metarhizium anisopliae* (NCIM 1311), *Metschnikowia fructicola*, *Myrothecium verrucaria*, *Neotyphodium lolii* AR1, *Neotyphodium lolii* AR37, *Neotyphodium lolii* AR6, *Neotyphodium lolii* NEA2, *Neotyphodium uncinatum*, *Paecilomyces fumorosoroseus* strain FE 9901, *Paecilomyces fumosoroseus*, *Paecilomyces lilacinus*, *Paecilomyces lilacinus* (IIHR PL-2), *Penicillium bilaii*, *Saccharomyces cerevisiae*, *Sclerotinia minor*, *Trichoderma asperellum* TV 1, *Trichoderma asperellum* strain ICC 012, *Trichoderma gamsii* strain ICC 080, *Trichoderma harzianum*, *Trichoderma harzianum* (IIHR-Th-2), *Trichoderma harzianum Rifai* strain T22, *Trichoderma koningii*, *Trichoderma lignorum*, *Trichoderma polysporum*, *Trichoderma* sp., *Trichoderma vixens* Gl-3, *Trichoderma viride*, *Trichoderma viride* (TNAU), *Verticillium lecanii*, or *Verticillium lecanii* (NCIM 1312).

In some embodiments, the purified bacterial population includes seed-origin bacterial endophytes from a non-*Bacillus* and/or a non-*Pseudomonas* genera and/or a non-*Rhizobium* genera, e.g., from one or more of *Achromobacter*, *Acidithiobacillus*, *Acidovorax*, *Acidovoraz*, *Acinetobacter*, *Aerococcus*, *Aeromonas*, *Agromyces*, *Ancylobacter*, *Arthrobacter*, *Azospirillum*, *Bdellovibrio*, *Bosea*, *Bradyrhizobium*, *Brevibacillus*, *Brevundimonas*, *Burkholderia*, *Cellulomonas*, *Cellvibrio*, *Chryseobacterium*, *Citrobacter*, *Clostridium*, *Corynebacterium*, *Cupriavidus*, *Curtobacterium*, *Curvibacter*, *Deinococcus*, *Desemzia*, *Devosia*, *Dokdonella*, *Dyella*, *Enhydrobacter*, *Enterobacter*, *Enterococcus*, *Erwinia*, *Escherichia*, *Finegoldia*, *Flavisolibacter*, *Flavobacterium*, *Frigoribacterium*, *Hafnia*, *Halomonas*, *Herbaspirillum*, *Klebsiella*, *Kocuria*, *Lactobacillus*, *Leclercia*, *Lentzea*, *Luteibacter*, *Luteimonas*, *Massilia*, *Methylobacterium*, *Microbacterium*, *Micrococcus*, *Microvirga*, *Mycobacterium*, *Neisseria*, *Nocardia*, *Oceanibaculum*, *Ochrobactrum*, *Oxalophagus*, *Paenibacillus*, *Panteoa*, *Pantoea*, *Plantibacter*, *Propionibacterium*, *Propioniciclava*, *Pseudonocardia*, *Pseudoxanthomonas*, *Psychrobacter*, *Rheinheimera*, *Rhodococcus*, *Roseateles*, *Ruminococcus*, *Sediminibacillus*, *Sediminibacterium*, *Serratia*, *Shigella*, *Shinella*, *Sphingobacterium*, *Sphingomonas*, *Sphingopyxis*, *Sphingosinicella*, *Staphylococcus*, *Stenotrophomonas*, *Strenotrophomonas*, *Streptomyces*, Tatumella, Tepidimonas, Thermomonas, Thiobacillus, Uncultured bacterium, Variovorax, or Xanthomonas.

In some embodiments, the purified bacterial population includes seed-origin bacterial endophytes from a genera selected from the group consisting of *Luteibacter*, *Sphingobium*, *Chryseobacterium*, *Curtobacterium*, *Micrococcus*, *Sphingomonas*, *Microbacterium*, *Methylobacterium*, *Stenotrophomonas*, *Xanthomonas*, *Agrobacterium*, *Paenibacillus*, *Staphylococcus*, *Enterobacter*, *Pantoea*, *Pseudomonas*, and *Bacillus*. In some embodiments, the purified bacterial populations includes seed-origin bacterial endophytes from a non-*Bacillus*, and/or a non-*Pseudomonas* genera and/or a non-*Rhizobium* genera, e.g., from one or more of *Luteibacter*, *Sphingobium*, *Chryseobacterium*, *Curtobacterium*, *Micrococcus*, *Sphingomonas*, *Microbacterium*, *Methylobacterium*, *Stenotrophomonas*, *Xanthomonas*, *Agrobacterium*, *Paenibacillus*, *Staphylococcus*, *Enterobacter*, or *Pantoea*.

In some embodiments, the seed-origin bacterial endophyte includes a 16S nucleic acid sequence that is at least 97% identical to at least one of the nucleic acid sequences referenced in Table 1 or Table 2 (SEQ ID NOs: 1-1448, e.g., SEQ ID NOs: 521-1448). For example, the seed-origin bacterial endophyte can include a 16S nucleic acid sequence that is at least 98% identical, at least 99% identical, or at least 99.5% identical to a 16S nucleic acid sequence referenced in Table 1 or Table 2 (SEQ ID NOs: 1-1448, e.g., SEQ ID NOs: 521-1448). In some embodiments, the seed-origin bacterial endophyte comprises a 16S nucleic acid sequence that is 100% identical to a 16S nucleic acid sequence referenced in Table 1 or Table 2 (SEQ ID NOs: 1-1448, e.g., SEQ ID NOs: 521-1448). In embodiments in which two or more seed-origin bacterial endophytes are used, the 16S nucleic acid sequence of each seed-origin bacterial endophyte can have more than 97% sequence identity to each other or can have less than 97% sequence identity to each other. In addition, in embodiments in which two or more seed-origin bacterial endophytes are used, the 16S nucleic acid sequence of one seed-origin bacterial endophyte can have more than 97% sequence identity to one of the nucleotide sequences set forth in SEQ ID NOs: 1-1448, and one seed-origin bacterial endophyte can have less than 97% sequence identity to one of the 16S nucleotide sequences set forth in SEQ ID NOs:1-1448.

In some embodiments, the seed-origin bacterial endophyte includes a 16S nucleic acid sequence that has less than 97% sequence identity to at least one of the nucleic acid sequences referenced in Table 1 or Table 2 (SEQ ID NOs: 1-1448).

TABLE 1

Representative endophytes from grass seeds, including their 16S rRNA sequences, assignment within OTU numbers, Genus, species, strain information, as well as GenBank Accession numbers.

| SEQ ID NO. | OTU # | Genus | Species | Strain | Accession No. |
|---|---|---|---|---|---|
| 1 | 37 | Burkholderia | fungorum | | JF753273 |
| 2 | 37 | Burkholderia | fungorum | | JF753274 |
| 3 | 27 | Burkholderia | gladioli | | JF753275 |
| 4 | 21 | Citrobacter | freundii | | JF753276 |
| 5 | 21 | Citrobacter | freundii | | JF753277 |
| 6 | 61 | Clostridium | acetobutylicum | | JF753278 |
| 7 | 61 | Clostridium | beijerinckii | | JF753279 |
| 8 | 0 | Enterobacter | absuriae | | JF753280 |
| 9 | 0 | Enterobacter | absuriae | | JF753281 |
| 10 | 0 | Enterobacter | aerogenes | | JF753282 |
| 11 | 0 | Enterobacter | aerogenes | | JF753283 |
| 12 | 18 | Enterobacter | asburiae | | JF753284 |
| 13 | 156 | Enterobacter | asburiae | | JF753285 |
| 14 | 0 | Enterobacter | asburiae | | JF753286 |
| 15 | 0 | Enterobacter | asburiae | | JF753287 |
| 16 | 0 | Enterobacter | asburiae | | JF753288 |
| 17 | 0 | Enterobacter | asburiae | | JF753289 |
| 18 | 0 | Enterobacter | asburiae | J2S4 | JF753290 |
| 19 | 18 | Enterobacter | asburiae | MY2 | JF753291 |
| 20 | 18 | Enterobacter | asburiae | MY2 | JF753292 |
| 21 | 21 | Enterobacter | asburiae | J2S4 | JF753293 |
| 22 | 18 | Enterobacter | cloacae | | JF753294 |
| 23 | 18 | Enterobacter | cloacae | | JF753295 |
| 24 | 177 | Enterobacter | ludwigii | AR1.22 | JF753296 |
| 25 | 56 | Enterobacter | sp. | Nj-68 | JF753297 |
| 26 | 18 | Escherichia | coli | | JF753298 |
| 27 | 18 | Escherichia | coli | | JF753299 |
| 28 | 18 | Escherichia | coli | | JF753300 |
| 29 | 18 | Escherichia | coli | NBRI1707 | JF753301 |
| 30 | 18 | Escherichia | coli | NBRI1707 | JF753302 |
| 31 | 18 | Escherichia | coli | NBRI1707 | JF753303 |
| 32 | 18 | Klebsiella | pneumoniae | 342 | JF753304 |
| 33 | 82 | Luteibacter | sp. | | JF753305 |
| 34 | 81 | Methylobacterium | sp. | | JF753306 |
| 35 | 31 | Paenibacillus | caespitis | | JF753307 |
| 36 | 49 | Paenibacillus | ruminocola | G22 | JF753308 |
| 37 | 18 | Panteoa | agglomerans | | JF753309 |
| 38 | 109 | Pantoea | agglomerans | | JF753310 |
| 39 | 146 | Pantoea | agglomerans | | JF753311 |
| 40 | 109 | Pantoea | agglomerans | 1.2244 | JF753312 |
| 41 | 84 | Pantoea | agglomerans | 1.2244 | JF753313 |
| 42 | 0 | Pantoea | agglomerans | 1.2244 | JF753314 |
| 43 | 0 | Pantoea | agglomerans | 1.2244 | JF753315 |
| 44 | 84 | Pantoea | agglomerans | 1.2244 | JF753316 |
| 45 | 7 | Pantoea | agglomerans | BJCP2 | JF753317 |
| 46 | 58 | Pantoea | agglomerans | BJCP2 | JF753318 |
| 47 | 146 | Pantoea | agglomerans | KJPB2 | JF753319 |
| 48 | 164 | Pantoea | agglomerans | KJPB2 | JF753320 |
| 49 | 0 | Pantoea | agglomerans | Sc-1 | JF753321 |
| 50 | 0 | Pantoea | agglomerans | Sc-1 | JF753322 |
| 51 | 0 | Pantoea | agglomerans | Sc-1 | JF753323 |
| 52 | 0 | Pantoea | agglomerans | Sc-1 | JF753324 |
| 53 | 0 | Pantoea | agglomerans | Sc-1 | JF753325 |
| 54 | 0 | Pantoea | agglomerans | Sc-1 | JF753326 |
| 55 | 0 | Pantoea | agglomerans | Sc-1 | JF753327 |
| 56 | 0 | Pantoea | agglomerans | Sc-1 | JF753328 |
| 57 | 0 | Pantoea | agglomerans | Sc-1 | JF753329 |
| 58 | 0 | Pantoea | agglomerans | Sc-1 | JF753330 |
| 59 | 0 | Pantoea | agglomerans | Sc-1 | JF753331 |
| 60 | 0 | Pantoea | agglomerans | Sc-1 | JF753332 |
| 61 | 0 | Pantoea | agglomerans | Sc-1 | JF753333 |
| 62 | 164 | Pantoea | agglomerans | TX4CB_114 | JF753334 |
| 63 | 0 | Pantoea | agglomerans | TX4CB_114 | JF753335 |
| 64 | 164 | Pantoea | agglomerans | 1.2244 | JF753336 |

TABLE 1-continued

Representative endophytes from grass seeds, including their 16S rRNA sequences, assignment within OTU numbers, Genus, species, strain information, as well as GenBank Accession numbers.

| SEQ ID NO. | OTU # | Genus | Species | Strain | Accession No. |
|---|---|---|---|---|---|
| 65 | 84 | Pantoea | agglomerans | 1.2244 | JF753337 |
| 66 | 84 | Pantoea | agglomerans | 1.2244 | JF753338 |
| 67 | 84 | Pantoea | agglomerans | 1.2244 | JF753339 |
| 68 | 84 | Pantoea | agglomerans | 1.2244 | JF753340 |
| 69 | 0 | Pantoea | agglomerans | 48b/90 | JF753341 |
| 70 | 127 | Pantoea | agglomerans | 48b/90 | JF753342 |
| 71 | 0 | Pantoea | agglomerans | 48b/90 | JF753343 |
| 72 | 7 | Pantoea | agglomerans | BJCP2 | JF753344 |
| 73 | 7 | Pantoea | agglomerans | BJCP2 | JF753345 |
| 74 | 0 | Pantoea | agglomerans | AN3 | JF753346 |
| 75 | 84 | Pantoea | agglomerans | KJPB2 | JF753347 |
| 76 | 164 | Pantoea | agglomerans | KJPB2 | JF753348 |
| 77 | 84 | Pantoea | agglomerans | KJPB2 | JF753349 |
| 78 | 164 | Pantoea | agglomerans | KJPB2 | JF753350 |
| 79 | 0 | Pantoea | agglomerans | KJPB2 | JF753351 |
| 80 | 0 | Pantoea | agglomerans | new*47con | JF753352 |
| 81 | 0 | Pantoea | agglomerans | Sc-1 | JF753353 |
| 82 | 0 | Pantoea | agglomerans | Sc-1 | JF753354 |
| 83 | 0 | Pantoea | agglomerans | Sc-1 | JF753355 |
| 84 | 0 | Pantoea | agglomerans | Sc-1 | JF753356 |
| 85 | 0 | Pantoea | agglomerans | Sc-1 | JF753357 |
| 86 | 173 | Pantoea | agglomerans | Sc-1 | JF753358 |
| 87 | 199 | Pantoea | ananatis | LMG 20103 | JF753359 |
| 88 | 0 | Pantoea | ananatis | LMG 20103 | JF753360 |
| 89 | 0 | Pantoea | ananatis | LMG 20103 | JF753361 |
| 90 | 0 | Pantoea | ananatis | LMG 20103 | JF753362 |
| 91 | 0 | Pantoea | ananatis | LMG 20103 | JF753363 |
| 92 | 0 | Pantoea | ananatis | LMG 20103 | JF753364 |
| 93 | 0 | Pantoea | ananatis | LMG 20103 | JF753365 |
| 94 | 0 | Pantoea | ananatis | LMG 20103 | JF753366 |
| 95 | 0 | Pantoea | ananatis | LMG 20106 | JF753367 |
| 96 | 158 | Pantoea | ananatis | SK-1 | JF753368 |
| 97 | 0 | Pantoea | ananatis | SK-1 | JF753369 |
| 98 | 0 | Pantoea | sp. | GJT-8 | JF753370 |
| 99 | 0 | Pantoea | sp. | GJT-8 | JF753371 |
| 100 | 0 | Pantoea | sp. | GJT-8 | JF753372 |
| 101 | 0 | Pantoea | sp. | GJT-8 | JF753373 |
| 102 | 0 | Pantoea | sp. | GJT-8 | JF753374 |
| 103 | 0 | Pantoea | sp. | GJT-8 | JF753375 |
| 104 | 0 | Pantoea | sp. | GJT-8 | JF753376 |
| 105 | 0 | Pantoea | sp. | GJT-8 | JF753377 |
| 106 | 0 | Pantoea | sp. | GJT-8 | JF753378 |
| 107 | 0 | Pantoea | sp. | GJT-8 | JF753379 |
| 108 | 1 | Pseudomonas | fluorescens | | JF753380 |
| 109 | 2 | Pseudomonas | oleovarans | | JF753381 |
| 110 | 2 | Pseudomonas | oryzihabitans | | JF753382 |
| 111 | 10 | Strenotrophomonas | maltophilia | | JF753383 |
| 112 | 105 | Strenotrophomonas | maltophilia | | JF753384 |
| 113 | 40 | Strenotrophomonas | maltophilia | | JF753385 |
| 114 | 10 | Strenotrophomonas | maltophilia | | JF753386 |
| 115 | 10 | Strenotrophomonas | maltophilia | | JF753387 |
| 116 | 185 | Strenotrophomonas | maltophilia | | JF753388 |
| 117 | 10 | Strenotrophomonas | maltophilia | | JF753389 |
| 118 | 10 | Strenotrophomonas | maltophilia | | JF753390 |
| 119 | 10 | Strenotrophomonas | maltophilia | | JF753391 |
| 120 | 10 | Strenotrophomonas | maltophilia | | JF753392 |
| 121 | 10 | Strenotrophomonas | maltophilia | | JF753393 |
| 122 | 10 | Strenotrophomonas | maltophilia | | JF753394 |
| 123 | 10 | Strenotrophomonas | maltophilia | | JF753395 |
| 124 | 153 | Strenotrophomonas | maltophilia | | JF753396 |
| 125 | 10 | Strenotrophomonas | maltophilia | | JF753397 |
| 126 | 10 | Strenotrophomonas | maltophilia | | JF753398 |
| 127 | 86 | Uncultured bacterium | Uncultured bacterium | SP6-0 | JF753399 |
| 128 | 188 | Uncultured bacterium | Uncultured bacterium | X-50 | JF753400 |
| 129 | 84 | Pantoea | agglomerans | 1.2244 | JF753401 |
| 130 | 179 | Rhodococcus | fascians | | JF753402 |
| 131 | 2 | Pseudomonas | oryzihabitans | | JF753403 |
| 132 | 84 | Pantoea | agglomerans | 1.2244 | JF753404 |
| 133 | 18 | Escherichia | coli | NBRI1707 | JF753405 |
| 134 | 25 | Methylobacterium | radiotolerans | | JF753406 |
| 135 | 18 | Escherichia | coli | NBRI1707 | JF753407 |
| 136 | 18 | Enterobacter | sp. | TSSAS2-21 | JF753408 |
| 137 | 18 | Enterobacter | sp. | FMB-1 | JF753409 |

TABLE 1-continued

Representative endophytes from grass seeds, including their 16S rRNA sequences, assignment within OTU numbers, Genus, species, strain information, as well as GenBank Accession numbers.

| SEQ ID NO. | OTU # | Genus | Species | Strain | Accession No. |
|---|---|---|---|---|---|
| 138 | 18 | Enterobacter | sp. | TSSAS2-21 | JF753410 |
| 139 | 101 | Sphingomonas | sp. | BF14 | JF753411 |
| 140 | 18 | Hafnia | alvei | | JF753412 |
| 141 | 149 | Escherichia | coli | NBRI1707 | JF753413 |
| 142 | 27 | Burkholderia | gladioli | pv. Agaricicola | JF753414 |
| 143 | 18 | Escherichia | coli | NBRI1707 | JF753415 |
| 144 | 25 | Methylobacterium | radiotolerans | | JF753416 |
| 145 | 194 | Micrococcus | luteus | NBSL29 | JF753417 |
| 146 | 37 | Burkholderia | phytofirmans | PsJN | JF753418 |
| 147 | 38 | Staphylococcus | warneri | R-36520 | JF753419 |
| 148 | 160 | Pseudomonas | fluorescens | | JF753420 |
| 149 | 18 | Enterobacter | cloacae | C111 | JF753421 |
| 150 | 161 | Methylobacterium | brachiatum | | JF753422 |
| 151 | 27 | Burkholderia | gladioli | pv. agaricicola | JF753423 |
| 152 | 18 | Escherichia | coli | NBRI1707 | JF753424 |
| 153 | 16 | Staphylococcus | sp. | SRC_DSF7 | JF753425 |
| 154 | 67 | Staphylococcus | epidermitis | | JF753426 |
| 155 | 64 | Methylobacterium | brachiatum | | JF753427 |
| 156 | 1 | Pseudomonas | putida | CM5002 | JF753428 |
| 157 | 37 | Burkholderia | phytofirmans | PsJN | JF753429 |
| 158 | 1 | Pseudomonas | putida | CM5002 | JF753430 |
| 159 | 101 | Sphingomonas | sp. | P5-5 | JF753431 |
| 160 | 84 | Pantoea | agglomerans | CLJ1 | JF753432 |
| 161 | 84 | Pantoea | agglomerans | KJPB2 | JF753433 |
| 162 | 7 | Pantoea | dispersa | CIP 102701 | JF753434 |
| 163 | 18 | Enterobacter | cloacae | R10-1A | JF753435 |
| 164 | 1 | Pseudomonas | putida | CM5002 | JF753436 |
| 165 | 1 | Pseudomonas | putida | CM5002 | JF753437 |
| 166 | 0 | Pantoea | agglomerans | KJPB2 | JF753438 |
| 167 | 143 | Pantoea | agglomerans | KJPB2 | JF753439 |
| 168 | 65 | Pseudomonas | putida | CM5002 | JF753440 |
| 169 | 1 | Pseudomonas | tolaasii | IExb | JF753441 |
| 170 | 84 | Pantoea | agglomerans | KJPB2 | JF753442 |
| 171 | 2 | Pseudomonas | oryzihabitans | | JF753443 |
| 172 | 1 | Pseudomonas | putida | CM5002 | JF753444 |
| 173 | 1 | Pseudomonas | putida | CM5002 | JF753445 |
| 174 | 143 | Pantoea | agglomerans | KJPB2 | JF753446 |
| 175 | 164 | Pantoea | agglomerans | KJPB2 | JF753447 |
| 176 | 56 | Enterobacter | asburiae | MY2 | JF753448 |
| 177 | 0 | Enterobacter | asburiae | NFSt10 | JF753449 |
| 178 | 25 | Methylobacterium | radiotolerans | | JF753450 |
| 179 | 7 | Pantoea | dispersa | NCPPB 2285 | JF753451 |
| 180 | 1 | Pseudomonas | putida | CM5002 | JF753452 |
| 181 | 72 | Cellulomonas | denverensis | | JF753453 |
| 182 | 102 | Arthrobacter | ramosus | | JF753454 |
| 183 | 72 | Cellulomonas | denverensis | | JF753455 |
| 184 | 0 | Pantoea | ananatis | LMG 20103 | JF753456 |
| 185 | 0 | Pantoea | ananatis | LMG 20103 | JF753457 |
| 186 | 102 | Arthrobacter | sp. | XY9 | JF753458 |
| 187 | 0 | Enterobacter | asburiae | | JF753459 |
| 188 | 0 | Enterobacter | cloaceae | | JF753460 |
| 189 | 196 | Enterobacter | hormaechei | | JF753461 |
| 190 | 7 | Pantoea | dispersa | NCPPB 2285 | JF753462 |
| 191 | 0 | Enterobacter | cloacae | TU | JF753463 |
| 192 | 10 | Stenotrophomonas | maltophilia | | JF753464 |
| 193 | 10 | Stenotrophomonas | maltophilia | | JF753465 |
| 194 | 21 | Klebsiella | pneumoniae | 342 | JF753466 |
| 195 | 0 | Citrobacter | freundii | GM1 | JF753467 |
| 196 | 31 | Paenibacillus | caespitis | | JF753468 |
| 197 | 31 | Paenibacillus | graminis | | JF753469 |
| 198 | 178 | Paenibacillus | sp. | P117 | JF753470 |
| 199 | 178 | Paenibacillus | sp. | MK17 | JF753471 |
| 200 | 72 | Cellulomonas | denverensis | | JF753472 |
| 201 | 28 | Microbacterium | sp. | 13635I | JF753473 |
| 202 | 31 | Paenibacillus | caespitis | | JF753474 |
| 203 | 31 | Paenibacillus | caespitis | | JF753475 |
| 204 | 196 | Enterobacter | asburiae | J2S4 | JF753476 |
| 205 | 66 | Rhizobium | sp. | HGR13 | JF753477 |
| 206 | 84 | Pantoea | agglomerans | KJPB2 | JF753478 |
| 207 | 84 | Pantoea | agglomerans | KJPB2 | JF753479 |
| 208 | 84 | Pantoea | agglomerans | Sc-1 | JF753480 |
| 209 | 84 | Pantoea | agglomerans | KJPB2 | JF753481 |
| 210 | 1 | Pseudomonas | putida | CM5002 | JF753482 |
| 211 | 2 | Pseudomonas | sp. | TE9 | JF753483 |
| 212 | 84 | Pantoea | agglomerans | 1.2244 | JF753484 |

TABLE 1-continued

Representative endophytes from grass seeds, including their 16S rRNA sequences, assignment within OTU numbers, Genus, species, strain information, as well as GenBank Accession numbers.

| SEQ ID NO. | OTU # | Genus | Species | Strain | Accession No. |
|---|---|---|---|---|---|
| 213 | 1 | Pseudomonas | synxantha | | JF753485 |
| 214 | 1 | Pseudomonas | fluorescens | | JF753486 |
| 215 | 1 | Pseudomonas | putida | CM5002 | JF753487 |
| 216 | 1 | Pseudomonas | fluorescens | PGPR1 | JF753488 |
| 217 | 0 | Pantoea | vagans | C9-1 | JF753489 |
| 218 | 10 | Stenotrophomonas | maltophilia | | JF753490 |
| 219 | 0 | Pantoea | agglomerans | 1.2244 | JF753491 |
| 220 | 37 | Burkholderia | phytofirmans | PSjN | JF753492 |
| 221 | 37 | Burkholderia | phytofirmans | PsJN | JF753493 |
| 222 | 92 | Streptomyces | sp. | KN-0260 | JF753494 |
| 223 | 64 | Methylobacterium | brachiatum | | JF753495 |
| 224 | 53 | Paenibacillus | sp. | IHB B 2257 | JF753496 |
| 225 | 0 | Pantoea | agglomerans | 1.2244 | JF753497 |
| 226 | 82 | Luteibacter | sp. | MDA0897 | JF753498 |
| 227 | 10 | Stenotrophomonas | maltophilia | | JF753499 |
| 228 | 7 | Pantoea | dispersa | NCPPB 2285 | JF753500 |
| 229 | 18 | Klebsiella | sp. | EH47 | JF753501 |
| 230 | 10 | Stenotrophomonas | maltophilia | | JF753502 |
| 231 | 10 | Stenotrophomonas | maltophilia | | JF753503 |
| 232 | 10 | Stenotrophomonas | maltophilia | | JF753504 |
| 233 | 10 | Stenotrophomonas | maltophilia | | JF753505 |
| 234 | 10 | Stenotrophomonas | maltophilia | | JF753506 |
| 235 | 0 | Pantoea | agglomerans | 1.2244 | JF753507 |
| 236 | 10 | Stenotrophomonas | maltophilia | | JF753508 |
| 237 | 192 | Enterobacter | asburiae | MY2 | JF753509 |
| 238 | 10 | Stenotrophomonas | maltophilia | | JF753510 |
| 239 | 22 | Bacillus | megaterium | NBAII-63 | JF753511 |
| 240 | 202 | Deinococcus | grandis | DSM | JF753512 |
| 241 | 204 | Azospirillum | zea | Gr24 | JF753513 |
| 242 | 30 | Rhodococcus | fascians | NKCM8906 | JF753514 |
| 243 | 28 | Microbacterium | sp. | VKM Ac-1389 | JF753515 |
| 244 | 41 | Bacillus | subtilis | | JF753516 |
| 245 | 41 | Bacillus | subtilis | TAT1-8 | JF753517 |
| 246 | 118 | Bacillus | asahai | NBPP91 | JF753518 |
| 247 | 64 | Methylobacterium | brachiatum | | JF753519 |
| 248 | 74 | Bradyrhizobium | japonicum | | JF753520 |
| 249 | 53 | Paenibacillus | sp. | IB-1067 | JF753521 |
| 250 | 120 | Paenibacillus | polymyxa | | JF753522 |
| 251 | 145 | Brevibacillus | agri | | JF753523 |
| 252 | 7 | Pantoea | agglomerans | ZFJ-6 | JF753524 |
| 253 | 56 | Enterobacter | sp. | pp9c | JF753525 |
| 254 | 110 | Sediminibacterium | sp. | I-28 | JF753526 |
| 255 | 200 | Bacillus | pumilus | ustb-06 | JF753527 |
| 256 | 39 | Bacillus | pumilus | PhyCEm-115 | JF753528 |
| 257 | 76 | Bacillus | circulans | WZ12 | JF753529 |
| 258 | 76 | Bacillus | nealsonii | PAB1C3 | JF753530 |
| 259 | 7 | Pantoea | agglomerans | ZFJ-6 | JF753531 |
| 260 | 39 | Bacillus | pumilus | CT3 | JF753532 |
| 261 | 18 | Enterobacter | sp. | G-2-10-2 | JF753533 |
| 262 | 7 | Pantoea | agglomerans | BJTZ1 | JF753534 |
| 263 | 120 | Paenibacillus | polymyxa | | JF753535 |
| 264 | 119 | Enterococcus | gallinarum | | JF753536 |
| 265 | 0 | Enterobacter | asburiae | M16 | JF753537 |
| 266 | 56 | Pantoea | agglomerans | WAB1925 | JF753538 |
| 267 | 113 | Microbacterium | schleiferi | | JF753539 |
| 268 | 71 | Sediminibacterium | sp. | I-28 | JF753540 |
| 269 | 119 | Enterococcus | gallinarum | | JF753541 |
| 270 | 64 | Methylobacterium | brachiatum | | JF753542 |
| 271 | 0 | Enterobacter | cloacae | M-5 | JF753543 |
| 272 | 39 | Bacillus | pumilus | CT3 | JF753544 |
| 273 | 56 | Enterobacter | cloacae | | JF753545 |
| 274 | 0 | Enterobacter | cloacae | M-5 | JF753546 |
| 275 | 0 | Enterobacter | cloacae | M-5 | JF753547 |
| 276 | 50 | Enterobacter | hormaechei | skg0061 | JF753548 |
| 277 | 170 | Pantoea | sp. | | JF753549 |
| 278 | 64 | Methylobacterium | brachiatum | | JF753550 |
| 279 | 106 | Enterobacter | asburiae | M16 | JF753551 |
| 280 | 176 | Bacillus | pumilus | NBJ7 | JF753552 |
| 281 | 1 | Pseudomonas | protegens | CHA0 | JN110435 |
| 282 | 10 | Stenotrophomonas | maltophilia | IAM 12423 | JN110431 |
| 283 | 10 | Stenotrophomonas | maltophilia | IAM 12423 | JN110437 |
| 284 | 9 | Ochrobactrum | tritici | SCII 24 | JN110432 |
| 285 | 9 | Ochrobactrum | grignonense | OgA9a | JN110441 |
| 286 | 46 | Sphingomonas | yanoikuyae | IFO 15102 | JN110436 |
| 287 | 104 | Flavobacterium | johnsoniae | DSM 2064 | JN110440 |

TABLE 1-continued

Representative endophytes from grass seeds, including their 16S rRNA sequences, assignment within OTU numbers, Genus, species, strain information, as well as GenBank Accession numbers.

| SEQ ID NO. | OTU # | Genus | Species | Strain | Accession No. |
|---|---|---|---|---|---|
| 288 | 24 | Paenibacillus | humicus | PC-147 | JN110433 |
| 289 | 169 | Agromyces | mediolanus | DSM 20152 | JN110439 |
| 290 | 3 | Curtobacterium | citreum | DSM 20528 | JN110438 |
| 291 | 3 | Curtobacterium | herbarum | DSM 14013 | JN110445 |
| 292 | 121 | Frigoribacterium | faeni | DSM 10309 | JN110443 |
| 293 | 134 | Microbacterium | oleivorans | DSM 16091 | JN110444 |
| 294 | 142 | Mycobacterium | abscessus | CIP 104536 | JN110430 |
| 295 | 142 | Mycobacterium | abscessus | CIP 104536 | JN110434 |
| 296 | 201 | Plantibacter | flavus | DSM 14012 | JN110442 |
| 297 | 83 | Enterobacter | cloacae subsp. cloacae | ATCC 13047 | JN110446 |
| 298 | 2 | Pseudomonas | oryzihabitans | IAM 1568 | JN110447 |
| 299 | 193 | Aeromonas | hydrophila subsp. dhakensis | LMG 19562 | JN110448 |
| 300 | 180 | Herbaspirillum | rubrisubalvicans | ICMP 5777T | JN110449 |
| 301 | 23 | Acinetobacter | beijerinckii | LUH 4759 | JN110450 |
| 302 | 66 | Rhizobium | radiobacter | IAM 12048 | JN110451 |
| 303 | 18 | Enterobacter | arachidis | Ah-143 | JN110452 |
| 304 | 83 | Escherichia | coli | O111:H str. 11128 | JN110453 |
| 305 | 10 | Stenotrophomonas | maltophilia | IAM 12423 | JN110454 |
| 306 | 84 | Pantoea | agglomerans | DSM3493 | JN110455 |
| 307 | 63 | Neisseria | meningitidis | M01-240149 | JN110456 |
| 308 | 1 | Pseudomonas | protegens | CHA0 | JN110457 |
| 309 | 89 | Dyella | ginsengisoli | Gsoil 3046 | JN110458 |
| 310 | 2 | Pseudomonas | putida | BIRD-1 | JN110459 |
| 311 | 19 | Bacillus | psychrosaccharolyticus | S156 | JN110460 |
| 312 | 129 | Deinococcus | ficus | CC-FR2-10 | JN110461 |
| 313 | 13 | Achromobacter | spanius | LMG 5911 | JN110462 |
| 314 | 0 | Tatumella | morbirosei | | JN167639 |
| 315 | 56 | Leclercia | adecarboxylata | | JN167641 |
| 316 | 18 | Enterobacter | dissolvens | | JN167642 |
| 317 | 56 | Enterobacter | cancerogenus | | JN167646 |
| 318 | 21 | Serratia | marcescens | | JN167643 |
| 319 | 0 | Erwinia | cypripedi | | JN167644 |
| 320 | 7 | Erwinia | aphidicola | | JN167651 |
| 321 | 46 | Sphingomonas | yanoikuyae | | JN167645 |
| 322 | 0 | Pantoea | anthophila | | JN167647 |
| 323 | 7 | Pantoea | dispersa | | JN167640 |
| 324 | 15 | Oxalophagus | oxalicus | | JN167648 |
| 325 | 14 | Paenibacillus | nanensis | | JN167650 |
| 326 | 5 | Bosea | vestrisii | | JN167652 |
| 327 | 69 | Rheinheimera | soli | | JN167653 |
| 328 | 26 | Acinetobacter | baumannii | | JN167654 |
| 329 | 23 | Acinetobacter | johnsonii | | JN167660 |
| 330 | 208 | Acinetobacter | beijerinckii | | JN167680 |
| 331 | 208 | Acinetobacter | schindleri | | JN167685 |
| 332 | 116 | Roseateles | depolymerans | | JN167655 |
| 333 | 116 | Roseateles | terrae | | JN167663 |
| 334 | 27 | Burkholderia | diffusa | | JN167657 |
| 335 | 211 | Sphingopyxis | panaciterrae | | JN167658 |
| 336 | 98 | Massilia | aerolata | | JN167682 |
| 337 | 51 | Massilia | albidiflava | | JN167661 |
| 338 | 1 | Pseudomonas | poae | | JN167662 |
| 339 | 75 | Ancylobacter | rudongensis | | JN167664 |
| 340 | 10 | Stenotrophomonas | pavanii | | JN167665 |
| 341 | 83 | Shigella | flexneri | | JN167666 |
| 342 | 91 | Bdellovibrio | bacteriovorus | | JN167671 |
| 343 | 56 | Enterobacter | cancerogenus | | JN167674 |
| 344 | 130 | Enhydrobacter | aerosaccus | | JN167675 |
| 345 | 100 | Variovorax | | boronicumulans | JN167676 |
| 346 | 128 | Oceanibaculum | pacificum | | JN167677 |
| 347 | 46 | Sphingomonas | yanoikuyae | | JN167683 |
| 348 | 157 | Devosia | riboflavina | | JN167684 |
| 349 | 18 | Escherichia | coli | | JN167686 |
| 350 | 190 | Sphingosinicella | | xenopeptidilytica | JN167688 |
| 351 | 120 | Paenibacillus | daejeonensis | | JN167679 |
| 352 | 6 | Paenibacillus | xylanilyticus | | JN167687 |
| 353 | 163 | Sediminibacillus | halophilus | | JN167689 |
| 354 | 44 | Corynebacterium | | pseudogenitalium | JN167659 |
| 355 | 123 | Nocardia | soli | | JN167670 |
| 356 | 206 | Lentzea | flaviverrucosa | | JN167672 |
| 357 | 198 | Flavobacterium | degerlachei | | JN167656 |
| 358 | 165 | Flavobacterium | aquatile | | JN167669 |
| 359 | 62 | Chryseobacterium | hominis | | JN167678 |

TABLE 1-continued

Representative endophytes from grass seeds, including their 16S rRNA sequences, assignment within OTU numbers, Genus, species, strain information, as well as GenBank Accession numbers.

| SEQ ID NO. | OTU # | Genus | Species | Strain | Accession No. |
|---|---|---|---|---|---|
| 360 | 186 | Uncultured bacterium | Uncultured bacterium | | JN167667 |
| 361 | 195 | Uncultured bacterium | Uncultured bacterium | | JN167681 |
| 362 | 21 | Klebsiella | variicola | | JN167690 |
| 363 | 18 | Klebsiella | pneumoniae | | JN167691 |
| 364 | 1 | Pseudomonas | plecoglossicida | | JN167693 |
| 365 | 10 | Stenotrophomonas | pavanii | | JN167694 |
| 366 | 101 | Sphingomonas | echinoides | | JN167695 |
| 367 | 66 | Rhizobium | massiliae | | JN167696 |
| 368 | 0 | Serratia | marcescens | | JN167697 |
| 369 | 101 | Sphingomonas | echinoides | | JN167698 |
| 370 | 114 | Sphingomonas | dokdonensis | | JN167701 |
| 371 | 7 | Pantoea | dispersa | | JN167699 |
| 372 | 82 | Luteibacter | anthropi | | JN167700 |
| 373 | 27 | Burkholderia | gladioli | | JN167702 |
| 374 | 56 | Leclercia | adecarboxylata | | JN167703 |
| 375 | 167 | Tepidimonas | aquatic | | JN167705 |
| 376 | 0 | Tatumella | morbirosei | | JN167706 |
| 377 | 56 | Enterobacter | cancerogenus | | JN167707 |
| 378 | 124 | Thermomonas | brevis | | JN167708 |
| 379 | 79 | Lactobacillus | iners | | JN167704 |
| 380 | 7 | Pantoea | dispersa | | JN167709 |
| 381 | 101 | Sphingomonas | echinoides | | JN167710 |
| 382 | 7 | Pantoea | dispersa | | JN167784 |
| 383 | 84 | Pantoea | agglomerans | | JN167785 |
| 384 | 101 | Sphingomonas | echinoides | | JN167786 |
| 385 | 101 | Sphingomonas | echinoides | | JN167713 |
| 386 | 18 | Shigella | flexneri | | JN167714 |
| 387 | 0 | Leclercia | adecarboxylata | | JN167716 |
| 388 | 29 | Pseudoxanthomonas | kaohsiungensis | | JN167717 |
| 389 | 57 | Psychrobacter | pulmonis | | JN167718 |
| 390 | 100 | Variovorax | boronicumulans | | JN167720 |
| 391 | 56 | Enterobacter | sp. | | JN167721 |
| 392 | 181 | Microvirga | aerophilus | | JN167727 |
| 393 | 132 | Microvirga | aerilata | | JN167734 |
| 394 | 7 | Erwinia | aphidicola | | JN167725 |
| 395 | 162 | Methylobacterium | platani | | JN167729 |
| 396 | 0 | Tatumella | morbirosei | | JN167730 |
| 397 | 37 | Burkholderia | phytofirmans | | JN167732 |
| 398 | 27 | Burkholderia | sp. | | JN167723 |
| 399 | 36 | Acidovorax | temperans | | JN167733 |
| 400 | 0 | Serratia | marcescens | | JN167743 |
| 401 | 56 | Serratia | ureilytica | | JN167737 |
| 402 | 23 | Acinetobacter | beijerinckii | | JN167738 |
| 403 | 26 | Acinetobacter | junii | | JN167739 |
| 404 | 23 | Acinetobacter | johnsonii | | JN167724 |
| 405 | 23 | Acinetobacter | kyonggiensis | | JN167726 |
| 406 | 152 | Halomonas | daqingensis | | JN167741 |
| 407 | 7 | Pantoea | dispersa | | JN167736 |
| 408 | 79 | Lactobacillus | iners | | JN167712 |
| 409 | 22 | Bacillus | aryabhattai | | JN167715 |
| 410 | 67 | Staphylococcus | hominis | | JN167722 |
| 411 | 67 | Staphylococcus | capitis | | JN167728 |
| 412 | 85 | Finegoldia | magna | | JN167735 |
| 413 | 20 | Ruminococcus | bromii | | JN167740 |
| 414 | 42 | Aerococcus | urinaeequi | | JN167742 |
| 415 | 32 | Propioniciclava | tarda | | JN167711 |
| 416 | 70 | Propionibacterium | acnes | | JN167719 |
| 417 | 107 | | Uncultured bacterium | | JN167731 |
| 418 | 99 | Brevundimonas | diminuta | | JN167744 |
| 419 | 99 | Brevundimonas | naejangsanensis | | JN167764 |
| 420 | 101 | Sphingomonas | echinoides | | JN167745 |
| 421 | 126 | Sphingomonas | koreensis | | JN167756 |
| 422 | 191 | Sphingomonas | humi | | JN167758 |
| 423 | 100 | Acidovorax | facilis | | JN167746 |
| 424 | 36 | Acidovoraz | temperans | | JN167757 |
| 425 | 136 | Shinella | zoogloeoides | | JN167747 |
| 426 | 116 | Roseateles | depolymerans | | JN167748 |
| 427 | 116 | Roseateles | terrae | | JN167752 |
| 428 | 69 | Rheinheimera | chironomi | | JN167749 |
| 429 | 69 | Rheinheimera | soli | | JN167775 |
| 430 | 23 | Acinetobacter | johnsonii | | JN167750 |
| 431 | 208 | Acinetobacter | schindleri | | JN167761 |
| 432 | 23 | Acinetobacter | lwoffii | | JN167765 |

TABLE 1-continued

Representative endophytes from grass seeds, including their 16S rRNA sequences, assignment within OTU numbers, Genus, species, strain information, as well as GenBank Accession numbers.

| SEQ ID NO. | OTU # | Genus | Species | Strain | Accession No. |
|---|---|---|---|---|---|
| 433 | 2 | Pseudomonas | stutzeri | | JN167751 |
| 434 | 184 | Thermomonas | koreensis | | JN167753 |
| 435 | 27 | Burkholderia | sp. | | JN167754 |
| 436 | 18 | Shigella | flexneri | | JN167760 |
| 437 | 97 | Cellvibrio | mixtus | | JN167766 |
| 438 | 21 | Serratia | marcescens | | JN167767 |
| 439 | 131 | Thiobacillus | aquaesulis | | JN167768 |
| 440 | 133 | Luteimonas | aestuarii | | JN167769 |
| 441 | 197 | Sphingosinicella | sp. | | JN167772 |
| 442 | 108 | Acidithiobacillus | albertensis | | JN167773 |
| 443 | 36 | Curvibacter | gracilis | | JN167774 |
| 444 | 47 | Devosia | insulae | | JN167777 |
| 445 | 93 | Cupriavidus | gilardii | | JN167778 |
| 446 | 140 | Methylobacterium | rhodesianum | | JN167779 |
| 447 | 89 | Dokdonella | sp. | | JN167780 |
| 448 | 150 | Desemzia | incerta | | JN167763 |
| 449 | 68 | Kocuria | rosea | | JN167770 |
| 450 | 123 | Nocardia | ignorata | | JN167771 |
| 451 | 182 | Pseudonocardia | aurantiaca | | JN167776 |
| 452 | 104 | Flavobacterium | johnsoniae | | JN167755 |
| 453 | 203 | Flavobacterium | mizutaii | | JN167762 |
| 454 | 73 | Flavisolibacter | ginsengiterrae | | JN167781 |
| 455 | 33 | Sphingobacterium | daejeonense | | JN167759 |
| 456 | 0 | Leclercia | adecarboxylata | | JN167782 |
| 457 | 56 | Enterobacter | cancerogenus | | JN167783 |
| 458 | 39 | Bacillus | altitudinis | | HQ432811 |
| 459 | 19 | Bacillus | simplex | | HQ432812 |
| 460 | 12 | Bacillus | thuringiensis | | HQ432813 |
| 461 | 6 | Paenibacillus | amylolyticus | | HQ432814 |
| 462 | 103 | Staphylococcus | aureus subsp. aureus | | HQ432815 |
| 463 | 146 | Pantoea | ananatis | | AB178169 |
| 464 | 56 | Pantoea | ananatis | | AB178170 |
| 465 | 12 | Bacillus | cereus | | AB178171 |
| 466 | 59 | Pantoea | ananatis | | AB178172 |
| 467 | 12 | Bacillus | cereus | | AB178173 |
| 468 | 45 | Sphingomonas | echinoides | | AB178174 |
| 469 | 45 | Sphingomonas | echinoides | | AB178175 |
| 470 | 45 | Sphingomonas | echinoides | | AB178176 |
| 471 | 45 | Sphingomonas | parapaucimobilis | | AB178177 |
| 472 | 12 | Bacillus | cereus | | AB178178 |
| 473 | 12 | Bacillus | cereus | | AB178179 |
| 474 | 12 | Bacillus | cereus | | AB178192 |
| 475 | 12 | Bacillus | cereus | | AB178193 |
| 476 | 12 | Bacillus | cereus | | AB178194 |
| 477 | 12 | Bacillus | cereus | | AB178195 |
| 478 | 12 | Bacillus | cereus | | AB178196 |
| 479 | 12 | Bacillus | cereus | | AB178197 |
| 480 | 12 | Bacillus | cereus | | AB178198 |
| 481 | 12 | Bacillus | cereus | | AB178199 |
| 482 | 12 | Bacillus | cereus | | AB178200 |
| 483 | 12 | Bacillus | cereus | | AB178201 |
| 484 | 12 | Bacillus | cereus | | AB178214 |
| 485 | 12 | Bacillus | cereus | | AB178215 |
| 486 | 12 | Bacillus | cereus | | AB178216 |
| 487 | 12 | Bacillus | cereus | | AB178217 |
| 488 | 12 | Bacillus | cereus | | AB178218 |
| 489 | 29 | Xanthomonas | translucens | pv. poae | AB242936 |
| 490 | 7 | Pantoea | ananatis | | AB242937 |
| 491 | 7 | Pantoea | ananatis | | AB242938 |
| 492 | 8 | Methylobacterium | aquaticum | | AB242939 |
| 493 | 8 | Methylobacterium | aquaticum | | AB242940 |
| 494 | 172 | Sphingomonas | melonis | | AB242941 |
| 495 | 45 | Sphingomonas | yabuuchiae | | AB242942 |
| 496 | 45 | Sphingomonas | yabuuchiae | | AB242943 |
| 497 | 8 | Methylobacterium | aquaticum | | AB242944 |
| 498 | 7 | Pantoea | ananatis | | AB242945 |
| 499 | 7 | Pantoea | ananatis | | AB242946 |
| 500 | 41 | Bacillus | subtilis | | AB242958 |
| 501 | 41 | Bacillus | subtilis | | AB242959 |
| 502 | 41 | Bacillus | subtilis | | AB242960 |
| 503 | 41 | Bacillus | subtilis | | AB242961 |
| 504 | 39 | Bacillus | pumilus | | AB242962 |
| 505 | 59 | Micrococcus | luteus | | AB242963 |
| 506 | 45 | Sphingomonas | yabuuchiae | | AB242964 |
| 507 | 148 | Sphingomonas | yabuuchiae | | AB242965 |

TABLE 1-continued

Representative endophytes from grass seeds, including their 16S rRNA sequences, assignment within OTU numbers, Genus, species, strain information, as well as GenBank Accession numbers.

| SEQ ID NO. | OTU # | Genus | Species | Strain | Accession No. |
|---|---|---|---|---|---|
| 508 | 212 | *Acidovorax* | sp. | | AB242966 |
| 509 | 3 | *Curtobacterium* | *flaccumfaciens* | pv. Basellae | AB242967 |
| 510 | 6 | *Paenibacillus* | *amylolyticus* | | AB242978 |
| 511 | 146 | *Pantoea* | *ananatis* | | AB242979 |
| 512 | 77 | *Pantoea* | *ananatis* | | AB242980 |
| 513 | 39 | *Bacillus* | *pumilus* | | AB242981 |
| 514 | 77 | *Pantoea* | *ananatis* | | AB242982 |
| 515 | 29 | *Xanthomonas* | *translucens* | | AB242983 |
| 516 | 39 | *Bacillus* | *pumilus* | | AB242984 |
| 517 | 3 | *Curtobacterium* | *flaccumfaciens* | pv. Basellae | AB242985 |
| 518 | 29 | *Xanthomonas* | *translucens* | pv. poae | AB242986 |
| 519 | 39 | *Bacillus* | *pumilus* | | AB242987 |
| 520 | 29 | *Xanthomonas* | *translucens* | pv. poae | AB242988 |

TABLE 2

Endophytic bacteria isolated from corn, rice and wheat seeds, including assignment to specific OTUs, corresponding Sequence ID numbers, Family, Genus, Taxonomic information and plant source from which the microbe was derived.

| Strain | OTU# | SEQ ID NO: | Seed-Origin Crop Type | Seed-Origin Cultivar Type | Source of seed-origin microbes | Family of Seed-Origin Microbe | Taxonomy of Seed-Origin Microbe |
|---|---|---|---|---|---|---|---|
| SYM00033 | 0 | 541 | Teosinte | Wild relative | Surface sterilized seeds | Enterobacteriaceae | *Enterobacter* sp. |
| SYM00173 | 0 | 593 | Rice | Modern | Surface sterilized seeds | Enterobacteriaceae | *Pantoea* sp. |
| SYM00176 | 0 | 596 | *Oryza nivara* | Wild relative | Surface sterilized seeds | Enterobacteriaceae | *Pantoea* sp. |
| SYM00284 | 0 | 633 | Maize | Modern | Surface sterilized seeds | Enterobacteriaceae | *Pantoea ananatis* |
| SYM00605 | 0 | 716 | Maize | Modern | Seed surface wash | Enterobacteriaceae | |
| SYM00607 | 0 | 717 | Maize | Modern | Seed surface wash | Enterobacteriaceae | |
| SYM00608 | 0 | 718 | Maize | Modern | Seed surface wash | Enterobacteriaceae | *Pantoea* sp. |
| SYM00620 | 0 | 720 | Teosinte | Wild relative | Seed surface wash | Enterobacteriaceae | *Enterobacter* sp. |
| SYM00658 | 0 | 736 | *Avena sterilis* | Wild relative | Seed surface wash | Enterobacteriaceae | |
| SYM00985 | 0 | 851 | Rice | Modern | Surface sterilized seeds | Enterobacteriaceae | |
| SYM01006 | 0 | 866 | Rice | Modern | Surface sterilized seeds | Enterobacteriaceae | |
| SYM01035 | 0 | 887 | *Avena sterilis* | Wild relative | Surface sterilized seeds | Enterobacteriaceae | |
| SYM01041 | 0 | 892 | Rice | Ancient Landrace | Surface sterilized seeds | Enterobacteriaceae | *Pantoea* sp. |
| SYM01158 | 0 | 937 | *Avena sterilis* | Wild relative | Roots & Seeds | Enterobacteriaceae | |
| SYM01173 | 0 | 943 | Rice | Ancient Landrace | Roots & Seeds | Enterobacteriaceae | |
| SYM01231 | 0 | 980 | Rice | Modern | Roots & Seeds | Enterobacteriaceae | |
| SYM00472 | 1 | 636 | Maize | Modern | Roots | Pseudomonadaceae | *Pseudomonas* sp. |
| SYM00660 | 1 | 737 | *Avena sterilis* | Wild relative | Seed surface wash | Pseudomonadaceae | *Pseudomonas* sp. |
| SYM00011 | 2 | 522 | Teosinte | Wild relative | Surface sterilized seeds | Pseudomonadaceae | *Pseudomonas* sp. |
| SYM00011b | 2 | 523 | Teosinte | Wild relative | Surface sterilized seeds | Pseudomonadaceae | *Pseudomonas* sp. |
| SYM00013 | 2 | 524 | Teosinte | Wild relative | Surface sterilized seeds | Pseudomonadaceae | *Pseudomonas* sp. |
| SYM00014 | 2 | 526 | Teosinte | Wild relative | Surface sterilized seeds | Pseudomonadaceae | *Pseudomonas* sp. |
| SYM00062 | 2 | 557 | Teosinte | Wild relative | Surface sterilized seeds | Pseudomonadaceae | *Pseudomonas* sp. |
| SYM00067 | 2 | 562 | Teosinte | Wild relative | Surface sterilized seeds | Pseudomonadaceae | *Pseudomonas* sp. |
| SYM00068 | 2 | 563 | Teosinte | Wild relative | Surface sterilized seeds | Pseudomonadaceae | *Pseudomonas* sp. |
| SYM00069 | 2 | 564 | Teosinte | Wild relative | Surface sterilized seeds | Pseudomonadaceae | *Pseudomonas* sp. |
| SYM00646 | 2 | 730 | Rice | Modern | Seed surface wash | Pseudomonadaceae | *Pseudomonas* sp. |
| SYM00649 | 2 | 733 | Rice | Modern | Seed surface wash | Pseudomonadaceae | *Pseudomonas* sp. |
| SYM00650 | 2 | 734 | Rice | Modern | Seed surface wash | Pseudomonadaceae | *Pseudomonas* sp. |
| SYM00657 | 2 | 735 | *Avena sterilis* | Wild relative | Seed surface wash | Pseudomonadaceae | *Pseudomonas* sp. |
| SYM00672 | 2 | 738 | *Oryza latifolia* | Wild relative | Seed surface wash | Pseudomonadaceae | *Pseudomonas* sp. |
| SYM00709 | 2 | 747 | Rice | Modern | Seed surface wash | Pseudomonadaceae | *Pseudomonas* sp. |
| SYM00926 | 2 | 804 | Rice | Ancient Landrace | Surface sterilized seeds | Pseudomonadaceae | *Pseudomonas* sp. |
| SYM00927 | 2 | 805 | Rice | Ancient Landrace | Surface sterilized seeds | Pseudomonadaceae | *Pseudomonas* sp. |
| SYM00946 | 2 | 821 | Rice | Modern | Surface sterilized seeds | Pseudomonadaceae | *Pseudomonas* sp. |
| SYM00955 | 2 | 828 | Rice | Ancient Landrace | Surface sterilized seeds | Pseudomonadaceae | *Pseudomonas* sp. |
| SYM00970 | 2 | 839 | Rice | Ancient Landrace | Surface sterilized seeds | Pseudomonadaceae | *Pseudomonas* sp. |
| SYM00971 | 2 | 840 | Rice | Ancient Landrace | Surface sterilized seeds | Pseudomonadaceae | *Pseudomonas* sp. |
| SYM00973 | 2 | 842 | Rice | Ancient Landrace | Surface sterilized seeds | Pseudomonadaceae | *Pseudomonas* sp. |
| SYM00993 | 2 | 857 | *Oryza officinalis* | Wild relative | Surface sterilized seeds | Pseudomonadaceae | *Pseudomonas* sp. |
| SYM01007 | 2 | 867 | Rice | Modern | Surface sterilized seeds | Pseudomonadaceae | *Pseudomonas* sp. |
| SYM01024 | 2 | 880 | *Oryza nivara* | Wild relative | Surface sterilized seeds | Pseudomonadaceae | *Pseudomonas* sp. |
| SYM01032 | 2 | 885 | *Avena sterilis* | Wild relative | Surface sterilized seeds | Pseudomonadaceae | *Pseudomonas* sp. |
| SYM01036 | 2 | 888 | Rice | Modern | Surface sterilized seeds | Pseudomonadaceae | *Pseudomonas* sp. |
| SYM01164 | 2 | 940 | Rice | Ancient Landrace | Roots & Seeds | Pseudomonadaceae | *Pseudomonas* sp. |
| SYM01171 | 2 | 942 | Rice | Ancient Landrace | Roots & Seeds | Pseudomonadaceae | *Pseudomonas* sp. |
| SYM01177 | 2 | 947 | Rice | Ancient Landrace | Roots & Seeds | Pseudomonadaceae | *Pseudomonas* sp. |
| SYM01178 | 2 | 948 | Rice | Ancient Landrace | Roots & Seeds | Pseudomonadaceae | *Pseudomonas* sp. |
| SYM01225 | 2 | 975 | Rice | Modern | Roots & Seeds | Pseudomonadaceae | *Pseudomonas* sp. |
| SYM01245 | 2 | 988 | Rice | Ancient Landrace | Roots & Seeds | Pseudomonadaceae | *Pseudomonas* sp. |

TABLE 2-continued

Endophytic bacteria isolated from corn, rice and wheat seeds, including assignment to specific OTUs, corresponding Sequence ID numbers, Family, Genus, Taxonomic information and plant source from which the microbe was derived.

| Strain | OTU# | SEQ ID NO: | Seed-Origin Crop Type | Seed-Origin Cultivar Type | Source of seed-origin microbes | Family of Seed-Origin Microbe | Taxonomy of Seed-Origin Microbe |
|---|---|---|---|---|---|---|---|
| SYM01251 | 2 | 989 | Rice | Ancient Landrace | Roots & Seeds | Pseudomonadaceae | *Pseudomonas* sp. |
| SYM01254 | 2 | 990 | Rice | Ancient Landrace | Roots & Seeds | Pseudomonadaceae | *Pseudomonas* sp. |
| SYM00013b | 3 | 525 | Teosinte | Wild relative | Surface sterilized seeds | Microbacteriaceae | *Curtobacterium* sp. |
| SYM00167 | 3 | 588 | Rice | Modern | Surface sterilized seeds | Microbacteriaceae | *Curtobacterium* sp. |
| SYM00171 | 3 | 591 | Rice | Modern | Surface sterilized seeds | Microbacteriaceae | *Curtobacterium* sp. |
| SYM00174 | 3 | 594 | Rye | Modern | Surface sterilized seeds | Microbacteriaceae | *Curtobacterium* sp. |
| SYM00178 | 3 | 598 | Rice | Ancient Landrace | Surface sterilized seeds | Microbacteriaceae | *Curtobacterium* sp. |
| SYM00180 | 3 | 600 | Rice | Ancient Landrace | Surface sterilized seeds | Microbacteriaceae | *Curtobacterium* sp. |
| SYM00181 | 3 | 601 | Rice | Ancient Landrace | Surface sterilized seeds | Microbacteriaceae | *Curtobacterium* sp. |
| SYM00235 | 3 | 622 | Rice | Modern | Surface sterilized seeds | Microbacteriaceae | *Curtobacterium* sp. |
| SYM00244 | 3 | 626 | Barley | Modern | Surface sterilized seeds | Microbacteriaceae | *Curtobacterium* sp. |
| SYM00525 | 3 | 654 | *Oryza nivara* | Wild relative | Seed surface wash | Microbacteriaceae | *Curtobacterium* sp. |
| SYM00625 | 3 | 724 | Maize | Modern | Seed surface wash | Microbacteriaceae | *Curtobacterium* sp. |
| SYM00645 | 3 | 729 | Rice | Modern | Seed surface wash | Microbacteriaceae | *Curtobacterium* sp. |
| SYM00647 | 3 | 731 | Rice | Modern | Seed surface wash | Microbacteriaceae | *Curtobacterium* sp. |
| SYM00673b | 3 | 739 | *Oryza latifolia* | Wild relative | Seed surface wash | Microbacteriaceae | *Curtobacterium* sp. |
| SYM00690 | 3 | 740 | Rice | Modern | Seed surface wash | Microbacteriaceae | *Curtobacterium* sp. |
| SYM00691 | 3 | 741 | Rice | Modern | Seed surface wash | Microbacteriaceae | *Curtobacterium* sp. |
| SYM00693 | 3 | 742 | Rice | Modern | Seed surface wash | Microbacteriaceae | *Curtobacterium* sp. |
| SYM00694b | 3 | 744 | Rice | Modern | Seed surface wash | Microbacteriaceae | *Curtobacterium* sp. |
| SYM00712 | 3 | 748 | Rice | Modern | Seed surface wash | Microbacteriaceae | *Curtobacterium* sp. |
| SYM00716 | 3 | 752 | Rice | Ancient Landrace | Seed surface wash | Microbacteriaceae | *Curtobacterium* sp. |
| SYM00722 | 3 | 753 | Rice | Ancient Landrace | Seed surface wash | Microbacteriaceae | *Curtobacterium* sp. |
| SYM00722B | 3 | 754 | Rice | Ancient Landrace | Seed surface wash | Microbacteriaceae | *Curtobacterium* sp. |
| SYM00731B | 3 | 756 | Rice | Ancient Landrace | Seed surface wash | Microbacteriaceae | *Curtobacterium* sp. |
| SYM00749 | 3 | 758 | Rice | Ancient Landrace | Surface sterilized seeds | Microbacteriaceae | *Curtobacterium* sp. |
| SYM00784 | 3 | 773 | Maize | Modern | Seed surface wash | Microbacteriaceae | *Curtobacterium* sp. |
| SYM00947 | 3 | 822 | Rice | Modern | Surface sterilized seeds | Microbacteriaceae | *Curtobacterium* sp. |
| SYM00949 | 3 | 823 | Rice | Modern | Surface sterilized seeds | Microbacteriaceae | *Curtobacterium* sp. |
| SYM00952 | 3 | 826 | Rice | Ancient Landrace | Surface sterilized seeds | Microbacteriaceae | *Curtobacterium* sp. |
| SYM00964 | 3 | 834 | Rice | Ancient Landrace | Surface sterilized seeds | Microbacteriaceae | *Curtobacterium* sp. |
| SYM00976 | 3 | 844 | Rice | Ancient Landrace | Surface sterilized seeds | Microbacteriaceae | *Curtobacterium* sp. |
| SYM00980 | 3 | 847 | Rice | Modern | Surface sterilized seeds | Microbacteriaceae | *Curtobacterium* sp. |
| SYM00984 | 3 | 850 | Rice | Modern | Surface sterilized seeds | Microbacteriaceae | *Curtobacterium* sp. |
| SYM00996 | 3 | 859 | *Oryza officinalis* | Wild relative | Surface sterilized seeds | Microbacteriaceae | *Curtobacterium* sp. |
| SYM01013 | 3 | 872 | Rice | Ancient Landrace | Surface sterilized seeds | Microbacteriaceae | *Curtobacterium* sp. |
| SYM01022 | 3 | 879 | *Oryza nivara* | Wild relative | Surface sterilized seeds | Microbacteriaceae | *Curtobacterium* sp. |
| SYM01025 | 3 | 881 | *Oryza nivara* | Wild relative | Surface sterilized seeds | Microbacteriaceae | *Curtobacterium* sp. |
| SYM01142 | 3 | 928 | Rice | Modern | Roots & Seeds | Microbacteriaceae | *Curtobacterium* sp. |
| SYM01144 | 3 | 929 | Rice | Modern | Roots & Seeds | Microbacteriaceae | *Curtobacterium* sp. |
| SYM01148 | 3 | 931 | Rice | Modern | Roots & Seeds | Microbacteriaceae | *Curtobacterium* sp. |
| SYM01151 | 3 | 932 | Rice | Modern | Roots & Seeds | Microbacteriaceae | *Curtobacterium* sp. |
| SYM01155 | 3 | 935 | Rice | Modern | Roots & Seeds | Microbacteriaceae | *Curtobacterium* sp. |
| SYM01156 | 3 | 936 | Rice | Modern | Roots & Seeds | Microbacteriaceae | *Curtobacterium* sp. |
| SYM01179 | 3 | 949 | Rice | Modern | Roots & Seeds | Microbacteriaceae | *Curtobacterium* sp. |
| SYM01181 | 3 | 951 | Rice | Modern | Roots & Seeds | Microbacteriaceae | *Curtobacterium* sp. |
| SYM01182 | 3 | 952 | Rice | Modern | Roots & Seeds | Microbacteriaceae | *Curtobacterium* sp. |
| SYM01183 | 3 | 953 | Rice | Modern | Roots & Seeds | Microbacteriaceae | *Curtobacterium* sp. |
| SYM01184 | 3 | 954 | Rice | Modern | Roots & Seeds | Microbacteriaceae | *Curtobacterium* sp. |
| SYM01185 | 3 | 955 | Rice | Modern | Roots & Seeds | Microbacteriaceae | *Curtobacterium* sp. |
| SYM01188 | 3 | 957 | Rice | Modern | Roots & Seeds | Microbacteriaceae | *Curtobacterium* sp. |
| SYM01198 | 3 | 962 | Rice | Modern | Roots & Seeds | Microbacteriaceae | *Curtobacterium* sp. |
| SYM01199 | 3 | 963 | Rice | Modern | Roots & Seeds | Microbacteriaceae | *Curtobacterium* sp. |
| SYM01201 | 3 | 964 | Rice | Modern | Roots & Seeds | Microbacteriaceae | *Curtobacterium* sp. |
| SYM01202 | 3 | 965 | Rice | Modern | Roots & Seeds | Microbacteriaceae | *Curtobacterium* sp. |
| SYM01204 | 3 | 966 | Rice | Modern | Roots & Seeds | Microbacteriaceae | *Curtobacterium* sp. |
| SYM01205 | 3 | 967 | Rice | Modern | Roots & Seeds | Microbacteriaceae | *Curtobacterium* sp. |
| SYM01207 | 3 | 969 | Rice | Modern | Roots & Seeds | Microbacteriaceae | *Curtobacterium* sp. |
| SYM01215 | 3 | 971 | Rice | Modern | Roots & Seeds | Microbacteriaceae | *Curtobacterium* sp. |
| SYM01218 | 3 | 973 | Rice | Modern | Roots & Seeds | Microbacteriaceae | *Curtobacterium* sp. |
| SYM01222 | 3 | 974 | Rice | Modern | Roots & Seeds | Microbacteriaceae | *Curtobacterium* sp. |
| SYM00188 | 6 | 605 | Maize | Modern | Leaves | Paenibacillaceae | *Paenibacillus* sp. |
| SYM00190 | 6 | 607 | Maize | Modern | Leaves | Paenibacillaceae | *Paenibacillus* sp. |
| SYM00195 | 6 | 610 | Maize | Modern | Leaves | Paenibacillaceae | *Paenibacillus* sp. |
| SYM00217 | 6 | 616 | Soybean | Modern | Roots | Paenibacillaceae | *Paenibacillus* sp. |
| SYM00227 | 6 | 619 | Soybean | Modern | Leaves | Paenibacillaceae | *Paenibacillus* sp. |
| SYM00292 | 6 | 634 | Maize | Modern | Surface sterilized seeds | Paenibacillaceae | *Paenibacillus taichungensis* |
| SYM00597 | 6 | 711 | Maize | Ancient Landrace | Seed surface wash | Paenibacillaceae | *Paenibacillus* sp. |
| SYM01108 | 6 | 915 | *Oryza nivara* | Wild relative | Surface sterilized seeds | Paenibacillaceae | *Paenibacillus* sp. |
| SYM01109 | 6 | 916 | *Oryza nivara* | Wild relative | Surface sterilized seeds | Paenibacillaceae | *Paenibacillus* sp. |
| SYM01110 | 6 | 917 | *Oryza nivara* | Wild relative | Surface sterilized seeds | Paenibacillaceae | *Paenibacillus* sp. |
| SYM01111 | 6 | 918 | *Oryza nivara* | Wild relative | Surface sterilized seeds | Paenibacillaceae | *Paenibacillus* sp. |
| SYM01112 | 6 | 919 | *Oryza nivara* | Wild relative | Surface sterilized seeds | Paenibacillaceae | *Paenibacillus* sp. |
| SYM01114 | 6 | 921 | Maize | Modern | Roots | Paenibacillaceae | *Paenibacillus* sp. |

TABLE 2-continued

Endophytic bacteria isolated from corn, rice and wheat seeds, including assignment to specific OTUs, corresponding
Sequence ID numbers, Family, Genus, Taxonomic information and plant source from which the microbe was derived.

| Strain | OTU# | SEQ ID NO: | Seed-Origin Crop Type | Seed-Origin Cultivar Type | Source of seed-origin microbes | Family of Seed-Origin Microbe | Taxonomy of Seed-Origin Microbe |
|---|---|---|---|---|---|---|---|
| SYM01117 | 6 | 922 | Maize | Ancient Landrace | Roots | Paenibacillaceae | *Paenibacillus* sp. |
| SYM01118 | 6 | 923 | Maize | Ancient Landrace | Roots | Paenibacillaceae | *Paenibacillus* sp. |
| SYM01127 | 6 | 925 | Teosinte | Wild relative | Roots | Paenibacillaceae | *Paenibacillus* sp. |
| SYM01256 | 6 | 991 | Maize | Ancient Landrace | Roots | Paenibacillaceae | *Paenibacillus* sp. |
| SYM00014b | 7 | 527 | Teosinte | Wild relative | Surface sterilized seeds | Enterobacteriaceae | *Erwinia* sp. |
| SYM00017b | 7 | 532 | Rice | Modern | Surface sterilized seeds | Enterobacteriaceae | *Pantoea* sp. |
| SYM00018 | 7 | 534 | Maize | Ancient Landrace | Surface sterilized seeds | Enterobacteriaceae | *Pantoea* sp. |
| SYM00020 | 7 | 535 | Maize | Ancient Landrace | Surface sterilized seeds | Enterobacteriaceae | *Pantoea* sp. |
| SYM00022 | 7 | 537 | Teosinte | Wild relative | Surface sterilized seeds | Enterobacteriaceae | *Pantoea* sp. |
| SYM00025 | 7 | 538 | Maize | Ancient Landrace | Surface sterilized seeds | Enterobacteriaceae | *Pantoea* sp. |
| SYM00026 | 7 | 539 | Maize | Ancient Landrace | Surface sterilized seeds | Enterobacteriaceae | *Pantoea* sp. |
| SYM00043 | 7 | 544 | Maize | Modern | Surface sterilized seeds | Enterobacteriaceae | *Pantoea* sp. |
| SYM00047 | 7 | 546 | Maize | Ancient Landrace | Surface sterilized seeds | Enterobacteriaceae | *Pantoea* sp. |
| SYM00049 | 7 | 547 | Maize | Ancient Landrace | Surface sterilized seeds | Enterobacteriaceae | *Pantoea* sp. |
| SYM00055 | 7 | 553 | Maize | Ancient Landrace | Surface sterilized seeds | Enterobacteriaceae | *Pantoea* sp. |
| SYM00057 | 7 | 554 | Maize | Ancient Landrace | Surface sterilized seeds | Enterobacteriaceae | *Pantoea* sp. |
| SYM00058 | 7 | 555 | Maize | Ancient Landrace | Surface sterilized seeds | Enterobacteriaceae | *Pantoea* sp. |
| SYM00078 | 7 | 568 | Maize | Ancient Landrace | Surface sterilized seeds | Enterobacteriaceae | *Pantoea* sp. |
| SYM00081 | 7 | 569 | Maize | Ancient Landrace | Seed surface wash | Enterobacteriaceae | *Pantoea* sp. |
| SYM00082a | 7 | 570 | Maize | Ancient Landrace | Seed surface wash | Enterobacteriaceae | *Pantoea* sp. |
| SYM00085 | 7 | 571 | Maize | Modern | Surface sterilized seeds | Enterobacteriaceae | *Pantoea* sp. |
| SYM00086 | 7 | 572 | Maize | Modern | Surface sterilized seeds | Enterobacteriaceae | *Pantoea* sp. |
| SYM00087 | 7 | 573 | Maize | Maize PI 485356 | Surface sterilized seeds | Enterobacteriaceae | *Pantoea* sp. |
| SYM00088 | 7 | 574 | Maize | Maize PI 485356 | Surface sterilized seeds | Enterobacteriaceae | *Pantoea* sp. |
| SYM00094 | 7 | 576 | Maize | Ancient Landrace | Surface sterilized seeds | Enterobacteriaceae | *Pantoea* sp. |
| SYM00095 | 7 | 577 | Maize | Ancient Landrace | Surface sterilized seeds | Enterobacteriaceae | *Pantoea* sp. |
| SYM00096 | 7 | 578 | Maize | Ancient Landrace | Surface sterilized seeds | Enterobacteriaceae | *Pantoea* sp. |
| SYM00100 | 7 | 579 | Maize | Ancient Landrace | Surface sterilized seeds | Enterobacteriaceae | *Pantoea* sp. |
| SYM00101 | 7 | 580 | Maize | Ancient Landrace | Surface sterilized seeds | Enterobacteriaceae | *Pantoea* sp. |
| SYM00502 | 7 | 639 | Maize | Ancient Landrace | Seed surface wash | Enterobacteriaceae | *Erwinia* sp. |
| SYM00506 | 7 | 641 | Maize | Ancient Landrace | Seed surface wash | Enterobacteriaceae | *Erwinia* sp. |
| SYM00506b | 7 | 642 | Maize | Ancient Landrace | Seed surface wash | Enterobacteriaceae | *Erwinia* sp. |
| SYM00511 | 7 | 647 | Maize | Ancient Landrace | Seed surface wash | Enterobacteriaceae | *Erwinia* sp. |
| SYM00514b | 7 | 649 | Maize | Ancient Landrace | Seed surface wash | Enterobacteriaceae | *Erwinia* sp. |
| SYM00514C | 7 | 650 | Maize | Ancient Landrace | Seed surface wash | Enterobacteriaceae | *Erwinia* sp. |
| SYM00514D | 7 | 651 | Maize | Ancient Landrace | Seed surface wash | Enterobacteriaceae | *Erwinia* sp. |
| SYM00731A | 7 | 755 | Rice | Ancient Landrace | Seed surface wash | Enterobacteriaceae | *Erwinia* sp. |
| SYM00785 | 7 | 774 | Maize | Modern | Seed surface wash | Enterobacteriaceae | *Erwinia* sp. |
| SYM01056 | 7 | 903 | Teosinte | Wild relative | Surface sterilized seeds | Enterobacteriaceae | *Erwinia* sp. |
| SYM01235 | 7 | 984 | *Oryza officinalis* | Wild relative | Roots & Seeds | Enterobacteriaceae | *Erwinia* sp. |
| SYM01238 | 7 | 986 | *Oryza officinalis* | Wild relative | Roots & Seeds | Enterobacteriaceae | *Erwinia* sp. |
| SYM00967 | 8 | 837 | Rice | Ancient Landrace | Surface sterilized seeds | Methylobacteriaceae | |
| SYM01233 | 8 | 982 | *Oryza officinalis* | Wild relative | Roots & Seeds | Methylobacteriaceae | |
| SYM00544 | 9 | 663 | Maize | Ancient Landrace | Seed surface wash | Brucellaceae | *Ochrobactrum* sp. |
| SYM00545B | 9 | 665 | Maize | Ancient Landrace | Seed surface wash | Brucellaceae | *Ochrobactrum* sp. |
| SYM00548 | 9 | 667 | Maize | Ancient Landrace | Seed surface wash | Brucellaceae | *Ochrobactrum* sp. |
| SYM00552 | 9 | 670 | Maize | Ancient Landrace | Seed surface wash | Brucellaceae | *Ochrobactrum* sp. |
| SYM00558 | 9 | 675 | Maize | Ancient Landrace | Seed surface wash | Brucellaceae | *Ochrobactrum* sp. |
| SYM00580A | 9 | 688 | Maize | Modern | Seed surface wash | Brucellaceae | *Ochrobactrum* sp. |
| SYM00580b | 9 | 689 | Maize | Modern | Seed surface wash | Brucellaceae | *Ochrobactrum* sp. |
| SYM00580d | 9 | 691 | Maize | Modern | Seed surface wash | Brucellaceae | *Ochrobactrum* sp. |
| SYM00581d | 9 | 698 | Maize | Modern | Seed surface wash | Brucellaceae | *Ochrobactrum* sp. |
| SYM00583 | 9 | 699 | Maize | Ancient Landrace | Seed surface wash | Brucellaceae | *Ochrobactrum* sp. |
| SYM00584 | 9 | 700 | Maize | Ancient Landrace | Seed surface wash | Brucellaceae | *Ochrobactrum* sp. |
| SYM00588 | 9 | 705 | Maize | Ancient Landrace | Seed surface wash | Brucellaceae | *Ochrobactrum* sp. |
| SYM00596 | 9 | 710 | Maize | Ancient Landrace | Seed surface wash | Brucellaceae | *Ochrobactrum* sp. |
| SYM00600 | 9 | 713 | Maize | Ancient Landrace | Seed surface wash | Brucellaceae | *Ochrobactrum* sp. |
| SYM00746 | 9 | 757 | Rice | Ancient Landrace | Surface sterilized seeds | Brucellaceae | *Ochrobactrum* sp. |
| SYM00752 | 9 | 759 | Maize | Modern | Seed surface wash | Brucellaceae | *Ochrobactrum* sp. |
| SYM00756 | 9 | 761 | Maize | Modern | Seed surface wash | Brucellaceae | *Ochrobactrum* sp. |
| SYM00763 | 9 | 767 | Maize | Modern | Seed surface wash | Brucellaceae | *Ochrobactrum* sp. |
| SYM00783 | 9 | 772 | Maize | Modern | Seed surface wash | Brucellaceae | *Ochrobactrum* sp. |
| SYM00812 | 9 | 775 | Rice | Modern | Seed surface wash | Brucellaceae | *Ochrobactrum* sp. |
| SYM00902 | 9 | 783 | Maize | Ancient Landrace | Surface sterilized seeds | Brucellaceae | *Ochrobactrum* sp. |
| SYM00923 | 9 | 802 | Maize | Modern | Surface sterilized seeds | Brucellaceae | *Ochrobactrum* sp. |
| SYM00935 | 9 | 810 | Rice | Modern | Surface sterilized seeds | Brucellaceae | *Ochrobactrum* sp. |
| SYM00937 | 9 | 812 | Rice | Modern | Surface sterilized seeds | Brucellaceae | *Ochrobactrum* sp. |
| SYM00954 | 9 | 827 | Rice | Ancient Landrace | Surface sterilized seeds | Brucellaceae | *Ochrobactrum* sp. |
| SYM01029 | 9 | 883 | *Avena sterilis* | Wild relative | Surface sterilized seeds | Brucellaceae | *Ochrobactrum* sp. |
| SYM01043 | 9 | 894 | Rice | Modern | Surface sterilized seeds | Brucellaceae | *Ochrobactrum* sp. |
| SYM01047 | 9 | 896 | *Oryza latifolia* | Wild relative | Surface sterilized seeds | Brucellaceae | *Ochrobactrum* sp. |
| SYM01052 | 9 | 899 | Maize | Ancient Landrace | Surface sterilized seeds | Brucellaceae | *Ochrobactrum* sp. |
| SYM01054 | 9 | 901 | Maize | Ancient Landrace | Surface sterilized seeds | Brucellaceae | *Ochrobactrum* sp. |
| SYM01055 | 9 | 902 | Maize | Ancient Landrace | Surface sterilized seeds | Brucellaceae | *Ochrobactrum* sp. |

TABLE 2-continued

Endophytic bacteria isolated from corn, rice and wheat seeds, including assignment to specific OTUs, corresponding Sequence ID numbers, Family, Genus, Taxonomic information and plant source from which the microbe was derived.

| Strain | OTU# | SEQ ID NO: | Seed-Origin Crop Type | Seed-Origin Cultivar Type | Source of seed-origin microbes | Family of Seed-Origin Microbe | Taxonomy of Seed-Origin Microbe |
| --- | --- | --- | --- | --- | --- | --- | --- |
| SYM01058 | 9 | 904 | Maize | Ancient Landrace | Surface sterilized seeds | Brucellaceae | *Ochrobactrum* sp. |
| SYM01064 | 9 | 906 | Maize | Ancient Landrace | Surface sterilized seeds | Brucellaceae | *Ochrobactrum* sp. |
| SYM01066 | 9 | 908 | Maize | Ancient Landrace | Surface sterilized seeds | Brucellaceae | *Ochrobactrum* sp. |
| SYM01069 | 9 | 909 | Maize | Modern | Surface sterilized seeds | Brucellaceae | *Ochrobactrum* sp. |
| SYM01079 | 9 | 913 | Maize | Modern | Surface sterilized seeds | Brucellaceae | *Ochrobactrum* sp. |
| SYM00064a | 10 | 560 | Teosinte | Wild relative | Surface sterilized seeds | Xanthomonadaceae | *Stenotrophomonas* sp. |
| SYM00183 | 10 | 603 | *Oryza glumipatula* | Wild relative | Surface sterilized seeds | Xanthomonadaceae | *Stenotrophomonas* sp. |
| SYM00184 | 10 | 604 | *Oryza glumipatula* | Wild relative | Surface sterilized seeds | Xanthomonadaceae | *Stenotrophomonas* sp. |
| SYM00905 | 10 | 786 | Maize | Modern | Surface sterilized seeds | Xanthomonadaceae | *Stenotrophomonas* sp. |
| SYM00543 | 12 | 662 | Maize | Ancient Landrace | Seed surface wash | Bacillaceae | *Bacillus* sp. |
| SYM00595 | 12 | 709 | Maize | Ancient Landrace | Seed surface wash | Bacillaceae | *Bacillus* sp. |
| SYM01227 | 12 | 977 | Rice | Modern | Roots & Seeds | Bacillaceae | *Bacillus* sp. |
| SYM00547 | 13 | 666 | Maize | Ancient Landrace | Seed surface wash | Alcaligenaceae | *Achromobacter* sp. |
| SYM00551 | 13 | 669 | Maize | Ancient Landrace | Seed surface wash | Alcaligenaceae | *Achromobacter* sp. |
| SYM00560 | 13 | 676 | Maize | Ancient Landrace | Seed surface wash | Alcaligenaceae | *Achromobacter* sp. |
| SYM00565B | 13 | 681 | Maize | Modern | Seed surface wash | Alcaligenaceae | *Achromobacter* sp. |
| SYM00580C | 13 | 690 | Maize | Modern | Seed surface wash | Alcaligenaceae | *Achromobacter* sp. |
| SYM00580i | 13 | 694 | Maize | Modern | Seed surface wash | Alcaligenaceae | *Achromobacter* sp. |
| SYM00585 | 13 | 701 | Maize | Ancient Landrace | Seed surface wash | Alcaligenaceae | *Achromobacter* sp. |
| SYM00586b | 13 | 702 | Maize | Ancient Landrace | Seed surface wash | Alcaligenaceae | *Achromobacter* sp. |
| SYM00588b | 13 | 706 | Maize | Ancient Landrace | Seed surface wash | Alcaligenaceae | *Achromobacter* sp. |
| SYM00591 | 13 | 708 | Maize | Ancient Landrace | Seed surface wash | Alcaligenaceae | *Achromobacter* sp. |
| SYM00602 | 13 | 715 | Maize | Modern | Seed surface wash | Alcaligenaceae | *Achromobacter* sp. |
| SYM00758 | 13 | 763 | Maize | Modern | Seed surface wash | Alcaligenaceae | *Achromobacter* sp. |
| SYM00761 | 13 | 765 | Maize | Modern | Seed surface wash | Alcaligenaceae | *Achromobacter* sp. |
| SYM00764 | 13 | 768 | Maize | Modern | Seed surface wash | Alcaligenaceae | *Achromobacter* sp. |
| SYM00765 | 13 | 769 | Maize | Modern | Seed surface wash | Alcaligenaceae | *Achromobacter* sp. |
| SYM00824 | 13 | 777 | Rice | Ancient Landrace | Seed surface wash | Alcaligenaceae | *Achromobacter* sp. |
| SYM00828 | 13 | 778 | Rice | Ancient Landrace | Seed surface wash | Alcaligenaceae | *Achromobacter* sp. |
| SYM00830 | 13 | 779 | Rice | Ancient Landrace | Seed surface wash | Alcaligenaceae | *Achromobacter* sp. |
| SYM00831 | 13 | 780 | Rice | Ancient Landrace | Seed surface wash | Alcaligenaceae | *Achromobacter* sp. |
| SYM00901 | 13 | 782 | Maize | Ancient Landrace | Surface sterilized seeds | Alcaligenaceae | *Achromobacter* sp. |
| SYM00903 | 13 | 784 | Maize | Modern | Surface sterilized seeds | Alcaligenaceae | *Achromobacter* sp. |
| SYM00904 | 13 | 785 | Maize | Modern | Surface sterilized seeds | Alcaligenaceae | *Achromobacter* sp. |
| SYM00907 | 13 | 787 | Maize | Modern | Surface sterilized seeds | Alcaligenaceae | *Achromobacter* sp. |
| SYM00908 | 13 | 788 | Maize | Ancient Landrace | Surface sterilized seeds | Alcaligenaceae | *Achromobacter* sp. |
| SYM00909 | 13 | 789 | Maize | Ancient Landrace | Surface sterilized seeds | Alcaligenaceae | *Achromobacter* sp. |
| SYM00910 | 13 | 790 | Maize | Modern | Surface sterilized seeds | Alcaligenaceae | *Achromobacter* sp. |
| SYM00914 | 13 | 794 | Maize | Modern | Surface sterilized seeds | Alcaligenaceae | *Achromobacter* sp. |
| SYM00917 | 13 | 796 | Maize | Modern | Surface sterilized seeds | Alcaligenaceae | *Achromobacter* sp. |
| SYM00929 | 13 | 806 | *Oryza latifolia* | Wild relative | Surface sterilized seeds | Alcaligenaceae | *Achromobacter* sp. |
| SYM00930 | 13 | 807 | Rice | Modern | Surface sterilized seeds | Alcaligenaceae | *Achromobacter* sp. |
| SYM00938 | 13 | 813 | Rice | Modern | Surface sterilized seeds | Alcaligenaceae | *Achromobacter* sp. |
| SYM00957 | 13 | 829 | Rice | Ancient Landrace | Surface sterilized seeds | Alcaligenaceae | *Achromobacter* sp. |
| SYM00959 | 13 | 830 | Rice | Ancient Landrace | Surface sterilized seeds | Alcaligenaceae | *Achromobacter* sp. |
| SYM01017 | 13 | 875 | Rice | Modern | Surface sterilized seeds | Alcaligenaceae | *Achromobacter* sp. |
| SYM01020 | 13 | 877 | Rice | Modern | Surface sterilized seeds | Alcaligenaceae | *Achromobacter* sp. |
| SYM01021 | 13 | 878 | *Oryza nivara* | Wild relative | Surface sterilized seeds | Alcaligenaceae | *Achromobacter* sp. |
| SYM01030 | 13 | 884 | *Avena sterilis* | Wild relative | Surface sterilized seeds | Alcaligenaceae | *Achromobacter* sp. |
| SYM00028 | 18 | 540 | Maize | Ancient Landrace | Surface sterilized seeds | Enterobacteriaceae | *Enterobacter* sp. |
| SYM00052 | 18 | 550 | Teosinte | Wild relative | Surface sterilized seeds | Enterobacteriaceae | *Enterobacter* sp. |
| SYM00053 | 18 | 551 | Teosinte | Wild relative | Surface sterilized seeds | Enterobacteriaceae | *Enterobacter* sp. |
| SYM00054 | 18 | 552 | Teosinte | Wild relative | Surface sterilized seeds | Enterobacteriaceae | *Enterobacter* sp. |
| SYM00175 | 18 | 595 | Winter rye | Modern | Surface sterilized seeds | Enterobacteriaceae | *Enterobacter* sp. |
| SYM00627 | 18 | 725 | Maize | Modern | Seed surface wash | Enterobacteriaceae | *Enterobacter* sp. |
| SYM00715 | 18 | 751 | Rice | Modern | Seed surface wash | Enterobacteriaceae | *Enterobacter* sp. |
| SYM00189 | 19 | 606 | Maize | Modern | Leaves | Bacillaceae | *Bacillus* sp. |
| SYM00192 | 19 | 608 | Maize | Modern | Leaves | Bacillaceae | *Bacillus* sp. |
| SYM00197 | 19 | 611 | Maize | Modern | Leaves | Bacillaceae | *Bacillus* sp. |
| SYM00201 | 19 | 612 | Maize | Maize | Roots | Bacillaceae | *Bacillus* sp. |
| SYM00202 | 19 | 613 | Maize | Maize | Roots | Bacillaceae | *Bacillus* sp. |
| SYM00215 | 19 | 615 | Soybean | Modern | Roots | Bacillaceae | *Bacillus* sp. |
| SYM00233 | 19 | 621 | Soybean | Modern | Leaves | Bacillaceae | *Bacillus* sp. |
| SYM00260 | 19 | 632 | Maize | Modern | Surface sterilized seeds | Bacillaceae | *Bacillus simplex* |
| SYM01113 | 19 | 920 | Maize | Modern | Roots | Bacillaceae | *Bacillus* sp. |
| SYM01119 | 19 | 924 | Maize | Ancient Landrace | Roots | Bacillaceae | *Bacillus* sp. |
| SYM00016b | 25 | 529 | Rice | Modern | Surface sterilized seeds | Methylobacteriaceae | *Methylobacterium* sp. |
| SYM00236 | 25 | 623 | Rice | Modern | Surface sterilized seeds | Methylobacteriaceae | *Methylobacterium* sp. |
| SYM00237 | 25 | 624 | Rice | Modern | Surface sterilized seeds | Methylobacteriaceae | *Methylobacterium* sp. |
| SYM00240 | 25 | 625 | Rice | Modern | Surface sterilized seeds | Methylobacteriaceae | *Methylobacterium* sp. |
| SYM00924 | 25 | 803 | Rice | Ancient Landrace | Surface sterilized seeds | Methylobacteriaceae | *Methylobacterium* sp. |
| SYM00936 | 25 | 811 | Rice | Modern | Surface sterilized seeds | Methylobacteriaceae | *Methylobacterium* sp. |
| SYM00950 | 25 | 824 | Rice | Ancient Landrace | Surface sterilized seeds | Methylobacteriaceae | *Methylobacterium* sp. |
| SYM00968 | 25 | 838 | Rice | Ancient Landrace | Surface sterilized seeds | Methylobacteriaceae | *Methylobacterium* sp. |

TABLE 2-continued

Endophytic bacteria isolated from corn, rice and wheat seeds, including assignment to specific OTUs, corresponding Sequence ID numbers, Family, Genus, Taxonomic information and plant source from which the microbe was derived.

| Strain | OTU# | SEQ ID NO: | Seed-Origin Crop Type | Seed-Origin Cultivar Type | Source of seed-origin microbes | Family of Seed-Origin Microbe | Taxonomy of Seed-Origin Microbe |
|---|---|---|---|---|---|---|---|
| SYM00986 | 25 | 852 | Rice | Modern | Surface sterilized seeds | Methylobacteriaceae | *Methylobacterium* sp. |
| SYM00998 | 25 | 861 | *Oryza officinalis* | Wild relative | Surface sterilized seeds | Methylobacteriaceae | *Methylobacterium* sp. |
| SYM00999 | 25 | 862 | *Oryza officinalis* | Wild relative | Surface sterilized seeds | Methylobacteriaceae | *Methylobacterium* sp. |
| SYM01003 | 25 | 864 | Rice | Modern | Surface sterilized seeds | Methylobacteriaceae | *Methylobacterium* sp. |
| SYM01008 | 25 | 868 | Rice | Modern | Surface sterilized seeds | Methylobacteriaceae | *Methylobacterium* sp. |
| SYM00501 | 27 | 638 | Maize | Ancient Landrace | Seed surface wash | Burkholderiaceae | *Burkholderia* sp. |
| SYM00504 | 27 | 640 | Maize | Ancient Landrace | Seed surface wash | Burkholderiaceae | *Burkholderia* sp. |
| SYM00536 | 27 | 656 | Maize | Ancient Landrace | Seed surface wash | Burkholderiaceae | *Burkholderia* sp. |
| SYM00536A | 27 | 657 | Maize | Ancient Landrace | Seed surface wash | Burkholderiaceae | *Burkholderia* sp. |
| SYM00538E | 27 | 659 | Maize | Ancient Landrace | Seed surface wash | Burkholderiaceae | *Burkholderia* sp. |
| SYM00566A | 27 | 682 | Maize | Modern | Seed surface wash | Burkholderiaceae | *Burkholderia* sp. |
| SYM00568 | 27 | 683 | Maize | Modern | Seed surface wash | Burkholderiaceae | *Burkholderia* sp. |
| SYM00570 | 27 | 684 | Maize | Modern | Seed surface wash | Burkholderiaceae | *Burkholderia* sp. |
| SYM00574 | 27 | 685 | Maize | Ancient Landrace | Seed surface wash | Burkholderiaceae | *Burkholderia* sp. |
| SYM00575 | 27 | 686 | Maize | Ancient Landrace | Seed surface wash | Burkholderiaceae | *Burkholderia* sp. |
| SYM00578 | 27 | 687 | Maize | Modern | Seed surface wash | Burkholderiaceae | *Burkholderia* sp. |
| SYM00621 | 27 | 721 | Maize | Modern | Seed surface wash | Burkholderiaceae | *Burkholderia* sp. |
| SYM00623 | 27 | 722 | Maize | Modern | Seed surface wash | Burkholderiaceae | *Burkholderia* sp. |
| SYM00624 | 27 | 723 | Maize | Modern | Seed surface wash | Burkholderiaceae | *Burkholderia* sp. |
| SYM00633 | 27 | 727 | Maize | Ancient Landrace | Seed surface wash | Burkholderiaceae | *Burkholderia* sp. |
| SYM00822 | 27 | 776 | Rice | Modern | Seed surface wash | Burkholderiaceae | *Burkholderia* sp. |
| SYM01010 | 27 | 869 | Rice | Ancient Landrace | Surface sterilized seeds | Burkholderiaceae | *Burkholderia* sp. |
| SYM01012 | 27 | 871 | Rice | Ancient Landrace | Surface sterilized seeds | Burkholderiaceae | *Burkholderia* sp. |
| SYM01015 | 27 | 873 | Rice | Ancient Landrace | Surface sterilized seeds | Burkholderiaceae | *Burkholderia* sp. |
| SYM01037 | 27 | 889 | Rice | Modern | Surface sterilized seeds | Burkholderiaceae | *Burkholderia* sp. |
| SYM00037 | 28 | 543 | Maize | Modern | Surface sterilized seeds | Microbacteriaceae | *Bacillus* sp. |
| SYM00051 | 28 | 549 | Teosinte | Wild relative | Surface sterilized seeds | Microbacteriaceae | *Microbacterium* sp. |
| SYM00104 | 28 | 582 | Maize | Ancient Landrace | Surface sterilized seeds | Microbacteriaceae | *Microbacterium* sp. |
| SYM00177 | 28 | 597 | *Oryza nivara* | Wild relative | Surface sterilized seeds | Microbacteriaceae | *Microbacterium* sp. |
| SYM00514A | 28 | 648 | Maize | Ancient Landrace | Seed surface wash | Microbacteriaceae | *Microbacterium* sp. |
| SYM00523 | 28 | 652 | *Oryza nivara* | Wild relative | Seed surface wash | Microbacteriaceae | *Microbacterium* sp. |
| SYM00538H | 28 | 660 | Maize | Ancient Landrace | Seed surface wash | Microbacteriaceae | *Microbacterium* sp. |
| SYM00542 | 28 | 661 | Maize | Ancient Landrace | Seed surface wash | Microbacteriaceae | *Microbacterium* sp. |
| SYM00556 | 28 | 674 | Maize | Ancient Landrace | Seed surface wash | Microbacteriaceae | *Microbacterium* sp. |
| SYM00581A | 28 | 695 | Maize | Modern | Seed surface wash | Microbacteriaceae | *Microbacterium* sp. |
| SYM00586c | 28 | 703 | Maize | Ancient Landrace | Seed surface wash | Microbacteriaceae | *Microbacterium* sp. |
| SYM00587 | 28 | 704 | Maize | Ancient Landrace | Seed surface wash | Microbacteriaceae | *Microbacterium* sp. |
| SYM00598 | 28 | 712 | Maize | Ancient Landrace | Seed surface wash | Microbacteriaceae | *Microbacterium* sp. |
| SYM00757 | 28 | 762 | Maize | Modern | Seed surface wash | Microbacteriaceae | *Microbacterium* sp. |
| SYM00760 | 28 | 764 | Maize | Modern | Seed surface wash | Microbacteriaceae | *Microbacterium* sp. |
| SYM00780 | 28 | 771 | Maize | Modern | Seed surface wash | Microbacteriaceae | *Microbacterium* sp. |
| SYM00832 | 28 | 781 | Rice | Ancient Landrace | Seed surface wash | Microbacteriaceae | *Microbacterium* sp. |
| SYM00911 | 28 | 791 | Maize | Modern | Surface sterilized seeds | Microbacteriaceae | *Microbacterium* sp. |
| SYM00912 | 28 | 792 | Maize | Ancient Landrace | Surface sterilized seeds | Microbacteriaceae | *Microbacterium* sp. |
| SYM00913 | 28 | 793 | Maize | Ancient Landrace | Surface sterilized seeds | Microbacteriaceae | *Microbacterium* sp. |
| SYM00915 | 28 | 795 | Maize | Modern | Surface sterilized seeds | Microbacteriaceae | *Microbacterium* sp. |
| SYM00918 | 28 | 797 | Maize | Ancient Landrace | Surface sterilized seeds | Microbacteriaceae | *Microbacterium* sp. |
| SYM00919 | 28 | 798 | Maize | Ancient Landrace | Surface sterilized seeds | Microbacteriaceae | *Microbacterium* sp. |
| SYM00920 | 28 | 799 | Maize | Ancient Landrace | Surface sterilized seeds | Microbacteriaceae | *Microbacterium* sp. |
| SYM00921 | 28 | 800 | Maize | Modern | Surface sterilized seeds | Microbacteriaceae | *Microbacterium* sp. |
| SYM00922 | 28 | 801 | Maize | Modern | Surface sterilized seeds | Microbacteriaceae | *Microbacterium* sp. |
| SYM00931 | 28 | 808 | Rice | Modern | Surface sterilized seeds | Microbacteriaceae | *Microbacterium* sp. |
| SYM00933 | 28 | 809 | Rice | Modern | Surface sterilized seeds | Microbacteriaceae | *Microbacterium* sp. |
| SYM00939 | 28 | 814 | Rice | Modern | Surface sterilized seeds | Microbacteriaceae | *Microbacterium* sp. |
| SYM00944 | 28 | 819 | Rice | Modern | Surface sterilized seeds | Microbacteriaceae | *Microbacterium* sp. |
| SYM00962 | 28 | 832 | Rice | Ancient Landrace | Surface sterilized seeds | Microbacteriaceae | *Microbacterium* sp. |
| SYM01000 | 28 | 863 | *Oryza officinalis* | Wild relative | Surface sterilized seeds | Microbacteriaceae | *Microbacterium* sp. |
| SYM01034 | 28 | 886 | *Avena sterilis* | Wild relative | Surface sterilized seeds | Microbacteriaceae | *Microbacterium* sp. |
| SYM01206 | 28 | 968 | Rice | Modern | Roots & Seeds | Microbacteriaceae | *Microbacterium* sp. |
| SYM00015 | 29 | 528 | Rice | Modern | Surface sterilized seeds | Xanthomonadaceae | *Xanthomonas* sp. |
| SYM00021 | 29 | 536 | Teosinte | Wild relative | Surface sterilized seeds | Xanthomonadaceae | *Xanthomonas* sp. |
| SYM00179 | 29 | 599 | Rice | Ancient Landrace | Surface sterilized seeds | Xanthomonadaceae | *Xanthomonas* sp. |
| SYM00182 | 29 | 602 | Rice | Ancient Landrace | Surface sterilized seeds | Xanthomonadaceae | *Xanthomonas* sp. |
| SYM00252 | 29 | 630 | Rice | Ancient Landrace | Surface sterilized seeds | Xanthomonadaceae | *Xanthomonas* sp. |
| SYM00977 | 29 | 845 | Rice | Ancient Landrace | Surface sterilized seeds | Xanthomonadaceae | *Xanthomonas* sp. |
| SYM00988 | 29 | 854 | Rice | Modern | Surface sterilized seeds | Xanthomonadaceae | *Xanthomonas* sp. |
| SYM00997 | 29 | 860 | *Oryza officinalis* | Wild relative | Surface sterilized seeds | Xanthomonadaceae | *Xanthomonas* sp. |
| SYM01018 | 29 | 876 | Rice | Modern | Surface sterilized seeds | Xanthomonadaceae | *Xanthomonas* sp. |
| SYM01028 | 29 | 882 | *Oryza nivara* | Wild relative | Surface sterilized seeds | Xanthomonadaceae | *Xanthomonas* sp. |
| SYM01146 | 29 | 930 | Rice | Modern | Roots & Seeds | Xanthomonadaceae | *Xanthomonas* sp. |
| SYM01153 | 29 | 933 | Rice | Modern | Roots & Seeds | Xanthomonadaceae | *Xanthomonas* sp. |
| SYM01154 | 29 | 934 | Rice | Modern | Roots & Seeds | Xanthomonadaceae | *Xanthomonas* sp. |
| SYM01162 | 29 | 939 | Rice | Ancient Landrace | Roots & Seeds | Xanthomonadaceae | *Xanthomonas* sp. |
| SYM01190 | 29 | 959 | Rice | Modern | Roots & Seeds | Xanthomonadaceae | *Xanthomonas* sp. |

TABLE 2-continued

Endophytic bacteria isolated from corn, rice and wheat seeds, including assignment to specific OTUs, corresponding Sequence ID numbers, Family, Genus, Taxonomic information and plant source from which the microbe was derived.

| Strain | OTU# | SEQ ID NO: | Seed-Origin Crop Type | Seed-Origin Cultivar Type | Source of seed-origin microbes | Family of Seed-Origin Microbe | Taxonomy of Seed-Origin Microbe |
|---|---|---|---|---|---|---|---|
| SYM00565A | 30 | 680 | Maize | Modern | Seed surface wash | Nocardiaceae | *Rhodococcus* sp. |
| SYM00580G | 30 | 693 | Maize | Modern | Seed surface wash | Nocardiaceae | *Rhodococcus* sp. |
| SYM00753 | 30 | 760 | Maize | Modern | Seed surface wash | Nocardiaceae | *Rhodococcus* sp. |
| SYM00762 | 30 | 766 | Maize | Modern | Seed surface wash | Nocardiaceae | *Rhodococcus* sp. |
| SYM00775 | 30 | 770 | Maize | Modern | Seed surface wash | Nocardiaceae | *Rhodococcus* sp. |
| SYM00943 | 30 | 818 | Rice | Modern | Surface sterilized seeds | Nocardiaceae | *Rhodococcus* sp. |
| SYM00951 | 30 | 825 | Rice | Ancient Landrace | Surface sterilized seeds | Nocardiaceae | *Rhodococcus* sp. |
| SYM01039 | 30 | 890 | Rice | Ancient Landrace | Surface sterilized seeds | Nocardiaceae | *Rhodococcus* sp. |
| SYM01040 | 30 | 891 | Rice | Ancient Landrace | Surface sterilized seeds | Nocardiaceae | *Rhodococcus* sp. |
| SYM01042 | 30 | 893 | Rice | Modern | Surface sterilized seeds | Nocardiaceae | *Rhodococcus* sp. |
| SYM01046 | 30 | 895 | Rice | Modern | Surface sterilized seeds | Nocardiaceae | *Rhodococcus* sp. |
| SYM01048 | 30 | 897 | *Oryza latifolia* | Wild relative | Surface sterilized seeds | Nocardiaceae | *Rhodococcus* sp. |
| SYM01053 | 30 | 900 | Maize | Modern | Surface sterilized seeds | Nocardiaceae | *Rhodococcus* sp. |
| SYM01063 | 30 | 905 | Maize | Modern | Surface sterilized seeds | Nocardiaceae | *Rhodococcus* sp. |
| SYM01065 | 30 | 907 | Maize | Ancient Landrace | Surface sterilized seeds | Nocardiaceae | *Rhodococcus* sp. |
| SYM01070 | 30 | 910 | Rice | Modern | Surface sterilized seeds | Nocardiaceae | *Rhodococcus* sp. |
| SYM01071 | 30 | 911 | Maize | Ancient Landrace | Surface sterilized seeds | Nocardiaceae | *Rhodococcus* sp. |
| SYM01078 | 30 | 912 | Rice | Modern | Surface sterilized seeds | Nocardiaceae | *Rhodococcus* sp. |
| SYM00589 | 31 | 707 | Maize | Ancient Landrace | Seed surface wash | Paenibacillaceae | *Paenibacillus* sp. |
| SYM00991 | 36 | 855 | Rice | Modern | Surface sterilized seeds | Comamonadaceae | *Acidovorax* sp. |
| SYM01236 | 36 | 985 | *Oryza officinalis* | Wild relative | Roots & Seeds | Comamonadaceae | *Acidovorax* sp. |
| SYM00057B | 37 | 1446 | Maize | Ancient Landrace | Surface sterilized seeds | Burkholderiaceae | *Burkholderia phytofirmans* |
| SYM00102 | 38 | 581 | Maize | Ancient Landrace | Surface sterilized seeds | Staphylococcaceae | *Staphylococcus* sp. |
| SYM00072 | 39 | 566 | Teosinte | Wild relative | Surface sterilized seeds | Bacillaceae | *Bacillus* sp. |
| SYM00075 | 39 | 567 | Teosinte | Wild relative | Surface sterilized seeds | Bacillaceae | *Bacillus* sp. |
| SYM00249 | 39 | 628 | Soybean | Modern | Surface sterilized seeds | Bacillaceae | *Bacillus* sp. |
| SYM00507 | 39 | 645 | Maize | Ancient Landrace | Seed surface wash | Bacillaceae | *Bacillus* sp. |
| SYM00553 | 39 | 671 | Maize | Ancient Landrace | Seed surface wash | Bacillaceae | *Bacillus* sp. |
| SYM00562 | 39 | 677 | Maize | Ancient Landrace | Seed surface wash | Bacillaceae | *Bacillus* sp. |
| SYM00564 | 39 | 679 | Maize | Ancient Landrace | Seed surface wash | Bacillaceae | *Bacillus* sp. |
| SYM00580E | 39 | 692 | Maize | Modern | Seed surface wash | Bacillaceae | *Bacillus* sp. |
| SYM00581b | 39 | 696 | Maize | Modern | Seed surface wash | Bacillaceae | *Bacillus* sp. |
| SYM00581c | 39 | 697 | Maize | Modern | Seed surface wash | Bacillaceae | *Bacillus* sp. |
| SYM00601 | 39 | 714 | Maize | Ancient Landrace | Seed surface wash | Bacillaceae | *Bacillus* sp. |
| SYM00036 | 41 | 542 | Maize | Modern | Surface sterilized seeds | Bacillaceae | *Bacillus* sp. |
| SYM00110 | 41 | 586 | Maize | Modern | Surface sterilized seeds | Bacillaceae | *Bacillus* sp. |
| SYM00193 | 41 | 609 | Maize | Modern | Leaves | Bacillaceae | *Bacillus* sp. |
| SYM00218 | 41 | 617 | Soybean | Modern | Roots | Bacillaceae | *Bacillus* sp. |
| SYM00250 | 41 | 629 | Soybean | Modern | Surface sterilized seeds | Bacillaceae | *Bacillus* sp. |
| SYM00697 | 41 | 745 | Rice | Modern | Seed surface wash | Bacillaceae | *Bacillus* sp. |
| SYM00704 | 41 | 746 | Rice | Modern | Seed surface wash | Bacillaceae | *Bacillus* sp. |
| SYM00017c | 45 | 533 | Rice | Modern | Surface sterilized seeds | Sphingomonadaceae | *Sphingomonas* sp. |
| SYM00062b | 45 | 558 | Teosinte | Wild relative | Surface sterilized seeds | Sphingomonadaceae | *Sphingomonas* sp. |
| SYM00065 | 45 | 561 | Teosinte | Wild relative | Surface sterilized seeds | Sphingomonadaceae | *Sphingomonas* sp. |
| SYM00168 | 45 | 589 | Rice | Modern | Surface sterilized seeds | Sphingomonadaceae | *Sphingomonas* sp. |
| SYM00169 | 45 | 590 | Rice | Modern | Surface sterilized seeds | Sphingomonadaceae | *Sphingomonas* sp. |
| SYM00942 | 45 | 817 | Rice | Modern | Surface sterilized seeds | Sphingomonadaceae | *Sphingomonas* sp. |
| SYM00994 | 45 | 858 | *Oryza officinalis* | Wild relative | Surface sterilized seeds | Sphingomonadaceae | *Sphingomonas* sp. |
| SYM01016 | 45 | 874 | Rice | Modern | Surface sterilized seeds | Sphingomonadaceae | *Sphingomonas* sp. |
| SYM01174 | 45 | 944 | Rice | Ancient Landrace | Roots & Seeds | Sphingomonadaceae | *Sphingomonas* sp. |
| SYM01176 | 45 | 946 | Rice | Ancient Landrace | Roots & Seeds | Sphingomonadaceae | *Sphingomonas* sp. |
| SYM01187 | 45 | 956 | Rice | Modern | Roots & Seeds | Sphingomonadaceae | *Sphingomonas* sp. |
| SYM01191 | 45 | 960 | Rice | Modern | Roots & Seeds | Sphingomonadaceae | *Sphingomonas* sp. |
| SYM01214 | 45 | 970 | Rice | Modern | Roots & Seeds | Sphingomonadaceae | *Sphingomonas* sp. |
| SYM01216 | 45 | 972 | Rice | Modern | Roots & Seeds | Sphingomonadaceae | *Sphingomonas* sp. |
| SYM00231 | 46 | 620 | Soybean | Modern | Leaves | Sphingomonadaceae | *Sphingobium* sp. |
| SYM00975 | 51 | 843 | Rice | Ancient Landrace | Surface sterilized seeds | Oxalobacteraceae | *Herbaspirillum* sp. |
| SYM00506c | 53 | 643 | Maize | Ancient Landrace | Seed surface wash | Paenibacillaceae | *Paenibacillus* sp. |
| SYM00506D | 53 | 644 | Maize | Ancient Landrace | Seed surface wash | Paenibacillaceae | *Paenibacillus* sp. |
| SYM00545 | 53 | 664 | Maize | Ancient Landrace | Seed surface wash | Paenibacillaceae | *Paenibacillus* sp. |
| SYM00549 | 53 | 668 | Maize | Ancient Landrace | Seed surface wash | Paenibacillaceae | *Paenibacillus* sp. |
| SYM00554 | 53 | 672 | Maize | Ancient Landrace | Seed surface wash | Paenibacillaceae | *Paenibacillus* sp. |
| SYM00555 | 53 | 673 | Maize | Ancient Landrace | Seed surface wash | Paenibacillaceae | *Paenibacillus* sp. |
| SYM00012 | 55 | 1447 | Teosinte | Wild relative | Surface sterilized seeds | Microbacteriaceae | *Microbacterium binotii* |
| SYM00046 | 56 | 545 | Maize | Ancient Landrace | Surface sterilized seeds | Enterobacteriaceae | *Enterobacter* sp. |
| SYM00050 | 56 | 548 | Maize | Ancient Landrace | Surface sterilized seeds | Enterobacteriaceae | *Enterobacter* sp. |
| SYM00628 | 56 | 726 | Maize | Modern | Seed surface wash | Enterobacteriaceae | *Enterobacter* sp. |
| SYM01049 | 56 | 898 | Teosinte | Wild relative | Surface sterilized seeds | Enterobacteriaceae | |
| SYM00106 | 59 | 583 | Maize | Ancient Landrace | Surface sterilized seeds | Micrococcaceae | *Micrococcus* sp. |
| SYM00107 | 59 | 584 | Maize | Ancient Landrace | Surface sterilized seeds | Micrococcaceae | *Micrococcus* sp. |
| SYM00108 | 59 | 585 | Maize | Ancient Landrace | Surface sterilized seeds | Micrococcaceae | *Micrococcus* sp. |
| SYM00254 | 59 | 631 | Maize | Modern | Surface sterilized seeds | Micrococcaceae | *Micrococcus* sp. |
| SYM00090 | 62 | 575 | Maize | Ancient Landrace | Surface sterilized seeds | Flavobacteriaceae | *Chryseobacterium* sp. |
| SYM00002 | 66 | 521 | Teosinte | Wild relative | Surface sterilized seeds | Rhizobiaceae | *Agrobacterium* sp. |

TABLE 2-continued

Endophytic bacteria isolated from corn, rice and wheat seeds, including assignment to specific OTUs, corresponding Sequence ID numbers, Family, Genus, Taxonomic information and plant source from which the microbe was derived.

| Strain | OTU# | SEQ ID NO: | Seed-Origin Crop Type | Seed-Origin Cultivar Type | Source of seed-origin microbes | Family of Seed-Origin Microbe | Taxonomy of Seed-Origin Microbe |
|---|---|---|---|---|---|---|---|
| SYM00017a | 66 | 531 | Rice | Modern | Surface sterilized seeds | Rhizobiaceae | *Agrobacterium* sp. |
| SYM00326 | 66 | 635 | Maize | Modern | Roots | Rhizobiaceae | *Agrobacterium tumefaciens* |
| SYM00714 | 66 | 750 | Rice | Modern | Seed surface wash | Rhizobiaceae | *Agrobacterium* sp. |
| SYM00983 | 66 | 849 | Rice | Modern | Surface sterilized seeds | Rhizobiaceae | *Agrobacterium* sp. |
| SYM01004 | 66 | 865 | Rice | Modern | Surface sterilized seeds | Rhizobiaceae | *Agrobacterium* sp. |
| SYM00060 | 67 | 556 | Maize | Ancient Landrace | Surface sterilized seeds | Staphylococcaceae | *Staphylococcus* sp. |
| SYM00113 | 67 | 587 | Maize | Modern | Surface sterilized seeds | Staphylococcaceae | *Staphylococcus* sp. |
| SYM01257 | 67 | 992 | Rice | Ancient Landrace | Roots & Seeds | Staphylococcaceae | *Staphylococcus* sp. |
| SYM01259 | 67 | 993 | Rice | Ancient Landrace | Roots & Seeds | Staphylococcaceae | *Staphylococcus* sp. |
| SYM00071 | 76 | 565 | Teosinte | Wild relative | Surface sterilized seeds | Bacillaceae | *Bacillus* sp. |
| SYM00204 | 76 | 614 | Maize | Maize | Roots | Bacillaceae | *Bacillus* sp. |
| SYM00563 | 76 | 678 | Maize | Ancient Landrace | Seed surface wash | Bacillaceae | *Bacillus* sp. |
| SYM00617 | 76 | 719 | Teosinte | Wild relative | Seed surface wash | Bacillaceae | *Bacillus* sp. |
| SYM00016c | 82 | 530 | Rice | Modern | Surface sterilized seeds | Xanthomonadaceae | *Luteibacter* sp. |
| SYM00960 | 82 | 831 | Rice | Ancient Landrace | Surface sterilized seeds | Xanthomonadaceae | *Luteibacter* sp. |
| SYM00965 | 82 | 835 | Rice | Ancient Landrace | Surface sterilized seeds | Xanthomonadaceae | *Luteibacter* sp. |
| SYM01167 | 82 | 941 | Rice | Ancient Landrace | Roots & Seeds | Xanthomonadaceae | *Luteibacter* sp. |
| SYM00940 | 83 | 815 | Rice | Modern | Surface sterilized seeds | Enterobacteriaceae | |
| SYM00941 | 83 | 816 | Rice | Modern | Surface sterilized seeds | Enterobacteriaceae | |
| SYM00963 | 83 | 833 | Rice | Ancient Landrace | Surface sterilized seeds | Enterobacteriaceae | |
| SYM00972 | 83 | 841 | Rice | Ancient Landrace | Surface sterilized seeds | Enterobacteriaceae | |
| SYM00987 | 83 | 853 | Rice | Modern | Surface sterilized seeds | Enterobacteriaceae | |
| SYM00713 | 84 | 749 | Rice | Modern | Seed surface wash | Enterobacteriaceae | *Erwinia* sp. |
| SYM00945 | 84 | 820 | Rice | Modern | Surface sterilized seeds | Enterobacteriaceae | |
| SYM01103 | 84 | 914 | Rice | Modern | Surface sterilized seeds | Enterobacteriaceae | |
| SYM01138 | 84 | 926 | *Oryza latifolia* | Wild relative | Roots & Seeds | Enterobacteriaceae | |
| SYM01139 | 84 | 927 | *Oryza latifolia* | Wild relative | Roots & Seeds | Enterobacteriaceae | |
| SYM01180 | 84 | 950 | Rice | Modern | Roots & Seeds | Enterobacteriaceae | |
| SYM01189 | 84 | 958 | Rice | Modern | Roots & Seeds | Enterobacteriaceae | |
| SYM01193 | 84 | 961 | Rice | Modern | Roots & Seeds | Enterobacteriaceae | |
| SYM01226 | 84 | 976 | Rice | Modern | Roots & Seeds | Enterobacteriaceae | |
| SYM01229 | 84 | 978 | Rice | Modern | Roots & Seeds | Enterobacteriaceae | *Pantoea* sp. |
| SYM01230 | 84 | 979 | Rice | Modern | Roots & Seeds | Enterobacteriaceae | |
| SYM00992 | 126 | 856 | *Oryza officinalis* | Wild relative | Surface sterilized seeds | Sphingomonadaceae | *Sphingomonas* sp. |
| SYM00063 | 134 | 559 | Teosinte | Wild relative | Surface sterilized seeds | Microbacteriaceae | *Microbacterium* sp. |
| SYM00226 | 134 | 618 | Soybean | Modern | Leaves | Microbacteriaceae | *Microbacterium* sp. |
| SYM00246 | 134 | 627 | Barley | Modern | Surface sterilized seeds | Microbacteriaceae | *Microbacterium* sp. |
| SYM00524 | 134 | 653 | *Oryza nivara* | Wild relative | Seed surface wash | Microbacteriaceae | *Microbacterium* sp. |
| SYM00694a | 134 | 743 | Rice | Modern | Seed surface wash | Microbacteriaceae | *Microbacterium* sp. |
| SYM01234 | 134 | 983 | *Oryza officinalis* | Wild relative | Roots & Seeds | Microbacteriaceae | *Microbacterium* sp. |
| SYM00199 | 135 | 1448 | Maize | Maize | Roots | Bacillaceae | *Bacillus* sp. |
| SYM00172 | 146 | 592 | Rice | Modern | Surface sterilized seeds | Enterobacteriaceae | *Pantoea* sp. |
| SYM00527 | 146 | 655 | *Oryza nivara* | Wild relative | Seed surface wash | Enterobacteriaceae | *Erwinia* sp. |
| SYM00644 | 146 | 728 | Rice | Modern | Seed surface wash | Enterobacteriaceae | *Erwinia* sp. |
| SYM00648 | 146 | 732 | Rice | Modern | Seed surface wash | Enterobacteriaceae | |
| SYM00966 | 146 | 836 | Rice | Ancient Landrace | Surface sterilized seeds | Enterobacteriaceae | |
| SYM00978 | 146 | 846 | Rice | Ancient Landrace | Surface sterilized seeds | Enterobacteriaceae | |
| SYM00981 | 146 | 848 | Rice | Modern | Surface sterilized seeds | Enterobacteriaceae | |
| SYM01011 | 146 | 870 | Rice | Ancient Landrace | Surface sterilized seeds | Enterobacteriaceae | *Erwinia* sp. |
| SYM01159 | 146 | 938 | *Avena sterilis* | Wild relative | Roots & Seeds | Enterobacteriaceae | |
| SYM01175 | 146 | 945 | Rice | Ancient Landrace | Roots & Seeds | Enterobacteriaceae | |
| SYM01232 | 146 | 981 | Rice | Modern | Roots & Seeds | Enterobacteriaceae | |
| SYM01244 | 146 | 987 | Rice | Ancient Landrace | Roots & Seeds | Enterobacteriaceae | |
| SYM00538A | 172 | 658 | Maize | Ancient Landrace | Seed surface wash | Sphingomonadaceae | *Sphingomonas* sp. |
| SYM00508 | 196 | 646 | Maize | Ancient Landrace | Seed surface wash | Enterobacteriaceae | |

Legend:
For "Source of seed-origin microbe" "Surface sterilized seeds" = seed-origin microbes isolated from seeds that were surface sterilized as described in the Examples;
"Seed surface wash" = microbes derived from the surface of seeds as described in the Examples;
"Roots" = seed-origin microbes isolated from roots of seeds that were germinated in sterile culture;
"Roots & Seeds" = seed-origin microbes isolated from roots and residual seed material that was generated by germinating seeds under sterile conditions;
"Leaves" = seed-origin microbes isolated from shoots and leaves that emerged from seeds that were germinated under sterile conditions.

As used herein, seed-origin endophytes can be obtained from seeds of many distinct plants. In one embodiment, the endophyte can be obtained from the seed of the same or different plant, and can be from the same or different cultivar or variety as the seed onto which it is to be coated. For example, seed endophytes from a particular corn variety can be isolated and coated onto the surface of a corn seed of the same variety. In one particular embodiment, the seed of the first plant that is to be coated with the endophyte can comprise a detectable amount of the same endophyte in the interior of the seed. In another embodiment, the seed of the first plant that is to be coated with the endophyte can comprise a detectable amount of the same endophyte in the exterior of the seed. For example, an uncoated reference seed may contain a detectable amount of the same endophyte within its seed. In yet another embodiment, the endophyte to be coated onto the seed of the plant is a microbe or of a microbial taxa that is detectably present in the interior and exterior of the seed from which the endophyte is derived.

In another embodiment, the endophyte can be obtained from a related species (e.g., an endophyte isolated from *Triticum monococcum* (einkorn wheat) can be coated onto the surface of a *T. aestivum* (common wheat) seed; or, an endophyte from *Hordeum vulgare* (barley) can be isolated and coated onto the seed of a member of the Triticeae family, for example, seeds of the rye plant, *Secale cereale*). In still another embodiment, the endophyte can be isolated from the seed of a plant that is distantly related to the seed onto which the endophyte is to be coated. For example, a tomato-derived endophyte is isolated and coated onto a rice seed.

In some embodiments, the present invention contemplates the use of endophytes that can confer a beneficial agronomic trait upon the seed or resulting plant onto which it is coated. In another embodiment, the seed endophytes useful for the present invention can also be isolated from seeds of plants adapted to a particular environment, including, but not limited to, an environment with water deficiency, salinity, acute and/or chronic heat stress, acute and/or chronic cold stress, nutrient deprived soils including, but not limited to, micronutrient deprived soils, macronutrient (e.g., potassium, phosphate, nitrogen) deprived soils, pathogen stress, including fungal, nematode, insect, viral, bacterial pathogen stress. In one example, the endophyte is isolated from the seed of a plant that grows in a water deficient environment.

The synthetic combination of the present invention contemplates the presence of an endophyte on the surface of the seed of the first plant. In one embodiment, the seed of the first plant is coated with at least 10 CFU of the endophyte per seed, for example, at least 20 CFU, at least 50 CFU, at least 100 CFU, at least 200 CFU, at least 300 CFU, at least 500 CFU, at least 1,000 CFU, at least 3,000 CFU, at least 10,000 CFU, at least 30,000 or more per seed. In another embodiment, the seed is coated with at least 10, for example, at least 20, at least 50, at least 100, at least 200, at least 300, at least 500, at least 1,000, at least 3,000, at least 10,000, at least 30,000, at least 100,000, at least 300,000, at least 1,000,000 or more of the endophyte as detected by the number of copies of a particular endophyte gene detected, for example, by quantitative PCR.

In some cases, the seed-origin endophyte is of monoclonal origin, providing high genetic uniformity of the endophyte population in an agricultural formulation or within a synthetic seed or plant combination with the endophyte.

In some cases, the bacterial endophytes described herein are capable of moving from one tissue type to another. For example, the present invention's detection and isolation of seed-origin endophytes within the mature tissues of cereal plants after coating on the exterior of a seed demonstrates their ability to move from seed exterior into the vegetative tissues of a maturing plant. Therefore, in one embodiment, the population of bacterial endophytes is capable of moving from the seed exterior into the vegetative tissues of a grass plant. In one embodiment, the seed endophyte which is coated onto the seed of a plant is capable, upon germination of the seed into a vegetative state, of localizing to a different tissue of the plant. For example, the endophyte can be capable of localizing to any one of the tissues in the plant, including: the root, adventitious root, seminal root, root hair, shoot, leaf, flower, bud, tassel, meristem, pollen, pistil, ovaries, stamen, fruit, stolon, rhizome, nodule, tuber, trichome, guard cells, hydathode, petal, sepal, glume, rachis, vascular cambium, phloem, and xylem. In one embodiment, the endophyte is capable of localizing to the root and/or the root hair of the plant. In another embodiment, the endophyte is capable of localizing to the photosynthetic tissues, for example, leaves and shoots of the plant. In other cases, the endophyte is localized to the vascular tissues of the plant, for example, in the xylem and phloem. In still another embodiment, the endophyte is capable of localizing to the reproductive tissues (flower, pollen, pistil, ovaries, stamen, fruit) of the plant. In another embodiment, the endophyte is capable of localizing to the root, shoots, leaves and reproductive tissues of the plant. In still another embodiment, the endophyte colonizes a fruit or seed tissue of the plant. In still another embodiment, the endophyte is able to colonize the plant such that it is present in the surface of the plant (i.e., its presence is detectably present on the plant exterior, or the episphere of the plant). In still other embodiments, the endophyte is capable of localizing to substantially all, or all, tissues of the plant. In certain embodiments, the endophyte is not localized to the root of a plant. In other cases, the endophyte is not localized to the photosynthetic tissues of the plant.

In some cases, the bacterial endophytes are capable of replicating within the host grass plant and colonizing the grass plant.

In addition, the bacterial endophytes described herein provide several key significant advantages over other plant-associated microbes.

Different environments can contain significantly different populations of endophytes and thus may provide reservoirs for desired seed-origin endophytes. Once a choice environment is selected, seeds of choice plants to be sampled can be identified by their healthy and/or robust growth, and can then be sampled at least 5 at a time by excavating the entire plants plus small root ball including roots and associated soil and any seeds or fruit present on the plant. The excavated material can be placed in a cool (4° C. environment) for storage, and then extraction of endophytes and DNA can be performed using methods described herein. Identification of choice environments or ecosystems for bioprospecting of plant associated endophytes from either wild plants or crop plants growing in the choice environments or ecosystems follows protocols described herein.

In one embodiment, the endophyte-associated plant is harvested from a soil type different than the normal soil type that the crop plant is grown on, for example from a gelisol (soils with permafrost within 2 m of the surface), for example from a histosol (organic soil), for example from a spodosol (acid forest soils with a subsurface accumulation of metal-humus complexes), for example from an andisol (soils formed in volcanic ash), for example from a oxisol (intensely weathered soils of tropical and subtropical environments), for example from a vertisol (clayey soils with high shrink/swell capacity), for example from an aridisol ($CaCO_3$-containing soils of arid environments with subsurface horizon development), for example from a ultisol (strongly leached soils with a subsurface zone of clay accumulation and <35% base saturation), for example from a mollisol (grassland soils with high base status), for example from an alfisol (moderately leached soils with a subsurface zone of clay accumulation and >35% base saturation), for example from a inceptisol (soils with weakly developed subsurface horizons), or for example from a entisol (soils with little or no morphological development).

In another embodiment, the endophyte-associated plant is harvested from an ecosystem where the agricultural plant is not normally found, for example, a tundra ecosystem as opposed to a temperate agricultural farm, for example from tropical and subtropical moist broadleaf forests (tropical and subtropical, humid), for example from tropical and subtropical dry broadleaf forests (tropical and subtropical, semihumid), for example from tropical and subtropical coniferous forests (tropical and subtropical, semihumid), for example from temperate broadleaf and mixed forests (temperate, humid), for example from temperate coniferous forests (temperate, humid to semihumid), for example from boreal forests/taiga (subarctic, humid), for example from tropical and subtropical grasslands, savannas, and shrublands (tropical and subtropical, semiarid), for example from temperate grasslands, savannas, and shrublands (temperate, semiarid), for example from flooded grasslands and savannas (temperate to tropical, fresh or brackish water inundated), for example from montane grasslands and shrublands (alpine or montane climate), for example from Mediterranean forests, woodlands, and scrub or sclerophyll forests (temperate warm, semihumid to semiarid with winter rainfall), for example from mangrove forests, and for example from deserts and xeric shrublands (temperate to tropical, arid).

In another embodiment, the endophyte-associated plant is harvested from a soil with an average pH range that is different from the optimal soil pH range of the crop plant, for example the plant may be harvested from an ultra acidic soil (<3.5), from an extreme acid soil (3.5-4.4), from a very strong acid soil (4.5-5.0), from a strong acid soil (5.1-5.5), from a moderate acid soil (5.6-6.0), from an slight acid soil (6.1-6.5), from an neutral soil (6.6-7.3), from an slightly alkaline soil (7.4-7.8), from an moderately alkaline soil (7.9-8.4), from a strongly alkaline soil (8.5-9.0), or from an very strongly alkaline soil (>9.0).

In one embodiment, the endophyte-associated plant is harvested from an environment with average air temperatures lower than the normal growing temperature of the crop plant, for example 2-5° C. colder than average, for example, at least 5-10° C. colder, at least 10-15° C. colder, at least at least 15-20° C. colder, at least 20-25° C. colder, at least 25-30° C. colder, at least 30-35° C. colder, at least 35-40° C. colder, at least 40-45° C. colder, at least 45-50° C. colder, at least 50-55° C. colder or more, when compared with crop plants grown under normal conditions during an average growing season.

In one embodiment, the endophyte-associated plant is harvested from an environment with average air temperatures higher than the normal growing temperature of the crop plant, for example 2-5° C. hotter than average, for example, at least 5-10° C. hotter, at least 10-15° C. hotter, at least at least 15-20° C. hotter, at least 20-25° C. hotter, at least 25-30° C. hotter, at least 30-35° C. hotter, at least 35-40° C. hotter, at least 40-45° C. hotter, at least 45-50° C. hotter, at least 50-55° C. hotter or more, when compared with crop plants grown under normal conditions during an average growing season.

In another embodiment, the endophyte-associated plant is harvested from an environment with average rainfall lower than the optimal average rainfall received by the crop plant, for example 2-5% less rainfall than average, for example, at least 5-10% less rainfall, at least 10-15% less rainfall, at least 15-20% less rainfall, at least 20-25% less rainfall, at least 25-30% less rainfall, at least 30-35% less rainfall, at least 35-40% less rainfall, at least 40-45% less rainfall, at least 45-50% less rainfall, at least 50-55% less rainfall, at least 55-60% less rainfall, at least 60-65% less rainfall, at least 65-70% less rainfall, at least 70-75% less rainfall, at least 80-85% less rainfall, at least 85-90% less rainfall, at least 90-95% less rainfall, or less, when compared with crop plants grown under normal conditions during an average growing season.

In one embodiment, the endophyte-associated plant is harvested from an environment with average rainfall higher than the optimal average rainfall of the crop plant, for example 2-5% more rainfall than average, for example, at least 5-10% more rainfall, at least 10-15% more rainfall, at least 15-20% more rainfall, at least 20-25% more rainfall, at least 25-30% more rainfall, at least 30-35% more rainfall, at least 35-40% more rainfall, at least 40-45% more rainfall, at least 45-50% more rainfall, at least 50-55% more rainfall, at least 55-60% more rainfall, at least 60-65% more rainfall, at least 65-70% more rainfall, at least 70-75% more rainfall, at least 80-85% more rainfall, at least 85-90% more rainfall, at least 90-95% more rainfall, at least 95-100% more rainfall, or even greater than 100% more rainfall, or even greater than 200% more rainfall, or even greater than 300% more rainfall, or even greater than 400% more rainfall, or even greater than 500% more rainfall, when compared with crop plants grown under normal conditions during an average growing season.

In another embodiment, the endophyte-associated plant is harvested from a soil type with different soil moisture classification than the normal soil type that the crop plant is grown on, for example from an aquic soil (soil is saturated with water and virtually free of gaseous oxygen for sufficient periods of time, such that there is evidence of poor aeration), for example from an udic soil (soil moisture is sufficiently high year-round in most years to meet plant requirement), for example from an ustic soil (soil moisture is intermediate between udic and aridic regimes; generally, plant-available moisture during the growing season, but severe periods of drought may occur), for example from an aridic soil (soil is dry for at least half of the growing season and moist for less than 90 consecutive days), for example from a xeric soil (soil moisture regime is found in Mediterranean-type climates, with cool, moist winters and warm, dry summers).

In one embodiment, the endophyte-associated plant is harvested from an environment with average rainfall lower than the optimal average rainfall of the crop plant, for example 2-95% less rainfall than average, for example, at least 5-90% less rainfall, at least 10-85% less rainfall, at least 15-80% less rainfall, at least 20-75% less rainfall, at least 25-70% less rainfall, at least 30-65% less rainfall, at least 35-60% less rainfall, at least 40-55% less rainfall, at least 45-50% less rainfall, when compared with crop plants grown under normal conditions during an average growing season.

In one embodiment, the endophyte-associated plant is harvested from an environment with average rainfall higher than the optimal average rainfall of the crop plant, for example 2-5% more rainfall than average, for example, at least 5-10% more rainfall, at least 10-15% more rainfall, at least 15-20% more rainfall, at least 20-25% more rainfall, at least 25-30% more rainfall, at least 30-35% more rainfall, at least 35-40% more rainfall, at least 40-45% more rainfall, at least 45-50% more rainfall, at least 50-55% more rainfall, at least 55-60% more rainfall, at least 60-65% more rainfall, at least 65-70% more rainfall, at least 70-75% more rainfall, at least 80-85% more rainfall, at least 85-90% more rainfall, at least 90-95% more rainfall, at least 95-100% more rainfall, or even greater than 100% more rainfall, or even greater than 200% more rainfall, or even greater than 300% more rainfall, or even greater than 400% more rainfall, or even greater than 500% more rainfall, when compared with crop plants grown under normal conditions during an average growing season.

In another embodiment, the endophyte-associated plant is harvested from an agricultural environment with a crop yield lower than the average crop yield expected from the crop plant grown under average cultivation practices on normal agricultural land, for example 2-5% lower yield than average, for example, at least 5-10% lower yield, at least 10-15% lower yield, at least 15-20% lower yield, at least 20-25% lower yield, at least 25-30% lower yield, at least 30-35% lower yield, at least 35-40% lower yield, at least 40-45% lower yield, at least 45-50% lower yield, at least 50-55% lower yield, at least 55-60% lower yield, at least 60-65% lower yield, at least 65-70% lower yield, at least 70-75% lower yield, at least 80-85% lower yield, at least 85-90% lower yield, at least 90-95% lower yield, or less, when compared with crop plants grown under normal conditions during an average growing season.

In a related embodiment, the endophyte-associated plant is harvested from an agricultural environment with a crop yield lower than the average crop yield expected from the crop plant grown under average cultivation practices on normal agricultural land, for example 2-95% lower yield than average, for example, at least 5-90% lower yield, at least 10-85% lower yield, at least 15-80% lower yield, at least 20-75% lower yield, at least 25-70% lower yield, at least 30-65% lower yield, at least 35-60% lower yield, at least 40-55% lower yield, at least 45-50% lower yield, when compared with crop plants grown under normal conditions during an average growing season.

In one embodiment, the endophyte-associated plant is harvested from an environment with average crop yield higher than the optimal average crop yield of the crop plant, for example 2-5% more yield than average, for example, at least 5-10% more yield, at least 10-15% more yield, at least 15-20% more yield, at least 20-25% more yield, at least 25-30% more yield, at least 30-35% more yield, at least 35-40% more yield, at least 40-45% more yield, at least 45-50% more yield, at least 50-55% more yield, at least 55-60% more yield, at least 60-65% more yield, at least 65-70% more yield, at least 70-75% more yield, at least 80-85% more yield, at least 85-90% more yield, at least 90-95% more yield, at least 95-100% more yield, or even greater than 100% more yield, or even greater than 200% more yield, or even greater than 300% more yield, or even greater than 400% more yield, or even greater than 500% more yield, when compared with crop plants grown under normal conditions during an average growing season.

In a related embodiment, the endophyte-associated plant is harvested from an environment with average crop yield higher than the optimal average crop yield of the crop plant, 2-500% more yield than average, 2-400% more yield than average, 2-300% more yield than average, 2-200% more yield than average, 2-95% more yield than average, for example, at least 5-90% more yield, at least 10-85% more yield, at least 15-80% more yield, at least 20-75% more yield, at least 25-70% more yield, at least 30-65% more yield, at least 35-60% more yield, at least 40-55% more yield, at least 45-50% more yield, when compared with crop plants grown under normal conditions during an average growing season.

In another embodiment, the endophyte-associated plant is harvested from an environment where soil contains lower total nitrogen than the optimum levels recommended in order to achieve average crop yields for a plant grown under average cultivation practices on normal agricultural land, for example 2-5% less nitrogen than average, for example, at least 5-10% less nitrogen, at least 10-15% less nitrogen, at least 15-20% less nitrogen, at least 20-25% less nitrogen, at least 25-30% less nitrogen, at least 30-35% less nitrogen, at least 35-40% less nitrogen, at least 40-45% less nitrogen, at least 45-50% less nitrogen, at least 50-55% less nitrogen, at least 55-60% less nitrogen, at least 60-65% less nitrogen, at least 65-70% less nitrogen, at least 70-75% less nitrogen, at least 80-85% less nitrogen, at least 85-90% less nitrogen, at least 90-95% less nitrogen, or less, when compared with crop plants grown under normal conditions during an average growing season.

In another embodiment, the endophyte-associated plant is harvested from an environment where soil contains higher total nitrogen than the optimum levels recommended in order to achieve average crop yields for a plant grown under average cultivation practices on normal agricultural land, for example 2-5% more nitrogen than average, for example, at least 5-10% more nitrogen, at least 10-15% more nitrogen, at least 15-20% more nitrogen, at least 20-25% more nitrogen, at least 25-30% more nitrogen, at least 30-35% more nitrogen, at least 35-40% more nitrogen, at least 40-45% more nitrogen, at least 45-50% more nitrogen, at least 50-55% more nitrogen, at least 55-60% more nitrogen, at least 60-65% more nitrogen, at least 65-70% more nitrogen, at least 70-75% more nitrogen, at least 80-85% more nitrogen, at least 85-90% more nitrogen, at least 90-95% more nitrogen, at least 95-100% more nitrogen, or even greater than 100% more nitrogen, or even greater than 200% more nitrogen, or even greater than 300% more nitrogen, or even greater than 400% more nitrogen, or even greater than 500% more nitrogen, when compared with crop plants grown under normal conditions during an average growing season.

In another embodiment, the endophyte-associated plant is harvested from an environment where soil contains lower total phosphorus than the optimum levels recommended in order to achieve average crop yields for a plant grown under average cultivation practices on normal agricultural land, for example 2-5% less phosphorus than average, for example, at least 5-10% less phosphorus, at least 10-15% less phosphorus, at least 15-20% less phosphorus, at least 20-25% less phosphorus, at least 25-30% less phosphorus, at least 30-35% less phosphorus, at least 35-40% less phosphorus, at least 40-45% less phosphorus, at least 45-50% less phosphorus, at least 50-55% less phosphorus, at least 55-60% less phosphorus, at least 60-65% less phosphorus, at least 65-70% less phosphorus, at least 70-75% less phosphorus, at least 80-85% less phosphorus, at least 85-90% less phosphorus, at least 90-95% less phosphorus, or less, when compared with crop plants grown under normal conditions during an average growing season.

In another embodiment, the endophyte-associated plant is harvested from an environment where soil contains higher total phosphorus than the optimum levels recommended in order to achieve average crop yields for a plant grown under average cultivation practices on normal agricultural land, for example 2-5% more phosphorus than average, for example, at least 5-10% more phosphorus, at least 10-15% more phosphorus, at least 15-20% more phosphorus, at least 20-25% more phosphorus, at least 25-30% more phosphorus, at least 30-35% more phosphorus, at least 35-40% more phosphorus, at least 40-45% more phosphorus, at least 45-50% more phosphorus, at least 50-55% more phosphorus, at least 55-60% more phosphorus, at least 60-65% more phosphorus, at least 65-70% more phosphorus, at least 70-75% more phosphorus, at least 80-85% more phosphorus, at least 85-90% more phosphorus, at least 90-95% more phosphorus, at least 95-100% more phosphorus, or even greater than 100% more phosphorus, or even greater than 200% more phosphorus, or even greater than 300% more phosphorus, or even greater than 400% more phosphorus, or even greater than 500% more phosphorus, when compared with crop plants grown under normal conditions during an average growing season.

In another embodiment, the endophyte-associated plant is harvested from an environment where soil contains lower total potassium than the optimum levels recommended in order to achieve average crop yields for a plant grown under average cultivation practices on normal agricultural land, for example 2-5% less potassium than average, for example, at least 5-10% less potassium, at least 10-15% less potassium, at least 15-20% less potassium, at least 20-25% less potassium, at least 25-30% less potassium, at least 30-35% less potassium, at least 35-40% less potassium, at least 40-45% less potassium, at least 45-50% less potassium, at least 50-55% less potassium, at least 55-60% less potassium, at least 60-65% less potassium, at least 65-70% less potassium, at least 70-75% less potassium, at least 80-85% less potassium, at least 85-90% less potassium, at least 90-95% less potassium, or less, when compared with crop plants grown under normal conditions during an average growing season.

In another embodiment, the endophyte-associated plant is harvested from an environment where soil contains higher total potassium than the optimum levels recommended in order to achieve average crop yields for a plant grown under average cultivation practices on normal agricultural land, for example 2-5% more potassium than average, for example, at least 5-10% more potassium, at least 10-15% more potassium, at least 15-20% more potassium, at least 20-25% more potassium, at least 25-30% more potassium, at least 30-35% more potassium, at least 35-40% more potassium, at least 40-45% more potassium, at least 45-50% more potassium, at least 50-55% more potassium, at least 55-60% more potassium, at least 60-65% more potassium, at least 65-70% more potassium, at least 70-75% more potassium, at least 80-85% more potassium, at least 85-90% more potassium, at least 90-95% more potassium, at least 95-100% more potassium, or even greater than 100% more potassium, or even greater than 200% more potassium, or even greater than 300% more potassium, or even greater than 400% more potassium, or even greater than 500% more potassium, when compared with crop plants grown under normal conditions during an average growing season.

In another embodiment, the endophyte-associated plant is harvested from an environment where soil contains lower total sulfur than the optimum levels recommended in order to achieve average crop yields for a plant grown under average cultivation practices on normal agricultural land, for example 2-5% less sulfur than average, for example, at least 5-10% less sulfur, at least 10-15% less sulfur, at least 15-20% less sulfur, at least 20-25% less sulfur, at least 25-30% less sulfur, at least 30-35% less sulfur, at least 35-40% less sulfur, at least 40-45% less sulfur, at least 45-50% less sulfur, at least 50-55% less sulfur, at least 55-60% less sulfur, at least 60-65% less sulfur, at least 65-70% less sulfur, at least 70-75% less sulfur, at least 80-85% less sulfur, at least 85-90% less sulfur, at least 90-95% less sulfur, or less, when compared with crop plants grown under normal conditions during an average growing season.

In another embodiment, the endophyte-associated plant is harvested from an environment where soil contains higher total sulfur than the optimum levels recommended in order to achieve average crop yields for a plant grown under average cultivation practices on normal agricultural land, for example 2-5% more sulfur than average, for example, at least 5-10% more sulfur, at least 10-15% more sulfur, at least 15-20% more sulfur, at least 20-25% more sulfur, at least 25-30% more sulfur, at least 30-35% more sulfur, at least 35-40% more sulfur, at least 40-45% more sulfur, at least 45-50% more sulfur, at least 50-55% more sulfur, at least 55-60% more sulfur, at least 60-65% more sulfur, at least 65-70% more sulfur, at least 70-75% more sulfur, at least 80-85% more sulfur, at least 85-90% more sulfur, at least 90-95% more sulfur, at least 95-100% more sulfur, or even greater than 100% more sulfur, or even greater than 200% more sulfur, or even greater than 300% more sulfur, or even greater than 400% more sulfur, or even greater than 500% more sulfur, when compared with crop plants grown under normal conditions during an average growing season.

In another embodiment, the endophyte-associated plant is harvested from an environment where soil contains lower total calcium than the optimum levels recommended in order to achieve average crop yields for a plant grown under average cultivation practices on normal agricultural land, for example 2-5% less calcium than average, for example, at least 5-10% less calcium, at least 10-15% less calcium, at least 15-20% less calcium, at least 20-25% less calcium, at least 25-30% less calcium, at least 30-35% less calcium, at least 35-40% less calcium, at least 40-45% less calcium, at least 45-50% less calcium, at least 50-55% less calcium, at least 55-60% less calcium, at least 60-65% less calcium, at least 65-70% less calcium, at least 70-75% less calcium, at least 80-85% less calcium, at least 85-90% less calcium, at least 90-95% less calcium, or less, when compared with crop plants grown under normal conditions during an average growing season.

In another embodiment, the endophyte-associated plant is harvested from an environment where soil contains lower total magnesium than the optimum levels recommended in order to achieve average crop yields for a plant grown under average cultivation practices on normal agricultural land, for example 2-5% less magnesium than average, for example, at least 5-10% less magnesium, at least 10-15% less magnesium, at least 15-20% less magnesium, at least 20-25% less magnesium, at least 25-30% less magnesium, at least 30-35% less magnesium, at least 35-40% less magnesium, at least 40-45% less magnesium, at least 45-50% less magnesium, at least 50-55% less magnesium, at least 55-60% less magnesium, at least 60-65% less magnesium, at least 65-70% less magnesium, at least 70-75% less magnesium, at least 80-85% less magnesium, at least 85-90% less magnesium, at least 90-95% less magnesium, or less, when compared with crop plants grown under normal conditions during an average growing season.

In another embodiment, the endophyte-associated plant is harvested from an environment where soil contains higher total sodium chloride (salt) than the optimum levels recommended in order to achieve average crop yields for a plant grown under average cultivation practices on normal agricultural land, for example 2-5% more salt than average, for example, at least 5-10% more salt, at least 10-15% more salt, at least 15-20% more salt, at least 20-25% more salt, at least 25-30% more salt, at least 30-35% more salt, at least 35-40% more salt, at least 40-45% more salt, at least 45-50% more salt, at least 50-55% more salt, at least 55-60% more salt, at least 60-65% more salt, at least 65-70% more salt, at least 70-75% more salt, at least 80-85% more salt, at least 85-90% more salt, at least 90-95% more salt, at least 95-100% more salt, or even greater than 100% more salt, or even greater than 200% more salt, or even greater than 300% more salt, or even greater than 400% more salt, or even greater than 500% more salt, when compared with crop plants grown under normal conditions during an average growing season.

Plants Useful for the Present Invention

In some embodiments, a bacterial endophyte of seed-origin can be introduced into an agricultural grass plant, i.e., a plant of the family Graminae (grasses). The grass plants into which the bacterial endophyte of seed-origin can be introduced may be any of the useful grasses belonging to the genera *Agropyron, Agrostis, Andropogon, Anthoxanthum, Arrhenatherum, Avena, Brachypodium, Bromus, Chloris, Cynodon, Dactylis, Elymus, Eragrostis, Festuca, Glyceria, Hierochloe, Hordeum, Lolium, Oryza, Panicum, Paspalum, Phalaris, Phleum, Poa, Setaria, Sorghum, Triticum, Zea* and *Zoysia*.

In another embodiment, the target plant is selected from the wheats, including, *Triticum monococcum, Triticum durum, Triticum turgidum, Triticum timopheevi* (Timopheevs Wheat) and *Triticum aestivum* (Bread Wheat).

In another embodiment, the target plant is a corn of the genus *Zea. Zea* is a genus of the family Graminae (Poaceae), commonly known as the grass family. The genus consists of some four species: *Zea mays*, cultivated corn and teosinte; *Zea diploperennis* Iltis et at., diploperennial teosinte; *Zea luxurians* (Durieu et Asch.) Bird; and *Zea perennis* (Hitchc.) Reeves et Mangelsd., perennial teosinte.

Accordingly, in one embodiment, the plant is selected from the group of Graminae (grasses), including grasses of the genera *Agropyron, Agrostis, Andropogon, Anthoxanthum, Arrhenatherum, Avena, Brachypodium, Bromus, Chloris, Cynodon, Dactylis, Elymus, Eragrostis, Festuca, Glyceria, Hierochloe, Hordeum*, including *Hordeum vulgare* L., *Hordeum distichon* L., and *Hordeum irregulare, Lolium, Oryza, Panicum, Paspalum, Phalaris, Phleum, Poa, Setaria, Sorghum, Triticum, Zea*, especially *Zea mays*, cultivated corn and teosinte, *Zea diploperennis* Iltis et at., diploperennial teosinte, *Zea luxurians* (Durieu et Asch.) Bird; and *Zea perennis* (Hitchc.) Reeves et Mangelsd., perennial teosinte, and *Zoysia*; wheats, including *Triticum monococcum, Triticum turgidum, Triticum timopheevi* (Timopheevs Wheat) and *Triticum aestivum* (Bread Wheat); rye grasses and bluegrasses, especially Kentucky bluegrass, Canada bluegrass, rough meadow grass, bulbous meadow grass, alpine meadow grass, wavy meadow grass, wood meadow grass, Balforth meadow grass, swamp meadow grass, broad leaf meadow grass, narrow leaf meadow grass, smooth meadow grass, spreading meadow grass and flattened meadow grass.

Commercial cultivars of agricultural plants can be used in the methods and compositions as described herein. Non-limiting examples of commercial cultivars are provided below.

Maize

Exemplary *Zea* cultivars provided herein include 39V07, 38H03AM1, P9675, P9675YXR, P9630AM1, P9990AM1, P9917, P9917AM1, P9910AM1, P9910AMRW, P9910AMX, P9910XR, P0062AMX, P0062XR, P0193AM, P0193HR, P0216HR, P0210HR, 36V51, 36V52, 36V53, 36V59, P0313AM1, P0313XR, P0463AM1, P0461AMX, P0461EXR, P0461XR, P0453AM, P0453HR, P0448, P0448AMRW, P0448AMX, P0448E, P0448EHR, P0448R, P0413AM1, P0413E, P0407AMXT, P0533AM1, P0533EXR, P0528AMX, P0528YXR, 35F40, P0652AMX, P0636AM1, P0636HR, P0621HR, P0621R, P0717HR, P0832AM1, P0832E, P0832EXR, P0832XR, 34F29, P0993AM1, P0993HR, P0993XR, P0987AM1, P0987HR, P0916EHR, 34R6, 7P1023AM-R, P1018EHR, P1018HR, 34F06, 34F07, P1184, P1162AM1, P1162AMRW-R, P1162AMX-R, P1162EXR, P1162XR, P1151 AM, P1151AM1, P1151R, P1142AMX, 33W80, 33W82, 33W84, 33W88AM1, P1281HR, P1253E, P1248AM, P1221AMX, P1221AMXT, P1215AM1, P1395, P1395AM1, P1395HR, P1395R, P1376XR, P1365AMX, P1360CHR, P1360HR, P1339AM1, P1324HR, 33Z74, 33T56, 33T57, 33M16, P1498, P1498AM, P1498HR, P1498R, P1480HR, P1477WHR, P1431W, P1431WR, P1420HR, 33G61, 33F12, P1555CHR, 33D42, 33D46, 33D49, P1659W, P1659WHR, 32D78, P1745HR, 32B16, P1995W, and P2088HR from Pioneer Hi-Bred, which are grown in geographical entities including Iowa. Exemplary *Zea* cultivars provided herein include P0115AM1, P0392AMX, P0496AMX, P0432AM1, P0413AM1, P0413AMRW, P0413E, P0413R, P0533AM1, P0636AM1, P0636YXR, 35K01, 35K02, 35K08, 35K09AM1, 35K10AMRW, 34M78, P0858AMX, P0832AMRW, P0832AMX, P0832E, P0832EXR, P0832R, P0993AM1, P0993HR, P0987AM1, P0987YXR, P0945YXR, P0916EHR, 34R65, P1023AM-R, P1023AMX-R, P1018AM, P1018AM1, P1018AMX, P1018E, P1018R, P1184, P1184AM, P1184AM1, P1184AMRW, P1184R, P1162AM1, P1162AMRW-R, P1162AMX-R, P1162EXR, P1151AM, P1151AM1, 34P91, P1292AMX, P1241AMX, P1221AMX, P1221AMXT, P1215AM1, P1395AM1, P1395AMRW, P1376XR, P1360CHR, P1360HR, P1352AMX, P1339AM1, P1319, P1319AM1, P1319HR, 33T55, 33T56, P1498, P1498AM, P1498CHR, P1498HR, P1498R, P1477W, P1477WHR, P1449XR, P1431W, P1431WR, 33F12, 33D42, P1690HR, P1659W, 32B09, 32B10, 32B16, P1995W, P1995WR, and P2088AM from Pioneer Hi-Bred, which are grown in geographical entities including Illinois.

Exemplary *Zea* cultivars provided herein include P8917XR, P9690AM, P9690HR, P0125R, P0231HR, P0365YHR, P0302CHR, P0474AM1, P0461EXR, P0591AM1, P0541AM1, P0541HR, 35F37, 35F38, 35F48AM1, 35F50AM, P0636AM1, P0636HR, P0636YXR, P0621HR, 35K01, P0876AM, P0876CHR, P0876HR, P0987, P0987AM, P0987AM1, P0987HR, P0987R, P0987YXR, P0916EHR, P0902AM1, P1023AM-R, P1023AMX-R, P1018EHR, P1173AM, P1173CHR, P1173HR, P1173R, P1151AM, P1151AM1, P1151HR, P1151R, P1151YXR, P1105YHR, P1292ER, P1266YHR, P1395AM, P1395AM1, P1395R, P1376XR, P1360HR, P1324HR, P1498AM, P1498AM1, P1498HR, P1498R, P1477W, P1477WHR, P1449XR, P1431W, 33G60, 33G61, 33F12, P1508CHR, 32T16, 33D42, 33D46, 33D47, 33D49, 33D53AM-R, 32T82, 32T84, P1690AM, P1690CHR, P1690HR, P1659W, P1659WHR, P1625CHR, P1625HR, P1768AMX, 32N74AM1, 32B09, 32B10, 32B11, 32B16, P1995W, P1995WR, 31G67AM1, 31G71, P2088AM, P2088YHR, and P2088YXR from Pioneer Hi-Bred, which are grown in geographical entities including Nebraska.

Exemplary *Zea* cultivars provided herein include P9690HR, P0115AM1, P0216HR, P0448E, P0432AM1, P0413AM1, P0413E, P0636AM1, P0636HR, P0636YHR, P0621HR, 35K01, 35K02, 35K08, 35K09AM1, 35K10AMRW, 34M78, P0858AMX, P0832AMX, P0832E, P0832R, P0993AM1, P0993HR, P0987, P0987AM, P0987AM1, P0987HR, P0987YXR, P0945YXR, P0916EHR, P1023AM-R, P1023AMX-R, P1018AM, P1018AM1, P1018AMX, P1018E, P1018R, P1184, P1184AM, P1184AM1, P1184R, P1162AM1, P1162AMRW-R, P1162AMX-R, P1151AM, P1151AM1, P1105YHR, 34P91, P1253E, P1221AMX, P1221AMXT, P1395, P1395AMRW, P1395HR, P1395R, P1376XR, P1360AM, P1360HR, P1352AMX, P1339AM1, P1319, P1319AM1, P1319HR, 33T54, 33T55, 33T56, 33T57, 33N58, P1498, P1498AM, P1498CHR, P1498HR, P1498R, P1477W, P1477WHR, P1449XR, P1431W, P1431WR, 33G60, 33F12, P1659W, P1659WHR, P1646YHR, P1636AM, P1636YHR, P1602YHR, 32D78, 32D79, P1745HR, 32B09, 32B10, 32B16, P1995W, P1995WR, 31P41, and P2088AM from Pioneer Hi-Bred, which are grown in geographical entities including Indiana.

Exemplary *Zea* cultivars provided herein include Gentry® SmartStax® RIB Complete®, including DKC48-12RIB Brand, DKC49-29RIB Brand, DKC53-56RIB Brand, DKC62-08RIB Brand, DKC63-33RIB Brand; DEKALB® Genuity® DroughtGard™ Hybrids, including DKC47-27RIB Brand, DKC50-57RIB Brand, DKC51-20RIB Brand, DKC63-55RIB Brand, DKC65-81RIB Brand; <89 Relative Maturity, including DKC31-10RIB Brand, DKC32-92RIB Brand, DKC33-78RIB Brand, DKC38-03RIB Brand, DKC39-07RIB Brand; 90-99 Relative Maturity, including DKC43-10RIB Brand, DKC44-13RIB Brand, DKC46-20RIB Brand, DKC48-12RIB Brand, DKC49-29RIB Brand; 101-103 Relative Maturity, including DKC51-20RIB Brand, DKC52-30RIB Brand, DKC53-56RIB Brand, DKC53-58RIB Brand, DKC53-78RIB Brand; 104-108 Relative Maturity, including DKC54-38RIB Brand, DKC57-75RIB Brand, DKC57-92RIB Brand, DKC58-87RIB Brand, DKC58-89RIB Brand; 110-111 Relative Maturity, including DKC60-63RIB Brand, DKC60-67RIB Brand, DKC61-16RIB Brand, DKC61-88RIB Brand, DKC61-89RIB Brand; 112-113 Relative Maturity, including DKC62-08RIB Brand, DKC62-97RIB Brand, DKC63-07RIB Brand, DKC63-33RIB Brand, DKC63-55RIB Brand; 114-116 Relative Maturity, including DKC64-69RIB Brand, DKC64-87RIB Brand, DKC65-19RIB Brand, DKC65-79RIB Brand, DKC66-40RIB Brand; 117+Relative Maturity, including DKC67-57RIB Brand, DKC67-58RIB Brand, DKC67-88RIB Brand, DKC68-05 Brand, and DKC69-29 Brand from DEKALB®, which are grown in geographical entities including the United States.

Wheat

Exemplary *Triticum* cultivars provided herein include Everest, TAM 111, Armour, TAM 112, Fuller, Duster, T158, Postrock, Endurance, Jagger, Winter Hawk, Art, Overley, Jagalene, Jackpot, Hatcher, Santa Fe, Danby, Billings, T81, TAM 110, AP503 CL2, Aspen, 2137, TAM 113, Hitch, TAM 101, CJ, Centerfield, SY Gold, and Above, which are grown in geographical entities including Kansas.

Exemplary *Triticum* cultivars provided herein include Barlow, Glenn, SY Scren, Faller, Prosper, Kelby, Brennan, RB07, Vantage, WB Mayville, Freyr, Jenna, Mott, Select, Steele-ND, Briggs, Howard, Reeder, Alsen, Rollag, Divide, Alkabo, Mountrail, Tioga, Lebsock, Grenora, Dilse, Ben, DG Max, Pierce, Monroe, DG Star, Jerry, Decade, Hawken, Wesley, Overland, CDC Falcon, SY Wolf, Harding, Darrell, WB Matlock, Millennium, and Boomer, which are grown in geographical entities including N. Dakota.

Exemplary *Triticum* cultivars provided herein include Yellowstone, Genou, CDC Falcon, Rampart, Ledger, Jerry, AP503 CL2, Hawken, Norris, Pryor, Jagalene, Carter, Morgan, Decade, WB Quake, Tiber, Willow Creek, Radiant, Neeley, Vanguard, Promontory, Overland, and Redwin, which are grown in geographical entities including Montana.

Exemplary *Triticum* cultivars provided herein include Duster, Endurance, Jagger, Fuller, O K Bullet, Jackpot, Everest, Billings, TAM 112, TAM 111, Big Max, Overley, Doans, Armour, Santa Fe, Garrison, Deliver, TAM 110, CJ, 2157, Custer, 2137, Scout, Centerfield, Triumph varieties, Dumas, TAM 401, Gallagher, Cutter, T-158, Ike, WB Hitch, Greer, AP 503 CL2, Ruby Lee, Pioneer 2548, Pioneer 2571, and Coker 762, which are grown in geographical entities including Oklahoma.

Exemplary *Triticum* cultivars provided herein include UI Stone, Diva, Petit, Jubilee, Louise, Alturas, Whit, Babe, Cataldo, Alpowa, BrundageCF, Brundage96, Bitterroot, Kaseberg, Amber, Bruneau, AP Legacy, Salute, Ladd, Junction, ORCF101, Mary, Masami, SY Ovation, Skiles, Rod, WB523, Legion, Eltan, WB528, Stephens, Otto, ORCF103, Rosalyn, Madsen, AP Badger, LCS Artdeco, ORCF102, Lambert, Goetze, WB456, WB1020M, AP700CL, Xerpha, Tubbs06, WB1066CL, Eddy, Finley, Juniper, Whetstone, Sprinterl, Paladin, DW, Buchanan, Farnum, Northwest 553, Peregrine, Rimrock, Declo, Esperia, Boundary, Bauermeister, Residence, Symphony, and Estica, which are grown in geographical entities including Washington state.

Exemplary *Triticum* cultivars provided herein include Wesley, Overland, Expedition, Clearfield, Smoky Hill, Arapahoe, Lyman, Hawken, Millennium, Jagalene, CDC Falcon, Alliance, Nekota, Briggs, RB07, Brick, Faller, Howard, Select, Traverse, Steele N D, Forge, Barlow, Butte86/Butte, Granger, Brennan, which are grown in geographical entities including South Dakota.

Barley

Exemplary barley cultivars provided herein include Azure, Beacon, Bere, Betzes, Bowman, Celebration, Centennial, Compana, Conlon, Diamant, Dickson, Drummond, Excel, Foster, Glenn, Golden Promise, Hazen, Highland barley, Kindred, Kindred L, Larker, Logan, Lux, Manchurian, Manscheuri, Mansury, Maris Otter, Morex, Nordal, Nordic, Optic, Park, Plumage Archer, Pearl, Pinnacle, Proctor, Pioneer, Rawson, Robust, Sioux, Stark, Tradition, Traill, Tregal, Trophy, Windich, and Yagan, which are grown throughout the world.

Exemplary barley cultivars provided herein include Tradition, Lacey, Robust, Celebration, Conlon, Pinnacle, Haybet, Legacy, Stellar-D, Innovation, Hays, Quest, Bowman, and Logan, which are grown in geographical entities including North Dakota.

Exemplary barley cultivars provided herein include AC METCALFE, HARRINGTON, CONRAD (B5057), LEGACY (B2978), MORAVIAN 69 (C69), MERIT (B4947), TRADITION (B2482), MORAVIAN 83 (C83), and CHARLES, which are grown in geographical entities including Idaho.

Exemplary barley cultivars provided herein include Harrington, Haybet, B 1202, Moravian, Baronesse, Hector, Bowman, Westford, B Merit, Gallatin, Horsford, Lewis, Stark, Piroline, Valier, B 2601, Legacy, Menuet, Robust, Chinook, and Clark, which are grown in geographical entities including Montana.

Exemplary barley cultivars provided herein include Champion, Bob, Baronesse, Radiant, Haybet, Belford, Camelot, BG, Camas, Gallatin, Copeland, AC Metcalfe, and Harrington, which are grown in geographical entities including Washington state.

Exemplary barley cultivars provided herein include Moravian 69, C-115, C-128, Scarlett, Baronesse, Hays, and Steptoe, which are grown in geographical entities including Colorado.

Transgenic Plants

The methods described herein can also be used with transgenic plants containing one or more exogenous transgenes, for example, to yield additional trait benefits conferred by the newly introduced endophytic microbes. Therefore, in one embodiment, a seed or seedling of a transgenic maize, wheat, rice, or barley plant is contacted with an endophytic microbe.

Methods of Using Seed-Origin Bacterial Endophytes

As described herein, purified bacterial populations that include one or more seed-origin bacterial endophytes and compositions containing the same (e.g., agricultural formulations) can be used to confer beneficial traits to the host plant including, for example, one or more of the following: increased root biomass, increased root length, increased height, increased shoot length, increased leaf number, increased water use efficiency, increased overall biomass, increase grain yield, increased photosynthesis rate, increased tolerance to drought, increased heat tolerance, increased salt tolerance, increased resistance to nematode stress, increased resistance to a fungal pathogen, increased resistance to a bacterial pathogen, increased resistance to a viral pathogen, a detectable modulation in the level of a metabolite, and a detectable modulation in the proteome relative to a reference plant. For example, in some embodiments, a purified bacterial population that includes a seed-origin bacterial endophyte can improve two or more such beneficial traits, e.g., water use efficiency and increased tolerance to drought. Such traits can be heritable by progeny of the agricultural plant to which the seed-origin bacterial endophyte was applied or by progeny of the agricultural plant that was grown from the seed associated with the seed-origin bacterial endophyte, In some cases, the seed-origin bacterial endophyte may produce one or more compounds and/or have one or more activities that are beneficial to the plant, e.g., one or more of the following: production of a metabolite, production of a phytohormone such as auxin, production of acetoin, production of an antimicrobial compound, production of a siderophore, production of a cellulase, production of a pectinase, production of a chitinase, production of a xylanase, nitrogen fixation, or mineral phosphate solubilization, For example, a seed-origin bacterial endophyte can producea phytohormone selected from the group consisting of an auxin, a cytokinin, a gibberellin, ethylene, a brassinosteroid, and abscisic acid. In one particular embodiment, the seed-origin bacterial endophyte produces auxin (e.g., indole-3-acetic acid (IAA)). Production of auxin can be assayed as described herein. Many of the microbes described herein are capable of producing the plant hormone auxin indole-3-acetic acid (IAA) when grown in culture. Auxin plays a key role in altering the physiology of the plant, including the extent of root growth. Therefore, in another embodiment, the bacterial endophytic population is disposed on the surface or within a tissue of the seed or seedling in an amount effective to detectably induce production of auxin in the agricultural plant. For example, the increase in auxin production can be at least 10%, for example, at least 20%, at least 30%, at least 40%, at least 50%, at least 60%, at least 75%, at least 100%, or more, when compared with a reference agricultural plant. In one embodiment, the increased auxin production can be detected in a tissue type selected from the group consisting of the root, shoot, leaves, and flowers.

In some embodiments, the seed-origin bacterial endophyte can produce a compound with antimicrobial properties. For example, the compound can have antibacterial properties, as determined by the growth assays provided herein. In one embodiment, the compound with antibacterial properties shows bacteriostatic or bactericidal activity against *E. coli* and/or *Bacillus* sp. In another embodiment, the seed-origin bacterial endophyte produces a compound with antifungal properties, for example, fungicidal or fungistatic activity against *S. cerevisiae* and/or *Rhizoctonia*.

In some embodiments, the seed-origin bacterial endophyte is capable of nitrogen fixation, and is thus capable of producing ammonium from atmospheric nitrogen. The ability of bacteria to fix nitrogen can be confirmed by testing for growth of the bacteria in nitrogen-free growth media, for example, LGI media, as described herein.

In some embodiments, the seed origin bacterial endophyte can produce a compound which increases the solubility of mineral phosphate in the medium, i.e., mineral phosphate solubilization, for example, using the growth assays described herein. In one embodiment, the seed-origin bacterial endophyte n produces a compound which allows the bacterium to grow in growth media containing $Ca_3HPO_4$ as the sole phosphate source.

In some embodiments, the seed-origin bacterial endophyte can produce a siderophore. Siderophores are small high-affinity iron chelating agents secreted by microorganisms that increase the bioavailability of iron. Siderophore production by the bacterial endophyte can be detected, for example, using the methods described herein, as well as elsewhere (Perez-Miranda et al., 2007, J Microbiol Methods. 70:127-31, incorporated herein by reference in its entirety).

In some embodiments, the seed-origin bacterial endophyte can produce a hydrolytic enzyme. For example, in one embodiment, a bacterial endophyte can produce a hydrolytic enzyme selected from the group consisting of a cellulase, a pectinase, a chitinase and a xylanase. Hydrolytic enzymes can be detected using the methods described herein (see also, cellulase: Quadt-Hallmann et al., (1997) Can. J. Microbiol., 43: 577-582; pectinase: Soares et al. (1999). Revista de Microbiolgia 30(4): 299-303; chitinase: Li et al., (2004) Mycologia 96: 526-536; and xylanase: Suto et al., (2002) J Biosci Bioeng. 93:88-90, each of which is incorporated by reference in its entirety).

In some embodiment, purified bacterial populations contain synergistic endophytic populations, e.g., synergistic seed-origin bacterial endophytes. As used herein, synergistic endophytic populations refer to two or more endophyte populations that produce one or more effects (e.g., two or more or three or more effects) that are greater than the sum of their individual effects. For example, in some embodiments, a purified bacterial population contains two or more different seed-origin bacterial endophytes that are capable of synergistically increasing at least one of e.g., production of a phytohormone such as auxin, production of acetoin, production of an antimicrobial compound, production of a siderophore, production of a cellulase, production of a pectinase, production of a chitinase, production of a xylanase, nitrogen fixation, or mineral phosphate solubilization in an agricultural grass plant. Synergistically increasing one or more of such properties can increase a beneficial trait in an agricultural grass plant, such as an increase in drought tolerance.

In some embodiments, a purified bacterial population containing one or more seed-origin bacterial endophytes can increase one or more properties such as production of a phytohormone such as auxin, production of acetoin, production of an antimicrobial compound, production of a siderophore, production of a cellulase, production of a pectinase, production of a chitinase, production of a xylanase, or mineral phosphate solubilization in an agricultural grass plant., without increasing nitrogen fixation in the agricultural grass plant.

In some embodiments, metabolites in grass plants can be modulated by making synthetic combinations of purified bacterial populations containing endophytic microbes such as seed-origin bacterial endophytes and a seed or seedling of an agricultural grass plant. For example, a bacterial endophyte described herein can cause a detectable modulation (e.g., an increase or decrease) in the level of various metabolites, e.g., indole-3-carboxylic acid, trans-zeatin, abscisic acid, phaseic acid, indole-3-acetic acid, indole-3-butyric acid, indole-3-acrylic acid, jasmonic acid, jasmonic acid methyl ester, dihydrophaseic acid, gibberellin A3, salicylic acid, upon colonization of a grass plant.

In some embodiments, the endophytic microbe modulates the level of the metabolite directly (e.g., the microbe itself produces the metabolite, resulting in an overall increase in the level of the metabolite found in the plant). In other cases, the agricultural grass plant, as a result of the association with the endophytic microbe (e.g., a seed-origin bacterial endophyte), exhibits a modulated level of the metabolite (e.g., the plant reduces the expression of a biosynthetic enzyme responsible for production of the metabolite as a result of the microbe inoculation). In still other cases, the modulation in the level of the metabolite is a consequence of the activity of both the microbe and the plant (e.g., the plant produces increased amounts of the metabolite when compared with a reference agricultural plant, and the endophytic microbe also produces the metabolite). Therefore, as used herein, a modulation in the level of a metabolite can be an alteration in the metabolite level through the actions of the microbe and/or the inoculated plant.

The levels of a metabolite can be measured in an agricultural plant, and compared with the levels of the metabolite in a reference agricultural plant, and grown under the same conditions as the inoculated plant. The uninoculated plant that is used as a reference agricultural plant is a plant which has not been applied with a formulation with the endophytic microbe (e.g., a formulation comprising a population of purified bacterial endophytes). The uninoculated plant used as the reference agricultural plant is generally the same species and cultivar as, and is isogenic to, the inoculated plant.

The metabolite whose levels are modulated (e.g., increased or decreased) in the endophyte-associated plant may serve as a primary nutrient (i.e., it provides nutrition for the humans and/or animals who consume the plant, plant tissue, or the commodity plant product derived therefrom, including, but not limited to, a sugar, a starch, a carbohydrate, a protein, an oil, a fatty acid, or a vitamin). The metabolite can be a compound that is important for plant growth, development or homeostasis (for example, a phytohormone such as an auxin, cytokinin, gibberellin, a brassinosteroid, ethylene, or abscisic acid, a signaling molecule, or an antioxidant). In other embodiments, the metabolite can have other functions. For example, in one embodiment, a metabolite can have bacteriostatic, bactericidal, fungistatic, fungicidal or antiviral properties. In other embodiments, the metabolite can have insect-repelling, insecticidal, nematode-repelling, or nematicidal properties. In still other embodiments, the metabolite can serve a role in protecting the plant from stresses, may help improve plant vigor or the general health of the plant. In yet another embodiment, the metabolite can be a useful compound for industrial production. For example, the metabolite may itself be a useful compound that is extracted for industrial use, or serve as an intermediate for the synthesis of other compounds used in industry. A level of a metabolite can be increased by 1%, for example, at least 10%, for example, at least 20%, at least 30%, at least 40%, at least 50%, at least 75%, at least 100%, at least 150%, at least 200%, at least 300% or more, when compared with a reference agricultural plant. In a particular embodiment, the level of the metabolite is increased within the agricultural plant or a portion thereof such that it is present at a concentration of at least 0.1 µg/g dry weight, for example, at least 0.3 µg/g dry weight, 1.0 µg/g dry weight, 3.0 µg/g dry weight, 10 µg/g dry weight, 30 µg/g dry weight, 100 µg/g dry weight, 300 µg/g dry weight, 1 mg/g dry weight, 3 mg/g dry weight, 10 mg/g dry weight, 30 mg/g dry weight, 100 mg/g dry weight or more, of the plant or portion thereof.

Likewise, the modulation can be a decrease in the level of a metabolite. The reduction can be in a metabolite affecting the taste of a plant or a commodity plant product derived from a plant (for example, a bitter tasting compound), or in a metabolite which makes a plant or the resulting commodity plant product otherwise less valuable (for example, reduction of oxalate content in certain plants, or compounds which are deleterious to human and/or animal health). The metabolite whose level is to be reduced can be a compound which affects quality of a commodity plant product (e.g., reduction of lignin levels). The level of metabolite in the agricultural grass plant or portion thereof can be, for example, decreased by at least 1%, for example, at least 10%, at least 20%, at least 30%, at least 40%, at least 50%, at least 75%, at least 80%, at least 85%, at least 90%, at least 95%, at least 97%, at least 99% or more, when compared with a reference agricultural plant in a reference environment.

In some embodiments, the seed-origin bacterial endophyte is capable of generating a bacterial network in the agricultural grass plant or surrounding environment of the plant, which network is capable of causing a detectable modulation in the level of a metabolite in the host plant.

In a particular embodiment, the metabolite can serve as a signaling or regulatory molecule. The signaling pathway can be associated with a response to a stress, for example, one of the stress conditions selected from the group consisting of drought stress, salt stress, heat stress, cold stress, low nutrient stress, nematode stress, insect herbivory stress, fungal pathogen stress, bacterial pathogen stress, and viral pathogen stress.

The inoculated agricultural plant is grown under conditions such that the level of one or more metabolites is modulated in the plant, wherein the modulation is indicative of increased resistance to a stress selected from the group consisting of drought stress, salt stress, heat stress, cold stress, low nutrient stress, nematode stress, insect herbivory stress, fungal pathogen stress, bacterial pathogen stress, and viral pathogen stress. The increased resistance can be measured at about 10 minutes after applying the stress, for example about 20 minutes, 30 minutes, about 45 minutes, about 1 hour, about 2 hours, about 4 hours, about 8 hours, about 12 hours, about 16 hours, about 20 hours, about 24 hours, about 36 hours, about 48 hours, about 72 hours, about 96 hours, about 120 hours, or about a week after applying the stress.

The metabolites or other compounds described herein can be detected using any suitable method including, but not limited to gel electrophoresis, liquid and gas phase chromatography, either alone or coupled to mass spectrometry (See, for example, the Examples sections below), NMR (See e.g., U.S. patent publication 20070055456, which is incorporated herein by reference in its entirety), immunoassays (enzyme-linked immunosorbent assays (ELISA)), chemical assays, spectroscopy and the like. In some embodiments, commercial systems for chromatography and NMR analysis are utilized.

In other embodiments, metabolites or other compounds are detected using optical imaging techniques such as magnetic resonance spectroscopy (MRS.), magnetic resonance imaging (MRI), CAT scans, ultra sound, MS-based tissue imaging or X-ray detection methods (e.g., energy dispersive x-ray fluorescence detection).

Any suitable method may be used to analyze the biological sample (e.g., seed or plant tissue) in order to determine the presence, absence or level(s) of the one or more metabolites or other compounds in the sample. Suitable methods include chromatography (e.g., HPLC, gas chromatography, liquid chromatography), mass spectrometry (e.g., MS, MS-MS), LC-MS, enzyme-linked immunosorbent assay (ELISA), antibody linkage, other immunochemical techniques, biochemical or enzymatic reactions or assays, and combinations thereof. The levels of one or more of the recited metabolites or compounds may be determined in the methods of the present invention. For example, the level(s) of one metabolites or compounds, two or more metabolites, three or more metabolites, four or more metabolites, five or more metabolites, six or more metabolites, seven or more metabolites, eight or more metabolites, nine or more metabolites, ten or more metabolites, or compounds etc., including a combination of some or all of the metabolites or compounds including, but not limited to those disclosed herein may be determined and used in such methods.

As shown in the Examples and otherwise herein, endophyte-inoculated plants display increased thermal tolerance, herbicide tolerance, drought resistance, insect resistance, fungus resistance, virus resistance, bacteria resistance, male sterility, cold tolerance, salt tolerance, increased yield, enhanced nutrient use efficiency, increased nitrogen use efficiency, increased protein content, increased fermentable carbohydrate content, reduced lignin content, increased antioxidant content, enhanced water use efficiency, increased vigor, increased germination efficiency, earlier or increased flowering, increased biomass, altered root-to-shoot biomass ratio, enhanced soil water retention, or a combination thereof. Therefore, in one embodiment, the bacterial endophytic population is disposed on the surface or within a tissue of the seed or seedling in an amount effective to increase the biomass of the plant, or a part or tissue of the plant grown from the seed or seedling. The increased biomass is useful in the production of commodity products derived from the plant. Such commodity products include an animal feed, a fish fodder, a cereal product, a processed human-food product, a sugar or an alcohol. Such products may be a fermentation product or a fermentable product, one such exemplary product is a biofuel. The increase in biomass can occur in a part of the plant (e.g., the root tissue, shoots, leaves, etc.), or can be an increase in overall biomass. Increased biomass production, such an increase meaning at least about 10%, 20%, 30%, 40%, 50%, 60%, 70%, 80%, 90%, 100%, or greater than 100% when compared with a reference agricultural plant. Such increase in overall biomass can be under relatively stress-free conditions. In other cases, the increase in biomass can be in plants grown under any number of abiotic or biotic stresses, including drought stress, salt stress, heat stress, cold stress, low nutrient stress, nematode stress, insect herbivory stress, fungal pathogen stress, bacterial pathogen stress, and viral pathogen stress. In one particular embodiment, the bacterial endophytic population is disposed in an amount effective to increase root biomass by at least 10%, for example, at least 20%, at least 30%, at least 40%, at least 50%, at least 60%, at least 75%, at least 100%, or more, when compared with a reference agricultural plant.

In another embodiment, the bacterial endophytic population is disposed on the surface or within a tissue of the seed or seedling in an amount effective to increase the rate of seed germination when compared with a reference agricultural plant. For example, the increase in seed germination can be at least 10%, for example, at least 20%, at least 30%, at least 40%, at least 50%, at least 60%, at least 75%, at least 100%, or more, when compared with a reference agricultural plant.

In other cases, the endophytic microbe is disposed on the seed or seedling in an amount effective to increase the average biomass of the fruit or cob from the resulting plant by at least 10%, for example, at least 20%, at least 30%, at least 40%, at least 50%, at least 75%, at least 100% or more, when compared with a reference agricultural plant.

As highlighted in the Examples section, plants inoculated with a bacterial endophytic population also show an increase in overall plant height. Therefore, in one embodiment, the present invention provides for a seed comprising a bacterial endophytic population which is disposed on the surface or within a tissue of the seed or seedling in an amount effective to increase the height of the plant. For example, the bacterial endophytic population is disposed in an amount effective to result in an increase in height of the agricultural plant such that is at least 10% greater, for example, at least 20% greater, at least 30% greater, at least 40% greater, at least 50% greater, at least 60% greater, at least 70% greater, at least 80% greater, at least 90% greater, at least 100% greater, at least 125% greater, at least 150% greater or more, when compared with a reference agricultural plant. Such an increase in height can be under relatively stress-free conditions. In other cases, the increase in height can be in plants grown under any number of abiotic or biotic stresses, including drought stress, salt stress, heat stress, cold stress, low nutrient stress, nematode stress, insect herbivory stress, fungal pathogen stress, bacterial pathogen stress, or viral pathogen stress.

The host plants inoculated with the bacterial endophytic population also show dramatic improvements in their ability to utilize water more efficiently. Water use efficiency is a parameter often correlated with drought tolerance. Water use efficiency (WUE) is a parameter often correlated with drought tolerance, and is the $CO_2$ assimilation rate per water transpired by the plant. An increase in biomass at low water availability may be due to relatively improved efficiency of growth or reduced water consumption. In selecting traits for improving crops, a decrease in water use, without a change in growth would have particular merit in an irrigated agricultural system where the water input costs were high. An increase in growth without a corresponding jump in water use would have applicability to all agricultural systems. In many agricultural systems where water supply is not limiting, an increase in growth, even if it came at the expense of an increase in water use also increases yield.

When soil water is depleted or if water is not available during periods of drought, crop yields are restricted. Plant water deficit develops if transpiration from leaves exceeds the supply of water from the roots. The available water supply is related to the amount of water held in the soil and the ability of the plant to reach that water with its root system. Transpiration of water from leaves is linked to the fixation of carbon dioxide by photosynthesis through the stomata. The two processes are positively correlated so that high carbon dioxide influx through photosynthesis is closely linked to water loss by transpiration. As water transpires from the leaf, leaf water potential is reduced and the stomata tend to close in a hydraulic process limiting the amount of photosynthesis. Since crop yield is dependent on the fixation of carbon dioxide in photosynthesis, water uptake and transpiration are contributing factors to crop yield. Plants which are able to use less water to fix the same amount of carbon dioxide or which are able to function normally at a lower water potential have the potential to conduct more photosynthesis and thereby to produce more biomass and economic yield in many agricultural systems. An increased water use efficiency of the plant relates in some cases to an increased fruit/kernel size or number.

Therefore, in one embodiment, the plants described herein exhibit an increased water use efficiency (WUE) when compared with a reference agricultural plant grown under the same conditions. For example, the plants grown from the seeds comprising the bacterial endophytic population can have at least 5% higher WUE, for example, at least 10% higher, at least 20% higher, at least 30% higher, at least 40% higher, at least 50% higher, at least 60% higher, at least 70% higher, at least 80% higher, at least 90% higher, at least 100% higher WUE than a reference agricultural plant grown under the same conditions. Such an increase in WUE can occur under conditions without water deficit, or under conditions of water deficit, for example, when the soil water content is less than or equal to 60% of water saturated soil, for example, less than or equal to 50%, less than or equal to 40%, less than or equal to 30%, less than or equal to 20%, less than or equal to 10% of water saturated soil on a weight basis.

In a related embodiment, the plant comprising the bacterial endophyte can have at least 10% higher relative water content (RWC), for example, at least 20% higher, at least 30% higher, at least 40% higher, at least 50% higher, at least 60% higher, at least 70% higher, at least 80% higher, at least 90% higher, at least 100% higher RWC than a reference agricultural plant grown under the same conditions.

Synthetic Combinations and Methods of Making

As shown in the Examples section below, the bacterial endophytic populations described herein are capable of colonizing a host plant. Successful colonization can be confirmed by detecting the presence of the bacterial population within the plant. For example, after applying the bacteria to the seeds, high titers of the bacteria can be detected in the roots and shoots of the plants that germinate from the seeds. In addition, significant quantities of the bacteria can be detected in the rhizosphere of the plants. Detecting the presence of the endophytic microbe inside the plant can be accomplished by measuring the viability of the microbe after surface sterilization of the seed or the plant: endophytic colonization results in an internal localization of the microbe, rendering it resistant to conditions of surface sterilization. The presence and quantity of the microbe can also be established using other means known in the art, for example, immunofluorescence microscopy using microbe specific antibodies, or fluorescence in situ hybridization (see, for example, Amann et al. (2001) Current Opinion in Biotechnology 12:231-236, incorporated herein by reference in its entirety). Alternatively, specific nucleic acid probes recognizing conserved sequences from the endophytic bacterium can be employed to amplify a region, for example by quantitative PCR, and correlated to CFUs by means of a standard curve.

In another embodiment, the endophytic microbe is disposed, for example, on the surface of a seed of an agricultural grass plant, in an amount effective to be detectable in the mature agricultural plant. In one embodiment, the endophytic microbe is disposed in an amount effective to be detectable in an amount of at least about 100 CFU, at least about 200 CFU, at least about 300 CFU, at least about 500 CFU, at least about 1,000 CFU, at least about 3,000 CFU, at least about 10,000 CFU, at least about 30,000 CFU, at least about 100,000 CFU or more in the mature agricultural plant.

In some cases, the endophytic microbe is capable of colonizing particular tissue types of the plant. In one embodiment, the endophytic microbe is disposed on the seed or seedling in an amount effective to be detectable within a target tissue of the mature agricultural plant selected from a fruit, a seed, a leaf, or a root, or portion thereof. For example, the endophytic microbe can be detected in an amount of at least about 100 CFU, at least about 200 CFU, at least about 300 CFU, at least about 500 CFU, at least about 1,000 CFU, at least about 3,000 CFU, at least about 10,000 CFU, at least about 30,000 CFU, at least about 100,000 CFU or more, in the target tissue of the mature agricultural plant.

Endophytes Compatible with Agrichemicals.

In certain embodiments, the endophyte is selected on the basis of its compatibility with commonly used agrichemicals. As mentioned earlier, plants, particularly agricultural plants, can be treated with a vast array of agrichemicals, including fungicides, biocides (anti-bacterial agents), herbicides, insecticides, nematicides, rodenticides, fertilizers, and other agents.

In some cases, it can be important for the endophyte to be compatible with agrichemicals, particularly those with fungicidal or antibacterial properties, in order to persist in the plant although, as mentioned earlier, there are many such fungicidal or antibacterial agents that do not penetrate the plant, at least at a concentration sufficient to interfere with the endophyte. Therefore, where a systemic fungicide or antibacterial agent is used in the plant, compatibility of the endophyte to be inoculated with such agents will be an important criterion.

In one embodiment, natural isolates of endophytes which are compatible with agrichemicals can be used to inoculate the plants according to the methods described herein. For example, fungal endophytes which are compatible with agriculturally employed fungicides can be isolated by plating a culture of the endophytes on a petri dish containing an effective concentration of the fungicide, and isolating colonies of the endophyte that are compatible with the fungicide. In another embodiment, an endophyte that is compatible with a fungicide is used for the methods described herein. For example, the endophyte can be compatible with at least one of the fungicides selected from the group consisting of: 2-(thiocyanatomethylthio)-benzothiazole, 2-phenylphenol, 8-hydroxyquinoline sulfate, ametoctradin, amisulbrom, antimycin, *Ampelomyces quisqualis*, azaconazole, azoxystrobin, *Bacillus subtilis*, benalaxyl, benomyl, benthiavalicarb-isopropyl, benzylaminobenzene-sulfonate (BABS) salt, bicarbonates, biphenyl, bismerthiazol, bitertanol, bixafen, blasticidin-S, borax, Bordeaux mixture, boscalid, bromuconazole, bupirimate, calcium polysulfide, captafol, captan, carbendazim, carboxin, carpropamid, carvone, chloroneb, chlorothalonil, chlozolinate, *Coniothyrium minitans*, copper hydroxide, copper octanoate, copper oxychloride, copper sulfate, copper sulfate (tribasic), cuprous oxide, cyazofamid, cyflufenamid, cymoxanil, cyproconazole, cyprodinil, dazomet, debacarb, diammonium ethylenebis-(dithiocarbamate), dichlofluanid, dichlorophen, diclocymet, diclomezine, dichloran, diethofencarb, difenoconazole, difenzoquat ion, diflumetorim, dimethomorph, dimoxystrobin, diniconazole, diniconazole-M, dinobuton, dinocap, diphenylamine, dithianon, dodemorph, dodemorph acetate, dodine, dodine free base, edifenphos, enestrobin, epoxiconazole, ethaboxam, ethoxyquin, etridiazole, famoxadone, fenamidone, fenarimol, fenbuconazole, fenfuram, fenhexamid, fenoxanil, fenpiclonil, fenpropidin, fenpropimorph, fentin, fentin acetate, fentin hydroxide, ferbam, ferimzone, fluazinam, fludioxonil, flumorph, fluopicolide, fluopyram, fluoroimide, fluoxastrobin, fluquinconazole, flusilazole, flusulfamide, flutianil, flutolanil, flutriafol, fluxapyroxad, folpet, formaldehyde, fosetyl, fosetyl-aluminium, fuberidazole, furalaxyl, furametpyr, guazatine, guazatine acetates, GY-81, hexachlorobenzene, hexaconazole, hymexazol, imazalil, imazalil sulfate, imibenconazole, iminoctadine, iminoctadine triacetate, iminoctadine tris(albesilate), ipconazole, iprobenfos, iprodione, iprovalicarb, isoprothiolane, isopyrazam, isotianil, kasugamycin, kasugamycin hydrochloride hydrate, kresoxim-methyl, mancopper, mancozeb, mandipropamid, maneb, mepanipyrim, mepronil, mercuric chloride, mercuric oxide, mercurous chloride, metalaxyl, mefenoxam, metalaxyl-M, metam, metam-ammonium, metam-potassium, metam-sodium, metconazole, methasulfocarb, methyl iodide, methyl isothiocyanate, metiram, metominostrobin, metrafenone, mildiomycin, myclobutanil, nabam, nitrothal-isopropyl, nuarimol, octhilinone, ofurace, oleic acid (fatty acids), orysastrobin, oxadixyl, oxine-copper, oxpoconazole fumarate, oxycarboxin, pefurazoate, penconazole, pencycuron, penflufen, pentachlorophenol, pentachlorophenyl laurate, penthiopyrad, phenylmercury acetate, phosphonic acid, phthalide, picoxystrobin, polyoxin B, polyoxins, polyoxorim, potassium bicarbonate, potassium hydroxyquinoline sulfate, probenazole, prochloraz, procymidone, propamocarb, propamocarb hydrochloride, propiconazole, propineb, proquinazid, prothioconazole, pyraclostrobin, pyrametostrobin, pyraoxystrobin, pyrazophos, pyribencarb, pyributicarb, pyrifenox, pyrimethanil, pyroquilon, quinoclamine, quinoxyfen, quintozene, *Reynoutria sachalinensis* extract, sedaxane, silthiofam, simeconazole, sodium 2-phenylphenoxide, sodium bicarbonate, sodium pentachlorophenoxide, spiroxamine, sulfur, SYP-Z071, SYP-Z048, tar oils, tebuconazole, tebufloquin, tecnazene, tetraconazole, thiabendazole, thifluzamide, thiophanate-methyl, thiram, tiadinil, tolclofos-methyl, tolylfluanid, triadimefon, triadimenol, triazoxide, tricyclazole, tridemorph, trifloxystrobin, triflumizole, triforine, triticonazole, validamycin, valifenalate, valiphenal, vinclozolin, zineb, ziram, zoxamide, *Candida oleophila, Fusarium oxysporum, Gliocladium* spp., *Phlebiopsis gigantea, Streptomyces griseoviridis, Trichoderma* spp., (RS)—N-(3,5-dichlorophenyl)-2-(methoxymethyl)-succinimide, 1,2-dichloropropane, 1,3-dichloro-1,1,3,3-tetrafluoroacetone hydrate, 1-chloro-2,4-dinitronaphthalene, 1-chloro-2-nitropropane, 2-(2-heptadecyl-2-imidazolin-1-yl)ethanol, 2,3-dihydro-5-phenyl-1,4-dithi-ine 1,1,4,4-tetraoxide, 2-methoxyethylmercury acetate, 2-methoxyethylmercury chloride, 2-methoxyethylmercury silicate, 3-(4-chlorophenyl)-5-methylrhodanine, 4-(2-nitroprop-1-enyl) phenyl thiocyanateme, ampropylfos, anilazine, azithiram, barium polysulfide, Bayer 32394, benodanil, benquinox, bentaluron, benzamacril; benzamacril-isobutyl, benzamorf, binapacryl, bis(methylmercury) sulfate, bis(tributyltin) oxide, buthiobate, cadmium calcium copper zinc chromate sulfate, carbamorph, CECA, chlobenthiazone, chloraniformethan, chlorfenazole, chlorquinox, climbazole, cyclafuramid, cypendazole, cyprofuram, decafentin, dichlone, dichlozoline, diclobutrazol, dimethirimol, dinocton, dinosulfon, dinoterbon, dipyrithione, ditalimfos, dodicin, drazoxolon, EBP, ESBP, etaconazole, etem, ethirim, fenaminosulf, fenapanil, fenitropan, 5-fluorocytosine and profungicides thereof, fluotrimazole, furcarbanil, furconazole, furconazole-cis, furmecyclox, furophanate, glyodine, griseofulvin, halacrinate, Hercules 3944, hexylthiofos, ICIA0858, isopamphos, isovaledione, mebenil, mecarbinzid, metazoxolon, methfuroxam, methylmercury dicyandiamide, metsulfovax, milneb, mucochloric anhydride, myclozolin, N-3,5-dichlorophenyl-succinimide, N-3-nitrophenylitaconimide, natamycin, N-ethylmercurio-4-toluenesulfonanilide, nickel bis(dimethyldithiocarbamate), OCH, phenylmercury dimethyldithiocarbamate, phenylmercury nitrate, phosdiphen, picolinamide UK-2A and derivatives thereof, prothiocarb; prothiocarb hydrochloride, pyracarbolid, pyridinitril, pyroxychlor, pyroxyfur, quinacetol; quinacetol sulfate, quinazamid, quinconazole, rabenzazole, salicylanilide, SSF-109, sultropen, tecoram, thiadifluor, thicyofen, thiochlorfenphim, thiophanate, thioquinox, tioxymid, triamiphos, triarimol, triazbutil, trichlamide, urbacid, XRD-563, and zarilamide, IK-1140.

In still another embodiment, an endophyte that is compatible with an antibacterial compound is used for the methods described herein. For example, the endophyte can be compatible with at least one of the antibiotics selected from the group consisting of: Amikacin, Gentamicin, Kanamycin, Neomycin, Netilmicin, Tobramycin, Paromomycin, Spectinomycin, Geldanamycin, Herbimycin, Rifaximin, streptomycin, Loracarbef, Ertapenem, Doripenem, Imipenem/Cilastatin, Meropenem, Cefadroxil, Cefazolin, Cefalotin or Cefalothin, Cefalexin, Cefaclor, Cefamandole, Cefoxitin, Cefprozil, Cefuroxime, Cefixime, Cefdinir, Cefditoren, Cefoperazone, Cefotaxime, Cefpodoxime, Ceftazidime, Ceftibuten, Ceftizoxime, Ceftriaxone, Cefepime, Ceftaroline fosamil, Ceftobiprole, Teicoplanin, Vancomycin, Telavancin, Clindamycin, Lincomycin, Daptomycin, Azithromycin, Clarithromycin, Dirithromycin, Erythromycin, Roxithromycin, Troleandomycin, Telithromycin, Spiramycin, Aztreonam, Furazolidone, Nitrofurantoin, Linezolid, Posizolid, Radezolid, Torezolid, Amoxicillin, Ampicillin, Azlocillin, Carbenicillin, Cloxacillin, Dicloxacillin, Flucloxacillin, Mezlocillin, Methicillin, Nafcillin, Oxacillin, Penicillin G, Penicillin V, Piperacillin, Penicillin G, Temocillin, Ticarcillin, Amoxicillin/clavulanate, Ampicillin/sulbactam, Piperacillin/tazobactam, Ticarcillin/clavulanate, Bacitracin, Colistin, Polymyxin B, Ciprofloxacin, Enoxacin, Gatifloxacin, Levofloxacin, Lomefloxacin, Moxifloxacin, Nalidixic acid, Norfloxacin, Ofloxacin, Trovafloxacin, Grepafloxacin, Sparfloxacin, Temafloxacin, Mafenide, Sulfacetamide, Sulfadiazine, Silver sulfadiazine, Sulfadimethoxine, Sulfamethizole, Sulfamethoxazole, Sulfanilimide (archaic), Sulfasalazine, Sulfisoxazole, Trimethoprim-Sulfamethoxazole (Co-trimoxazole) (TMP-SMX), Sulfonamidochrysoidine (archaic), Demeclocycline, Doxycycline, Minocycline, Oxytetracycline, Tetracycline, Clofazimine, Dapsone, Capreomycin, Cycloserine, Ethambutol, Ethionamide, Isoniazid, Pyrazinamide, Rifampicin (Rifampin in US), Rifabutin, Rifapentine, Streptomycin, Arsphenamine, Chloramphenicol, Fosfomycin, Fusidic acid, Metronidazole, Mupirocin, Platensimycin, Quinupristin/Dalfopristin, Thiamphenicol, Tigecycline, Tinidazole, and Trimethoprim. Fungicide compatible endophytes can also be isolated by selection on liquid medium. The culture of endophytes can be plated on petri dishes without any forms of mutagenesis; alternatively, the endophytes can be mutagenized using any means known in the art. For example, microbial cultures can be exposed to UV light, gamma-irradiation, or chemical mutagens such as ethylmethanesulfonate (EMS) prior to selection on fungicide containing media. Finally, where the mechanism of action of a particular fungicide is known, the target gene can be specifically mutated (either by gene deletion, gene replacement, site-directed mutagenesis, etc.) to generate an endophyte that is resilient against that particular fungicide. It is noted that the above-described methods can be used to isolate fungi that are compatible with both fungistatic and fungicidal compounds.

It will also be appreciated by one skilled in the art that a plant may be exposed to multiple types of fungicides or antibacterial compounds, either simultaneously or in succession, for example at different stages of plant growth. Where the target plant is likely to be exposed to multiple fungicidal and/or antibacterial agents, an endophyte that is compatible with many or all of these agrichemicals can be used to inoculate the plant. An endophyte that is compatible with several fungicidal agents can be isolated, for example, by serial selection. An endophyte that is compatible with the first fungicidal agent is isolated as described above (with or without prior mutagenesis). A culture of the resulting endophyte can then be selected for the ability to grow on liquid or solid media containing the second antifungal compound (again, with or without prior mutagenesis). Colonies isolated from the second selection are then tested to confirm its compatibility to both antifungal compounds.

Likewise, bacterial endophytes that are compatible to biocides (including herbicides such as glyphosate or antibacterial compounds, whether bacteriostatic or bactericidal) that are agriculturally employed can be isolated using methods similar to those described for isolating fungicide compatible endophytes. In one embodiment, mutagenesis of the microbial population can be performed prior to selection with an antibacterial agent. In another embodiment, selection is performed on the microbial population without prior mutagenesis. In still another embodiment, serial selection is performed on an endophyte: the endophyte is first selected for compatibility to a first antibacterial agent. The isolated compatible endophyte is then cultured and selected for compatibility to the second antibacterial agent. Any colony thus isolated is tested for compatibility to each, or both antibacterial agents to confirm compatibility with these two agents.

Compatibility with an antimicrobial agent can be determined by a number of means known in the art, including the comparison of the minimal inhibitory concentration (MIC) of the unmodified and modified endophyte. Therefore, in one embodiment, the present invention discloses an isolated modified endophyte derived from an endophyte isolated from within a plant or tissue thereof, wherein the endophyte is modified such that it exhibits at least 3 fold greater, for example, at least 5 fold greater, at least 10 fold greater, at least 20 fold greater, at least 30 fold greater or more MIC to an antimicrobial agent when compared with the unmodified endophyte.

In one particular aspect, disclosed herein are bacterial endophytes with enhanced compatibility to the herbicide glyphosate. In one embodiment, the bacterial endophyte has a doubling time in growth medium containing at least 1 mM glyphosate, for example, at least 2 mM glyphosate, at least 5 mM glyphosate, at least 10 mM glyphosate, at least 15 mM glyphosate or more, that is no more than 250%, for example, no more than 200%, no more than 175%, no more than 150%, or no more than 125%, of the doubling time of the endophyte in the same growth medium containing no glyphosate. In one particular embodiment, the bacterial endophyte has a doubling time in growth medium containing 5 mM glyphosate that is no more than 150% the doubling time of the endophyte in the same growth medium containing no glyphosate.

In another embodiment, the bacterial endophyte has a doubling time in a plant tissue containing at least 10 ppm glyphosate, for example, at least 15 ppm glyphosate, at least 20 ppm glyphosate, at least 30 ppm glyphosate, at least 40 ppm glyphosate or more, that is no more than 250%, for example, no more than 200%, no more than 175%, no more than 150%, or no more than 125%, of the doubling time of the endophyte in a reference plant tissue containing no glyphosate. In one particular embodiment, the bacterial endophyte has a doubling time in a plant tissue containing 40 ppm glyphosate that is no more than 150% the doubling time of the endophyte in a reference plant tissue containing no glyphosate.

The selection process described above can be repeated to identify isolates of the endophyte that are compatible with a multitude of antifungal or antibacterial agents.

Candidate isolates can be tested to ensure that the selection for agrichemical compatibility did not result in loss of a desired microbial bioactivity. Isolates of the endophyte that are compatible with commonly employed fungicides can be selected as described above. The resulting compatible endophyte can be compared with the parental endophyte on plants in its ability to promote germination.

The agrichemical compatible endophytes generated as described above can be detected in samples. For example, where a transgene was introduced to render the endophyte compatible with the agrichemical(s), the transgene can be used as a target gene for amplification and detection by PCR. In addition, where point mutations or deletions to a portion of a specific gene or a number of genes results in compatibility with the agrichemical(s), the unique point mutations can likewise be detected by PCR or other means known in the art. Such methods allow the detection of the microbe even if it is no longer viable. Thus, commodity plant products produced using the agrichemical compatible microbes described herein can readily be identified by employing these and related methods of nucleic acid detection.

Beneficial Attributes of Synthetic Combinations of Cereal Seeds and Seed-Origin Endophytes Improved Attributes Conferred by the Endophyte.

The present invention contemplates the establishment of a microbial symbiont in a plant. In one embodiment, the microbial association results in a detectable change to the seed or plant. The detectable change can be an improvement in a number of agronomic traits (e.g., improved general health, increased response to biotic or abiotic stresses, or enhanced properties of the plant or a plant part, including fruits and grains). Alternatively, the detectable change can be a physiological or biological change that can be measured by methods known in the art. The detectable changes are described in more detail in the sections below. As used herein, an endophyte is considered to have conferred an improved agricultural trait whether or not the improved trait arose from the plant, the endophyte, or the concerted action between the plant and endophyte. Therefore, for example, whether a beneficial hormone or chemical is produced by the plant or endophyte, for purposes of the present invention, the endophyte will be considered to have conferred an improved agronomic trait upon the host plant.

In some aspects, provided herein, are methods for producing a seed of a plant with a heritably altered trait. The trait of the plant can be altered without known genetic modification of the plant genome, and comprises the following steps. First, a preparation of an isolated endophyte which is exogenous to the seed of the plant is provided, and optionally processed to produce a microbial preparation. The microbial preparation is then contacted with the plant. The plants are then allowed to go to seed, and the seeds, which contain the endophytes on and/or in the seed are collected. The endophytes contained within the seed are viably incorporated into the seed.

The method of the present invention can facilitate crop productivity by enhancing germination, seedling vigor and biomass in comparison with a non-treated control. Moreover, the introduction of the beneficial microorganisms to within the seed instead of by, e.g., seed coating, makes the endophytes less susceptible to environmental perturbation and more compatible with chemical seed coatings (e.g., pesticides and herbicides). Using endophyte colonized seeds, the plant growth and biomass increases are statistically similar to those obtained using conventional inoculation methods e.g., exogenous seed soaking and soil inoculation (that are more laborious and less practicable in certain circumstances).

Improved General Health.

Also described herein are plants, and fields of plants, that are associated with beneficial bacterial and/or fungal endophytes, such that the overall fitness, productivity or health of the plant or a portion thereof, is maintained, increased and/or improved over a period of time. Improvement in overall plant health can be assessed using numerous physiological parameters including, but not limited to, height, overall biomass, root and/or shoot biomass, seed germination, seedling survival, photosynthetic efficiency, transpiration rate, seed/fruit number or mass, plant grain or fruit yield, leaf chlorophyll content, photosynthetic rate, root length, or any combination thereof. Improved plant health, or improved field health, can also be demonstrated through improved resistance or response to a given stress, either biotic or abiotic stress, or a combination of one or more abiotic stresses, as provided herein.

Other Abiotic Stresses.

Disclosed herein are endophyte-associated plants with increased resistance to an abiotic stress. Exemplary abiotic stresses include, but are not limited to:

Drought and Heat Tolerance.

In some cases, a plant resulting from seeds containing the endophyte can exhibit a physiological change, such as a decreased change in photosynthetic activity (expressed, for example, as $\Delta Fv/Fm$) after exposure to heat shock or drought conditions as compared to a corresponding control, genetically identical plant that does not contain the endophytes grown in the same conditions. In some cases, the endophyte-associated plant as disclosed herein can exhibit an increased change in photosynthetic activity $\Delta Fv(\Delta Fv/Fm)$ after heat-shock or drought stress treatment, for example 1, 2, 3, 4, 5, 6, 7 days or more after the heat-shock or drought stress treatment, or until photosynthesis ceases, as compared with corresponding control plant of similar developmental stage but not containing the endophytes. For example, a plant having an endophyte able to confer heat and/or drought-tolerance can exhibit a $\Delta Fv/Fm$ of from about 0.1 to about 0.8 after exposure to heat-shock or drought stress or a $\Delta Fv/Fm$ range of from about 0.03 to about 0.8 under one day, or 1, 2, 3, 4, 5, 6, 7, or over 7 days post heat-shock or drought stress treatment, or until photosynthesis ceases. In some embodiments, stress-induced reductions in photosynthetic activity can be reduced by at least about 0.25% (for example, at least about 0.5%, at least about 1%, at least about 2%, at least about 3, at least about 5%, at least about 8%, at least about 10%, at least about 15%, at least about 20%, at least about 25%, at least about 30%, at least about 40%, at least about 50%, at least about 60%, at least about 75%, at least about 80%, at least about 80%, at least about 90%, at least about 95%, at least about 99% or at least 100%) as compared to the photosynthetic activity decrease in a corresponding reference agricultural plant following heat shock conditions. Significance of the difference between the endophyte-associated and reference agricultural plants can be established upon demonstrating statistical significance, for example at $p<0.05$ with an appropriate parametric or non-parametric statistic, e.g., Chi-square test, Student's t-test, Mann-Whitney test, or F-test based on the assumption or known facts that the endophyte-associated plant and reference agricultural plant have identical or near identical genomes.

In some embodiments, the plants contain endophytes able to confer novel heat and/or drought-tolerance in sufficient quantity, such that increased growth under conditions of heat or drought stress is observed. For example, a heat and/or drought-tolerance endophyte population described herein can be present in sufficient quantity in a plant, resulting in increased growth as compared to a plant that does not contain the endophyte, when grown under drought conditions or heat shock conditions, or following such conditions. Growth can be assessed with physiological parameters including, but not limited to, height, overall biomass, root and/or shoot biomass, seed germination, seedling survival, photosynthetic efficiency, transpiration rate, seed/fruit number or mass, plant grain or fruit yield, leaf chlorophyll content, photosynthetic rate, root length, or any combination thereof.

In some cases, a plant resulting from seeds containing an endophyte that includes a novel heat and/or drought tolerance endophyte population described herein exhibits a difference in the physiological parameter that is at least about 5% greater, for example at least about 5%, at least about 8%, at least about 10%, at least about 15%, at least about 20%, at least about 25%, at least about 30%, at least about 40%, at least about 50%, at least about 60%, at least about 75%, at least about 80%, at least about 80%, at least about 90%, or at least 100%, at least about 200%, at least about 300%, at least about 400% or greater than a reference agricultural plant grown under similar conditions.

In various embodiments, the endophytes introduced into altered seed microbiota can confer in the resulting plant thermal tolerance, herbicide tolerance, drought resistance, insect resistance, fungus resistance, virus resistance, bacteria resistance, male sterility, cold tolerance, salt tolerance, increased yield, enhanced nutrient use efficiency, increased nitrogen use efficiency, increased protein content, increased fermentable carbohydrate content, reduced lignin content, increased antioxidant content, enhanced water use efficiency, increased vigor, increased germination efficiency, earlier or increased flowering, increased biomass, altered root-to-shoot biomass ratio, enhanced soil water retention, or a combination thereof. A difference between endophyte-associated plant and a reference agricultural plant can also be measured using other methods known in the art (see, for example, Haake et al. (2002) *Plant Physiol.* 130: 639-648)

Salt Stress.

In other embodiments, endophytes able to confer increased tolerance to salinity stress can be introduced into plants. The resulting plants containing the endophytes can exhibit increased resistance to salt stress, whether measured in terms of survival under saline conditions, or overall growth during, or following salt stress. The physiological parameters of plant health recited above, including height, overall biomass, root and/or shoot biomass, seed germination, seedling survival, photosynthetic efficiency, transpiration rate, seed/fruit number or mass, plant grain or fruit yield, leaf chlorophyll content, photosynthetic rate, root length, or any combination thereof, can be used to measure growth, and compared with the growth rate of reference agricultural plants (e.g., isogenic plants without the endophytes) grown under identical conditions. In some cases, a plant resulting from seeds containing an endophyte able to confer salt tolerance described herein exhibits a difference in the physiological parameter that is at least about 5% greater, for example at least about 5%, at least about 8%, at least about 10%, at least about 15%, at least about 20%, at least about 25%, at least about 30%, at least about 40%, at least about 50%, at least about 60%, at least about 75%, at least about 80%, at least about 80%, at least about 90%, or at least 100%, at least about 200%, at least about 300%, at least about 400% or greater than a reference agricultural plant grown under the same sodium concentration in the soil.

In other instances, endophyte-associated plants and reference agricultural plants can be grown in soil or growth media containing different concentration of sodium to establish the inhibitory concentration of sodium (expressed, for example, as the concentration in which growth of the plant is inhibited by 50% when compared with plants grown under no sodium stress). Therefore, in another embodiment, a plant resulting from seeds containing an endophyte able to confer salt tolerance described herein exhibits an increase in the inhibitory sodium concentration by at least 10 mM, for example at least 15 mM, at least 20 mM, at least 30 mM, at least 40 mM, at least 50 mM, at least 60 mM, at least 70 mM, at least 80 mM, at least 90 mM, at least 100 mM or more, when compared with the reference agricultural plants.

High Metal Content.

Plants are sessile organisms and therefore must contend with the environment in which they are placed. While plants have adapted many mechanisms to deal with chemicals and substances that may be deleterious to their health, heavy metals represent a class of toxins which are highly relevant for plant growth and agriculture. Plants use a number of mechanisms to cope with toxic levels of heavy metals (for example, nickel, cadmium, lead, mercury, arsenic, or aluminum) in the soil, including excretion and internal sequestration. For agricultural purposes, it is important to have plants that are able to tolerate otherwise hostile conditions, for example soils containing elevated levels of toxic heavy metals. Endophytes that are able to confer increased heavy metal tolerance may do so by enhancing sequestration of the metal in certain compartments. Use of such endophytes in a plant would allow the development of novel plant-endophyte combinations for purposes of environmental remediation (also known as phytoremediation). Therefore, in one embodiment, the plant containing the endophyte able to confer increased metal tolerance exhibits a difference in a physiological parameter that is at least about 5% greater, for example at least about 5%, at least about 8%, at least about 10%, at least about 15%, at least about 20%, at least about 25%, at least about 30%, at least about 40%, at least about 50%, at least about 60%, at least about 75%, at least about 80%, at least about 80%, at least about 90%, or at least 100%, at least about 200%, at least about 300%, at least about 400% or greater than a reference agricultural plant grown under the same heavy metal concentration in the soil.

Alternatively, the inhibitory concentration of the heavy metal can be determined for the endophyte-associated plant and compared with a reference agricultural plant under the same conditions. Therefore, in one embodiment, the plants resulting from seeds containing an endophyte able to confer heavy metal tolerance described herein exhibit an increase in the inhibitory sodium concentration by at least 0.1 mM, for example at least 0.3 mM, at least 0.5 mM, at least 1 mM, at least 2 mM, at least 5 mM, at least 10 mM, at least 15 mM, at least 20 mM, at least 30 mM, at least 50 mM or more, when compared with the reference agricultural plants.

Finally, plants inoculated with endophytes that are able to confer increased metal tolerance exhibits an increase in overall metal accumulation by at least 10%, for example at least 15%, at least 20%, at least 30%, at least 40%, at least 50%, at least 60%, at least 75%, at least 100%, at least 150%, at least 200%, at least 300% or more, when compared with uninoculated plants grown under the same conditions.

Low Nutrient Stress.

The endophytes described herein may also confer to the plant an increased ability to grow in nutrient limiting conditions, for example by solubilizing or otherwise making available to the plants macronutrients or micronutrients that are complexed, insoluble, or otherwise in an unavailable form. In one embodiment, a plant is inoculated with an endophyte that confers increased ability to liberate and/or otherwise provide to the plant with nutrients selected from the group consisting of phosphate, nitrogen, potassium, iron, manganese, calcium, molybdenum, vitamins, or other micronutrients. Such a plant can exhibit increased growth in soil containing limiting amounts of such nutrients when compared with reference agricultural plant. Differences between the endophyte-associated plant and reference agricultural plant can be measured by comparing the biomass of the two plant types grown under limiting conditions, or by measuring the physical parameters described above. Therefore, in one embodiment, the plant containing the endophyte able to confer increased tolerance to nutrient limiting conditions exhibits a difference in a physiological parameter that is at least about 5% greater, for example at least about 5%, at least about 8%, at least about 10%, at least about 15%, at least about 20%, at least about 25%, at least about 30%, at least about 40%, at least about 50%, at least about 60%, at least about 75%, at least about 80%, at least about 80%, at least about 90%, or at least about 100%, at least about 200%, at least about 300%, at least about 400% or greater than a reference agricultural plant grown under the same heavy metal concentration in the soil.

Cold Stress.

In some cases, endophytes can confer to the plant the ability to tolerate cold stress. Many known methods exist for the measurement of a plant's tolerance to cold stress (as reviewed, for example, in Thomashow (2001) Plant Physiol. 125: 89-93, and Gilmour et al. (2000) Plant Physiol. 124: 1854-1865, both of which are incorporated herein by reference in their entirety). As used herein, cold stress refers to both the stress induced by chilling (0° C.-15° C.) and freezing (<0° C.). Some cultivars of agricultural plants can be particularly sensitive to cold stress, but cold tolerance traits may be multigenic, making the breeding process difficult. Endophytes able to confer cold tolerance would potentially reduce the damage suffered by farmers on an annual basis. Improved response to cold stress can be measured by survival of plants, the amount of necrosis of parts of the plant, or a change in crop yield loss, as well as the physiological parameters used in other examples. Therefore, in one embodiment, the plant containing the endophyte able to confer increased cold tolerance exhibits a difference in a physiological parameter that is at least about 5% greater, for example at least about 5%, at least about 8%, at least about 10%, at least about 15%, at least about 20%, at least about 25%, at least about 30%, at least about 40%, at least about 50%, at least about 60%, at least about 75%, at least about 80%, at least about 80%, at least about 90%, or at least 100%, at least about 200%, at least about 300%, at least about 400% or greater than a reference agricultural plant grown under the same conditions of cold stress.

Biotic Stress.

In other embodiments, the bacterial endophyte protects the plant from a biotic stress, for example, insect infestation, nematode infestation, bacterial infection, fungal infection, oomycete infection, protozoal infection, viral infection, and herbivore grazing, or a combination thereof.

Insect Herbivory.

There is an abundance of insect pest species that can infect or infest a wide variety of plants. Pest infestation can lead to significant damage. Insect pests that infest plant species are particularly problematic in agriculture as they can cause serious damage to crops and significantly reduce plant yields. A wide variety of different types of plant are susceptible to pest infestation including commercial crops such as cotton, soybean, wheat, barley, and corn.

In some cases, the endophytes described herein may confer upon the host plant the ability to repel insect herbivores. In other cases, the endophytes may produce, or induce the production in the plant of, compounds which are insecticidal or insect repellant. The insect may be any one of the common pathogenic insects affecting plants, particularly agricultural plants. Examples include, but are not limited to: *Leptinotarsa* spp. (e.g., *L. decemlineata* (Colorado potato beetle), *L. juncta* (false potato beetle), or *L. texana* (Texan false potato beetle)); *Nilaparvata* spp. (e.g., *N. lugens* (brown planthopper)); *Laode/phax* spp. (e.g., *L. striatellus* (small brown planthopper)); *Nephotettix* spp. (e.g., *N. virescens* or *N. cincticeps* (green leafhopper), or *N. nigropictus* (rice leafhopper)); *Sogatella* spp. (e.g., *S. furcifera* (whitebacked planthopper)); *Chilo* spp. (e.g., *C. suppressalis* (rice striped stem borer), *C. auricilius* (gold-fringed stem borer), or *C. polychrysus* (dark-headed stem borer)); *Sesamia* spp. (e.g., *S. inferens* (pink rice borer)); *Tryporyza* spp. (e.g., *T. innotata* (white rice borer), or *T. incertulas* (yellow rice borer)); *Anthonomus* spp. (e.g., *A. grandis* (boll weevil)); *Phaedon* spp. (e.g., *P. cochleariae* (mustard leaf beetle)); *Epilachna* spp. (e.g., *E. varivetis* (Mexican bean beetle)); *Tribolium* spp. (e.g., *T. castaneum* (red floor beetle)); *Diabrotica* spp. (e.g., *D. virgifera* (western corn rootworm), *D. barberi* (northern corn rootworm), *D. undecimpunctata howardi* (southern corn rootworm), *D. virgifera zeae* (Mexican corn rootworm); *Ostrinia* spp. (e.g., *O. nubilalis* (European corn borer)); *Anaphothrips* spp. (e.g., *A. obscrurus* (grass *thrips*)); *Pectinophora* spp. (e.g., *P. gossypiella* (pink bollworm)); *Heliothis* spp. (e.g., *H. virescens* (tobacco budworm)); *Trialeurodes* spp. (e.g., *T. abutiloneus* (banded-winged whitefly) *T. vaporariorum* (greenhouse whitefly)); *Bemisia* spp. (e.g., *B. argentifolii* (silverleaf whitefly)); *Aphis* spp. (e.g., *A. gossypii* (cotton aphid)); *Lygus* spp. (e.g., *L. lineolaris* (tarnished plant bug) or *L. hesperus* (western tarnished plant bug)); *Euschistus* spp. (e.g., *E. conspersus* (conspires stink bug)); *Chlorochroa* spp. (e.g., *C. sayi* (Say stinkbug)); *Nezara* spp. (e.g., *N. viridula* (southern green stinkbug)); *Thrips* spp. (e.g., *T. tabaci* (onion *thrips*)); *Frankliniella* spp. (e.g., *F. fusca* (tobacco *thrips*), or *F. occidentalis* (western flower *thrips*)); *Acheta* spp. (e.g., *A. domesticus* (house cricket)); *Myzus* spp. (e.g., *M. persicae* (green peach aphid)); *Macrosiphum* spp. (e.g., *M. euphorbiae* (potato aphid)); *Blissus* spp. (e.g., *B. leucopterus* (chinch bug)); *Acrosternum* spp. (e.g., *A. hilare* (green stink bug)); *Chilotraea* spp. (e.g., *C. polychrysa* (rice stalk borer)); *Lissorhoptrus* spp. (e.g., *L. oryzophilus* (rice water weevil)); *Rhopalosiphum* spp. (e.g., *R. maidis* (corn leaf aphid)); and *Anuraphis* spp. (e.g., *A. maidiradicis* (corn root aphid)).

The endophyte-associated plant can be tested for its ability to resist, or otherwise repel, pathogenic insects by measuring, for example, overall plant biomass, biomass of the fruit or grain, percentage of intact leaves, or other physiological parameters described herein, and comparing with a reference agricultural plant. In one embodiment, the endophyte-associated plant exhibits at least 5% greater biomass, for example, at least 10%, at least 15%, at least 20%, at least 30%, at least 40%, at least 50%, at least 75%, at least 100% or more biomass, than the reference agricultural plant grown under the same conditions (e.g., grown side-by-side, or adjacent to, the endophyte-associated plants). In other embodiments, the endophyte-associated plant exhibits at least 5% greater fruit or grain yield, for example, at least 10%, at least 15%, at least 20%, at least 30%, at least 40%, at least 50%, at least 75%, at least 100% or more fruit or grain yield, than the reference agricultural plant grown under the same conditions (e.g., grown side-by-side, or adjacent to, the endophyte-associated plants).

Nematodes. Nematodes are microscopic roundworms that feed on the roots, fluids, leaves and stems of more than 2,000 row crops, vegetables, fruits, and ornamental plants, causing an estimated $100 billion crop loss worldwide and accounting for 13% of global crop losses due to disease. A variety of parasitic nematode species infect crop plants, including root-knot nematodes (RKN), cyst- and lesion-forming nematodes. Root-knot nematodes, which are characterized by causing root gall formation at feeding sites, have a relatively broad host range and are therefore parasitic on a large number of crop species. The cyst- and lesion-forming nematode species have a more limited host range, but still cause considerable losses in susceptible crops.

Signs of nematode damage include stunting and yellowing of leaves, and wilting of the plants during hot periods. Nematode infestation, however, can cause significant yield losses without any obvious above-ground disease symptoms. The primary causes of yield reduction are due to underground root damage. Roots infected by SCN are dwarfed or stunted. Nematode infestation also can decrease the number of nitrogen-fixing nodules on the roots, and may make the roots more susceptible to attacks by other soilborne plant nematodes.

In one embodiment, the endophyte-associated plant has an increased resistance to a nematode when compared with a reference agricultural plant. As before with insect herbivores, biomass of the plant or a portion of the plant, or any of the other physiological parameters mentioned elsewhere, can be compared with the reference agricultural plant grown under the same conditions. Particularly useful measurements include overall plant biomass, biomass and/or size of the fruit or grain, and root biomass. In one embodiment, the endophyte-associated plant exhibits at least 5% greater biomass, for example, at least 10%, at least 15%, at least 20%, at least 30%, at least 40%, at least 50%, at least 75%, at least 100% or more biomass, than the reference agricultural plant grown under the same conditions (e.g., grown side-by-side, or adjacent to, the endophyte-associated plants, under conditions of nematode challenge). In another embodiment, the endophyte-associated plant exhibits at least 5% greater root biomass, for example, at least 10%, at least 15%, at least 20%, at least 30%, at least 40%, at least 50%, at least 75%, at least 100% or more root biomass, than the reference agricultural plant grown under the same conditions (e.g., grown side-by-side, or adjacent to, the endophyte-associated plants, under conditions of nematode challenge). In still another embodiment, the endophyte-associated plant exhibits at least 5% greater fruit or grain yield, for example, at least 10%, at least 15%, at least 20%, at least 30%, at least 40%, at least 50%, at least 75%, at least 100% or more fruit or grain yield, than the reference agricultural plant grown under the same conditions (e.g., grown side-by-side, or adjacent to, the endophyte-associated plants, under conditions of nematode challenge).

Fungal Pathogens.

Fungal diseases are responsible for yearly losses of over $10 Billion on agricultural crops in the US, represent 42% of global crop losses due to disease, and are caused by a large variety of biologically diverse pathogens. Different strategies have traditionally been used to control them. Resistance traits have been bred into agriculturally important varieties, thus providing various levels of resistance against either a narrow range of pathogen isolates or races, or against a broader range. However, this involves the long and labor intensive process of introducing desirable traits into commercial lines by genetic crosses and, due to the risk of pests evolving to overcome natural plant resistance, a constant effort to breed new resistance traits into commercial lines is required. Alternatively, fungal diseases have been controlled by the application of chemical fungicides. This strategy usually results in efficient control, but is also associated with the possible development of resistant pathogens and can be associated with a negative impact on the environment. Moreover, in certain crops, such as barley and wheat, the control of fungal pathogens by chemical fungicides is difficult or impractical.

The present invention contemplates the use of endophytes which are able to confer resistance to fungal pathogens to the host plant. Increased resistance to fungal inoculation can be measured, for example, using any of the physiological parameters presented above, by comparing with reference agricultural plants. In one embodiment, the endophyte-associated plant exhibits at least 5% greater biomass, for example, at least 10%, at least 15%, at least 20%, at least 30%, at least 40%, at least 50%, at least 75%, at least 100% or more biomass, than the reference agricultural plant grown under the same conditions (e.g., grown side-by-side, or adjacent to, the endophyte-associated plants, infected with the fungal pathogen). In still another embodiment, the endophyte-associated plant exhibits at least 5% greater fruit or grain yield, for example, at least 10%, at least 15%, at least 20%, at least 30%, at least 40%, at least 50%, at least 75%, at least 100% or more fruit or grain yield, than the reference agricultural plant grown under the same conditions (e.g., grown side-by-side, or adjacent to, the endophyte-associated plants, infected with the fungal pathogen). In another embodiment, the endophyte-associated plant exhibits at least a 5% reduction in for hyphal growth, for example, at least 10%, at least 15%, at least 20%, at least 30%, at least 40%, at least 50%, at least 75%, at least 90% reduction or more, in hyphal growth, than the reference agricultural plant grown under the same conditions (e.g., grown side-by-side, or adjacent to, the endophyte-associated plants, infected with the fungal pathogen).

Viral Pathogens.

Plant viruses are estimated to account for 18% of global crop losses due to disease. There are numerous examples of viral pathogens affecting agricultural productivity. Examples include the American wheat striate mosaic virus (AWSMV) (wheat striate mosaic), Barley stripe mosaic virus (BSMV), Barley yellow dwarf virus (BYDV), Brome mosaic virus (BMV), Cereal chlorotic mottle virus (CCMV), Corn chlorotic vein banding virus (CCVBV), Brazilian maize mosaic virus, Corn lethal necrosis Virus complex from Maize chlorotic mottle virus, (MCMV), Maize dwarf mosaic virus (MDMV), A or B Wheat streak mosaic virus (WSMV), Cucumber mosaic virus (CMV), *Cynodon* chlorotic streak virus (CCSV), Johnsongrass mosaic virus (JGMV), Maize bushy stunt *Mycoplasma*-like organism (MLO) associated virus, Maize chlorotic dwarf Maize chlorotic dwarf virus (MCDV), Maize chlorotic mottle virus (MCMV), Maize dwarf mosaic virus (MDMV), strains A, D, E and F, Maize leaf fleck virus (MLFV), Maize line virus (MLV), Maize mosaic (corn leaf stripe, Maize mosaic virus (MMV), enanismo rayado), Maize mottle and chlorotic stunt virus, Maize pellucid ringspot virus (MPRV), Maize raya gruesa virus (MRGV), Maize rayado fino (fine striping) virus (MRFV), Maize red stripe virus (MRSV), Maize ring mottle virus (MRMV), Maize rio cuarto virus (MRCV), Maize rough dwarf virus (MRDV), Cereal tillering disease virus, Maize sterile stunt virus, barley yellow striate virus, Maize streak virus (MSV), Maize stripe virus, Maize chloroticstripe virus, maize hoja blanca virus, Maize stunting virus; Maize tassel abortion virus (MTAV), Maize vein enation virus (MVEV), Maize wallaby ear virus (MWEV), Maize white leaf virus, Maize white line mosaic virus (MWLMV), Millet red leaf virus (MRLV), Northern cereal mosaic virus (NCMV), Oat pseudorosette virus, (zakuklivanie), Oat sterile dwarf virus (OSDV), Rice black-streaked dwarf virus (RBSDV), Rice stripe virus (RSV), Sorghum mosaic virus (SrMV), Sugarcane mosaic virus (SCMV) strains H, 1 and M, Sugarcane Fiji disease virus (FDV), Sugarcane mosaic virus (SCMV) strains A, B, D, E, SC, BC, Sabi and MB (formerly MDMV-B), and Wheat spot mosaic virus (WSMV). In one embodiment, the endophyte-associated plant provides protection against viral pathogens such that there is at least 5% greater biomass, for example, at least 10%, at least 15%, at least 20%, at least 30%, at least 40%, at least 50%, at least 75%, at least 100% or more biomass, than the reference agricultural plant grown under the same conditions. In still another embodiment, the endophyte-associated plant exhibits at least 5% greater fruit or grain yield, for example, at least 10%, at least 15%, at least 20%, at least 30%, at least 40%, at least 50%, at least 75%, at least 100% or more fruit or grain yield when challenged with a virus, than the reference agricultural plant grown under the same conditions. In yet another embodiment, the endophyte-associated plant exhibits at least 5% lower viral titer, for example, at least 10%, at least 15%, at least 20%, at least 30%, at least 40%, at least 50%, at least 75%, at least 100% lower viral titer when challenged with a virus, than the reference agricultural plant grown under the same conditions.

Bacterial Pathogens.

Likewise, bacterial pathogens are a significant problem negatively affecting agricultural productivity and accounting for 27% of global crop losses due to plant disease. In one embodiment, the endophyte-associated plant described herein provides protection against bacterial pathogens such that there is at least 5% greater biomass, for example, at least 10%, at least 15%, at least 20%, at least 30%, at least 40%, at least 50%, at least 75%, at least 100% or more biomass, than the reference agricultural plant grown under the same conditions. In still another embodiment, the endophyte-associated plant exhibits at least 5% greater fruit or grain yield, for example, at least 10%, at least 15%, at least 20%, at least 30%, at least 40%, at least 50%, at least 75%, at least 100% or more fruit or grain yield when challenged with a bacterial pathogen, than the reference agricultural plant grown under the same conditions. In yet another embodiment, the endophyte-associated plant exhibits at least 5% lower bacterial count, for example, at least 10%, at least 15%, at least 20%, at least 30%, at least 40%, at least 50%, at least 75%, at least 100% lower bacterial count when challenged with a bacteria, than the reference agricultural plant grown under the same conditions.

Improvement of Other Traits.

In other embodiments, the inoculated endophyte can confer other beneficial traits to the plant. Improved traits can include an improved nutritional content of the plant or plant part used for human consumption. In one embodiment, the endophyte-associated plant is able to produce a detectable change in the content of at least one nutrient. Examples of such nutrients include amino acid, protein, oil (including any one of Oleic acid, Linoleic acid, Alpha-linolenic acid, Saturated fatty acids, Palmitic acid, Stearic acid and Trans fats), carbohydrate (including sugars such as sucrose, glucose and fructose, starch, or dietary fiber), Vitamin A, Thiamine (vit. B1), Riboflavin (vit. B2), Niacin (vit. B3), Pantothenic acid (B5), Vitamin B6, Folate (vit. B9), Choline, Vitamin C, Vitamin E, Vitamin K, Calcium, Iron, Magnesium, Manganese, Phosphorus, Potassium, Sodium, Zinc. In one embodiment, the endophyte-associated plant or part thereof contains at least 10% more nutrient, for example, at least 20%, at least 30%, at least 40%, at least 50%, at least 60%, at least 70%, at least 80%, at least 90%, at least 100%, at least 150%, at least 200%, at least 300% or more, of the nutrient when compared with reference agricultural plants.

In other cases, the improved trait can include reduced content of a harmful or undesirable substance when compared with reference agricultural plants. Such compounds include those which are harmful when ingested in large quantities or are bitter tasting (for example, oxalic acid, amygdalin, certain alkaloids such as solanine, caffeine, nicotine, quinine and morphine, tannins, cyanide). As such, in one embodiment, the endophyte-associated plant or part thereof contains at least 10% less of the undesirable substance, for example, at least 20%, at least 30%, at least 40%, at least 50%, at least 60%, at least 70%, at least 80%, at least 90%, at least 95%, at least 98%, at least 99% less of the undesirable substance when compared with reference agricultural plant. In a related embodiment, the improved trait can include improved taste of the plant or a part of the plant, including the fruit or seed. In a related embodiment, the improved trait can include reduction of undesirable compounds produced by other endophytes in plants, such as degradation of *Fusarium* produced deoxynivalenol (also known as vomitoxin and a virulence factor involved in *Fusarium* head blight of maize and wheat) in a part of the plant, including the fruit or seed.

In other cases, the improved trait can be an increase in overall biomass of the plant or a part of the plant, including its fruit or seed.

The endophyte-associated plant can also have an altered hormone status or altered levels of hormone production when compared with a reference agricultural plant. An alteration in hormonal status may affect many physiological parameters, including flowering time, water efficiency, apical dominance and/or lateral shoot branching, increase in root hair, and alteration in fruit ripening.

The association between the endophyte and the plant can also be detected using other methods known in the art. For example, the biochemical, metabolomics, proteomic, genomic, epigenomic and/or transcriptomic profiles of endophyte-associated plants can be compared with reference agricultural plants under the same conditions.

Metabolomic differences between the plants can be detected using methods known in the art. For example, a biological sample (whole tissue, exudate, phloem sap, xylem sap, root exudate, etc.) from the endophyte-associated and reference agricultural plants can be analyzed essentially as described in Fiehn et al., (2000) Nature Biotechnol., 18, 1157-1161, or Roessner et al., (2001) Plant Cell, 13, 11-29. Such metabolomic methods can be used to detect differences in levels in hormone, nutrients, secondary metabolites, root exudates, phloem sap content, xylem sap content, heavy metal content, and the like. Such methods are also useful for detecting alterations in microbial content and status; for example, the presence and levels of bacterial/fungal signaling molecules (e.g., autoinducers and pheromones), which can indicate the status of group-based behavior of endophytes based on, for example, population density (see, for example Daniels et al., (2006). PNAS 103: 14965-14970. Eberhard et al., (1981). Biochemistry 20 (9): 2444-2449). Transcriptome analysis (reviewed, for example, in Usadel & Fernie, (2013). Front Plant Sci. 4:48) of endophyte-associated and reference agricultural plants can also be performed to detect changes in expression of at least one transcript, or a set or network of genes upon endophyte association. Similarly, epigenetic changes can be detected using methylated DNA immunoprecipitation followed by high-throughput sequencing (Vining et al., (2013) BMC Plant Biol. 13:92).

Combinations of Endophytic Microbes

Combinations of endophytic microbes such as seed-origin bacterial endophytes can be selected by any one or more of several criteria. In one embodiment, compatible endophytic populations are selected. As used herein, compatibility refers to microbial populations which do not significantly interfere with the growth and propagation of the other. Incompatible microbial populations can arise, for example, where one of the populations produces or secrets a compound which is toxic or deleterious to the growth of the other population(s). Incompatibility arising from production of deleterious compounds/agents can be detected using methods known in the art, and as described herein elsewhere. Similarly, the distinct populations can compete for limited resources in a way that makes co-existence difficult.

In another embodiment, combinations are selected on the basis of compounds produced by each population. For example, the first population is capable of producing siderophores, and another population is capable of producing anti-fungal compounds. In one embodiment, the first population of bacterial endophytes is capable of a function selected from the group consisting of auxin production, nitrogen fixation, production of an antimicrobial compound, siderophore production, mineral phosphate solubilization, cellulase production, chitinase production, xylanase production, and acetoin production. In another embodiment, the second population of bacterial endophytes is capable of a function selected from the group consisting of auxin production, nitrogen fixation, production of an antimicrobial compound, siderophore production, mineral phosphate solubilization, cellulase production, chitinase production, xylanase production, and acetoin production. In still another embodiment, the first and second populations are capable of at least one different function.

In still another embodiment, the combinations are selected which display distinct localization in the plant after colonization. For example, the first population can colonize, and in some cases preferentially colonize, the root tissue, while a second population can be selected on the basis of its preferential colonization of the aerial parts of the agricultural plant. Therefore, in one embodiment, the first population is capable of colonizing one or more of the tissues selected from the group consisting of a root, shoot, leaf, flower, and seed. In another embodiment, the second population is capable of colonizing one or more tissues selected from the group consisting of root, shoot, leaf, flower, and seed. In still another embodiment, the first and second populations are capable of colonizing a different tissue within the agricultural grass plant.

In still another embodiment, the combinations of endophytes are selected which confer one or more distinct fitness traits on the inoculated agricultural plant, either individually or in synergistic association with other endophytes. Alternatively, two or more endophytes induce the colonization of a third endophyte. For example, the first population is selected on the basis that it confers significant increase in biomass, while the second population promotes increased drought tolerance on the inoculated agricultural plant. Therefore, in one embodiment, the first population is capable of conferring at least one trait selected from the group consisting of thermal tolerance, herbicide tolerance, drought resistance, insect resistance, fungus resistance, virus resistance, bacteria resistance, male sterility, cold tolerance, salt tolerance, increased yield, enhanced nutrient use efficiency, increased nitrogen use efficiency, increased fermentable carbohydrate content, reduced lignin content, increased antioxidant content, enhanced water use efficiency, increased vigor, increased germination efficiency, earlier or increased flowering, increased biomass, altered root-to-shoot biomass ratio, enhanced soil water retention, or a combination thereof. In another embodiment, the second population is capable of conferring a trait selected from the group consisting of thermal tolerance, herbicide tolerance, drought resistance, insect resistance, fungus resistance, virus resistance, bacteria resistance, male sterility, cold tolerance, salt tolerance, increased yield, enhanced nutrient use efficiency, increased nitrogen use efficiency, increased fermentable carbohydrate content, reduced lignin content, increased antioxidant content, enhanced water use efficiency, increased vigor, increased germination efficiency, earlier or increased flowering, increased biomass, altered root-to-shoot biomass ratio, enhanced soil water retention, or a combination thereof. In still another embodiment, each of the first and second population is capable of conferring a different trait selected from the group consisting of thermal tolerance, herbicide tolerance, drought resistance, insect resistance, fungus resistance, virus resistance, bacteria resistance, male sterility, cold tolerance, salt tolerance, increased yield, enhanced nutrient use efficiency, increased nitrogen use efficiency, increased fermentable carbohydrate content, reduced lignin content, increased antioxidant content, enhanced water use efficiency, increased vigor, increased germination efficiency, earlier or increased flowering, increased biomass, altered root-to-shoot biomass ratio, enhanced soil water retention, or a combination thereof.

The combinations of endophytes can also be selected based on combinations of the above criteria. For example, the first population can be selected on the basis of the compound it produces (e.g., its ability to fix nitrogen, thus providing a potential nitrogen source to the plant), while the second population is selected on the basis of its ability to confer increased resistance of the plant to a pathogen (e.g., a fungal pathogen).

Formulations/Seed Coating Compositions

The purified bacterial populations described herein can be formulated using an agriculturally compatible carrier. The formulation useful for these embodiments generally typically include at least one member selected from the group consisting of a tackifier, a microbial stabilizer, a fungicide, an antibacterial agent, an herbicide, a nematicide, an insecticide, a plant growth regulator, a rodenticide, a desiccant, and a nutrient.

In some cases, the purified bacterial population is mixed with an agriculturally compatible carrier. The carrier can be a solid carrier or liquid carrier, and in various forms including microspheres, powders, emulsions and the like. The carrier may be any one or more of a number of carriers that confer a variety of properties, such as increased stability, wettability, or dispersability. Wetting agents such as natural or synthetic surfactants, which can be nonionic or ionic surfactants, or a combination thereof can be included in a composition of the invention. Water-in-oil emulsions can also be used to formulate a composition that includes the purified bacterial population (see, for example, U.S. Pat. No. 7,485,451, which is incorporated herein by reference in its entirety). Suitable formulations that may be prepared include wettable powders, granules, gels, agar strips or pellets, thickeners, and the like, microencapsulated particles, and the like, liquids such as aqueous flowables, aqueous suspensions, water-in-oil emulsions, etc. The formulation may include grain or legume products, for example, ground grain or beans, broth or flour derived from grain or beans, starch, sugar, or oil.

In some embodiments, the agricultural carrier may be soil or a plant growth medium. Other agricultural carriers that may be used include water, fertilizers, plant-based oils, humectants, or combinations thereof. Alternatively, the agricultural carrier may be a solid, such as diatomaceous earth, loam, silica, alginate, clay, bentonite, vermiculite, seed cases, other plant and animal products, or combinations, including granules, pellets, or suspensions. Mixtures of any of the aforementioned ingredients are also contemplated as carriers, such as but not limited to, pesta (flour and kaolin clay), agar or flour-based pellets in loam, sand, or clay, etc. Formulations may include food sources for the cultured organisms, such as barley, rice, or other biological materials such as seed, plant parts, sugar cane bagasse, hulls or stalks from grain processing, ground plant material or wood from building site refuse, sawdust or small fibers from recycling of paper, fabric, or wood. Other suitable formulations will be known to those skilled in the art.

In one embodiment, the formulation can include a tackifier or adherent. Such agents are useful for combining the bacterial population of the invention with carriers that can contain other compounds (e.g., control agents that are not biologic), to yield a coating composition. Such compositions help create coatings around the plant or seed to maintain contact between the microbe and other agents with the plant or plant part. In one embodiment, adherents are selected from the group consisting of: alginate, gums, starches, lecithins, formononetin, polyvinyl alcohol, alkali formononetinate, hesperetin, polyvinyl acetate, cephalins, Gum Arabic, Xanthan Gum, Mineral Oil, Polyethylene Glycol (PEG), Polyvinyl pyrrolidone (PVP), Arabino-galactan, Methyl Cellulose, PEG 400, Chitosan, Polyacrylamide, Polyacrylate, Polyacrylonitrile, Glycerol, Triethylene glycol, Vinyl Acetate, Gellan Gum, Polystyrene, Polyvinyl, Carboxymethyl cellulose, Gum Ghatti, and polyoxyethylene-polyoxybutylene block copolymers. Other examples of adherent compositions that can be used in the synthetic preparation include those described in EP 0818135, CA 1229497, WO 2013090628, EP 0192342, WO 2008103422 and CA 1041788, each of which is incorporated herein by reference in its entirety.

The formulation can also contain a surfactant. Non-limiting examples of surfactants include nitrogen-surfactant blends such as Prefer 28 (Cenex), Surf-N(US), Inhance (Brandt), P-28 (Wilfarm) and Patrol (Helena); esterified seed oils include Sun-It II (AmCy), MSO (UAP), Scoil (Agsco), Hasten (Wilfarm) and Mes-100 (Drexel); and organo-silicone surfactants include Silwet L77 (UAP), Silikin (Terra), Dyne-Amic (Helena), Kinetic (Helena), Sylgard 309 (Wilbur-Ellis) and Century (Precision). In one embodiment, the surfactant is present at a concentration of between 0.01% v/v to 10% v/v. In another embodiment, the surfactant is present at a concentration of between 0.1% v/v to 1% v/v.

In certain cases, the formulation includes a microbial stabilizer. Such an agent can include a desiccant. As used herein, a "desiccant" can include any compound or mixture of compounds that can be classified as a desiccant regardless of whether the compound or compounds are used in such concentrations that they in fact have a desiccating effect on the liquid inoculant. Such desiccants are ideally compatible with the bacterial population used, and should promote the ability of the microbial population to survive application on the seeds and to survive desiccation. Examples of suitable desiccants include one or more of trehalose, sucrose, glycerol, and Methylene glycol. Other suitable desiccants include, but are not limited to, non reducing sugars and sugar alcohols (e.g., mannitol or sorbitol). The amount of desiccant introduced into the formulation can range from about 5% to about 50% by weight/volume, for example, between about 10% to about 40%, between about 15% and about 35%, or between about 20% and about 30%.

In some cases, it is advantageous for the formulation to contain agents such as a fungicide, an antibacterial agent, an herbicide, a nematicide, an insecticide, a plant growth regulator, a rodenticide, or a nutrient. Such agents are ideally compatible with the agricultural seed or seedling onto which the formulation is applied (e.g., it should not be deleterious to the growth or health of the plant). Furthermore, the agent is ideally one which does not cause safety concerns for human, animal or industrial use (e.g., no safety issues, or the compound is sufficiently labile that the commodity plant product derived from the plant contains negligible amounts of the compound).

In the liquid form, for example, solutions or suspensions, the bacterial endophytic populations of the present invention can be mixed or suspended in water or in aqueous solutions. Suitable liquid diluents or carriers include water, aqueous solutions, petroleum distillates, or other liquid carriers.

Solid compositions can be prepared by dispersing the bacterial endophytic populations of the invention in and on an appropriately divided solid carrier, such as peat, wheat, bran, vermiculite, clay, talc, bentonite, diatomaceous earth, fuller's earth, pasteurized soil, and the like. When such formulations are used as wettable powders, biologically compatible dispersing agents such as non-ionic, anionic, amphoteric, or cationic dispersing and emulsifying agents can be used.

The solid carriers used upon formulation include, for example, mineral carriers such as kaolin clay, pyrophillite, bentonite, montmorillonite, diatomaceous earth, acid white soil, vermiculite, and pearlite, and inorganic salts such as ammonium sulfate, ammonium phosphate, ammonium nitrate, urea, ammonium chloride, and calcium carbonate. Also, organic fine powders such as wheat flour, wheat bran, and rice bran may be used. The liquid carriers include vegetable oils such as soybean oil and cottonseed oil, glycerol, ethylene glycol, polyethylene glycol, propylene glycol, polypropylene glycol, etc.

In one particular embodiment, the formulation is ideally suited for coating of the endophytic microbial population onto seeds. The bacterial endophytic populations described in the present invention are capable of conferring many fitness benefits to the host plants. The ability to confer such benefits by coating the bacterial populations on the surface of seeds has many potential advantages, particularly when used in a commercial (agricultural) scale.

The bacterial endophytic populations herein can be combined with one or more of the agents described above to yield a formulation suitable for combining with an agricultural seed or seedling. The bacterial population can be obtained from growth in culture, for example, using a synthetic growth medium. In addition, the microbe can be cultured on solid media, for example on petri dishes, scraped off and suspended into the preparation. Microbes at different growth phases can be used. For example, microbes at lag phase, early-log phase, mid-log phase, late-log phase, stationary phase, early death phase, or death phase can be used.

The formulations comprising the bacterial endophytic population of the present invention typically contains between about 0.1 to 95% by weight, for example, between about 1% and 90%, between about 3% and 75%, between about 5% and 60%, between about 10% and 50% in wet weight of the bacterial population of the present invention. It is preferred that the formulation contains at least about $10^3$ CFU per ml of formulation, for example, at least about $10^4$, at least about $10^5$, at least about $10^6$, at least 10' CFU, at least $10^8$ CFU per ml of formulation.

Population of Seeds

In another aspect, the invention provides for a substantially uniform population of seeds comprising a plurality of seeds comprising the bacterial endophytic population, as described herein above. Substantial uniformity can be determined in many ways. In some cases, at least 10%, for example, at least 20%, at least 30%, at least 40%, at least 50%, at least 60%, at least 70%, at least 75%, at least 80%, at least 90%, at least 95% or more of the seeds in the population, contains the bacterial endophytic population in an amount effective to colonize the plant disposed on the surface of the seeds. In other cases, at least 10%, for example, at least 20%, at least 30%, at least 40%, at least 50%, at least 60%, at least 70%, at least 75%, at least 80%, at least 90%, at least 95% or more of the seeds in the population, contains at least 1, 10, or 100 CFU on the seed surface or per gram of seed, for example, at least 200 CFU, at least 300 CFU, at least 1,000 CFU, at least 3,000 CFU, at least 10,000 CFU, at least 30,000 CFU, at least 100,000 CFU, at least 300,000 CFU, or at least 1,000,000 CFU per seed or more.

In a particular embodiment, the population of seeds is packaged in a bag or container suitable for commercial sale. Such a bag contains a unit weight or count of the seeds comprising the bacterial endophytic population as described herein, and further comprises a label. In one embodiment, the bag or container contains at least 1,000 seeds, for example, at least 5,000 seeds, at least 10,000 seeds, at least 20,000 seeds, at least 30,000 seeds, at least 50,000 seeds, at least 70,000 seeds, at least 80,000 seeds, at least 90,000 seeds or more. In another embodiment, the bag or container can comprise a discrete weight of seeds, for example, at least 1 lb, at least 2 lbs, at least 5 lbs, at least 10 lbs, at least 30 lbs, at least 50 lbs, at least 70 lbs or more. The bag or container comprises a label describing the seeds and/or said bacterial endophytic population. The label can contain additional information, for example, the information selected from the group consisting of: net weight, lot number, geographic origin of the seeds, test date, germination rate, inert matter content, and the amount of noxious weeds, if any. Suitable containers or packages include those traditionally used in plant seed commercialization. The invention also contemplates other containers with more sophisticated storage capabilities (e.g., with microbiologically tight wrappings or with gas- or water-proof containments).

In some cases, a sub-population of seeds comprising the bacterial endophytic population is further selected on the basis of increased uniformity, for example, on the basis of uniformity of microbial population. For example, individual seeds of pools collected from individual cobs, individual plants, individual plots (representing plants inoculated on the same day) or individual fields can be tested for uniformity of microbial density, and only those pools meeting specifications (e.g., at least 80% of tested seeds have minimum density, as determined by quantitative methods described elsewhere) are combined to provide the agricultural seed sub-population.

The methods described herein can also comprise a validating step. The validating step can entail, for example, growing some seeds collected from the inoculated plants into mature agricultural plants, and testing those individual plants for uniformity. Such validating step can be performed on individual seeds collected from cobs, individual plants, individual plots (representing plants inoculated on the same day) or individual fields, and tested as described above to identify pools meeting the required specifications.

In some embodiments, methods described herein include planting a synthetic combination described herein. Suitable planters include an air seeder and/or fertilizer apparatus used in agricultural operations to apply particulate materials including one or more of the following, seed, fertilizer and/or inoculants, into soil during the planting operation. Seeder/fertilizer devices can include a tool bar having ground-engaging openers thereon, behind which is towed a wheeled cart that includes one or more containment tanks or bins and associated metering means to respectively contain and meter therefrom particulate materials. See, e.g., U.S. Pat. No. 7,555,990.

In certain embodiments, a composition described herein may be in the form of a liquid, a slurry, a solid, or a powder (wettable powder or dry powder). In another embodiment, a composition may be in the form of a seed coating. Compositions in liquid, slurry, or powder (e.g., wettable powder) form may be suitable for coating seeds. When used to coat seeds, the composition may be applied to the seeds and allowed to dry. In embodiments wherein the composition is a powder (e.g., a wettable powder), a liquid, such as water, may need to be added to the powder before application to a seed.

In still another embodiment, the methods can include introducing into the soil an inoculum of one or more of the endophyte populations described herein. Such methods can include introducing into the soil one or more of the compositions described herein.

The inoculum(s) or compositions may be introduced into the soil according to methods known to those skilled in the art. Non-limiting examples include in-furrow introduction, spraying, coating seeds, foliar introduction, etc. In a particular embodiment, the introducing step comprises in-furrow introduction of the inoculum or compositions described herein.

In one embodiment, seeds may be treated with composition(s) described herein in several ways but preferably via spraying or dripping. Spray and drip treatment may be conducted by formulating compositions described herein and spraying or dripping the composition(s) onto a seed(s) via a continuous treating system (which is calibrated to apply treatment at a predefined rate in proportion to the continuous flow of seed), such as a drum-type of treater. Batch systems, in which a predetermined batch size of seed and composition(s) as described herein are delivered into a mixer, may also be employed. Systems and apparati for performing these processes are commercially available from numerous suppliers, e.g., Bayer CropScience (Gustafson).

In another embodiment, the treatment entails coating seeds. One such process involves coating the inside wall of a round container with the composition(s) described herein, adding seeds, then rotating the container to cause the seeds to contact the wall and the composition(s), a process known in the art as "container coating". Seeds can be coated by combinations of coating methods. Soaking typically entails using liquid forms of the compositions described. For example, seeds can be soaked for about 1 minute to about 24 hours (e.g., for at least 1 min, 5 min, 10 min, 20 min, 40 min, 80 min, 3 hr, 6 hr, 12 hr, 24 hr).

Population of Plants/Agricultural Fields

A major focus of crop improvement efforts has been to select varieties with traits that give, in addition to the highest return, the greatest homogeneity and uniformity. While inbreeding can yield plants with substantial genetic identity, heterogeneity with respect to plant height, flowering time, and time to seed, remain impediments to obtaining a homogeneous field of plants. The inevitable plant-to-plant variability are caused by a multitude of factors, including uneven environmental conditions and management practices. Another possible source of variability can, in some cases, be due to the heterogeneity of the microbial population inhabit the plants. By providing bacterial endophytic populations onto seeds and seedlings, the resulting plants generated by germinating the seeds and seedlings have a more consistent microbial composition, and thus are expected to yield a more uniform population of plants.

Therefore, in another aspect, the invention provides a substantially uniform population of plants. The population can include at least 100 plants, for example, at least 300 plants, at least 1,000 plants, at least 3,000 plants, at least 10,000 plants, at least 30,000 plants, at least 100,000 plants or more. The plants are grown from the seeds comprising the bacterial endophytic population as described herein. The increased uniformity of the plants can be measured in a number of different ways.

In one embodiment, there is an increased uniformity with respect to the microbes within the plant population. For example, in one embodiment, a substantial portion of the population of plants, for example at least 10%, at least 20%, at least 30%, at least 40%, at least 50%, at least 60%, at least 70%, at least 75%, at least 80%, at least 90%, at least 95% or more of the seeds or plants in a population, contains a threshold number of the bacterial endophytic population. The threshold number can be at least 10 CFU, at least 100 CFU, for example at least 300 CFU, at least 1,000 CFU, at least 3,000 CFU, at least 10,000 CFU, at least 30,000 CFU, at least 100,000 CFU or more, in the plant or a part of the plant. Alternatively, in a substantial portion of the population of plants, for example, in at least 1%, at least 10%, at least 20%, at least 30%, at least 40%, at least 50%, at least 60%, at least 70%, at least 75%, at least 80%, at least 90%, at least 95% or more of the plants in the population, the bacterial endophyte population that is provided to the seed or seedling represents at least 0.1%, at least 1%, at least 5%, at least 10%, at least 20%, at least 30%, at least 40%, at least 50%, at least 60%, at least 70%, at least 80%, at least 90%, at least 95%, at least 99%, or 100% of the total microbe population in the plant/seed.

In one embodiment, there is increased genetic uniformity of a substantial proportion or all detectable microbes within the taxa, genus, or species of the seed-origin microbe relative to an uninoculated control. This increased uniformity can be a result of the seed-origin microbe being of monoclonal origin or otherwise deriving from a seed-origin microbial population comprising a more uniform genome sequence and plasmid repertoire than would be present in the microbial population a plant that derives its microbial community largely via assimilation of diverse soil symbionts.

In another embodiment, there is an increased uniformity with respect to a physiological parameter of the plants within the population. In some cases, there can be an increased uniformity in the height of the plants when compared with a population of reference agricultural plants grown under the same conditions. For example, there can be a reduction in the standard deviation in the height of the plants in the population of at least 5%, for example, at least 10%, at least 15%, at least 20%, at least 30%, at least 40%, at least 50%, at least 60% or more, when compared with a population of reference agricultural plants grown under the same conditions. In other cases, there can be a reduction in the standard deviation in the flowering time of the plants in the population of at least 5%, for example, at least 10%, at least 15%, at least 20%, at least 30%, at least 40%, at least 50%, at least 60% or more, when compared with a population of reference agricultural plants grown under the same conditions.

Commodity Plant Product

The present invention provides a commodity plant product, as well as methods for producing a commodity plant product, that is derived from a plant of the present invention. As used herein, a "commodity plant product" refers to any composition or product that is comprised of material derived from a plant, seed, plant cell, or plant part of the present invention. Commodity plant products may be sold to consumers and can be viable or nonviable. Nonviable commodity products include but are not limited to nonviable seeds and grains; processed seeds, seed parts, and plant parts; dehydrated plant tissue, frozen plant tissue, and processed plant tissue; seeds and plant parts processed for animal feed for terrestrial and/or aquatic animal consumption, oil, meal, flour, flakes, bran, fiber, paper, tea, coffee, silage, crushed of whole grain, and any other food for human or animal consumption; and biomasses and fuel products; and raw material in industry. Industrial uses of oils derived from the agricultural plants described herein include ingredients for paints, plastics, fibers, detergents, cosmetics, lubricants, and biodiesel fuel. Soybean oil may be split, inter-esterified, sulfurized, epoxidized, polymerized, ethoxylated, or cleaved. Designing and producing soybean oil derivatives with improved functionality and improved oliochemistry is a rapidly growing field. The typical mixture of triglycerides is usually split and separated into pure fatty acids, which are then combined with petroleum-derived alcohols or acids, nitrogen, sulfonates, chlorine, or with fatty alcohols derived from fats and oils to produce the desired type of oil or fat. Commodity plant products also include industrial compounds, such as a wide variety of resins used in the formulation of adhesives, films, plastics, paints, coatings and foams.

The invention will be further described in the following examples, which do not limit the scope of the invention described in the claims.

EXAMPLES

Example 1—Isolation of Bacterial Endophytes from Seeds, Seedlings, and Plants

In order to better understand the role played by seed-borne endophytic microbes in improving the vigor, general health and stress resilience of host plants, a systematic screen was initiated to isolate and characterize endophytic microbes from seeds of commercially significant grass plants.

Diverse types of maize, wheat, rice, and other seeds were acquired and screened for cultivatable microbes. 49 distinct cultivars of maize and teosinte accessions were sourced from the USDA via GRIN (National Genetic Resources Program at http://www.ars-grin.gov/) or purchased from the Sustainable Seed Company (Covelo, Calif.). Similarly, 5 distinct wheat cultivars and wheat relatives were sourced from the USDA via GRIN (National Genetic Resources Program at http://www.ars-grin.gov/) or purchased from a Whole Foods in Cambridge, Mass. Seeds of rice and rice relatives (23 in total) were sourced from the USDA via GRIN (National Genetic Resources Program at http://www.ars-grin.gov/) or purchased from a Whole Foods in Cambridge, Mass. Seeds of several other species of plants, including sorghum, millet, oat, rye, teff, etc., were sourced from the USDA via GRIN (National Genetic Resources Program at the world wide web at ars-grin.gov/), the Sustainable Seed Company or purchased from a Whole Foods in Cambridge, Mass.

Pools of 5 seeds were soaked in 10 mL of sterile water contained in sterile 15 mL conical tubes for 24 hours. Some maize and rice accessions were sampled for seed surface microbes. In these cases, after 24 hours of soaking, 50 µL aliquots of undiluted, 100× dilute and 10000× dilute soaking water was plated onto R2A agar [Proteose peptone (0.5 g/L), Casamino acids (0.5 g/L), Yeast extract (0.5 g/L), Dextrose (0.5 g/L) Soluble starch (0.5 g/L), Dipotassium phosphate (0.3 g/L), Magnesium sulfate $7H_2O$ (0.05 g/L), Sodium pyruvate (0.3 g/L), Agar (15 g/L), Final pH 7±0.2 @ 25° C.] to culture oligotrophic bacteria, while the same volumes and dilutions were also plated onto potato dextrose agar (PDA) [Potato Infusion from 200 g/L, Dextrose 20 g/L, Agar 15 g/L, Final pH: 5.6±0.2 at 25° C.] to culture copiotrophic bacteria and fungi. All seeds in the study were sampled for endophytes by surface sterilization, trituration, and culturing of the mash. Seeds were surface sterilized by washing with 70% EtOH, rinsing with water, then washing with a 3% solution of sodium hypochlorite followed by 3 rinses in sterile water. All wash and rinse steps were 5 minutes with constant shaking at 130 rpm. Seeds were then blotted on R2A agar which was incubated at 30° C. for 7 days in order to confirm successful surface sterilization. Following the sterilization process, batches of seeds were ground with a sterile mortar and pestle in sterile R2A broth, while seeds of maize, rice and soy were also grown in sterile conditions and the roots or shoots of seedlings (without further sterilization) were crushed by bead beating in a Fastprep24 machine with 3 carbide beads, 1 mL of R2A broth in a 15 mL Falcon tube shaking at 6M/s for 60 seconds. Extracts of surface washes, crushed seed, or macerated seedling tissue were serially diluted by factors of 1 to $10^{-3}$ and spread onto quadrants on R2A, PDA, LGI or V8 juice agar in order to isolate cultivable seed-borne microorganisms. Plates were incubated at 28° C. for 7 days, monitoring for the appearance of colonies daily. After a week, plates were photographed and different morphotypes of colonies were identified and labeled. These were then selected for identification by sequencing, backing up by freezing at −80° C. as glycerol stock, and assaying for beneficial functions as described herein.

Plating and Scoring of Microbes

After 7 days of growth, most bacterial colonies had grown large and distinct enough to allow differentiation based on colony size, shape, color and texture. Photographs of each plate were taken, and on the basis of color and morphotype, different colonies were identified by number for later reference. These strains were also streaked out onto either R2A or PDA to check for purity, and clean cultures were then scraped with a loop off the plate, resuspended in a mixture of R2A and glycerol, and frozen away in quadruplicate at −80° C. for later.

Example 2—Sequence Analysis & Phylogenetic Assignment

To accurately characterize the isolated bacterial endophytes, colonies were submitted for marker gene sequencing, and the sequences were analyzed to provide taxonomic classifications. Colonies were subjected to 16S rRNA gene PCR amplification using a 27f/1492r primer set, and Sanger sequencing of paired ends was performed at Genewiz (South Plainfield, N.J.). Raw chromatograms were converted to sequences, and corresponding quality scores were assigned using TraceTuner v3.0.6beta (U.S. Pat. No. 6,681,186, incorporated herein by reference). These sequences were quality filtered using PRINSEQ v0.20.3 [Schmieder and Edwards (2011) Bioinformatics. 2011; 27:863-864, incorporated herein by reference] with left and right trim quality score thresholds of 30 and a quality window of 20 bp. Sequences without paired reads were discarded from further processing. Paired end quality filtered sequences were merged using USEARCH v7.0 [Edgar (2010) Nature methods 10:996-8]. Taxonomic classifications were assigned to the sequences using the RDP classifier [Wang et al., (2007) Applied and environmental microbiology 73:5261-7, incorporated herein by reference] trained on the Greengenes database [McDonald et al. (2012), ISME journal 6:610-8, incorporated herein by reference]. The resulting 473 microbes, representing 44 distinct OTUs (using a 97% similarity threshold) are provided in Table 2.

Example 3—In-Vitro Testing of Bacterial Endophytes

A total of 242 seed-origin bacterial endophytes representing 44 distinct OTUs as described above were seeded onto 96 well plates and tested for various activities and/or production of compounds, as described below. Colonies or wells with no detectable activity were scored as "−", low activity as "1," moderate activity as "2" and strong activity as "3." The results of these in vitro assays are summarized in Table 3.

Production of Auxin (SD)

To allow isolates to grow and accumulate auxin, bacterial strains were inoculated into 250 µL of R2A broth supplemented with L-tryptophan (5 mM) in 350 µL deep, transparent flat bottom, 96 well culture plates. The plates were sealed with a breathable membrane and incubated at 28° C. under static conditions for 3 days. After 3 days the OD600 and OD530 nm were measured on a plate reader to check for bacterial growth. After measuring these ODs, 50 µL of yellowish Salkowski reagent (0.01 M $FeCl_3$ in 35% $HClO_4$ (perchloric acid. #311421, Sigma) were added to each well and incubated in the dark for 30 minutes before measuring the OD530 nm measured to detect pink/red color.

Auxin is an important plant hormone, which can promote cell enlargement and inhibit branch development (meristem activity) in above ground plant tissues, while below ground it has the opposite effect, promoting root branching and growth. Interestingly, plant auxin is manufactured above ground and transported to the roots. It thus follows that plant and especially root inhabiting microbes which produce significant amounts of auxin will be able to promote root branching and development even under conditions where the plant reduces its own production of auxin. Such conditions can exist for example when soil is flooded and roots encounter an anoxic environment which slows or stops root metabolism.

Seed-origin bacteria were screened for their ability to produce auxins as possible root growth promoting agents. A very large number of bacteria showed a detectable level of pink or red colour development (the diagnostic feature of the assay suggesting auxin or indolic compound production)—169 out of 247. 89 strains had particularly strong production of auxin or indole compounds. *Erwinia* and *Pantoea* species are very similar if not identical taxonomic groups and can thus be considered together—of a total of 38 isolates, 23 had moderate or strong production of auxin or indole compounds in vitro. Many of these *Erwinia* and *Pantoea* strains were isolated from inside surface sterilized seeds, suggesting they may be able to colonize the inside of the emerging root (first plant part to emerge the seed) and stimulate root growth for by producing auxins on the inside of the plant.

Another important group of auxin producing seed-origin bacteria were *Pseudomonas* species, 9 of the 14 isolated showed significant production of indoles in this assay. Ochrobactrum species were also detected as strong producers of indolic compounds in this assay, with 15 of 18 showing moderate to strong color change (although all 18 had detectable colour change in this assay). Strongly auxin producing strains of *Pseudomonas* and Ochrobactrum species were isolated from seed surfaces.

Mineral Phosphate Solubilization

Microbes were plated on tricalcium phosphate media as described in Rodriguez et al., (2001) J Biotechnol 84: 155-161 (incorporated herein by reference). This was prepared as follows: 10 g/L glucose, 0.373 g/L $NH_4NO_3$, 0.41 g/L $MgSO_4$, 0.295 g/L NaCl, 0.003 $FeCl_3$, 0.7 g/L $Ca_3HPO_4$, 100 mM Tris and 20 g/L Agar, pH 7, then autoclaved and poured into square Petri plates. After 3 days of growth at 28° C. in darkness, clear halos were measured around colonies able to solubilize the tricalcium phosphate. This was an agar based assay looking for halos around colonies which signify the solubilization of opaque tri-calcium phosphate, which resulted in a large number (95) of isolates having detectable levels of phosphate solubilization (Table 3). Of these, at least 36 had moderate to high levels of phosphate solubilization, including several *Enterobacter* and *Pantoea* species.

Growth on Nitrogen Free LGI Media

All glassware was cleaned with 6 M HCl before media preparation. A new 96 well plate (300 ul well volume) was filled with 250 ul/well of sterile LGI broth [per L, 50 g Sucrose, 0.01 g $FeCl_3$-$6H_2O$, 0.8 g $K_3PO_4$, 0.2 g $CaCl2$, 0.2 g $MgSO_4$-$7H_2O$, 0.002 g $Na_2MoO_4$-$2H_2O$, pH 7.5]. Bacteria were inoculated into the 96 wells simultaneously with a flame-sterilized 96 pin replicator. The plate was sealed with a breathable membrane, incubated at 28° C. without shaking for 5 days, and OD600 readings taken with a 96 well plate reader.

A nitrogen fixing plant associated bacterium is able theoretically to add to the host's nitrogen metabolism, and the most famous beneficial plant associated bacteria, *rhizobia*, are able to do this within specially adapted organs on the roots of leguminous plants. The seed associated bacteria in this study may be able to fix nitrogen in association with the developing seedling, whether they colonize the plant's surfaces or interior and thereby add to the plant's nitrogen nutrition.

In total, of the 247 isolates there were 34 (14%) which had detectable growth under nitrogen limiting conditions (Table 3).

TABLE 3

Functional assays to examine the potential for seed-origin microbes to confer novel functions to crops.

| Sym Strain ID | OTU # | SEQ ID NO: | Taxonomy | Antagonizes E. coli | Antagonizes S. cerevisciae | Shows Cellulolytic activity | Shows Pectinolytic activity | Secretes siderophores | Phosphate Solubilization | Growth on Nitrogen Free LGI | ACC Deaminase Activity | Produces Auxin/Indoles | Produces Acetoin |
|---|---|---|---|---|---|---|---|---|---|---|---|---|---|
| SYM00033 | 0 | 541 | *Enterobacter* sp. | — | — | 1 | 1 | 1 | 2 | — | — | 3 | — |
| SYM00173 | 0 | 593 | *Pantoea* sp. | 2 | — | 1 | 1 | — | 2 | Yes | — | 3 | 1 |
| SYM00176 | 0 | 596 | *Pantoea* sp. | 1 | — | 1 | 1 | 2 | 1 | — | — | 2 | 1 |
| SYM00605 | 0 | 716 | | — | — | 1 | 1 | 2 | 2 | — | — | 1 | — |
| SYM00607 | 0 | 717 | | — | — | — | — | 2 | 2 | — | — | 1 | 2 |
| SYM00608 | 0 | 718 | *Pantoea* sp. | — | — | — | — | 1 | — | — | 1 | 1 | 1 |
| SYM00620 | 0 | 720 | *Enterobacter* sp. | — | 1 | 1 | 1 | — | 1 | — | — | 2 | 2 |
| SYM00658 | 0 | 736 | | 1 | 1 | 1 | 1 | — | 2 | — | 1 | 2 | 3 |
| SYM00660 | 1 | 737 | *Pseudomonas* sp. | — | 1 | 2 | 2 | 1 | — | — | 1 | — | 1 |
| SYM00011 | 2 | 522 | *Pseudomonas* sp. | — | — | — | — | — | 1 | Yes | — | 2 | — |
| SYM00011b | 2 | 523 | *Pseudomonas* sp. | — | — | — | — | — | — | — | — | — | 1 |
| SYM00013 | 2 | 524 | *Pseudomonas* sp. | — | — | 2 | 2 | 2 | — | Yes | — | 2 | — |
| SYM00014 | 2 | 526 | *Pseudomonas* sp. | — | — | 2 | 2 | 1 | — | Yes | — | 2 | — |
| SYM00062 | 2 | 557 | *Pseudomonas* sp. | — | — | 2 | 2 | 2 | — | — | 1 | 2 | — |
| SYM00068 | 2 | 563 | *Pseudomonas* sp. | — | — | 2 | 2 | 2 | 1 | — | 3 | 2 | — |
| SYM00069 | 2 | 564 | *Pseudomonas* sp. | — | — | — | — | — | — | — | — | — | 2 |
| SYM00646 | 2 | 730 | *Pseudomonas* sp. | — | — | 2 | 2 | 3 | — | — | — | 2 | — |
| SYM00649 | 2 | 733 | *Pseudomonas* sp. | — | — | 2 | 2 | 1 | — | — | 3 | 2 | — |
| SYM00650 | 2 | 734 | *Pseudomonas* sp. | — | 1 | 2 | 2 | — | — | — | 3 | 2 | — |
| SYM00657 | 2 | 735 | *Pseudomonas* sp. | — | — | 2 | 2 | — | — | — | 3 | 2 | — |
| SYM00672 | 2 | 738 | *Pseudomonas* sp. | — | — | 2 | 2 | 2 | 1 | — | 3 | 1 | — |
| SYM00709 | 2 | 747 | *Pseudomonas* sp. | — | — | 3 | 3 | — | — | — | — | — | 3 |
| SYM00013b | 3 | 525 | *Curtobacterium* sp. | — | — | — | — | — | — | — | — | — | 1 |
| SYM00167 | 3 | 588 | *Curtobacterium* sp. | — | — | — | — | — | — | — | — | 1 | — |
| SYM00171 | 3 | 591 | *Curtobacterium* sp. | — | — | — | — | 2 | — | — | — | 1 | — |
| SYM00174 | 3 | 594 | *Curtobacterium* sp. | — | — | — | — | — | — | — | — | 1 | 1 |
| SYM00178 | 3 | 598 | *Curtobacterium* sp. | — | — | 1 | 1 | 1 | — | — | — | — | 1 |
| SYM00180 | 3 | 600 | *Curtobacterium* sp. | — | — | — | — | — | — | — | — | — | 1 |
| SYM00181 | 3 | 601 | *Curtobacterium* sp. | — | — | — | — | — | — | — | — | — | 2 |
| SYM00235 | 3 | 622 | *Curtobacterium* sp. | — | — | 1 | 1 | — | 1 | Yes | — | 3 | 3 |
| SYM00244 | 3 | 626 | *Curtobacterium* sp. | — | — | 1 | 1 | — | 1 | — | — | — | 1 |
| SYM00525 | 3 | 654 | *Curtobacterium* sp. | — | — | — | — | — | — | — | — | 2 | 1 |
| SYM00625 | 3 | 724 | *Curtobacterium* sp. | — | — | 2 | 2 | — | — | — | 1 | 1 | — |
| SYM00645 | 3 | 729 | *Curtobacterium* sp. | — | — | — | — | 3 | — | — | 3 | 1 | — |
| SYM00647 | 3 | 731 | *Curtobacterium* sp. | — | — | 1 | 1 | — | — | — | — | 1 | 3 |
| SYM00690 | 3 | 740 | *Curtobacterium* sp. | — | — | — | — | — | — | — | 1 | 1 | 1 |
| SYM00691 | 3 | 741 | *Curtobacterium* sp. | — | — | — | — | — | — | — | 1 | — | 1 |
| SYM00693 | 3 | 742 | *Curtobacterium* sp. | — | — | 1 | 1 | — | — | — | 1 | — | 1 |
| SYM00712 | 3 | 748 | *Curtobacterium* sp. | — | — | 1 | 1 | — | — | — | 1 | 1 | — |
| SYM00716 | 3 | 752 | *Curtobacterium* sp. | — | — | — | — | — | — | — | 1 | 1 | 1 |
| SYM00722 | 3 | 753 | *Curtobacterium* sp. | — | — | 1 | 1 | — | — | — | 1 | 1 | — |
| SYM00731B | 3 | 756 | *Curtobacterium* sp. | — | — | — | — | — | — | — | 1 | 1 | — |
| SYM00784 | 3 | 773 | *Curtobacterium* sp. | 2 | — | — | — | — | — | — | — | 1 | — |
| SYM00188 | 6 | 605 | *Paenibacillus* sp. | — | — | — | — | — | — | — | — | — | 2 |
| SYM00190 | 6 | 607 | *Paenibacillus* sp. | — | — | 1 | 1 | — | 1 | — | — | — | — |
| SYM00195 | 6 | 610 | *Paenibacillus* sp. | — | — | — | — | — | 2 | — | — | — | 2 |
| SYM00217 | 6 | 616 | *Paenibacillus* sp. | — | — | — | — | — | 2 | — | — | — | — |
| SYM00227 | 6 | 619 | *Paenibacillus* sp. | — | — | 1 | 1 | — | 1 | — | 1 | — | — |
| SYM00597 | 6 | 711 | *Paenibacillus* sp. | — | — | — | — | — | 1 | — | — | — | 3 |
| SYM00017b | 7 | 532 | *Pantoea* sp. | — | — | 1 | 1 | — | 2 | — | — | 3 | — |
| SYM00018 | 7 | 534 | *Pantoea* sp. | — | — | — | — | — | — | — | — | 3 | — |
| SYM00020 | 7 | 535 | *Pantoea* sp. | — | — | — | — | — | 1 | Yes | — | 3 | — |
| SYM00022 | 7 | 537 | *Pantoea* sp. | — | — | 1 | 1 | 1 | — | — | — | 2 | — |

TABLE 3-continued

Functional assays to examine the potential for seed-origin microbes to confer novel functions to crops.

| Sym Strain ID | OTU # | SEQ ID NO: | Taxonomy | Antagonizes E. coli | Antagonizes S. cerevisciae | Shows Cellulolytic activity | Shows Pectinolytic activity | Secretes siderophores | Phosphate Solubilization | Growth on Nitrogen Free LGI | ACC Deaminase Activity | Produces Auxin/ Indoles | Produces Acetoin |
|---|---|---|---|---|---|---|---|---|---|---|---|---|---|
| SYM00025 | 7 | 538 | Pantoea sp. | — | — | 1 | 1 | — | — | — | — | 2 | 1 |
| SYM00043 | 7 | 544 | Pantoea sp. | — | — | 1 | 1 | 1 | 2 | Yes | — | 1 | — |
| SYM00047 | 7 | 546 | Pantoea sp. | — | — | 1 | 1 | — | 2 | — | — | 1 | 1 |
| SYM00049 | 7 | 547 | Pantoea sp. | — | — | — | — | 1 | — | — | — | 3 | 1 |
| SYM00055 | 7 | 553 | Pantoea sp. | — | — | 1 | 1 | 1 | 2 | — | — | — | — |
| SYM00057 | 7 | 554 | Pantoea sp. | — | — | — | — | — | — | — | — | — | 1 |
| SYM00058 | 7 | 555 | Pantoea sp. | — | — | — | — | — | — | — | — | — | 3 |
| SYM00078 | 7 | 568 | Pantoea sp. | 3 | 1 | 1 | 1 | 1 | 2 | Yes | — | 3 | — |
| SYM00081 | 7 | 569 | Pantoea sp. | — | — | 1 | 1 | 1 | 2 | Yes | — | 1 | — |
| SYM00082a | 7 | 570 | Pantoea sp. | — | — | — | — | 1 | — | Yes | — | 1 | — |
| SYM00085 | 7 | 571 | Pantoea sp. | — | — | 1 | 1 | 1 | 2 | — | — | 1 | 1 |
| SYM00086 | 7 | 572 | Pantoea sp. | — | — | 1 | 1 | 1 | 2 | — | — | 1 | 1 |
| SYM00088 | 7 | 574 | Pantoea sp. | — | — | — | — | — | — | — | — | — | 3 |
| SYM00094 | 7 | 576 | Pantoea sp. | — | — | 1 | 1 | 1 | 2 | Yes | — | 1 | 1 |
| SYM00095 | 7 | 577 | Pantoea sp. | — | — | 1 | 1 | 1 | 2 | Yes | — | 1 | 1 |
| SYM00096 | 7 | 578 | Pantoea sp. | — | — | 1 | 1 | 1 | — | — | — | 1 | 1 |
| SYM00100 | 7 | 579 | Pantoea sp. | 1 | 1 | 1 | 1 | 1 | 1 | — | — | 3 | — |
| SYM00101 | 7 | 580 | Pantoea sp. | — | — | — | — | 1 | — | — | — | 2 | — |
| SYM00502 | 7 | 639 | Erwinia sp. | — | — | — | — | 1 | 1 | — | — | 3 | — |
| SYM00506 | 7 | 641 | Erwinia sp. | — | — | 1 | 1 | 1 | 1 | — | — | 3 | 1 |
| SYM00506b | 7 | 642 | Erwinia sp. | — | 1 | 1 | 1 | 1 | 1 | — | — | 3 | 3 |
| SYM00511 | 7 | 647 | Erwinia sp. | — | — | — | — | — | — | — | — | 2 | 1 |
| SYM00514b | 7 | 649 | Erwinia sp. | — | — | — | — | — | 2 | — | — | 3 | 3 |
| SYM00514C | 7 | 650 | Erwinia sp. | — | — | — | — | — | — | — | 3 | — | 1 |
| SYM00514D | 7 | 651 | Erwinia sp. | — | — | — | — | — | — | — | — | 2 | 3 |
| SYM00731A | 7 | 755 | Erwinia sp. | — | — | 1 | 1 | — | 1 | — | 1 | 2 | — |
| SYM00785 | 7 | 774 | Erwinia sp. | 1 | 1 | 1 | 1 | — | 2 | — | 1 | 2 | — |
| SYM00544 | 9 | 663 | Ochrobactrum sp. | — | 1 | — | — | — | 1 | — | — | 3 | — |
| SYM00545B | 9 | 665 | Ochrobactrum sp. | — | 1 | — | — | — | — | — | — | 2 | — |
| SYM00548 | 9 | 667 | Ochrobactrum sp. | — | 1 | — | — | — | 1 | — | — | 2 | — |
| SYM00552 | 9 | 670 | Ochrobactrum sp. | — | 1 | — | — | — | — | — | — | 2 | 1 |
| SYM00558 | 9 | 675 | Ochrobactrum sp. | — | 1 | — | — | — | 1 | — | — | 2 | — |
| SYM00580b | 9 | 689 | Ochrobactrum sp. | — | 1 | — | — | — | — | — | — | 1 | — |
| SYM00580d | 9 | 691 | Ochrobactrum sp. | — | 1 | — | — | — | — | — | — | 2 | — |
| SYM00583 | 9 | 699 | Ochrobactrum sp. | — | 1 | — | — | — | 1 | — | — | 2 | — |
| SYM00584 | 9 | 700 | Ochrobactrum sp. | — | — | — | — | — | 1 | — | — | 2 | — |
| SYM00588 | 9 | 705 | Ochrobactrum sp. | — | 1 | — | — | — | 2 | — | — | 2 | 2 |
| SYM00596 | 9 | 710 | Ochrobactrum sp. | — | 1 | — | — | — | 1 | — | — | 2 | 3 |
| SYM00600 | 9 | 713 | Ochrobactrum sp. | — | 1 | — | — | — | 2 | — | — | 2 | — |
| SYM00746 | 9 | 757 | Ochrobactrum sp. | 1 | 1 | — | — | — | 1 | — | 1 | 1 | 1 |
| SYM00752 | 9 | 759 | Ochrobactrum sp. | 1 | 1 | — | — | — | 1 | — | 1 | 2 | — |
| SYM00756 | 9 | 761 | Ochrobactrum sp. | 1 | — | — | — | — | 1 | — | 1 | 1 | — |
| SYM00763 | 9 | 767 | Ochrobactrum sp. | 1 | — | — | — | — | 1 | — | — | 2 | — |
| SYM00783 | 9 | 772 | Ochrobactrum sp. | 1 | 1 | — | — | — | 1 | — | — | 2 | — |
| SYM00812 | 9 | 775 | Ochrobactrum sp. | — | — | — | — | — | — | — | — | 2 | — |
| SYM00064a | 10 | 560 | Stenotrophomonas sp. | — | — | — | — | — | — | — | — | 1 | — |
| SYM00183 | 10 | 603 | Stenotrophomonas sp. | — | — | — | — | — | — | — | — | 1 | 2 |
| SYM00184 | 10 | 604 | Stenotrophomonas sp. | — | — | — | — | — | — | — | — | 1 | 3 |
| SYM00543 | 12 | 662 | Bacillus sp. | 1 | 1 | — | — | — | — | — | — | 1 | — |
| SYM00595 | 12 | 709 | Bacillus sp. | 1 | 1 | — | — | — | — | — | — | 1 | — |
| SYM00580C | 13 | 690 | Achromobacter sp. | — | — | — | — | 1 | — | — | 1 | 1 | — |
| SYM00547 | 13 | 666 | Achromobacter sp. | — | — | — | — | 2 | — | — | 1 | 1 | — |
| SYM00551 | 13 | 669 | Achromobacter sp. | — | 1 | — | — | 1 | — | — | 2 | 1 | — |
| SYM00560 | 13 | 676 | Achromobacter sp. | — | — | — | — | 1 | — | — | — | 2 | — |
| SYM00565B | 13 | 681 | Achromobacter sp. | — | — | — | — | 1 | 1 | — | 1 | 1 | 1 |
| SYM00580i | 13 | 694 | Achromobacter sp. | — | 1 | — | — | — | — | — | — | 1 | — |
| SYM00585 | 13 | 701 | Achromobacter sp. | — | — | — | — | 1 | 2 | — | 1 | 2 | — |
| SYM00586b | 13 | 702 | Achromobacter sp. | — | 1 | — | — | 2 | — | — | — | 2 | — |
| SYM00588b | 13 | 706 | Achromobacter sp. | — | — | — | — | — | — | — | — | 3 | 2 |
| SYM00591 | 13 | 708 | Achromobacter sp. | — | — | — | — | — | — | — | 3 | 1 | — |
| SYM00602 | 13 | 715 | Achromobacter sp. | — | — | — | — | 3 | — | — | — | 1 | 2 |
| SYM00758 | 13 | 763 | Achromobacter sp. | — | — | — | — | — | — | — | 3 | 1 | — |
| SYM00761 | 13 | 765 | Achromobacter sp. | — | — | — | — | 1 | — | — | 1 | — | — |
| SYM00764 | 13 | 768 | Achromobacter sp. | — | — | — | — | 1 | — | — | 1 | 1 | — |
| SYM00765 | 13 | 769 | Achromobacter sp. | — | — | — | — | — | — | — | — | — | 3 |
| SYM00824 | 13 | 777 | Achromobacter sp. | — | 1 | — | — | — | — | — | 3 | 1 | — |
| SYM00828 | 13 | 778 | Achromobacter sp. | — | — | — | — | 1 | — | — | — | 1 | — |
| SYM00830 | 13 | 779 | Achromobacter sp. | — | — | — | — | — | — | — | 3 | 1 | — |
| SYM00831 | 13 | 780 | Achromobacter sp. | — | — | — | — | 1 | 1 | — | 1 | 1 | — |
| SYM00028 | 18 | 540 | Enterobacter sp. | 1 | 1 | 1 | 1 | — | 1 | — | — | 1 | 3 |
| SYM00052 | 18 | 550 | Enterobacter sp. | — | — | 1 | 1 | — | 1 | — | — | 1 | 1 |

TABLE 3-continued

Functional assays to examine the potential for seed-origin microbes to confer novel functions to crops.

| Sym Strain ID | OTU # | SEQ ID NO: | Taxonomy | Antagonizes E. coli | Antagonizes S. cerevisciae | Shows Cellulolytic activity | Shows Pectinolytic activity | Secretes siderophores | Phosphate Solubilization | Growth on Nitrogen Free LGI | ACC Deaminase Activity | Produces Auxin/ Indoles | Produces Acetoin |
|---|---|---|---|---|---|---|---|---|---|---|---|---|---|
| SYM00053 | 18 | 551 | Enterobacter sp. | — | — | 1 | 1 | — | 1 | — | — | — | 1 |
| SYM00054 | 18 | 552 | Enterobacter sp. | — | — | — | — | 1 | — | — | — | — | 3 |
| SYM00175 | 18 | 595 | Enterobacter sp. | — | — | 1 | 1 | 1 | 2 | Yes | — | 1 | — |
| SYM00627 | 18 | 725 | Enterobacter sp. | 1 | 2 | 1 | 1 | — | 2 | — | 1 | — | 3 |
| SYM00715 | 18 | 751 | Enterobacter sp. | — | — | — | — | — | 2 | — | 1 | — | 2 |
| SYM00189 | 19 | 606 | Bacillus sp. | — | — | — | — | — | — | — | — | — | — |
| SYM00192 | 19 | 608 | Bacillus sp. | — | — | — | — | — | — | — | — | — | 1 |
| SYM00197 | 19 | 611 | Bacillus sp. | — | — | — | — | — | — | — | — | — | — |
| SYM00201 | 19 | 612 | Bacillus sp. | — | — | — | — | — | — | — | — | 1 | 2 |
| SYM00202 | 19 | 613 | Bacillus sp. | — | — | — | — | — | 2 | — | — | 1 | — |
| SYM00215 | 19 | 615 | Bacillus sp. | — | — | — | — | — | — | — | — | — | — |
| SYM00233 | 19 | 621 | Bacillus sp. | — | — | — | — | — | — | Yes | — | 2 | 3 |
| SYM00016b | 25 | 529 | Methylobacterium sp. | — | — | 1 | 1 | — | — | — | — | 1 | 1 |
| SYM00236 | 25 | 623 | Methylobacterium sp. | — | — | 1 | 1 | — | 1 | Yes | 1 | — | — |
| SYM00237 | 25 | 624 | Methylobacterium sp. | — | — | 1 | 1 | — | 1 | Yes | 1 | 2 | — |
| SYM00240 | 25 | 625 | Methylobacterium sp. | — | — | 1 | 1 | — | 1 | Yes | 3 | — | — |
| SYM00501 | 27 | 638 | Burkholderia sp. | 3 | 1 | — | — | 2 | — | — | 3 | 2 | — |
| SYM00504 | 27 | 640 | Burkholderia sp. | 3 | 1 | — | — | 2 | — | — | 3 | 2 | — |
| SYM00536 | 27 | 656 | Burkholderia sp. | 3 | 1 | — | — | 3 | 1 | — | 1 | 2 | — |
| SYM00538E | 27 | 659 | Burkholderia sp. | 1 | 1 | — | — | 2 | 1 | — | 3 | 1 | — |
| SYM00566A | 27 | 682 | Burkholderia sp. | 2 | 1 | — | — | 2 | — | — | 3 | — | 3 |
| SYM00568 | 27 | 683 | Burkholderia sp. | 2 | 1 | — | — | 2 | — | — | 3 | 1 | — |
| SYM00570 | 27 | 684 | Burkholderia sp. | 2 | 1 | — | — | 2 | 1 | — | 3 | 1 | — |
| SYM00574 | 27 | 685 | Burkholderia sp. | 2 | 1 | — | — | 2 | 1 | — | 3 | 1 | 1 |
| SYM00575 | 27 | 686 | Burkholderia sp. | 3 | 1 | — | — | 2 | 1 | — | 3 | 1 | — |
| SYM00578 | 27 | 687 | Burkholderia sp. | 2 | 1 | — | — | 2 | 2 | — | 3 | — | — |
| SYM00621 | 27 | 721 | Burkholderia sp. | 1 | 1 | — | — | 3 | — | — | 3 | 1 | — |
| SYM00623 | 27 | 722 | Burkholderia sp. | 1 | 1 | — | — | 3 | — | — | 3 | — | — |
| SYM00624 | 27 | 723 | Burkholderia sp. | 1 | 1 | — | — | 3 | — | — | 3 | — | — |
| SYM00633 | 27 | 727 | Burkholderia sp. | 1 | 1 | 1 | 1 | — | 2 | — | 1 | 3 | 3 |
| SYM00822 | 27 | 776 | Burkholderia sp. | — | — | — | — | 3 | 1 | — | — | — | — |
| SYM00037 | 28 | 543 | Bacillus sp. | — | — | — | — | — | — | — | — | — | 2 |
| SYM00051 | 28 | 549 | Microbacterium sp. | — | 2 | — | — | 2 | — | — | — | 2 | 2 |
| SYM00104 | 28 | 582 | Microbacterium sp. | 1 | — | — | — | — | — | Yes | — | — | — |
| SYM00177 | 28 | 597 | Microbacterium sp. | — | — | — | — | — | — | — | — | 1 | 3 |
| SYM00514A | 28 | 648 | Microbacterium sp. | — | — | — | — | — | — | — | — | 2 | 2 |
| SYM00523 | 28 | 652 | Microbacterium sp. | — | — | — | — | — | — | — | — | 2 | 2 |
| SYM00538H | 28 | 660 | Microbacterium sp. | — | — | — | — | — | — | — | — | — | 2 |
| SYM00542 | 28 | 661 | Microbacterium sp. | — | — | 1 | 1 | — | — | — | — | 1 | 1 |
| SYM00556 | 28 | 674 | Microbacterium sp. | — | — | 1 | 1 | — | — | — | — | 3 | — |
| SYM00581A | 28 | 695 | Microbacterium sp. | — | — | — | — | — | — | — | — | 2 | 3 |
| SYM00586c | 28 | 703 | Microbacterium sp. | — | — | 1 | 1 | — | — | — | — | 2 | 2 |
| SYM00587 | 28 | 704 | Microbacterium sp. | — | — | 2 | 2 | — | — | — | — | 2 | 1 |
| SYM00598 | 28 | 712 | Microbacterium sp. | — | — | — | — | — | — | — | — | 1 | 2 |
| SYM00757 | 28 | 762 | Microbacterium sp. | — | — | — | — | — | — | — | 1 | — | 3 |
| SYM00760 | 28 | 764 | Microbacterium sp. | — | — | — | — | — | — | — | 1 | — | 2 |
| SYM00780 | 28 | 771 | Microbacterium sp. | — | — | — | — | — | 1 | — | — | 1 | — |
| SYM00832 | 28 | 781 | Microbacterium sp. | 1 | — | — | — | — | — | — | — | — | 1 |
| SYM00015 | 29 | 528 | Xanthomonas sp. | 1 | — | 2 | 2 | 2 | — | Yes | — | 1 | 1 |
| SYM00021 | 29 | 536 | Xanthomonas sp. | 2 | — | 3 | 3 | 2 | — | — | — | 2 | — |
| SYM00179 | 29 | 599 | Xanthomonas sp. | 1 | — | 2 | 2 | — | 1 | — | — | 1 | 1 |
| SYM00182 | 29 | 602 | Xanthomonas sp. | 1 | — | 1 | 1 | — | 1 | — | 1 | 3 | 3 |
| SYM00252 | 29 | 630 | Xanthomonas sp. | — | — | — | — | — | — | Yes | — | — | — |
| SYM00565A | 30 | 680 | Rhodococcus sp. | — | 1 | — | — | — | 1 | — | — | — | — |
| SYM00580G | 30 | 693 | Rhodococcus sp. | — | 1 | — | — | 2 | 1 | — | — | 1 | — |
| SYM00753 | 30 | 760 | Rhodococcus sp. | 1 | 1 | — | — | — | — | Yes | 1 | 1 | 2 |
| SYM00762 | 30 | 766 | Rhodococcus sp. | 1 | — | — | — | 1 | 1 | Yes | — | 1 | — |
| SYM00775 | 30 | 770 | Rhodococcus sp. | 1 | 1 | — | — | 2 | 1 | Yes | 1 | 1 | — |
| SYM00589 | 31 | 707 | Paenibacillus sp. | — | — | — | — | — | — | — | — | 3 | 2 |
| SYM00057B | 37 | 1446 | Burkholderia phytofirmans | — | 1 | 1 | 1 | 1 | 1 | Yes | 3 | 1 | — |
| SYM00102 | 38 | 581 | Staphylococcus sp. | — | — | — | — | — | — | — | — | — | 2 |
| SYM00072 | 39 | 566 | Bacillus sp. | 2 | — | — | — | — | — | — | — | — | 3 |
| SYM00075 | 39 | 567 | Bacillus sp. | 2 | — | — | — | — | — | — | — | — | 3 |
| SYM00249 | 39 | 628 | Bacillus sp. | — | — | — | — | — | — | — | — | — | — |
| SYM00507 | 39 | 645 | Bacillus sp. | 2 | 1 | — | — | — | — | — | — | 2 | 1 |
| SYM00553 | 39 | 671 | Bacillus sp. | — | 1 | — | — | — | — | — | — | — | 1 |
| SYM00562 | 39 | 677 | Bacillus sp. | 2 | — | — | — | — | — | — | — | — | — |
| SYM00564 | 39 | 679 | Bacillus sp. | 2 | 1 | — | — | — | — | — | — | — | — |
| SYM00580E | 39 | 692 | Bacillus sp. | — | 1 | — | — | 1 | — | — | — | — | 1 |
| SYM00581b | 39 | 696 | Bacillus sp. | 2 | — | — | — | — | — | — | — | 2 | 3 |

TABLE 3-continued

Functional assays to examine the potential for seed-origin microbes to confer novel functions to crops.

| Sym Strain ID | OTU # | SEQ ID NO: | Taxonomy | Antagonizes E. coli | Antagonizes S. cerevisciae | Shows Cellulolytic activity | Shows Pectinolytic activity | Secretes siderophores | Phosphate Solubilization | Growth on Nitrogen Free LGI | ACC Deaminase Activity | Produces Auxin/ Indoles | Produces Acetoin |
|---|---|---|---|---|---|---|---|---|---|---|---|---|---|
| SYM00581c | 39 | 697 | Bacillus sp. | — | — | — | — | — | — | — | 1 | 1 | 3 |
| SYM00601 | 39 | 714 | Bacillus sp. | 1 | — | — | — | — | — | — | — | — | 3 |
| SYM00036 | 41 | 542 | Bacillus sp. | 3 | 2 | — | — | — | — | — | — | — | 3 |
| SYM00110 | 41 | 586 | Bacillus sp. | 3 | 1 | — | — | — | — | Yes | — | 1 | — |
| SYM00193 | 41 | 609 | Bacillus sp. | 3 | — | — | — | — | — | — | — | — | 1 |
| SYM00218 | 41 | 617 | Bacillus sp. | 3 | 1 | — | — | — | 1 | — | — | — | — |
| SYM00250 | 41 | 629 | Bacillus sp. | — | 1 | — | — | — | 1 | Yes | — | — | — |
| SYM00697 | 41 | 745 | Bacillus sp. | 3 | 3 | — | — | — | — | — | — | — | 3 |
| SYM00704 | 41 | 746 | Bacillus sp. | 3 | 3 | — | — | — | — | — | — | — | 3 |
| SYM00017c | 45 | 533 | Sphingomonas sp. | — | — | 1 | 1 | — | — | Yes | — | 2 | 1 |
| SYM00062b | 45 | 558 | Sphingomonas sp. | — | — | 1 | 1 | — | — | — | — | 3 | 1 |
| SYM00065 | 45 | 561 | Sphingomonas sp. | — | — | — | — | — | — | — | — | — | 1 |
| SYM00168 | 45 | 589 | Sphingomonas sp. | — | 1 | 2 | 2 | — | 2 | Yes | — | 2 | 1 |
| SYM00169 | 45 | 590 | Sphingomonas sp. | — | 1 | 2 | 2 | — | 2 | Yes | — | 3 | 3 |
| SYM00231 | 46 | 620 | Sphingobium sp. | — | 1 | 2 | 2 | 1 | 2 | Yes | — | 2 | — |
| SYM00975 | 51 | 843 | Herbaspirillum sp. | — | — | — | — | 2 | 2 | — | — | — | 3 |
| SYM00506c | 53 | 643 | Paenibacillus sp. | — | — | — | — | — | — | — | — | 3 | 1 |
| SYM00506D | 53 | 644 | Paenibacillus sp. | — | — | — | — | — | — | — | — | 2 | — |
| SYM00545 | 53 | 664 | Paenibacillus sp. | — | 1 | — | — | — | — | — | — | 2 | — |
| SYM00549 | 53 | 668 | Paenibacillus sp. | — | — | — | — | — | — | — | — | 1 | — |
| SYM00554 | 53 | 672 | Paenibacillus sp. | — | 1 | — | — | — | — | — | — | 1 | 1 |
| SYM00555 | 53 | 673 | Paenibacillus sp. | — | 1 | — | — | — | — | — | — | — | — |
| SYM00012 | 55 | 1447 | Microbacterium binotii | 1 | — | — | — | — | 1 | — | — | 1 | 1 |
| SYM00046 | 56 | 545 | Enterobacter sp. | 1 | 3 | 1 | 1 | 2 | 1 | — | — | 1 | 3 |
| SYM00050 | 56 | 548 | Enterobacter sp. | — | 2 | 1 | 1 | 1 | 1 | — | — | 2 | 2 |
| SYM00628 | 56 | 726 | Enterobacter sp. | 1 | 1 | 1 | 1 | — | 1 | — | 1 | 3 | 3 |
| SYM00106 | 59 | 583 | Micrococcus sp. | — | — | 1 | 1 | — | — | Yes | — | — | — |
| SYM00107 | 59 | 584 | Micrococcus sp. | — | — | — | — | — | — | Yes | — | — | 1 |
| SYM00108 | 59 | 585 | Micrococcus sp. | — | — | 1 | 1 | — | — | Yes | — | — | — |
| SYM00090 | 62 | 575 | Chryseobacterium sp. | 1 | — | — | — | 1 | — | — | — | — | — |
| SYM00002 | 66 | 521 | Agrobacterium sp. | — | — | 2 | 2 | — | — | — | — | 3 | — |
| SYM00017a | 66 | 531 | Agrobacterium sp. | — | — | 2 | 2 | — | — | — | — | 3 | — |
| SYM00714 | 66 | 750 | Agrobacterium sp. | — | — | 1 | 1 | — | — | — | 1 | 2 | — |
| SYM00060 | 67 | 556 | Staphylococcus sp. | — | — | — | — | — | — | — | — | — | 3 |
| SYM00071 | 76 | 565 | Bacillus sp. | — | — | — | — | — | — | — | — | — | 2 |
| SYM00204 | 76 | 614 | Bacillus sp. | — | — | — | — | — | — | — | — | — | — |
| SYM00563 | 76 | 678 | Bacillus sp. | — | — | — | — | — | — | — | — | — | — |
| SYM00617 | 76 | 719 | Bacillus sp. | — | — | — | — | — | — | — | — | 1 | 2 |
| SYM00960 | 82 | 831 | Luteibacter sp. | — | — | — | — | 2 | — | — | — | — | 3 |
| SYM00940 | 83 | 815 | | — | — | — | — | — | 1 | — | — | — | 3 |
| SYM00713 | 84 | 749 | Erwinia sp. | — | 1 | 1 | 1 | 1 | 1 | — | 1 | 2 | 1 |
| SYM00992 | 126 | 856 | Sphingomonas sp. | — | — | — | — | — | 2 | — | — | — | 2 |
| SYM00063 | 134 | 559 | Microbacterium sp. | 1 | — | — | — | — | — | — | — | 1 | 3 |
| SYM00226 | 134 | 618 | Microbacterium sp. | — | — | — | — | — | — | — | — | — | — |
| SYM00246 | 134 | 627 | Microbacterium sp. | — | 1 | — | — | — | — | — | — | 1 | 1 |
| SYM00524 | 134 | 653 | Microbacterium sp. | — | — | — | — | — | — | — | — | 1 | 3 |
| SYM00199 | 135 | 1448 | Bacillus sp. | — | — | — | — | — | 2 | — | — | — | — |
| SYM00172 | 146 | 592 | Pantoea sp. | 2 | — | 1 | 1 | 3 | 2 | Yes | — | 3 | 3 |
| SYM00527 | 146 | 655 | Erwinia sp. | — | — | 1 | 1 | — | 1 | — | — | 3 | 1 |
| SYM00644 | 146 | 728 | Erwinia sp. | — | — | 1 | 1 | 1 | 1 | — | 3 | 2 | 2 |
| SYM00648 | 146 | 732 | | 1 | 1 | — | — | 1 | 2 | — | 1 | 1 | 3 |
| SYM00538A | 172 | 658 | Sphingomonas sp. | — | — | 1 | 1 | — | — | — | — | 2 | — |
| SYM00508 | 196 | 646 | | — | — | 1 | 1 | — | 1 | — | — | 2 | — |

Legend:
"—" indicates no significant increase;
"1" = low activity;
"2" = medium activity;
"3" = high activity All of these groups are known to have representatives with the potential to fix atmospheric nitrogen; however chief among these were *Bacillus, Burkholderia, Enterobacter, Methylobacteria,* and *Pseudomonas*.

| Genus | Seed-origin isolates growing on N Free Media |
|---|---|
| *Bacillus* sp. | 3 |
| *Burkholderia* sp. | 1 |
| *Curtobacterium* sp. | 1 |
| *Enterobacter* sp. | 1 |
| *Methylobacterium* sp. | 3 |
| *Microbacterium* sp. | 1 |
| *Micrococcus* sp. | 3 |
| *Pantoea* sp. | 9 |
| *Pseudomonas* sp. | 3 |
| *Rhodococcus* sp. | 3 |
| *Sphingobium* sp. | 1 |
| *Sphingomonas* sp. | 3 |
| *Xanthomonas* sp. | 2 |

ACC Deaminase Activity

Microbes were assayed for growth with ACC as their sole source of nitrogen. Prior to media preparation all glassware was cleaned with 6 M HCl. A 2 M filter sterilized solution of ACC (#1373A, Research Organics, USA) was prepared in water. 2 µl/mL of this was added to autoclaved LGI broth (see above), and 250 µL aliquots were placed in a brand new (clean) 96 well plate. The plate was inoculated with a 96 pin library replicator, sealed with a breathable membrane, incubated at 28° C. without shaking for 5 days, and OD600 readings taken. Only wells that were significantly more turbid than their corresponding nitrogen free LGI wells were considered to display ACC deaminase activity.

Plant stress reactions are strongly impacted by the plant's own production and overproduction of the gaseous hormone ethylene. Ethylene is metabolized from its precursor 1-aminocyclopropane-1-carboxylate (ACC) which can be diverted from ethylene metabolism by microbial and plant enzymes having ACC deaminase activity. As the name implies, ACC deaminase removes molecular nitrogen from the ethylene precursor, removing it as a substrate for production of the plant stress hormone and providing for the microbe a source of valuable nitrogen nutrition. It is somewhat surprising, but this microbial ability to inhibit ethylene production is very important for plant health as damage to growth and productivity under various stress conditions is believed to result from the plant's own over-production of ethylene (Journal of Industrial Microbiology & Biotechnology, October 2007, Volume 34, Issue 10, pp 635-648).

In total, of the 247 isolates there were 68 (28%) which had greater growth on nitrogen free LGI media supplemented with ACC, than in nitrogen free LGI. Of these, only 11% had very high ACC deaminase activity and these were mostly strains of *Achromobacter, Burkholderia,* and *Pseudomonas*. Chief amongst these were *Burkholderia* species which held ACC deaminase as their most distinctive in vitro characteristic—94% or 15 out of 16 *Burkholderia* isolates had ACC deaminase activity. Of *Burkholderia* isolates, 81% had strong ACC deaminase activity, while only 42% of *Achromobacter* species (5 of 12 isolates) had strong ACC deaminase activity, and next were *Pseudomonas* where only 5 of 14 isolates (42%) had strong activity. Many *Curtobacteria* isolates appeared to have ACC deaminase activity as well, however these were all rated low (as 1) and thus of less interest than the preceeding groups of isolates.

| Genus | Seed-Origin Isolates growing on ACC as the sole Nitrogen Source |
|---|---|
| *Achromobacter* sp. | 12 |
| *Agrobacterium* sp. | 1 |
| *Bacillus* sp. | 1 |
| *Burkholderia* sp. | 15 |
| *Curtobacterium* sp. | 9 |
| *Enterobacter* sp. | 3 |
| *Erwinia* sp. | 5 |
| *Methylobacterium* sp. | 3 |
| *Microbacterium* sp. | 2 |
| *Ochrobactrum* sp. | 3 |
| *Pantoea* sp. | 1 |
| *Pseudomonas* sp. | 7 |
| *Rhodococcus* sp. | 2 |
| *Xanthomonas* sp. | 1 |

Acetoin and Diacetyl Production

The method was adapted from Phalip et al., (1994) J Basic Microbiol 34: 277-280. (incorporated herein by reference). 250 ml of autoclaved R2A broth supplemented with 0.5% glucose was aliquoted into a 96 well plate (#07-200-700, Fisher). The bacterial endophytes from a glycerol stock plate were inoculated into the plate using a flame-sterilized 96 pin replicator, sealed with a breathable membrane, then incubated for 3 days without shaking at 28° C. At day 5, 50 µl/well was added of freshly blended Barritt's Reagents A and B [5 g/L creatine mixed 3:1 (v/v) with freshly prepared ∝-naphthol (75 g/L in 2.5 M sodium hydroxide)]. After 15 minutes, plates were scored for red or pink coloration relative to a copper colored negative control (measured as 525 nm absorption on a plate reader).

A large number of seed-origin bacteria showed a detectable level of pink or red color development (126 out of 247; See Table 3). 70 of 247 isolates had strong production of acetoin or butanediol as detected by this assay. *Bacillus* (13 of 33), *Enterobacter* (8 or 16) and *Microbacterium* (12 of 21) species were the most intense producers of acetoin/butanediol in this collection. In addition, two of the three isolates of *Stenotrophomonas* included in this study were also strong acetoin/butanediol producers.

Siderophore Production

To ensure no contaminating iron was carried over from previous experiments, all glassware was deferrated with 6 M HCl and water prior to media preparation [Cox (1994) Methods Enzymol 235: 315-329, incorporated herein by reference]. In this cleaned glassware, R2A broth media, which is iron limited, was prepared and poured (250 ul/well) into 96 well plates and the plate then inoculated with bacteria using a 96 pin plate replicator. After 3 days of incubation at 28° C. without shaking, to each well was added 100 ul of O-CAS preparation without gelling agent [Perez-Miranda et al. (2007), J Microbiol Methods 70: 127-131, incorporated herein by reference]. One liter of O-CAS reagent was prepared using the cleaned glassware by mixing 60.5 mg of chrome azurol S (CAS), 72.9 mg of hexadecyltrimethyl ammonium bromide (HDTMA), 30.24 g of finely crushed Piperazine-1,4-bis-2-ethanesulfonic acid (PIPES) with 10 ml of 1 mM $FeCl_3.6H_2O$ in 10 mM HCl solvent. The PIPES had to be finely powdered and mixed gently with stirring (not shaking) to avoid producing bubbles, until a deep blue color was achieved. 15 minutes after adding the reagent to each well, color change was scored by looking for purple halos (catechol type siderophores) or orange colonies (hydroxamate siderophores) relative to the deep blue of the O-CAS.

Siderophore production by bacteria on a plant surface or inside a plant may both show that a microbe is equipped to grow in a nutrient limited environment, and perhaps protect the plant environment from invasion by other, perhaps undesirable microbes. We searched for two types of siderophore which result in purple color change (catechol type siderophores) or orange color change (hydroxamate siderophores) after addition of the blue O-Cas reagent to 96 well plates. A large number of bacteria showed a detectable level of color change relative to the deep blue of the O-CAS; 80 out of 247. Notably, 32 of 247 strains had strong production of siderophores. Interestingly, strong siderophore producers included a large number (14) of the 16 *Burkholderia* isolates. Many isolates of *Achromobacter* (9 of 12) and *Pantoea* (15 of 26) were able to induce weak colour change in the O-CAS material.

| Genus | Seed-origin Isolates Producing Strong Siderophores |
|---|---|
| *Achromobacter* sp. | 3 |
| *Burkholderia* sp. | 14 |
| *Curtobacterium* sp. | 2 |
| *Enterobacter* sp. | 1 |
| *Microbacterium* sp. | 1 |
| *Pantoea* sp. | 2 |
| *Pseudomonas* sp. | 5 |
| *Rhodococcus* sp. | 2 |
| *Xanthomonas* sp. | 2 |

Pectinase Activity

Iodine reacts with pectin to form a dark blue-colored complex, leaving clear halos as evidence of extracellular enzyme activity. Adapting a previous protocol [Soares et al. (1999) Rev de Microbiol 30: 299-303, incorporated herein by reference] 0.2% (w/v) of citrus pectin (#76280, Sigma) and 0.1% triton X-100 were added to R2A media, autoclaved and poured into 150 mm plates. Bacteria were inoculated using a 96 pin plate replicator. After 3 days of culturing in the darkness at 25° C., pectinase activity was visualized by flooding the plate with Gram's iodine. Positive colonies were surrounded by clear halos. In our study, a large number, roughly 83 of the 247 isolates, had detectable pectinase activity, and 21 of these isolates had moderate to strong results visualized as medium to large halos—caused by copious diffusion of enzyme away from the bacteria.

Cellulase Activity

Iodine reacts with cellulose to form a dark brown/blue-colored complex, leaving clear halos as evidence of extracellular enzyme activity. Adapting a previous protocol [Kasana et al. (2008), Curr Microbiol 57: 503-507, incorporated herein by reference] 0.2% carboxymethylcellulose (CMC) sodium salt (#C5678, Sigma) and 0.1% triton X-100 were added to a starch free variant of R2A media, autoclaved and poured into 150 mm plates. Bacteria were inoculated using a 96 pin plate replicator. After 3 days of culturing in the darkness at 25° C., cellulose activity was visualized by flooding the plate with Gram's iodine. Positive colonies were surrounded by clear halos.

In our study, a large number, roughly 83 of the 247 isolates, had detectable cellulose activity, and 21 of these isolates had moderate to strong results visualized as medium to large halos—caused by copious diffusion of enzyme away from the bacteria.

Antibiosis

Briefly, colonies of either *E. coli* DH5a (bacterial tester) or yeast strain *Saccharomyces cerevisiae* AH109 (fungal tester) were resuspended in 1 mL R2A broth to an OD600 of 0.2, and 40 µL of this was mixed with 40 mL of warm R2A agar for pouring a single rectangular Petri dish. Seed derived bacteria were inoculated onto plates using a flame sterilized 96 pin plate replicator, incubated for 3 days at 28° C. Antibiosis was scored by observing clear halos around endophyte colonies.

A total of 59 and 72 isolates showed antibiosis activity against either *E. coli* or yeast, respectively (Table 3). Antibiotic production by bacteria on a plant surface or inside a plant may both show that a microbe is ecologically aggressive (a survivor) and it may mean that it can help protect a plant against pathogens. Interestingly, three groups of bacteria, the *Bacilli, Enterobacters* and *Burkholderia* both had a large proportion of isolates (up to 45%, 50% and 88% respectively) which were inhibiting growth of *E. coli* and yeast, suggestive of a common mechanism of antiobiosis such as production and secretion of a broad spectrum antibiotic. As antibiosis effects were detected in the same 14 strains of *Burkholderia* that produced siderophores, *Burkholderia* mediated antibiosis may have been be caused by localized iron starvation, inhibiting both yeast and *E. coli* growth. A large number of Ochrobacterum isolates also had antagonism towards yeast growth.

Example 4—Seed Endophyte Establishment and Persistence in Corn and Wheat

Seed endophytes colonize plant tissues and as part of their life cycle they can establish inside roots and disperse systemically throughout the plant vascular system and colonize stems, leaves, flowers and seeds. In order to track the fate of individual strains they are labeled with a marker such as Green Fluorescent Proteins (GFP) encoded in a multi copy plasmid. A strain is transformed with the plasmid encoding the expression of GFP that can be detected by flow cytometry with excitation with a blue laser at 488 nm and light emission at 530 nm or fluorescent microscopy. The transformed strain will fluoresce green and thus can be readily discriminated from the native microbial community as indigenous green fluorescence does not occur in seed endophytes or microbial species associated with the rhizosphere or soils. Seeds are inoculated with such bacteria which colonize the germinating seed allowing the establishment, detection and enumeration of the GFP-labeled strain in specific tissues such as roots, stems and flowers as the plants develop and mature. Through the plant's life cycle and reproductive stages the tissues can be analyzed for the presence of the GFP labeled seed-origin endophyte. This demonstrates that bacteria's ability to colonize and persist in vegetative plant tissues, in addition to seed surfaces and interiors where it was originally inoculated. Seed endophytes will be capable of propagation outside the seed and to be re-established on seeds to colonize new plant generations.

Figure 1B:
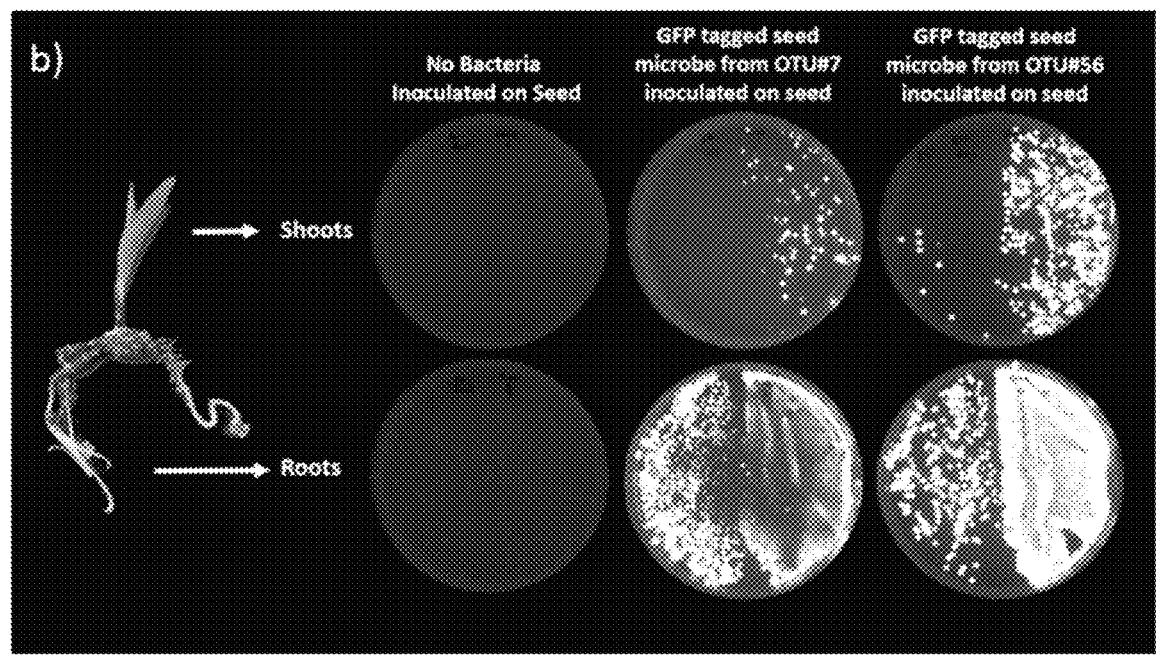
FIG. 1B depicts an alternative approach to observe plant colonization by seed-origin endophytes by tagging the microbes with a kanamycin resistance and GFP containing plasmid. These microbes were coated onto unsterilized maize seed, which was dried in a 50 mL conical tube and stored at room temperature for a week before being planted in cups containing sterile sand in a greenhouse. After a week of growth, shoots and roots were macerated using bead beating, serially diluted to 10× and 1,000× before plating and colony counting under UV to determine green fluorescing CFUs per plant on TSA plates containing kanamycin. Control plant extracts were plated on kanamycin free agar and developed non-GFP containing colonies of several undescribed microbes.

A strain of *Pantoea* representing OTU #7 and an *Enterobacter* representing OTU #56 were successfully electroporated with the broad gram negative host range plasmid, pDSK-GFPuv [Wang et al. (2007), New Phytol 174(1): 212-23, incorporated herein by reference]. This is a low copy plasmid, driving constitutive expression of very bright fluorescing GFP under UV light, in addition to carrying a constitutively expressed kanamycin resistance gene which can allow for selection against background, non-tagged microbes inherent in plant samples. These pDSK-GFPuv transformed bacteria were grown overnight in a volume of 10 mL of 50% TSB and the next day, CFUs were counted by serial dilution and plating on 50% TSA plates. At this time, 10 g of 58PM36 seed (Blue River Hybrid maize) in a sterile 50 mL conical tube was flooded with a mixture of 10 µl of plantability polymer Flo Rite 1706 and 500 µl of the GFP plasmid containing OTU #7 or OTU #56 bacteria in R2A broth. After vigorous shaking to ensure even coating of seed with bacteria, tubes were sealed and left at 25° C. for 7 days, at which time CFUs of bacteria still surviving on seed were assessed by carbide bead beating with a Fastprep24 machine for 60 seconds at 5M/seconds. Each 15 mL Falcon tube contained 3 seeds, 2 beads and 1 mL of sterile R2A broth in the. After agitation, 20 µL of the supernatant was then serially diluted, and 50 µL of the 10× diluted and 50 µL of the 1,000× diluted plated on halves of 50% TSA plates. Two of each seed type including untreated, OTU #7-GFP and OTU #56-GFP inoculated seeds were then planted 3 cm deep in 70% ethanol cleaned pots containing heat sterilized quartz sand, and watered daily with autoclaved water for 7 days as seedlings developed. At this time, seedlings were removed and shaken free from sand, cut into roots or shoots, weighed, placed in 15 mL Falcon tubes along with two carbide beads and either 1 mL of 50% TSB for shoots or 2 mL of 50% TSB for roots. These were then homogenized by shaking on the Fastprep24 for 120 seconds at 5M/second. 20 µL of shoot and root homogenates were then serially diluted, and 50 µL of the 10× diluted and 50 µL of the 1,000× diluted plated on halves of 50% TSA plates. Uninoculated seed were plated on antibiotic free TSA, but OTU #7-GFP and OTU #56-GFP plant extracts were placed on TSA plates containing 50 µg/ml of kanamycin. See FIG. 1B for an example of the two GFP fluorescing strains on kanamycin containing TSA plates.

Based on colony counting of serial dilutions, OTU #7-GFP inoculum was at a level of $2.74 \times 10^9$ CFU/mL (approximately $5.08 \times 10^7$ CFU/seed) when applied to seeds, and after 7 days at room temperature each seed still had about $4.44 \times 10^5$ CFUs per seed. After 7 days of growth in a greenhouse exposed to fluctuations in light, heat, moisture and atmosphere, OTU #7-GFP inoculated seeds developed into a seedling with an average of $1.24 \times 10^6$ CFU/g of root tissue and $7.93 \times 10^5$ CFU/g of shoot tissue. Thus after planting seeds with approximately $4.44 \times 10^5$ CFU of OTU #7-GFP each, seedlings germinated and grew into plantlets containing an average of $1.02 \times 10^6$ CFU GFP labelled bacteria. This represents an almost three fold increase of bacterial numbers and suggests active growth and colonization of these bacteria in the plant, rather than passive survival for a week until the time of harvest.

OTU #56-GFP inoculum was at a level of $1.69 \times 10^9$ CFU/mL (approximately $3.13 \times 10^7$ CFU/seed) when applied to seeds, and 7 days later each seed still had about $2.21 \times 10^6$ CFUs living on its surface. After 7 days of growth in a greenhouse exposed to fluctuations in light, heat, moisture and atmosphere, OTU #56-GFP inoculated seeds developed into seedlings with an average of $4.71 \times 10^6$ CFU/g of root tissue and $2.03 \times 10^4$ CFU/g of shoot tissue. Thus after planting seeds with approximately $2.21 \times 10^6$ CFU of OTU #7-GFP each, seedlings germinated and grew into plantlets containing an average of $6.06 \times 10^5$ CFU GFP labelled bacteria.

Taken together, these two experiments successfully showed that seed derived endophytes are able to survive on a maize seed surface in large numbers under non-sterile greenhouse conditions for at least a week and are able to colonize and persist on the developing plant over time where they will have ongoing opportunities to influence and improve plant growth, health and productivity.

Example 5—Colonization of Grass Plants

The establishment of plant-microbe interactions is contingent on close proximity. The microbiome of the host plant consists of microorganisms inside tissues as well as those living on the surface and surrounding rhizosphere. The present invention describes, among other methods, the colonization of the plant by application of endophytic microbes of the seed surface. The experiments described in this section are aimed at confirming successful colonization of plants by endophytic bacteria by direct recovery of viable colonies from various tissues of the inoculated plant. The experiments were designed to reduce background microbes by the use of surface-sterilized seeds, and planting and growing the seeds in a sterile environment, to improve the observable colonization of the plant with the inoculated bacterium.

Experimental Description

Corn seeds of cultivar 58PM36 (Blue River Hybrid) were surface-sterilizing by exposing them to chlorine gas overnight, using the methods described elsewhere. Sterile seeds were then inoculated with submerged in 0.5 OD overnight cultures [Tryptic Soy Broth] of strains SYM00254 (a *Micrococcus* sp. of OTU 59), SYM00284 (a *Pantoea* sp. of OTU 0), SYM00290 (an *Actinobacter* of OTU 154), or SYM00292 (a *Paenibacillus* sp. of OTU 6) and allowed to briefly air dry. The seeds were then placed in tubes filled partially with a sterile sand-vermiculite mixture [(1:1 wt/wt)] and covered with 1 inch of the mixture, watered with sterile water, sealed and incubated in a greenhouse for 7 days. After this incubation time, various tissues of the grown plants were harvested and used as donors to isolate bacteria by placing tissue section in a homogenizer [TSB 20%] and mechanical mixing. The slurry was then serially diluted in 10-fold steps to $10^{-3}$ and dilutions 1 through $10^{-3}$ were plated on TSA 20% plates (1.3% agar). Plates were incubated overnight and pictures were taken of the resulting plates as well as colony counts for CFUs.

Experimental Results

Successful inoculation of corn plants by the endophytic bacteria allowed the recovery of viable, culturable cells as identified on TSA agar plates. Controls experiments using uninoculated, surface sterilized seeds were conducted and showed few, if any, bacterial cells were cultivatable from the inside suggesting inoculation with extra microbes would be easily detectable by culturing. Non surface sterilized seeds meanwhile showed a large diversity of colony types including both bacteria and fungi which drowned out the detection by culturing of inoculated bacteria, whereas the plants grown from surface-sterilized seeds showed a dominance of the inoculated strains readily identified by the colony morphology.

Finally, significant quantities of viable colonies were recovered from roots, shoots or seeds of corn plants inoculated with SYM00254, SYM00284, SYM00290, or SYM00292 (Table 10, FIG. 1A), confirming the successful colonization of these tissues of corn plants inoculated with the various strains. Microbes living on the seed surface can be eliminated by surface sterilization as was done here. The elimination of this background allows for the quantitation of the cells of interest.

TABLE 10

Confirmed colonization of seed origin strains in corn shoot and root tissue at 7 days after seed inoculation.

| Seed-origin microbes | Shoot tissue | Root tissue |
| --- | --- | --- |
| SYM00254 | ++ | +++ |
| SYM00284 | +++ | +++ |
| SYM00290 | + | +++ |
| SYM00292 | ++ | +++ |

+—<$10^4$ cells per tissue type;
++—$10^4$ to $10^6$ cells per tissue type;
+++—>$10^6$ cells per tissue type.

Example 6—Testing of Seed-Origin Bacterial Endophyte Populations on Plants

The results shown above demonstrate that many of the endophytic bacteria described herein possess activities that could impart beneficial traits to a plant upon colonization. First, many of the bacteria described here are capable of producing compounds that could be beneficial to the plant, as detected using the in vitro assays described above. In addition, several representative bacteria were tested and found to successfully colonize corn plants as demonstrated in the example above. The aim of the experiments in this section addresses the ability of the bacterial endophytes to confer beneficial traits on a host plant. Several different methods were used to ascertain this. First, plants inoculated with bacteria were tested under conditions without any stress to determine whether the microbe confers an increase in vigor. Second, endophyte-inoculated plants were tested under specific stress conditions (e.g., salt stress, heat stress, drought stress, and combinations thereof) to test whether the bacteria confer an increase in tolerance to these stresses. These growth tests were performed using three different means: using growth assays on water-agar plates; using growth assays on sterile filter papers; and growth assays on magenta boxes.

Experimental Description

Surface sterilization of seeds—Un-treated organic maize seeds (Blue River hybrids, 40R73) and wheat seeds (Briggs, developed by South Dakota University) were sterilized overnight with chlorine gas as follows: 200 g of seeds were weighed and placed in a 250 mL glass bottle. The opened bottle and its cap were placed in a dessicator jar in a fume hood. A beaker containing 100 mL of commercial bleach (8.25% sodium hypochlorite) was placed in the dessicator jar. Immediately prior to sealing the jar, 3 mL of concentrated hydrochloric acid (34-37.5%) was carefully added to the bleach. The sterilization was left to proceed for 18-24 h. After sterilization, the bottle was closed with its sterilized cap, and reopened in a sterile flow hood. The opened bottle was left in the sterile hood for a couple hours to air out the seeds and remove chlorine gas leftover. The bottle was then closed and the seeds stored at room temperature in the dark until use.

Seedling Vigor Assessment in Normal and Stressed Conditions on Water Agar

Bacterial endophytes isolated from seeds as described herein were tested for their ability to promote plant growth under normal and stressed conditions by inoculating maize and wheat seeds with those endophytes and germinating them on water agar. For each bacterial endophyte tested, 5 mL of liquid R2A medium was inoculated with a single colony and the culture grown at room temperature on a shaker to an OD (600 nm) of between 0.8 and 1.2.

Figure 2:
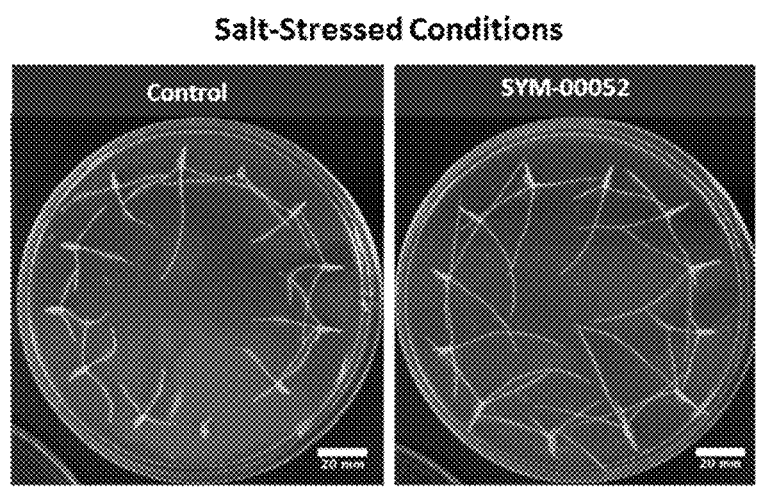
FIG. 2 contains representative photographs of seedlings. The seedlings inoculated with SYM-00052 (right) outperformed un-inoculated control seedlings (left) under salt stress conditions with 100 mM NaCl in media. This provides an example of seed-origin microbes conferring growth promotion to wheat seeds grown under salt stress.
Figure 3:
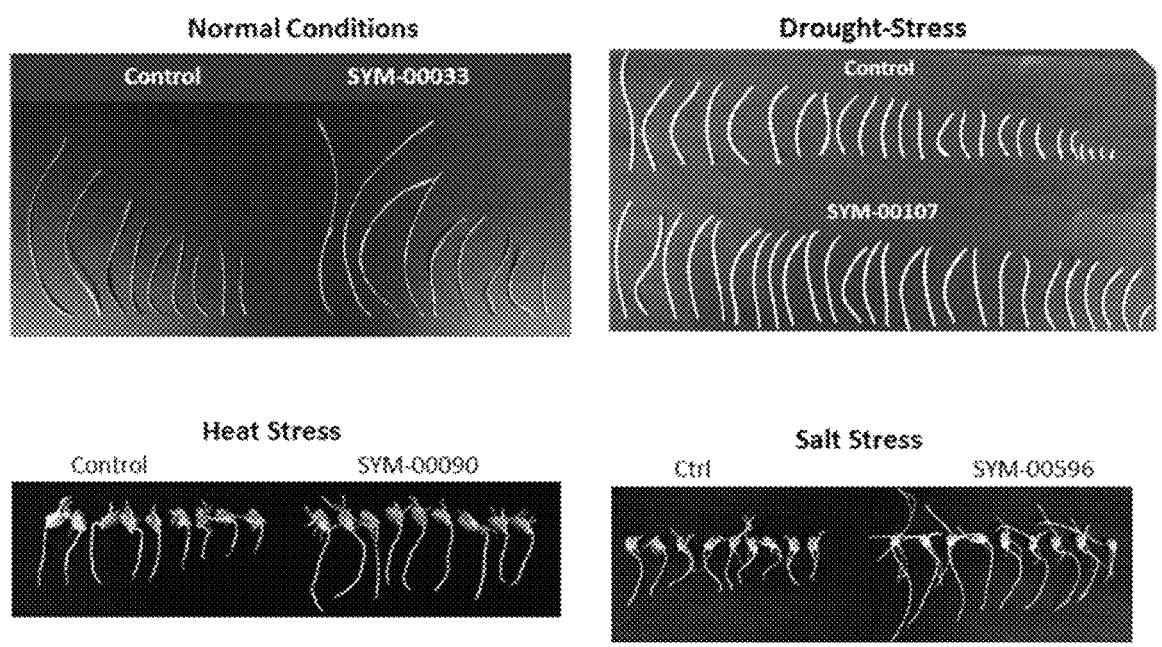
FIG. 3 contains representative photographs of seedlings. Improved vigor or growth of wheat (above) and corn (below) plants inoculated with seed-borne endophytes was observed. Top left: wheat seeds were inoculated with SYM00033 and germinated under normal conditions. Top right: wheat seedlings inoculated with SYM00107 show enhanced growth under drought stress compared to uninoculated controls. Bottom left: SYM00090 inoculated corn seeds show improved growth under heat stress when compared with controls. Bottom right: corn seedlings inoculated with SYM00596 display enhanced growth under salt stress.
Figure 4:
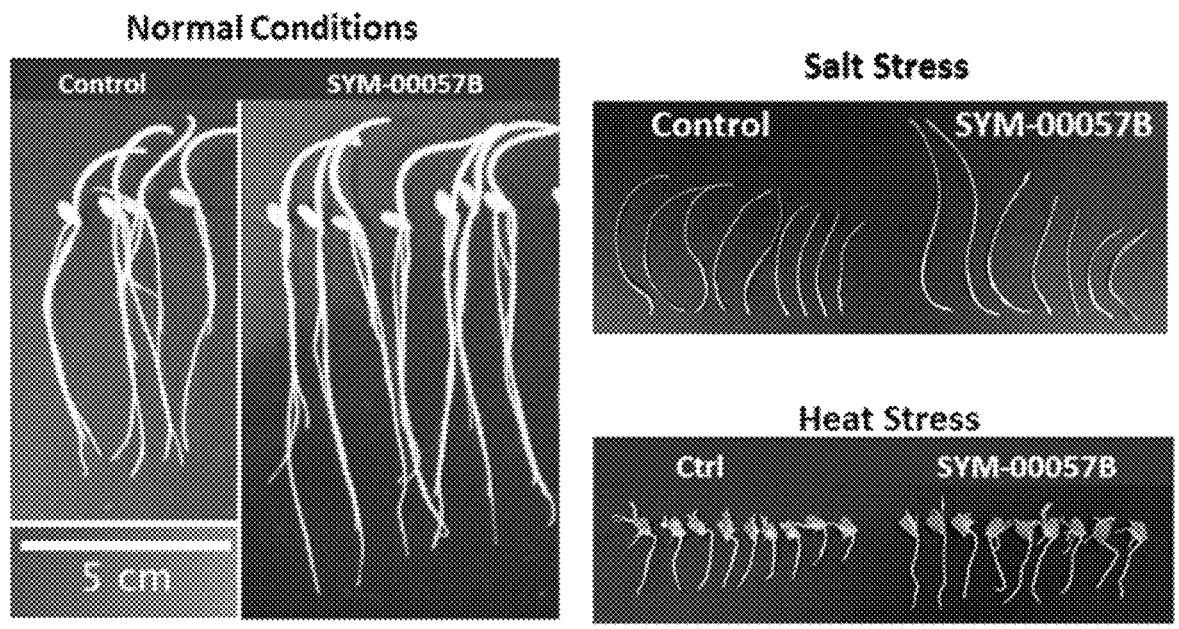
FIG. 4 contains representative photographs depicting seeds of wheat (Briggs cultivar) that were inoculated with the endophyte SYM00057B and grown under normal conditions (left), grown in the presence of 100 mM NaCl (top right), or under heat stress (bottom right). Increase in root length of wheat plants inoculated with seed-borne endophytes.
Figure 5:
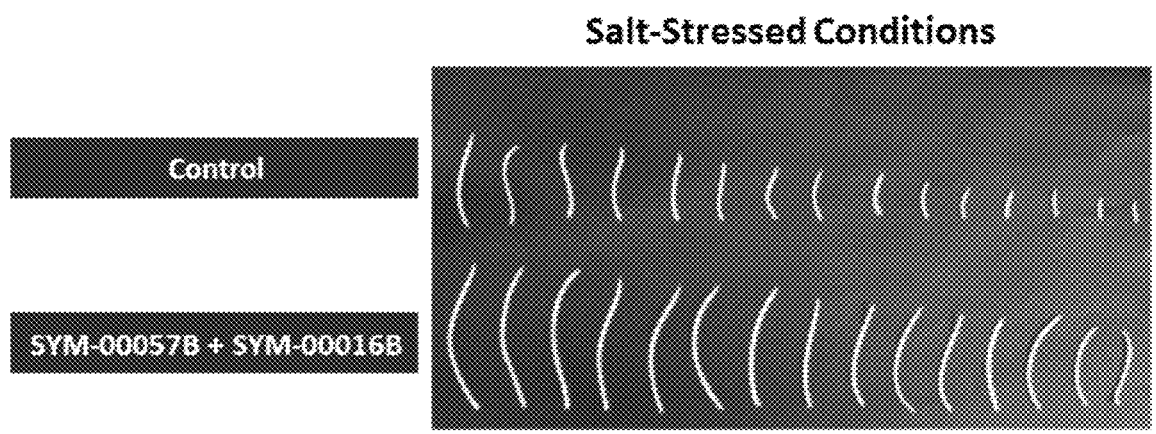
FIG. 5 contains representative photographs depicting wheat seeds inoculated with a combination of SYM00057B and SYM00016B (bottom row) show enhanced growth under salt stress conditions when compared with controls (top row). Combinations of seed-origin microbes confer improved vigor to wheat.
Figure 6:
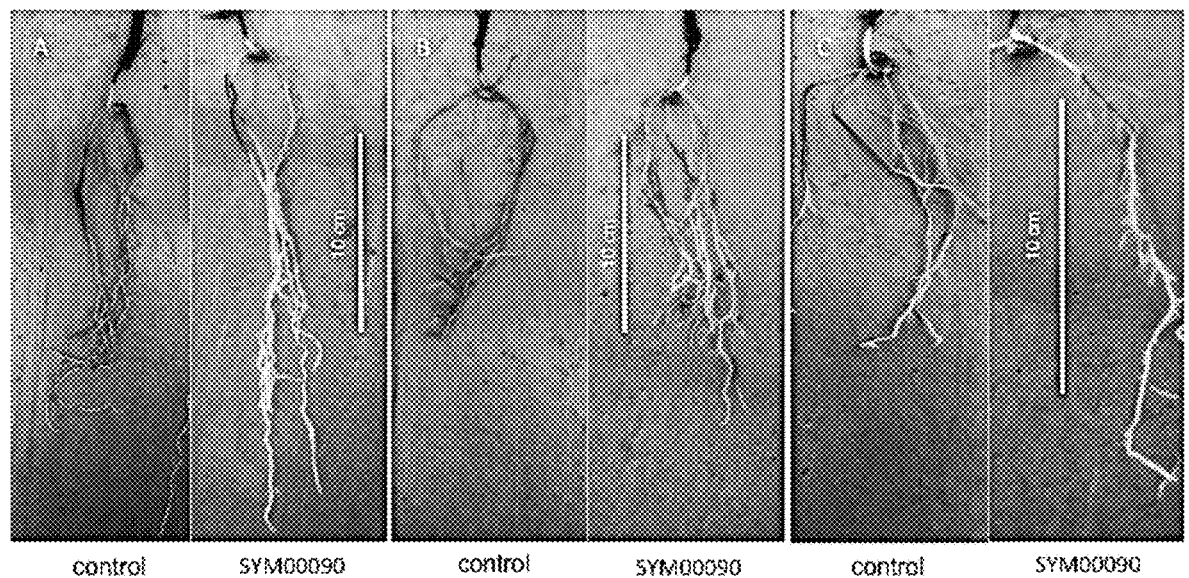
FIG. 6 contains representative photographs of roots of plants that germinated from uninoculated (control) and inoculated seeds (Sym00090) and were exposed to A) normal, B) drought and C) cold conditions. For normal conditions, plants were kept on a growth chamber set up to 22° C., 60% relative humidity and 14 h light/10 dark cycle for 15 days after planting. For drought, water was removed from bottom container in double-decker Magenta box one week after planting and the sand was let to dry. Harvesting was done at 7 days after water was removed, when wilting symptoms appeared. For cold, the air temperature was set to 5° C., one week after planting and maintained for 7 days. The roots of the inoculated plant are not only larger but also show a larger amount of lateral roots and root-hairs.

Sterilized maize and wheat seeds were placed on water agar plates (1.3% bacto agar) in a laminar flow hood, using forceps previously flamed. A drop of inoculum with an OD comprised between 0.8 and 1.2 (corresponding to about $10^8$ CFU/mL) was placed on each seed (50 uL for maize, 30 uL for wheat, representing approximately $5.10^6$ and $3.10^6$ CFUs for maize and wheat, respectively). For each treatment, 3 plates were prepared with 12 seeds each, arranged as show in on FIG. 2 to insure position uniformity. Plates were sealed with surgical tape, randomized to avoid position effects and placed in a growth chamber set at 22° C., 60% relative humidity, in the dark for four days. After four days, a picture of each plate was taken and the root length of each seedling was measured using the imaging software ImageJ. The percentage difference between the treated plants and the mock-treated (R2A control) was then calculated. For growth under salt stress, the water agar plates were supplemented with 100 mM NaCl. For growth under heat stress, the plates were placed at 40° C., 60% humidity after two days of growth, and left for an additional two days.

Seedling Vigor Assays Under Normal and Stressed Conditions on Filter Paper

Filter papers were autoclaved and placed into Petri dishes, and then presoaked with treatment solutions. To simulate normal conditions, 3-4 mL sterile water was added to the filters. Drought and saline stresses were induced by adding 3-4 mL 8% PEG 6000 solution or 50 or 100 mM NaCl to the filter papers. Surface sterilized seeds were incubated in bacterial inocula for at least one hour prior to plating. Nine seeds were plated in triplicate for each condition tested, including room temperature and heat stress (40° C.) for both normal and saline conditions. During initial stages of the experiment, plates were sealed with parafilm to inhibit evaporative water loss and premature drying of the filter papers. Plates were incubated in the dark at room temperature for two days following which heat treatment plates were shifted to 40° C. for 4-6 days. Parafilm was removed from all plates after 3-5 days. After 5-8 days, seedlings were scored by manually measuring root length for corn and shoot length for wheat and recording the mass of pooled seedlings from individual replicates.

Experimental Results

Plant vigor and improved stress resilience are important components of providing fitness to a plant in an agricultural setting. These can be measured in germination assays to test the improvement on the plant phenotype as conferred by microbial inoculation. The collection of seed-origin endophytes produced a measurable response in corn (Tables 4a and 4b), and wheat (Table 5a and Table 5b) when inoculated as compared to non-inoculated controls. For example, from 48 bacterial strains, representing 44 OTUs tested in these germination assays, only 2 did not produce a favorable phenotype in any of the measured multiple parameters such as root length, weight, or shoot length in wheat. This suggests that the strains play an intimate role modulating and improving plant vigor and conferring stress resilience to the host plant. In wheat under normal conditions (vigor), 73% of the strains tested showed some level of effect and 43% a strong plant response suggesting the physiology and ecological niches of the strain collection can be associated to a beneficial plant role. The stress responses in the strain collection can be seen by the ability of a subgroup to confer a beneficial response under different conditions such as heat and salt and drought. These can be applicable to products for arid and marginal lands. In a large proportion of cases for the tested strains, the beneficial effect was measurable in both crops indicating that the strains are capable of colonizing multiple varieties and plant species. This can play a role in their mechanisms for dispersal and colonization from one seed into a mature plant but also as part of the life cycle to establish an ample distribution range and ecological persistence in nature. This may translate also into relevant features in agriculture. For drought responses in corn it was found that 73% of the strains were improving in the filter paper assay as measured by root length and weight. In some cases it was possible to see additive effects for stress responses comparing heat, salt and the combination of heat and salt in the same assay, however not always in a cumulative benefit. For vigor in corn 81% of the strains showed improvements when tested in filter paper or water agar assays.

The phenotypes conferred by the inoculation and improvement in plant development are visible by comparing for example the root length, shoot length and weight of the seedling with non-inoculated controls as illustrated by FIGS. 3, 4, 5, and 6.

Individual tests for stress response for corn showed in average 57% of the strains an increase in weight over control in heat and salt, 51% for heat-salt and 40% for drought on weight gain. For wheat under salt conditions 54% of the strains produced an effect on root length, 77% of the strains a shoot length effect and 50% a weight gain. Drought tests were scored for shoot length and weight with a 59% of the strains showing increase in shoot length and 43% weight increase.

Table 4. Systematic assessment of effects of seed-origin microbes on corn seed vigor under normal and stressed conditions. Legend: "—" indicates no significant increase relative to uninoculated control; "1"=0-5% increase relative to uninoculated control; "2"=5-10% increase relative to uninoculated control; "3"=>10% increase relative to uninoculated control TABLE 4(a)

Assay for seedling vigor in water agar conditions

| Strain | OTU# | Corn cultivar A Weight Normal | Corn cultivar A Root length Normal | Corn-organic Root Length normal | Corn-organic Root Length salt |
|---|---|---|---|---|---|
| SYM00002 | 66 | | | 2 | 2 |
| SYM00011 | 2 | | | — | 1 |
| SYM00012 | 55 | | | 2 | 2 |
| SYM00017c | 45 | | 1 | 3 | — |
| SYM00028 | 18 | | | 2 | |
| SYM00049 | 7 | 2 | 1 | 3 | 1 |
| SYM00052 | 18 | | | 1 | — |
| SYM00057b | 37 | | | 3 | 2 |
| SYM00060 | 67 | | | 1 | |
| SYM00064a | 10 | | | 2 | 2 |
| SYM00071 | 76 | | | 1 | |
| SYM00075 | 39 | 2 | | — | — |
| SYM00090 | 62 | | | — | 1 |
| SYM00167 | 3 | | | 1 | 1 |
| SYM00188 | 6 | | 1 | 3 | — |
| SYM00192 | 19 | | | 1 | 2 |
| SYM00199 | 135 | | | 1 | 1 |
| SYM00231 | 46 | | | 2 | — |

TABLE 4(b)

Assay for seedling vigor on filter paper.

| Strain | OTU # | ROOT LENGTH Corn organic Filter paper normal | heat | salt | heat-salt | drought | SEEDLING WEIGHT Corn organic Filter paper normal | heat | salt | heat-salt | drought |
|---|---|---|---|---|---|---|---|---|---|---|---|
| SYM00002 | 66 | 1 | 3 | — | — | 3 | 2 | 3 | 1 | — | 1 |
| SYM00011 | 2 | | | | | 2 | — | — | — | — | 2 |
| SYM00012 | 55 | — | 1 | — | — | — | 2 | 2 | — | 2 | — |
| SYM00017c | 45 | 1 | — | 3 | 2 | 2 | — | 1 | 1 | 2 | — |
| SYM00028 | 18 | — | — | — | — | 3 | 1 | — | 2 | 3 | — |
| SYM00033 | 0 | — | 1 | 3 | 2 | 2 | 1 | 3 | — | 2 | — |
| SYM00049 | 7 | 1 | 3 | 1 | 2 | 1 | — | — | — | 1 | — |
| SYM00052 | 18 | | | | | 2 | — | — | — | — | 1 |
| SYM00057b | 37 | 1 | 1 | — | 1 | 1 | 1 | 3 | 1 | 1 | 1 |
| SYM00071 | 76 | — | 1 | 2 | 3 | — | 2 | 1 | 2 | 3 | — |
| SYM00075 | 39 | | | | | — | — | — | — | — | 3 |
| SYM00090 | 62 | 2 | 2 | 2 | — | 1 | 3 | 3 | 1 | 1 | — |
| SYM00102 | 38 | — | 2 | 3 | 3 | — | — | 1 | — | 3 | — |
| SYM00107 | 59 | — | 1 | — | — | — | 1 | — | — | 3 | 1 |
| SYM00167 | 3 | 2 | 2 | 1 | 3 | 1 | 1 | 3 | — | 2 | — |
| SYM00172 | 146 | — | — | — | 1 | — | — | — | — | — | — |
| SYM00188 | 6 | — | 1 | 2 | — | — | 1 | 2 | 1 | 3 | — |
| SYM00192 | 19 | — | 2 | — | 3 | — | 1 | 2 | 1 | 3 | — |
| SYM00199 | 135 | — | 3 | — | 3 | — | 1 | 3 | 1 | 3 | — |
| SYM00218 | 41 | | | | | — | — | — | 1 | — | 3 |
| SYM00231 | 46 | | | | | — | — | — | — | — | 1 |
| SYM00508 | 196 | — | — | — | — | — | 1 | — | — | — | — |
| SYM00547 | 13 | 2 | 1 | 3 | — | 1 | 1 | — | — | — | 1 |
| SYM00554 | 53 | — | 3 | — | 3 | — | — | 2 | — | 3 | — |
| SYM00589 | 31 | — | 2 | 3 | 3 | — | 1 | 3 | 1 | 3 | — |
| SYM00595 | 12 | 1 | 3 | 2 | 2 | — | 1 | 3 | 1 | 3 | — |
| SYM00596 | 9 | 1 | 3 | 3 | 3 | 1 | — | 3 | — | 3 | — |
| SYM00660 | 1 | — | 2 | 1 | 1 | 2 | — | 2 | — | — | 2 |
| SYM00713 | 84 | — | — | — | — | 2 | — | — | — | — | — |
| SYM00775 | 30 | — | — | 3 | — | — | 2 | 2 | — | 3 | 2 |
| SYM00940 | 83 | — | — | — | — | 1 | 1 | 1 | — | — | 1 |

TABLE 4(b)-continued

Assay for seedling vigor on filter paper.

| | | ROOT LENGTH Corn organic Filter paper | | | | | SEEDLING WEIGHT Corn organic Filter paper | | | | |
|---|---|---|---|---|---|---|---|---|---|---|---|
| Strain | OTU # | normal | heat | salt | heat-salt | drought | normal | heat | salt | heat-salt | drought |
| SYM00967 | 8 | — | — | 3 | — | 3 | 1 | 1 | 1 | — | 1 |
| SYM00975 | 51 | 2 | — | 3 | — | 3 | 1 | 1 | — | — | 2 |
| SYM00991 | 36 | — | — | — | 3 | — | 1 | — | — | — | 1 |
| SYM00992 | 126 | 1 | — | — | — | 3 | — | — | — | — | — |

Table 5. Wheat Stress/Vigor Test

TABLE 5(a)

Wheat seedling vigor assessment using water agar assay.

| | | Root Length Wheat Briggs Water-agar | | |
|---|---|---|---|---|
| Strain | OTU# | Normal | Heat | Salt |
| SYM00002 | 66 | 3 | — | 3 |
| SYM00011 | 2 | 3 | 3 | 3 |
| SYM00012 | 55 | 3 | 1 | 3 |
| SYM00015 | 29 | — | 1 | — |
| SYM00016b | 25 | 2 | 3 | 3 |
| SYM00017c | 45 | 3 | 2 | 3 |
| SYM00021 | 29 | 3 | — | — |
| SYM00028 | 18 | 3 | — | 2 |
| SYM00033 | 0 | 3 | — | 3 |
| SYM00046 | 56 | 3 | — | — |
| SYM00049 | 7 | 3 | 2 | 2 |
| SYM00052 | 18 | 1 | — | 3 |
| SYM00057b | 37 | 3 | 3 | 3 |
| SYM00060 | 67 | 2 | — | — |
| SYM00063 | 134 | 1 | — | — |
| SYM00064a | 10 | 3 | — | — |
| SYM00071 | 76 | 3 | — | — |
| SYM00075 | 39 | 3 | — | — |
| SYM00090 | 62 | 3 | 2 | 1 |
| SYM00102 | 38 | 2 | — | — |
| SYM00107 | 59 | 2 | 3 | — |
| SYM00167 | 3 | 3 | — | 3 |
| SYM00168 | 45 | 3 | — | 1 |
| SYM00183 | 10 | 3 | — | — |
| SYM00188 | 6 | 1 | — | — |
| SYM00192 | 19 | 3 | 1 | — |
| SYM00199 | 135 | 3 | 1 | 3 |
| SYM00218 | 41 | 3 | 1 | — |
| SYM00508 | 196 | 3 | 3 | 1 |
| SYM00538A | 172 | 1 | — | 1 |
| SYM00547 | 13 | 2 | 3 | 2 |
| SYM00589 | 31 | — | 3 | 1 |
| SYM00595 | 12 | — | 3 | — |
| SYM00596 | 9 | 1 | 3 | 1 |
| SYM00660 | 1 | — | — | 2 |
| SYM00713 | 84 | 2 | — | 1 |
| SYM00775 | 30 | — | 2 | — |
| SYM00940 | 83 | — | 1 | — |
| SYM00965 | 82 | 2 | — | 1 |
| SYM00967 | 8 | 2 | 3 | 3 |
| SYM00975 | 51 | 1 | — | 2 |
| SYM00992 | 126 | — | — | 3 |

Legend:
"—" indicates no significant increase relative to uninoculated control;
"1" = 0-5% increase relative to uninoculated control;
"2" = 5-10% increase relative to uninoculated control;
"3" = >10% increase relative to uninoculated control TABLE 5(b)

Wheat seedling vigor using filter paper assay.

| | | WHEAT BRIGGS FILTER PAPER | | | | | |
|---|---|---|---|---|---|---|---|
| | | Shoot Length | | | Weight | | |
| Strain | OTU # | Normal | Salt | Drought | Normal | Salt | Drought |
| SYM00002 | 66 | — | 1 | — | — | 2 | — |
| SYM00011 | 2 | 3 | 1 | 3 | 3 | — | 2 |
| SYM00012 | 55 | — | 2 | 3 | 2 | — | 1 |
| SYM00016b | 25 | | | | | | |
| SYM00017c | 45 | — | 1 | — | — | 1 | 2 |
| SYM00028 | 18 | — | 3 | 3 | — | 3 | 3 |
| SYM00033 | 0 | 3 | 1 | 2 | — | — | 1 |
| SYM00049 | 7 | 3 | — | 3 | 2 | — | 2 |
| SYM00052 | 18 | 1 | — | 1 | 3 | — | — |
| SYM00057b | 37 | 3 | 3 | 1 | 2 | — | 3 |
| SYM00064a | 10 | — | 2 | 2 | — | — | — |
| SYM00071 | 76 | 2 | 3 | 3 | — | 3 | 1 |
| SYM00075 | 39 | — | 1 | 3 | — | — | 3 |
| SYM00090 | 62 | — | — | 3 | — | — | 3 |
| SYM00102 | 38 | — | 3 | 3 | 2 | 3 | — |
| SYM00107 | 59 | 1 | 3 | 3 | 2 | 3 | 3 |
| SYM00167 | 3 | 2 | 2 | 1 | — | — | 2 |
| SYM00168 | 45 | | | | | | |
| SYM00172 | 146 | | | — | | | 3 |
| SYM00188 | 6 | 1 | 3 | — | — | 3 | — |
| SYM00192 | 19 | — | 3 | — | 2 | 3 | — |
| SYM00199 | 135 | — | — | 1 | 2 | — | — |
| SYM00218 | 41 | — | 2 | 3 | 3 | — | 3 |
| SYM00231 | 46 | — | — | 3 | 3 | 3 | 3 |
| SYM00508 | 196 | — | 3 | — | — | 2 | — |
| SYM00538A | 172 | | | | | | |
| SYM00547 | 13 | | | 1 | | | — |
| SYM00554 | 53 | — | 3 | — | — | 3 | — |
| SYM00589 | 31 | — | — | — | — | — | — |
| SYM00595 | 12 | 1 | 3 | 3 | 2 | 3 | — |
| SYM00596 | 9 | 1 | 3 | 3 | 1 | 3 | 2 |
| SYM00660 | 1 | | | 3 | | | — |
| SYM00713 | 84 | | | 1 | | | — |
| SYM00965 | 82 | | | | | | |
| SYM00967 | 8 | | — | | | — | |
| SYM00975 | 51 | | — | | | — | |
| SYM00992 | 126 | | — | | | — | |

Legend:
"—" indicates no increase relative to uninoculated control;
"1" = 0-5% increase;
"2" = 5-10% increase;
"3" = >10% increase Growth Test of Inoculated Plants in Magenta Boxes Representative endophytes isolated from seeds as described herein were tested for their ability to promote plant growth under normal and stressed conditions by inoculating maize seeds with those endophytes and growing them inside Conviron Growth chambers (Conviron Corp., Asheville, N.C.) on double-decker Magenta boxes essentially as described in Rodriguez et al. ISME Journal (2008) 2, 404-416, which is incorporated herein by reference in its entirety. Briefly, the double-deckers were made by drilling a hole 8 mm in diameter in the center of a GA-7 plant culture vessel (Magenta boxes, Sigma, St. Louis), top-knotting and weaving through a 14 cm length of cotton rope to the bottom chamber to act as a wick and adding a defined amount of playground sand in the upper chamber. Peter's 20:20:20 plant nutrient solution (Peters Fertilizer Co., Fogelsville, Pa.) is added to the bottom chamber and a tight-fitting lid is added to the top and the whole system autoclaved and sterilized prior to planting with not-inoculated or endophyte-treated seeds.

Maize seeds were surface sterilized with chlorine gas as described herein. Sterilized maize seeds were soaked for one hour on the appropriate bacterial culture before planting. Each bacterial culture was grown on a shaking incubator 20% Tryptic soy broth (TSB) until reaching ~0.5 optical density, measured at 600 nm wavelength. Non-inoculated controls were soaked on sterile 20% TSB. Three seeds were planted on each double-decker Magenta box and three boxes were used per treatment (endophytic bacteria×environmental condition). The double-deckers were placed inside a Conviron Growth chamber with a setting of 60% humidity and kept in the dark for four days, until they started germinating. Upon germination, plants were grown in a cycle of light (~400 mE×m^-2×s^-1) for 14 hrs. and dark for 10 hrs. When the leaves were fully expanded, approximately 8 days after seeding, the plants were assigned to one of 3 chambers were conditions were as follows: for Control conditions, plants were kept at 22° C.; for cold, plants were subjected to 5° C. during the light part of the daily cycle and near zero degrees during the dark part; for drought, the plants were maintained in the control chamber, but the liquid from the lower part of the double decker was emptied and the soil was allowed to dry; for heat conditions, the light intensity was set to a maximum of ~600 mE×m^-2×s^-1, while the temperature was set to 40° C. for 12 hrs. out of the 14 hrs. of light and 45 degrees during the two hrs. around noon, during the dark cycle the temperature was set to 30° C. The air humidity was maintained at 60% in all chambers. The conditions were maintained for one week at the end of which conductance was measured using an SC-1 Leaf Porometer (Decagon Devices Inc., Pullman, Wash.) in the plants maintained under control and drought conditions and all the plants were harvested, photographed and dried in a convention oven at 45° C. to estimate dried biomass. Shoot and root lengths were measured digitally using the software ImageJ version 1.48u4 (Rasband http://imagej.nih.gov).

Average measurements were compared against those for uninoculated controls for each treatment. The results obtained with the water agar assay are summarized in Table 7. Several bacterial endophytes provided significant plant growth improvement under normal and/or stressed conditions in maize. Notably, strain SYM90 provided growth improvement under normal, drought and cold conditions, mainly in the form of increased root length. Strains SYM00183, SYM00015, SYM00167 and SYM00168 also increased root length under drought conditions relative to non-inoculated controls. Almost all the endophytic bacteria tested provided increase gain in biomass under cold conditions. The magnitude of the difference in the conductance between normal conditions and drought conditions was significantly larger in the plants inoculated with SYM231 relative to the non-inoculated controls, suggesting an improved water balance potentially related to closure of stomata.

TABLE 7

Summary of results of testing synthetic combinations of seed-origin endophytes and corn in plant growth tests on Magenta boxes.

| Plant vigor and stress resilience in Corn | | Root length | | |
|---|---|---|---|---|
| Strain | OTU# | normal | drought | cold |
| SYM00090 | 62 | 2 | 3 | 3 |
| SYM00016b | 25 | — | — | — |
| SYM00231 | 46 | — | 2 | 1 |
| SYM00183 | 10 | 3 | 3 | 2 |
| SYM00015 | 29 | 3 | 3 | — |
| SYM00167 | 3 | 2 | 2 | — |
| SYM00168 | 45 | 2 | 3 | 1 |

Legend:
"—" indicates no significant increase relative to uninoculated control;
"1" = 0-5% increase relative to uninoculated control;
"2" = 5-10% increase relative to uninoculated control;
"3" = >10% increase relative to uninoculated control.

Dose Response

Initial experiments described above were conducted to determine whether the microbe conferred beneficial traits to the colonized plant. We next sought to determine the amount of the microbe that is effective to confer any such benefit. In this example, selected microbial cultures were diluted to OD600 of 1.0, 0.1 and 0.01 (approximately $10^8$, $10^7$, $10^6$ CFUs/mL respectively) and applied onto wheat seeds (Briggs) using the water agar assay previously described.

SYM00011, SYM00033 and SYM00057B cultures were grown from a single colony in 5 mL of liquid R2A medium at room temperature on a shaker to stationary phase. The absorbance at 600 nm was measured and adjusted to an $OD_{600}$ of 1.0 (~$10^8$ CFUs/mL) in R2A media. Two additional dilutions at OD 0.1 and 0.01 (~$10^7$ and $10^6$ CFUs/mL respectively) were prepared by diluting the initial inoculum 10 and 100 times, again in R2A media.

Wheat seeds (Briggs) were sterilized overnight with chlorine gas and placed on water agar plates as described above. A 30 μL drop of inoculum was placed on each seed, representing approximately $3.0 \times 10^6$, $3.0 \times 10^5$ and $3.0 \times 10^4$ CFUs per seed for OD1, OD0.1 and OD0.01 inoculums, respectively. For each treatment, 3 plates were prepared with 12 seeds each. Plates were sealed with surgical tape, randomized to avoid position effects and placed in a growth chamber set at 22° C., 60% relative humidity, in the dark for four days. After four days, a picture of each plate was taken and the root length of each seedling was measured using the imaging software ImageJ (NIH). The percentage difference between the treated plants and the mock-treated (R2A control) was then calculated.

Figure 7:
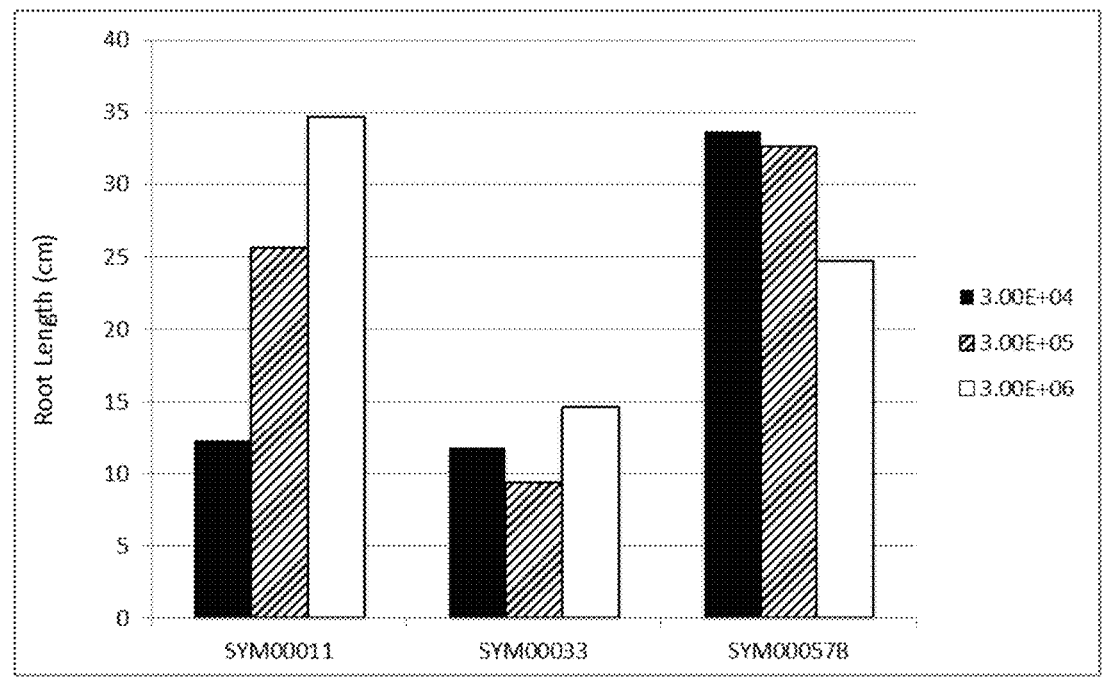
FIG. 7 is a graph depicting that seed-origin microbes show beneficial effects across a wide range of administered doses. Sterilized wheat seeds were inoculated with 3.0×104, 3.0×105 and 3.0×106 CFU/seed of endophytic microbes SYM00011, SYM00033 and SYM00057B. Shown are root lengths of each treatment, represented as a percentage increase over mock-inoculated controls.

All doses of the microbes at different concentration provided an increase in root length over the mock-treated controls as shown in FIG. 7. The optimal dose of microbes to confer a growth benefit to wheat varied for SYM00011, SYM00033 and SYM00057B. For SYM00011, we observed a positive correlation between the bacterial concentration of the inoculum and the growth benefits conferred to the plant, with ~$3.0 \times 10^6$ CFUs/seed (30 μL of OD600 of 1.0) being the most effective bacterial amount with a 35% increase in growth. For SYM00057B, plants treated with all three doses had similar root lengths, with the least concentrated inoculum ($3 \times 10^4$ CFUs/seed), being the most effective amount, suggesting saturation at a lower concentration. Similarly, all three concentrations of SYM00033 provided similar benefits, also suggesting saturation at $3 \times 10^4$ CFU/seed.

Inoculation with Strain Combinations

Microbial species colonizing habitats such as the seed-origin endophytic microbes described herein are likely to interact with other microbes as well as with the host in exchanging carbon, energy and other metabolites. The electron flow and metabolism may involve multiple species for complete transfer, which would support the establishment of synergistic communities or assemblages. In certain cases, the beneficial effect of a single microbial inoculant from seeds can be magnified by the presence of a second synergistic strain favoring the establishment and persistence of the binary assemblage and their competence. To create assemblages or combinations of available strains in a collection, several approaches were followed, including:

1. Strains with similar or differing functionalities identified by in vitro testing. Plant growth promoting activities encompass multiple microbial mechanisms to affect plant physiology. These microbial attributes can be tested in vitro such as auxin production, production of glycosylhydrolases (such as xylanase, cellulase, pectinase, and chitinase, ACC deaminase activity), mineral phosphate solubilization, siderophore production, nitrogen fixation and antibiosis against plant pathogens among others. By combining strains with similar or differing functionalities, the plant benefit are improved as compared to the individual members.

2. Combinations based on strain origin or co-occurrence. Based on their isolation from the same seed two strains may form an efficient microbial assemblage that can be provided heterologously to novel hosts.

3. Strains with demonstrated germination vigor and/or stress resilience. Seedling germination assays allow testing plant early development, establishment of the seed endophytes in the plant and quantifiable beneficial effect in root length, weight or shoot length as compared to non-inoculated controls and the same strains inoculated as singles.

4. Strains isolated from different hosts that may work synergistically. We isolated seed-origin endophytes from multiple plant hosts. Members of this group are capable of showing beneficial effects on inoculated plants when combined as compared to their individual effects.

5. One member from 3 and one member of 4. Seed endophytes showing increased plant vigor and stress resilience are combined with novel seed endophyte strains and their synergistic interaction amplifies the individual responses.

These combinations were tested with the collection of seed endophytes representing the 44 OTUs in vigor and stress resilience assays in corn (Table 6a) and wheat (Table 6b).

Table 6. Assessing the Effects of Creating Synthetic Combinations of Multiple Seed-Origin Endophytes with Seeds TABLE 6(a)

Corn seedling vigor assessment using filter paper assay.

| | | Root Length | | | | | Weight | | | | |
|---|---|---|---|---|---|---|---|---|---|---|---|
| Strain 1 | Strain 2 | Norm | Heat | Salt | Heat-salt | Drought | Norm | Heat | Salt | Heat-salt | Drought |
| SYM11 | SYM46 | — | — | — | — | 1 | — | 2 | — | — | 1 |
| SYM17c | SYM46 | — | — | — | — | 3 | — | — | — | — | 1 |
| SYM33 | SYM46 | — | — | — | 3 | 3 | — | 2 | — | — | 1 |
| SYM49 | SYM46 | — | — | — | — | — | — | — | — | — | 2 |
| SYM2 | SYM46 | — | — | — | — | 3 | — | 1 | — | — | 1 |
| SYM172 | SYM46 | — | — | 2 | — | — | — | — | — | — | — |
| SYM231 | SYM46 | — | — | — | — | 3 | — | — | 1 | — | 1 |
| SYM11 | SYM50 | — | — | 2 | 2 | 3 | — | 3 | — | — | 2 |
| SYM17c | SYM50 | 1 | — | 1 | 1 | 2 | — | — | 1 | — | 1 |
| SYM33 | SYM50 | — | — | — | 1 | 1 | — | 1 | — | — | 2 |
| SYM49 | SYM50 | — | — | 1 | 3 | — | — | — | — | — | — |
| SYM2 | SYM50 | — | 1 | — | 2 | — | 2 | — | — | — | — |
| SYM172 | SYM50 | — | 3 | 1 | 3 | — | — | 1 | — | — | — |
| SYM231 | SYM50 | — | 2 | 1 | 2 | — | — | 2 | — | — | — |
| SYM17c | SYM90 | — | 3 | 1 | 3 | — | 1 | — | — | — | 2 |
| SYM17c | SYM231 | 1 | 3 | 1 | 3 | 1 | 1 | 1 | — | — | — |
| SYM231 | SYM90 | — | — | — | 3 | — | 3 | 1 | — | — | — |
| SYM11 | SYM16b | — | 2 | 3 | 3 | 1 | 2 | — | — | — | 1 |
| SYM11 | SYM90 | 1 | — | 3 | 3 | 3 | 1 | 1 | — | — | 1 |
| SYM11 | SYM102 | — | 3 | 3 | 3 | 3 | 2 | 1 | — | — | 2 |
| SYM11 | SYM188 | — | 3 | 1 | 3 | 3 | — | — | — | — | 2 |
| SYM16b | SYM90 | | | | | | | | | | 3 |
| SYM90 | SYM102 | 1 | 3 | 3 | 3 | 3 | 3 | 1 | — | — | 3 |
| SYM102 | SYM188 | 1 | 2 | 1 | 3 | — | — | 1 | — | — | — |
| SYM589 | SYM90 | 1 | — | — | 3 | 3 | — | — | — | — | — |
| SYM596 | SYM90 | 2 | 3 | 1 | 3 | 3 | 3 | — | — | — | — |
| SYM218 | SYM90 | | | | | | | | | | 3 |
| SYM57b | SYM90 | 1 | 3 | — | 3 | 3 | 2 | — | — | — | 1 |
| SYM589 | SYM231 | 3 | 3 | — | 3 | 3 | 1 | — | — | — | — |
| SYM596 | SYM231 | 1 | — | 2 | 3 | 3 | 2 | 3 | — | — | 1 |
| SYM102 | SYM231 | — | — | 1 | 3 | 3 | 1 | — | — | — | — |
| SYM57b | SYM231 | 2 | 2 | 1 | 3 | 3 | 2 | — | 1 | — | — |

Legend:
"—" indicates no significant increase relative to uninoculated control;
"1" = 0-5% increase relative to uninoculated control;
"2" = 5-10% increase relative to uninoculated control;
"3" = >10% increase relative to uninoculated control.

TABLE 6(b)

Wheat seedling vigor assessment using filter paper assay.

| | | Root Length | | | Shoot Length | | | Weight | | |
|---|---|---|---|---|---|---|---|---|---|---|
| Strain 1 | Strain 2 | Normal | Heat | Salt | Normal | Salt | Drought | Normal | Salt | Drought |
| SYM 175 | SYM50 | — | — | — | — | 3 | 3 | — | 3 | 3 |
| SYM63b | SYM50 | 1 | — | — | 2 | 3 | 3 | 2 | 3 | 3 |
| SYM63b | SYM192 | 3 | — | — | 2 | — | — | 2 | — | — |
| SYM2 | SYM17c | 3 | — | 1 | 1 | 3 | 3 | 1 | 3 | 3 |
| SYM167 | SYM17c | — | — | — | 2 | 3 | 3 | 2 | 3 | 3 |
| SYM188 | SYM16b | — | — | — | 3 | — | 3 | 3 | — | 3 |
| SYM49 | SYM16b | 3 | — | — | 3 | — | 3 | 3 | — | 3 |
| SYM57b | SYM16b | 1 | 2 | — | 2 | 3 | 3 | 2 | 3 | 3 |
| SYM57b | SYM192 | 2 | — | 1 | — | 3 | 3 | — | 3 | 3 |
| SYM11 | SYM46 | 3 | | | | | — | | | — |
| SYM17c | SYM46 | 2 | | | | | — | | | 1 |
| SYM33 | SYM46 | 3 | | | | | — | | | — |
| SYM49 | SYM46 | 1 | | | | | — | | | — |
| SYM2 | SYM46 | 3 | | | | | 1 | | | — |
| SYM172 | SYM46 | — | | | | | — | | | — |
| SYM231 | SYM46 | 1 | | | | | — | | | — |
| SYM11 | SYM50 | — | | | | | — | | | — |
| SYM17c | SYM50 | — | | | | | — | | | — |
| SYM33 | SYM50 | — | | | | | — | | | 1 |
| SYM49 | SYM50 | 3 | | | | | — | | | — |
| SYM2 | SYM50 | 3 | | | | | — | | | — |
| SYM172 | SYM50 | — | | | | | — | | | 1 |
| SYM231 | SYM50 | 1 | | | | | — | | | 1 |
| SYM965 | SYM17c | 3 | | | | | | | | |
| SYM965 | SYM90 | 2 | | | | | | | | |
| SYM965 | SYM231 | 3 | | | | | | | | |
| SYM17c | SYM90 | 3 | | | | | | | | |
| SYM17c | SYM231 | 3 | | | | | | | | |
| SYM231 | SYM90 | 3 | | | | | | | | |
| SYM11 | SYM16b | 2 | | | | | | | | |
| SYM11 | SYM90 | 3 | | | | | | | | |
| SYM11 | SYM102 | 3 | | | | | | | | |
| SYM11 | SYM188 | 3 | | | | | | | | |
| SYM16b | SYM90 | 3 | | | | | | | | |
| SYM16b | SYM102 | 3 | | | | | | | | |
| SYM16b | SYM188 | 3 | | | | | | | | |
| SYM90 | SYM102 | 2 | | | | | | | | |
| SYM90 | SYM188 | 2 | | | | | | | | |
| SYM102 | SYM188 | 3 | | | | | | | | |
| SYM2 | SYM90 | 3 | | | | | | | | |
| SYM589 | SYM90 | — | | | | | | | | |
| SYM596 | SYM90 | 1 | | | | | | | | |
| SYM218 | SYM90 | 3 | | | | | | | | |
| SYM57b | SYM90 | 3 | | | | | | | | |
| SYM2 | SYM231 | 1 | | | | | | | | |
| SYM589 | SYM231 | 1 | | | | | | | | |
| SYM596 | SYM231 | 3 | | | | | | | | |
| SYM218 | SYM231 | 2 | | | | | | | | |
| SYM102 | SYM231 | 1 | | | | | | | | |
| SYM57b | SYM231 | 3 | | | | | | | | |

Legend:
"—" indicates no significant increase relative to uninoculated control;
"1" = 0-5% increase relative to uninoculated control;
"2" = 5-10% increase relative to uninoculated control;
"3" = >10% increase relative to uninoculated control A total of 50 binary combinations of strains were tested for vigor and stress resilience for heat, salt, heat-salt or drought and scored for improved vigor and/or stress resilience. Visible increase in shoot length for wheat was observed when the binaries were paired based on their seed origin for isolation and also based on the selection from the vigor and stress resilience assays suggesting that additive effects can be observed as compared to the effect from individual stresses. Other interesting response was observed for corn when inoculated with the binary formed by SYM00090 related to *Chryseobacterium*, a representative member of OTU 62 and SYM00231 related to *Sphingobium* and a representative member of OTU 46 provided protection against heat-salt stress in corn and vigor in wheat as measured for root length in both assays. Other combinations with strains was based on the production of auxin for strains SYM00011, SYM00017c, SYM00033, SYM00049, SYM00002, SYM00062b, SYM00172 and SYM00231 paired with cellulolytic and petcinolytic from strain SYM00050 showed an enhancement in the heat-salt resilience as compared to the same set of auxin producing strains paired with SYM00046 where drought stress was enhanced compared to the previous set. The drought resilience enhancement seen in seedling phenotypes in wheat as compared to controls is the result of the plant response to inoculation and molecular mechanisms for interaction between plant and bacteria. One example is the up-regulation of the protein pectin esterase on inoculated plants and the recognition of that protein in drought protection in plants. In addition, combinations of the 4 strains SYM00017b, SYM00049, SYM00057b and SYM00188 in corn increased dramatically the production of the plant hormone Abscisic acid as compared to individual strains indicating a more beneficial effect at molecular level with assemblages.

Example 7—Proteomic Analysis of Inoculated Plants

As shown in some of the earlier examples, endophytic microbes described herein are capable of conferring significant beneficial traits on the inoculated agricultural plant. In order to explore the pathways augmented or otherwise modified by the endophyte, we performed proteomic analysis on extracts of wheat and corn plants grown on water agar. Sterilized wheat and corn seeds were either mock-inoculated with R2A medium, or inoculated with selected endophytes SYM00011, SYM00016, SYM00057B, SYM00218, using conditions previously described. The seeds were subjected to the growth parameters as summarized below.

| Sample # | Crop | Test | Condition |
|---|---|---|---|
| 1 | Wheat (Briggs) | R2A (mock control) | Normal |
| 2 | Wheat (Briggs) | SYM00218 | Normal |
| 3 | Wheat (Briggs) | R2A (mock control) | Heat |
| 4 | Wheat (Briggs) | SYM00011 | Heat |
| 5 | Wheat (Briggs) | SYM00016 | Heat |
| 6 | Wheat (Briggs) | SYM00057B | Heat |
| 7 | Corn (40R73) | R2A (mock control) | Normal |
| 8 | Corn (40R73) | SYM00057B | Normal |

Sample Collection:

After 4 days of growth, 12 whole seedlings (including roots, seeds and hypocotyls) per treatment were collected in a 50 mL falcon tube using sterile forceps and immediately snap-frozen in liquid nitrogen to minimize protein degradation and proteomic changes during sample collection (such as wound responses from using the forceps). The frozen samples were then homogenized using a pestle and mortar previously cooled in liquid nitrogen and transferred to a 15 mL falcon tube on dry ice. The homogenized samples were stored at −80° C. until further processing.

Sample Preparation 1 mL of 5% SDS 1 mM DTT was added to 1 mL of homogenized tissue and the samples were boiled for 5 mins. The samples were cooled on ice and 2 mL of 8M urea solution was added. The samples were spun for 20 mins. at 14,000 rpm and the soluble phase recovered. A 25% volume of 100% TCA solution was added to the soluble phase, left on ice for 20 mins. and centrifuged for 10 mins. at 14,000 rpm. The protein pellet was washed twice with ice-cold acetone and solubilized in 125 µL 0.2M NaOH and neutralized with 125 µL of 1M Tris-Cl pH 8.0. Protein solutions were diluted in THE (50 mM Tris-Cl pH8.0, 100 mM NaCl, 1 mM EDTA) buffer. RapiGest SF reagent (Waters Corp., Milford, Mass.) was added to the mix to a final concentration of 0.1% and samples were boiled for 5 min. TCEP (Tris (2-carboxyethyl) phosphine) was added to 1 mM (final concentration) and the samples were incubated at 37° C. for 30 min. Subsequently, the samples were carboxymethylated with 0.5 mg/ml of iodoacetamide for 30 min at 37° C. followed by neutralization with 2 mM TCEP (final concentration). Proteins samples prepared as above were digested with trypsin (trypsin:protein ratio—1:50) overnight at 37° C. RapiGest was degraded and removed by treating the samples with 250 mM HCl at 37° C. for 1 h followed by centrifugation at 14,000 rpm for 30 min at 4° C. The soluble fraction was then added to a new tube and the peptides were extracted and desalted using Aspire RP30 desalting columns (Thermo Scientific). The trypsinized samples were labeled with isobaric tags (iTRAQ, ABSCIEX, Ross et al 2004), where each sample was labeled with a specific tag to its peptides.

Mass Spectrometry Analysis

Each set of experiments (samples 1 to 6; samples 7 and 8) was then pooled and fractionated using high pH reverse phase chromatography (HPRP-Xterra C18 reverse phase, 4.6 mm×10 mm 5 µm particle (Waters)). The chromatography conditions were as follows: the column was heated to 37° C. and a linear gradient from 5-35% B (Buffer A-20 mM ammonium formate pH10 aqueous, Buffer B-20 mM ammonium formate pH10 in 80% ACN-water) was applied for 80 min at 0.5 ml/min flow rate. A total of 30 fractions of 0.5 ml volume where collected for LC-MS/MS analysis. Each of these fractions was analyzed by high-pressure liquid chromatography (HPLC) coupled with tandem mass spectroscopy (LC-MS/MS) using nano-spray ionization. The nano-spray ionization experiments were performed using a TripleTof 5600 hybrid mass spectrometer (AB SCIEX Concord, Ontario, Canada)) interfaced with nano-scale reversed-phase HPLC (Tempo, Applied Biosystems (Life Technologies), CA, USA) using a 10 cm-180 micron ID glass capillary packed with 5 µm C18 Zorbax™ beads (Agilent Technologies, Santa Clara, Calif.). Peptides were eluted from the C18 column into the mass spectrometer using a linear gradient (5-30%) of ACN (Acetonitrile) at a flow rate of 550 µl/min for 100 min. The buffers used to create the ACN gradient were: Buffer A (98% H2O, 2% ACN, 0.2% formic acid, and 0.005% TFA) and Buffer B (100% ACN, 0.2% formic acid, and 0.005% TFA). MS/MS data were acquired in a data-dependent manner in which the MS1 data was acquired for 250 ms at m/z of 400 to 1250 Da and the MS/MS data was acquired from m/z of 50 to 2,000 Da. For Independent data acquisition (IDA) parameters MS1-TOF 250 ms, followed by 50 MS2 events of 25 ms each. The IDA criteria, over 200 counts threshold, charge state +2-4 with 4s exclusion. Finally, the collected data were analyzed using Protein Pilot 4.0 (AB SCIEX) for peptide identifications and quantification.

Results:

The proteomics analysis of wheat inoculated with endophytic bacteria (SYM11, SYM16B and SYM57B) grown under heat stress and maize inoculated with SYM57B grown under normal condition revealed three major pathways augmented or otherwise modified by the endophyte: growth promotion, resistance against oxidative stress and mechanisms involved in symbiosis enhancement (Table 8 and Table 9).

TABLE 8

Proteins showing differential levels of expression under heat stress in endophyte-inoculated wheat (var. Briggs) seedlings relative to not-inoculated control seedlings.
UP-REGULATED PROTEINS IN RESPONSE TO ENDOPHYTIC BACTERIA

| Growth promotion | | | Ratio Treatment/Control | | |
|---|---|---|---|---|---|
| Accession number | Gene name | Pathway | SYM-00011 | SYM-00016B | SYM-00057B |
| gi\|474293349 | Acid beta-fructofuranosidase | mobilization of sucrose | 0.5-1Fold | 1-2Fold | 1-2Fold |
| gi\|473798701 | ATP synthase subunit beta, mitochondrial | ATP synthesis | 1-2Fold | 1-2Fold | |
| gi\|473945263 | Fructan 1-exohydrolase | mobilization of fructans | | | 1-2Fold |
| gi\|473798921 | Glutamine synthetase cytosolic isozyme 1-2 | Amino acid biosynthesis | | 1-2Fold | 1-2Fold |
| gi\|474427549 | Dynamin-related protein 1E | Cell division | 1-2Fold | 1-2Fold | 1-2Fold |
| gi\|474154210 | Histone H1 | Cell division | 1-2Fold | 1-2Fold | 1-2Fold |
| gi\|474396419 | Histone H1 | Cell division | | 1-2Fold | 1-2Fold |
| gi\|474315053 | Histone H2A | Cell division | 1-2Fold | 1-2Fold | >2Fold |
| gi\|474114390 | Histone H2A | Cell division | | | 1-2Fold |
| gi\|474408930 | Histone H2A.1 | Cell division | 1-2Fold | | >2Fold |
| gi\|474247555 | Protein H2A.7 | Cell division | 1-2Fold | 0.5-1Fold | |
| gi\|474400621 | Histone H4 | Cell division | 1-2Fold | | 1-2Fold |
| gi\|474160133 | Serine carboxypeptidase-like protein | Amino acid release | 1-2Fold | 1-2Fold | 1-2Fold |
| gi\|474397165 | Serine carboxypeptidase-like 51 | Amino acid release | >2Fold | 1-2Fold | |
| gi\|474449933 | Pectinesterase 1 | Cell wall remodeling | 1-2Fold | | >2Fold |
| gi\|474193958 | Peptidyl-prolyl cis-trans isomerase CYP40 | Juvenile phase of vegetative development | 1-2Fold | >2Fold | >2Fold |
| gi\|473956589 | Ribonucleoside-diphosphate reductase | DNA synthesis | 0.1-0.5Fold | 0.1-0.5Fold | >10Fold |
| gi\|474326915 | Villin-4 | Cell elongation | >2Fold | >10Fold | >2Fold |
| gi\|474156626 | Glutenin, low molecular weight subunit | Protein storage - affected by heat | 1-2Fold | 1-2Fold | |

| Resistance against abiotic stress | | | Ratio Treatment/Control | | |
|---|---|---|---|---|---|
| Accession number | Gene name | Function | SYM-00011 | SYM-00016B | SYM-00057B |
| gi\|474449933 | Pectinesterase 1 | Resistance to drought | 1-2Fold | | >2Fold |
| gi\|474381202 | Peroxiredoxin Q, chloroplastic | Resistance to oxidative stress | 0.5-1Fold | 0.5-1Fold | >2Fold |
| gi\|474299547 | Glutathione S-transferase DHAR3, chloroplastic | Resistance to oxidative stress | 1-2Fold | 1-2Fold | >2Fold |
| gi\|474276683 | Peroxidase 12 | Resistance to oxidative stress | 1-2Fold | 1-2Fold | 1-2Fold |
| gi\|474414579 | 3-hydroxybenzoate 6-hydroxylase 1 | Degradation of toxic organic compounds | 1-2Fold | >2Fold | 1-2Fold |
| gi\|474323467 | BAHD acyltransferase DCR | Cutin formation - dessication resistance | 1-2Fold | 1-2Fold | 0.1-0.5Fold |
| gi\|473999626 | 5'-methylthioadenosine/S-adenosylhomocysteine nucleosidase | Negative feedback on ethylene production | 0.5-1Fold | 0.5-1Fold | 0.5-1Fold |
| gi\|474326305 | Aldehyde dehydrogenase family 2 member C4 | Controls acetaldehyde accumulation | 0.5-1Fold | 0.5-1Fold | 0.5-1Fold |
| gi\|474041937 | putative protein phosphatase 2C 45 | Regulates ABA signaling | | 0.5-1Fold | |
| gi\|473894812 | DEAD-box ATP-dependent RNA helicase 40 ("DEAD" disclosed as SEQ ID NO: 1449) | mRNA decay and ribosome biogenesis | | 0.1-0.5Fold | |

| Symbiosis enhancement | | | Ratio Treatment/Control | | |
|---|---|---|---|---|---|
| Accession number | Gene name | Function | SYM-00011 | SYM-00016B | SYM-00057B |
| gi\|474407144 | Enolase 1 | Glycolisis of sugars required by endophyte | 0.5-1Fold | 0.5-1Fold | |
| gi\|474119301 | Protochlorophyllide reductase B, chloroplastic | Affected by symbiosis | | 0.5-1Fold | |
| gi\|474213532 | Elicitor-responsive protein 1 | Microbe response signaling | 0.5-1Fold | 0.5-1Fold | 1-2Fold |

TABLE 9

Proteins showing differential levels of expression under normal condition in endophyte-inoculated corn (40R73) seedlings relative to not-inoculated control seedlings.

| Growth promotion | | | |
|---|---|---|---|
| Accession number | Gene name | Pathway | SYM-00057B/control |
| gi\|413950290 | putative peptidyl-prolyl cis-trans isomerase | Organ development | >2-fold |
| gi\|414876902 | ATP-dependent Clp protease proteolytic subunit | Chloroplast component | >2-fold |
| gi\|413948820 | Translation elongation factor Tu isoformm 3 | Protein biosynthesis | 1-2 fold |
| gi\|414878150 | Chaperone protein dnaJ 15 | Positive gravitropism | <0.5-fold |
| gi\|413954599 | translation elongation/initiation factor | Embryo development ends seed dormancy | <0.5-fold |

| Resistance against abiotic stress | | | |
|---|---|---|---|
| Accession number | Gene name | Function | SYM-00057B/control |
| gi\|414867473 | Glutathione S-transferase GSTU6 | Resistance to oxidative stress | 1-2 fold |
| gi\|414876903 | Calmodulin2 | ABA-induced antioxidant defense | <0.5-fold |
| gi\|413920116 | Ras protein Rab-18 | ABA inducible, accumulates in cold stress | 0.5-1 fold |
| gi\|413926351 | DNA repair protein RAD23-1 isoform 3 | Nucleotide-excision repair | 0.5-1 fold |

| Symbiosis enhancement | | | |
|---|---|---|---|
| Accession number | Gene name | Function | SYM-00057B/control |
| gi\|413920282 | Hydroquinone glucosyltransferase | Upregulated in Rhizobia symbiosis | >10-fold |
| gi\|413939151 | replication factor C subunit 3 | Negative regulation of defense response | >10-fold |
| gi\|413946904 | NEDD8-activating enzyme E1 catalytic subunit | Protein neddylation - microbe response | >10-fold |
| gi\|413951445 | delta3,5-delta2,4-dienoyl-CoA isomerase | Peroxisome component - defense | >10-fold |
| gi\|413925737 | Proteasome subunit alpha type | Response to compatible symbiotic bacteria | >2-fold |
| gi\|413957021 | Ras protein RHN1 | Legume homolog involved in nodulation | >2-fold |
| gi\|414875813 | Early nodulin 20 | Root nodule formation | >2-fold |
| gi\|414886632 | Putative plant regulator RWP-RK family protein | Nodule inception protein | 1-2 fold |
| gi\|413955359 | putative metacaspase family protein | Programmed cell death regulation | 0.5-1 fold |
| gi\|413920552 | win1 | Defense response to bacteria and fungi | <0.5-fold |
| gi\|413948744 | protein brittle-1 | Response to nematodes | <0.5-fold |
| gi\|414869634 | Proteasome subunit beta type | Regulation of hypersensitive response | 0.5-1 fold |

Growth Promotion:

Proteins involved in the breakdown of seed stored reserves and playing important roles in the stimulation of continued growth during germination were up-regulated by endophytes. This class of proteins includes beta-fructofuranosidases, fructan 1-exohydrolases and carboxypeptidases involved in the mobilization of sucrose, fructans and insoluble proteins respectively, for the release of glucose, fructose and amino acids [Fincher (1989). Annu. Rev. Plant Physiol. Plant Mol. Biol. 40:305-46, incorporated herein by reference in its entirety]. Those results show that bacterial endophytes induce a faster release of nutrients from the seed, leading to augmented growth at early stage of plant development. The levels of proteins playing a role in cell proliferation and elongation were also increased in endophyte-inoculated seedlings. This class of proteins includes dynamins, histones, a ribonucleoside-diphosphate reductase, pectinesterases and villins, involved in cell division, chromatin structure, DNA synthesis, cell wall remodeling and elongation respectively [Hepler et al. (2001) Annu. Rev. Cell Dev. Biol. 2001. 17:159-87, Kang et al. (2003) The Plant Cell 15: 899-913, Imoto et al. (2005) Plant Mol. Biol. 58:177-192, incorporated herein by reference in their entirety). Those results demonstrate that, in response to the endophytic bacteria tested, the two types of plant growth, proliferation and elongation, are promoted, leading to substantial growth enhancement.

Resistance Against Stress:

A number of proteins involved in resistance against stress were significantly up-regulated in wheat under stress induction and the presence of endophytes. The level of several proteins playing a role in resistance against oxidative stress by scavenging reactive oxygen species was higher in inoculated plants including glutathione S-transferases (GST), peroxidase and ascorbate oxidase [Apel and Hirt (2004) Annu. Rev. Plant Biol. 55:373-99, incorporated herein by reference in its entirety]. Those results shows that in addition to plant growth, the endophytes tested promoted the general pathways involved in resistance against oxidative stress. The proteomics data-set also revealed the strong induction of a pectinesterase by SYM11 and SYM57B in wheat that might play a role in drought resistance as previously described (WO2013122473, incorporated herein by reference in its entirety).

Symbiosis Enhancement:

In corn under normal conditions, only GST was up-regulated, while other abscisic acid (ABA) and stress inducible proteins were down-regulated. The down-regulation of ABA and stress inducible proteins in corn was positively correlated with the down-regulation of proteins associated to programmed cell death, pathogen resistance and hypersensitive response. Moreover, the replication factor C, subunit 3 that negatively regulates plant defense was significantly overexpressed in the SYM57b inoculated corn seedlings. Those results are consistent with the conventional wisdom that, under normal condition, the establishment of symbioses with beneficial microbes involves decrease in the expression of genes associated to the plant defense system [Samac and Graham (2007) Plant Physiol. 144:582-587, incorporated herein by reference in its entirety].

In addition, several proteins directly associated with beneficial symbioses are up-regulated in the wheat and corn. It is intriguing that several of these proteins are homologous to proteins involved in nodule formation in legumes. Many genes involved in nodulation, such as nodulation receptor kinases are broadly distributed in the plant kingdom, even in plants incapable of forming nodules, as is the case of maize [Endre et al. (2002) Nature 417:962-966, incorporated herein by reference in its entirety]. Some of these conserved receptors may sense bacterial signals in symbiotic associations other than Legume-*Rhizobia* and this may explain why the nodulation factors from *Badyrhizobium japonicum* are able to enhance seed germination and root growth in corn [Suleimanov et al. (2002) J. Exp. Bot. 53:1929-1934, incorporated herein by reference in its entirety].

Example 8—Analysis of Hormone Levels in Inoculated Plants

As shown in some of the earlier examples, endophytic microbes described herein are capable of conferring significant beneficial traits on the inoculated agricultural plant. In order to explore the possibility that seed endosymbionts augment or modify hormone levels in planta, a metabolomic analysis was performed of 12 phytohormones (indole-3-carboxylic acid, trans-zeatin, abscisic acid, phaseic acid, indole-3-acetic acid, indole-3-butyric acid, indole-3-acrylic acid, jasmonic acid, jasmonic acid methyl ester, dihydrophaseic acid, gibberellin A3, salicylic acid) in wheat and corn plants grown on water agar under normal condition and inoculated by SYM57B or a mix of selected endophytes (see table below). The mixes of endophytes inoculums were obtained by mixing equal volume of the different bacterial cultures.

| Crop | Treatment |
|---|---|
| Wheat (Briggs) | R2A (mock control) |
| Wheat (Briggs) | SYM57B |
| Wheat (Briggs) | Mix (SYM11 + SYM17C + SYM49 + SYM57B) |
| Corn (40R73) | R2A (mock control) |
| Corn (40R73) | SYM57B |
| Corn (40R73) | Mix (SYM17C + SYM49 + SYM57B + SYM188) |

Samples Analyzed for Plant Hormone Profiling
Methods
Sample Preparation 4-day old whole wheat and corn seedlings (including roots, seed and hypocotyl) were finely ground in liquid nitrogen by mortar and pestle then aliquoted into 1.5 mL microcentrifuge tubes and weighed. Phytohormones were extracted from ground sprouts using a protein precipitation protocol where cold extraction solvent (80% aqueous methanol with 1% acetic acid) containing internal standards was added to the finely ground plant material (4004, solvent for every 100 mg ground plant tissue). Samples were kept on ice during the addition of extraction solvent. Samples were then vortexed for 60 min at medium-high speed at 4° C., then centrifuged for 15 min at 13,000 g at 4° C. The resultant supernatant was removed and analyzed by LC-MS/MS.
LC-MS/MS Phytohormones were chromatographically separated using a Waters nanoAcquity UPLC system on a Waters Atlantis dC18 column (3 µM, 300 µM×150 mm) held at 40° C. Samples were held at 4° C. in the auto-sampler. Water (buffer A) and acetonitrile (buffer B), both with 0.1% formic acid, were used as buffers. The flow rate was 11.5 µL/min and injection volume 1 µL. Each sample was injected twice and hormone levels averaged. Phytohormones were analyzed by selected reaction monitoring (SRM) on a Waters Xevo TQ-S mass spectrometer in both negative and positive ion modes. The UPLC gradient was as follows: time (t)=0 min, 10% B; t=0.5 min, 10% B; t=5.5 min, 95% B; t=7.5 min, 95% B; t=8 min, 10% B. The column was equilibrated for three minutes before each injection.
Results Inoculation of wheat and corn with seed-origin endophytes significantly altered the level of several plant hormones, including indole-3-carboxylic acid, trans-zeatin, abscisic acid, phaseic acid and indole-3-acetic acid. In addition, the combination of multiple seed endosymbionts further modified the plant hormone profiling of inoculated plants. In particular, the level of abscisic acid and indole-3-carboxylic acid, the decarboxylated form of auxin, was augmented by 63% and 98% respectively in corn inoculated with the mixed endophytes.

Example 9—Field Trial Planting & Assessment of Plant Health Under Stress

Planting & Setup of Field Trials in Normal and Stressed Conditions

To determine whether a microbe or combination of microbes is capable of promoting plant growth in the field, a field trial was conducted using representative endophytic microbes described herein. The trial involved testing individual microbial strains and combinations of strains by treating and planting the seeds of a variety of plants (including, but not limited to maize, wheat, cotton, and barley), with one or two varieties or cultivars of each plant tested. A typical trial was laid out as a randomized complete block design, with each combination microbial treatment and plant variety replicated six times in the trial.

Trials were conducted across various geographies including field sites in major producing regions of South Dakota, Nebraska, Saskatchewan and Austria, on both dry and irrigated land to test responses in both well-watered and drought-stressed conditions. Trials may also be conducted in geographies with hotter growing seasons, where temperatures can reach up to 95° F. for five or more consecutive days, in order to assess responses under heat stress. Trials may also be conducted in geographies prone to higher levels of microbial, nematode or insect pathogens in order to assess responses under pathogen stress Fertilizer and herbicides are applied according to soil test results and locally recommended practice. Fertilizer may be applied at 25%, 50% or 75% of recommended levels to assess responses under nutrient stress.

For maize, typical field plots were 10'×'40' with 4 evenly spaced rows, seeded at a rate of approximately 34,000 seeds per acre. Each randomized complete block trial included an untreated control and a mock-formulation control, as well as additional untreated border plots on the 40' ends. For wheat, typical field plots were 5'×50' with 7 evenly spaced rows, seeded at a rate of approximately 90 lbs per acre. Each randomized complete block trial included an untreated control and a mock-formulation control.

Measurement of Biomass

Biomass of field plots is assessed by selecting 10 plants per plot for maize or 20 plants per plot for wheat at random from the middle two rows at harvest, removing the plants from the soil and cleaning off any residual soil. Plants are then divided into aerial and root sections and weighed to obtain fresh weight. Plants are then be dried in a vacuum oven overnight and weighed again to obtain dry weight.

Measurement of Yield, Grain Moisture, Test Weight

Yield of field plots is measured at the end of the growing season by harvesting the plots with an appropriate harvester. For maize, only the middle two rows are harvested. For wheat, all 7 rows may be harvested, or only the middle 5 may be used. Test weight and moisture of the grain may be recorded by the harvester, or subsamples of the harvested grain may be used for manual test weight assessment and moisture analysis in a DICKEY-John® grain moisture analyzer (Dickey-John Corp., Chatham, Ill.), using parameters recommended by the manufacturer.

Measurement of Emergence & Plant Height

Emergence in the field plots was assessed for wheat by counting the number of emerged plants in the middle 10' section of the middle two rows and reporting the total number plants emerged. Emergence counts were done every four days starting with the day of emergence of the first plants and ending when 50% or more of the plants in the plot had reached Feekes scale 2. Emergence in the field was assessed for maize by doing a full count of all emerged plants in the plot and reporting the number of emerged plants as a percentage of the number of seeds planted in that plot. Two emergence counts were done, one at the emergence of the first plants and a second count five days later.

Figure 8:
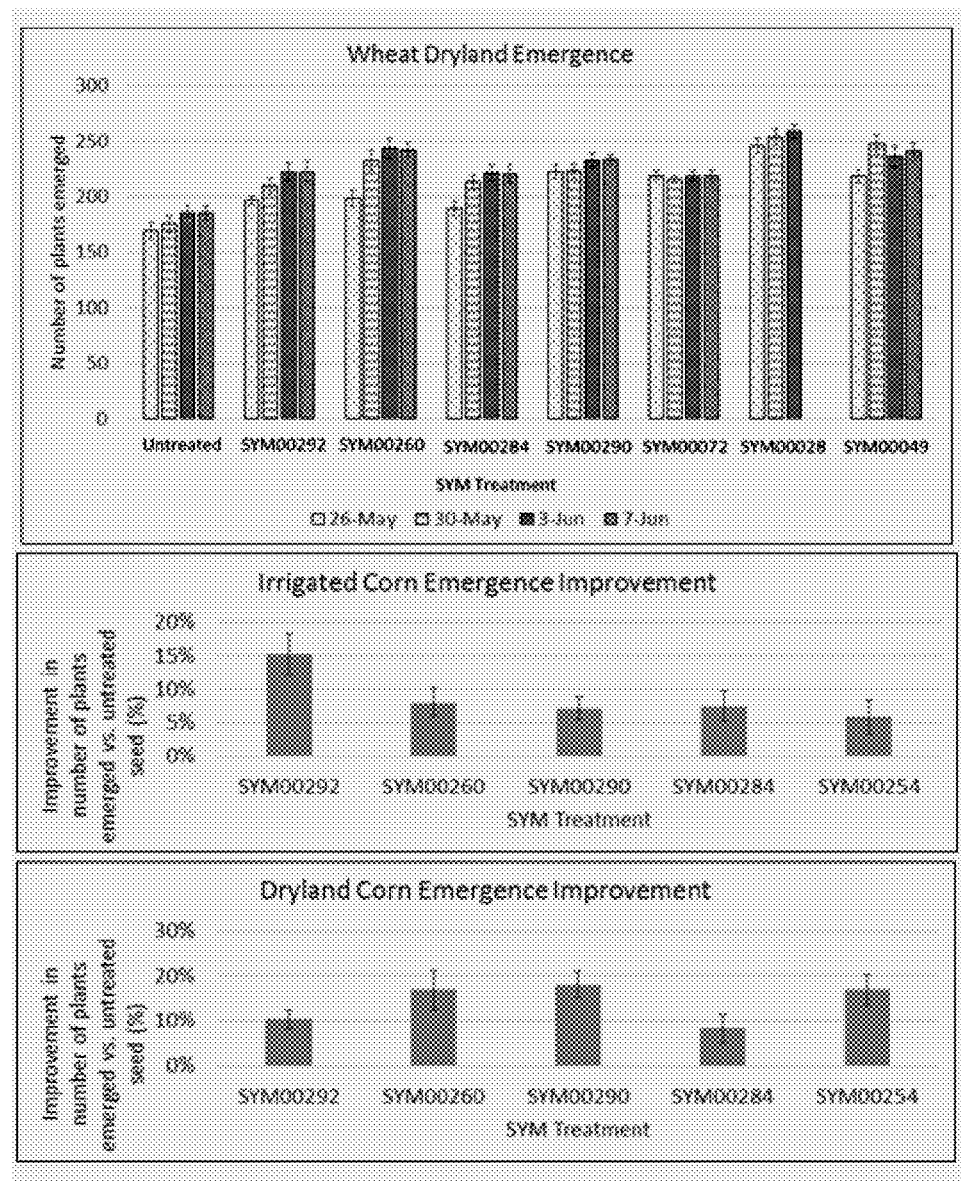
FIG. 8 contains three graphs depicting the field testing of seed-origin microbes for benefits to cereal crop emergence. Top panel: Number of wheat plants emerging in the middle 10' section of the middle 2 rows of each test plot. Numbers reported are an average of counts of 6 replicate plots for each treatment. All SYM strains show improvement in emergence over the untreated control. Middle panel: Improvement in the number of corn plants emerging in the dryland test plots over the untreated control. Emergence numbers were calculated as an average of counts of 6 replicate plots for each treatment. All SYM strains show improvement in emergence over the untreated control, with SYM00260, SYM00290 and SYM00254 all showing improvements greater than 15%. Bottom panel: Improvement in the number of corn plants emerged in the irrigated test plots over the untreated control. Emergence numbers were calculated as an average of counts of 6 replicate plots for each treatment. All SYM strains show improvement in emergence over the untreated control, with SYM00292 showing an improvement of 15%.

Emergence of wheat in a field trial on four different days is shown in the top panel of FIG. 8. The numbers reported are an average of emergence counts of 6 replicate plots for each treatment. All SYM strains show improvement in emergence over the untreated control, with SYM00028 showing the greatest improvement.

Emergence of corn in a field trial is shown in the middle panel of FIG. 8 (for a dryland trial) and in the bottom panel FIG. 8 (for an irrigated trial). The numbers are reported as a percent increase over an untreated control and were calculated as an average of emergence counts of 6 replicate plots for each treatment. All SYM strains show improvement in emergence over the untreated control. SYM00260, SYM00290 and SYM00254 showed the best performance in the dryland trial, and SYM00292 showed the best performance in the irrigated trial.

Measurement of Flowering Time

The day of flowering for a particular plot is recorded when 50% or more of the plants in the plot have reached the flowering stage.

SPAD Measurement

Chlorophyll values, for example, SPAD readings are conducted on wheat by measuring 10 plants per plot at random from the middle two rows. The first measurement is done at flowering, with a second measurement done two weeks later on the same 10 plants in each plot. The SPAD reading is taken on the flag leaf on each plant, for example, as measured with SPAD502 supplied by Minolta Co., Ltd., at approximately three quarters of the leaf length from the leaf base and avoiding the midrib of the leaf. SPAD readings are conducted on maize by measuring 10 plants per plot at random from the middle two rows. The first measurement is done at flowering (VT stage), with a second measurement done two weeks later on the same 10 plants in each plot. The SPAD reading is taken on the topmost leaf under the tassel, approximately 0.5 inch from the edge of the leaf and three quarters of the leaf length from the leaf base.

Stand Count & Lodging Assessment

Stand count and percent lodging are assessed in wheat by counting the total number of tillers and the number of broken stalks in the middle two rows on the day of harvest. Stand count and percent lodging are assessed in maize by counting the number of standing plants and the number of stalks broken below the ear in the middle two rows on the day of harvest.

Sterilization of Seed Surfaces from Microorganisms Using Disinfecting Chemicals

Example Description

In order to isolate and characterize endophytic microorganisms, all microorganisms living on the surface of the plant, plant tissue, or plant structure must be removed. After a pre-wash to remove all loosely attached microorganisms, the surfaces are sterilized with disinfecting chemicals, and the plant tissue is tested for sterility.

Experimental Description Surface sterilization of seeds is performed as described by Bacon and Hinton, "Isolation, In Planta Detection, and Uses of Endophytic Bacteria for Plant Protection", Chapter in *Manual of Environmental Microbiology*, 3rd Edition (2007): 638-647, with some modifications. Briefly, batches of seeds are first given a prewash to remove as many of the surface bacteria as possible by vigorously washing them in sterile 0.05M phosphate buffer (pH 7.2). If the seeds have been treated with pesticides, the prewash buffer contains 0.01% Tween 20 or 0.05% Triton X-100, and is followed by 3-5 washes in 75-90% ethanol. They then are allowed to imbibe in 1× sterile phosphate-buffered saline (PBS) at 4° C. for 24 h (or different times depending on the seed variety). After imbibing, they are surface sterilized by immersion in 70% ethanol for 5 min, 10% bleach solution for 3-15 minutes (depending on seed), and rinsed twice with autoclaved distilled water. Alternatively, samples can be surface-sterilized by using 1% chloramine for 3 minutes followed by 70% ethanol for 5 minute and rinsed twice with sterile distilled water. Alternatively, seeds can be sterilized by submerging them in 10% hydrogen peroxide for 5 min-1 hour and then rinsed twice with sterile distilled water. Samples are blotted dry using autoclaved paper towels. Once sterilized, a few seeds of each batch are aseptically imprinted onto Tryptic Soy Agar (TSA) and Potato Dextrose agar (PDA) in a Petri dish using sterile forceps: one of the sides of the seed is pressed first, then the seed is turned onto its other side on another part of the plate, and then removed. These plates are stored in the dark for five days and checked daily for bacterial and/or fungal growth. If the batch of seeds proves to retain microbes, the whole batch is destroyed and the experiment re-started with new seeds.

Other plant tissues are surface-sterilized and tested for sterility essentially as described for seeds, with some modifications:

1. Leaves: Leaves are detached and pre-washed as described for seeds. Then they are placed in 1% chloramine for 30 minutes, or in full strength commercial bleach for 5 minutes, and washed twice in 3-5 times in distilled sterile water for 3 minutes. Samples are blotted dry using autoclaved paper towels. 5 grams of leaf tissue are then transferred to a sterile blender and processed as described for seeds with 50 mL of R2A broth.

2. Roots: Roots are removed from the plants and pre-washed twice as described for seeds to remove all attached soil. Roots are surface-sterilized in 1% chloramine solution for up to 30 minutes (or alternatively 10% bleach) and washed 3-5 times in distilled sterile water for 3 minutes. The roots are then immersed for 30 minutes in sterile 0.05 M phosphate buffer (pH 7.2) and then rinsed several times. 5 g of root tissue are then transferred to an sterile blender and processed as described for seeds with 50 mL of R2A broth.

3. Stems: A portion of the plant stem is cut from the plant pre-washed as described for seeds. It is then surface sterilized as described for the roots and washed twice in distilled sterile water for 3 minutes. 5 g from the inside of the stem are removed by cutting the outside layer with a sterile blade and processed as described for seeds.

Sterilization of Seed or Plant Surface from Bacteria Using Antibiotic Agents

Seeds are surface sterilized with antibacterial compounds such as sodium hypochlorite, copper oxychloride, copper hydroxide, copper sulfate, chlorothalonil, cuprous oxide, streptomycin, copper ammonium carbonate, copper diammonia diacetate complex, copper octanoate, oxytetracycline, fosetyl-AL or chloropicrin. Seed is soaked in an aqueous solution or commercial formulation containing one or more of these compounds for 30 seconds to 12 hours in a plastic container. The solution may also be administered to seedlings or plants by spraying or soaking leaves or other aerial parts of the plant, after which the plant tissues are sprayed or rinsed with water to remove residual fungicide. After surface sterilization, the seed is removed from the antibacterial formulation and washed 3-5 times with sterile distilled water.

Sterilization of Seed or Plant Surface from Fungi Using Fungicidal Agents

Seeds are surface sterilized by use of contact fungicides such as captan, maneb, thiram, fludioxonil, and others. Seed is soaked in an aqueous solution or commercial formulation containing one or more of these compounds for 30 seconds to 12 hours in a plastic container. After surface sterilization, the seed is removed from the fungicide solution and washed 3-5 times with sterile distilled water. The solution of fungicides may also be administered to seedlings or plants by spraying or soaking leaves or other aerial parts of the plant, after which the plant tissues are sprayed or rinsed with water to remove residual fungicide. Systemic fungicides such as azoxystrobin, carboxin, mefenoxam, metalaxyl, thiabendazole, trifloxystrobin, difenoconazole, ipconazole, tebuconazole or triticonazole may also be used only when it is desirable to also sterilize interior tissues.

Isolation of Bacteria and Fungi from the Interior of Seeds

Example Description

Isolation of fungi and bacteria (including endophytes) from the interior of surface-sterilized seeds is done using techniques known in the art. Surface sterilized seeds are ground, diluted in liquid media, and this suspension is used to inoculate solid media plates. These are incubated under different conditions at room temperature.

Experiment Description

Approximately fifty surface-sterilized seeds are transferred aseptically to a sterile blender and ground. The ground seeds are resuspended in 50 mL of sterile R2A broth, and incubated for 4 h at room temperature. Ten 1 mL aliquots of the seed homogenates are collected and centrifuged, their supernatants discarded and the pellets gently resuspended in 1 mL of sterile 0.05 phosphate buffer; 0.5 mL of 50% glycerol is added to each of five tubes. These are stored at −80C for possible further characterization (i.e. if the plates become too overcrowded with one microorganism, the frozen aliquots can be used to plate lower dilutions of the homogenate). The remaining aliquots are diluted down twice in hundred-fold dilutions to $10^{-4}$. 100 microliters of the 1, $10^{-2}$, and $10^{-4}$ dilutions are used to inoculate three Petri dishes containing the following media in order to isolate of bacteria and/or fungi:

1. Tryptic Soy agar
2. R2A agar
3. Potato dextrose agar
4. Sabouraud Agar
5. Other media depending on target microorganism The plates are divided into three sets comprising each media type and incubated in different environments. The first set is incubated aerobically, the second under anaerobic conditions, and the third under microaerophilic conditions and all are inspected daily for up to 5 days. 1-2 individual colonies per morphotype are isolated and streaked for purity onto fresh plates of the same media/environment from which the microorganism was isolated. Plates are incubated at room temperature for 2-5 days. Once an isolate grows it is streaked once more for purity onto a fresh plate of the same media to ensure purity and incubated under the same environmental conditions.

From the second streaked plate, isolates are stored in Tryptic soy broth +15% glycerol at −80° C. for further characterization, by first scraping 2-3 colonies (about 10 μL) from the plate into a cryogenic tube containing 1.5 mL of the above-mentioned media and gently resuspending the cells. Alternatively, isolates are propagated in specialized media as recommended for the particular taxon of microorganism. The microbes obtained represent those that live in the seeds of the plant accession.

Isolation of Bacteria and Fungi from Plant Interior Tissues

Example Description

Isolation of fungi and bacteria (including endophytes) from surface-sterilized plant tissues is done using techniques known in the art. Surface sterilized plant tissues are ground, diluted in liquid media, and then this suspension is used to inoculate solid media plates. These are incubated under different environmental conditions at room temperature.

Experiment Description

Approximately fifty grams of surface-sterilized plant tissue are transferred aseptically to a sterile blender and ground. The ground tissue is resuspended in 50 mL of sterile R2A broth, and incubated for 4 h at room temperature. Ten 1 mL aliquots of the plant tissue homogenates are collected and centrifuged, their supernatants discarded and the pellets gently resuspended in 1 mL of sterile 0.05 phosphate buffer. 0.5 mL of 50% Glycerol is added to each of five tubes. These are stored at −80° C. for possible further characterization (i.e. if the plates become too overcrowded with one microorganism, the frozen aliquots can be used to plate lower dilutions of the homogenate). The remaining aliquots are diluted down twice in hundred-fold dilutions to $10^{-4}$. One hundred microliters of the 1, $10^{-2}$, and $10^{-4}$ dilutions are used to inoculate three Petri dishes containing the following media in order to isolate of bacteria and/or fungi:

1. Tryptic Soy agar
2. R2A agar
3. Potato dextrose agar
4. Sabouraud Agar
5. Other media depending on target microorganism Plates are divided into three sets comprising each media type and incubated in different environments. The first set is incubated aerobically, the second under anaerobic conditions, and the third under microaerophilic conditions and all are inspected daily for up to 5 days. 1-2 individual colonies per morphotype are isolated and streaked for purity onto fresh plates of the same media/environment from which the microorganism was isolated. Plates are incubated at room temperature for 2-5 days. Once an isolate grows it is streaked once more for purity onto a fresh plate of the same media to ensure purity and incubated under the same environmental conditions.

From the second streaked plate, isolates are stored in Tryptic soy broth +15% glycerol at −80° C. for further characterization, by first scraping 2-3 colonies (about 10 μL) from the plate into a cryogenic tube containing 1.5 mL of the above-mentioned media and gently resuspending the cells. Alternatively, isolates are propagated in specialized media as recommended for the particular taxon of microorganism. The catalog of microbes thus isolated constitutes a good representation of the microbes found in the growing plant tissues.

Isolation of Bacteria and Fungi from Plant or Seed Surfaces

To collect phyllosphere, rhizosphere, or spermosphere material for culturing of microbes, unwashed shoot, roots or seeds are shaken free/cleaned of any attached soil and stuffed into sterile 50 mL Falcon tubes. To these, 10 mL of sterile 0.1 M sodium phosphate buffer is added and shaken, followed by 5 minutes of sonication to dislodge microbes from plant surfaces, with the resulting cloudy or muddy wash collected in a separate 15 mL Falcon tube. 100 μL of this microbe filled wash can be directly spread onto agar plates or nutrient broth for culturing and enrichment, or it can be further diluted with sterile 0.1 M sodium phosphate buffer by 10×, 100×, 1,000×, 10,000× and even 100,000×, before microbial culturing on agar plates or nutrient broth.

Glycerol stock preparations of the plant surface wash solution should be made at this point by mixing 1 mL of the soil wash solution and 0.5 mL of sterile, 80% glycerol, flash freezing the preparation in a cryotube dipped in liquid nitrogen, and storing at −80° C. Nutrient broth inoculated with a mixture of plant surface bacteria should form a stable, mixed community of microbes which can be used in plant inoculation experiments described herein, subcultured in subsequent broth incubations, or spread on agar plates and separated into individual colonies which can be tested via methods described herein.

Characterization of Fungal and Bacterial Isolates

Example Description

Characterization of fungi and bacteria isolated from surface-sterilized or non-sterilized plant or seed tissues is done using techniques known in the art. These techniques take advantage of differential staining of microorganisms, morphological characteristics of cells, spores, or colonies, biochemical reactions that provide differential characterization, and DNA amplification and sequencing of diagnostic regions of genes, among other methods.

Experimental Description

Isolates of bacteria and/or fungi isolated as described herein (including endophytic bacteria and fungi) are categorized into three types: bacterial isolates, fungal isolates, and unknown isolates (since yeast colonies can resemble bacterial colonies in some cases) based on colony morphology, formation of visible mycelia, and/or formation of spores. To determine if an unknown isolate is bacterial or fungal, microscopic analysis of the isolates is performed. Some of the analyses known to the art to differentiate microorganisms include the 10% KOH test, positive staining with Lactophenol cotton blue, Gram staining, and growth on media with selective agents. The distinguishing features observed by these tests are relative cell size (yeast size is much larger than bacterial size), formation of hyphae and spores (filamentous bacteria form smaller hyphae than fungi, and do not form structures containing spores), or growth under selection agents (most bacteria can grow in the presence of antifungal compounds like nystatin, while most fungi cannot; likewise, most fungi are unaffected by the presence of broad-spectrum antibiotics like chloramphenicol and spectinomycin).

To identify the isolates, DNA sequence analysis of conserved genomic regions like the ribosomal DNA loci is performed. To obtain DNA to perform PCR amplifications, some cellular growth from solid media (approximately 5-10 μL) is resuspended in 30 μL of sterile Tris/EDTA buffer (pH 8.0). Samples are heated to 98° C. for 10 minutes followed by cooling down to 4° C. for 1 minute in a thermocycler. This cycle is repeated twice. Samples are then centrifuged at ~13,000 RCF for 1-5 minutes and used as DNA template for PCR reactions. Below is a series of primer combinations that can be used to identify isolates to a genus level.

| Primer 1 | Primer 2 | Target |
|---|---|---|
| V4_515F (5'-GTGCCAGCMGC CGCGGTAA- 3') (SEQ ID NO: 1450) | V4_806R (5'-GGACTACHVGGG TWTCTAAT-3') (SEQ ID NO: 1451) | The $4^{th}$ Variable region of the bacterial 16S rDNA (Caporaso, J. Gregory, et al. *The ISME journal* 6.8 (2012): 1621-1624.) |
| 27F (5'-AGAGTTTGATCC TGGCTCAG-3') (SEQ ID NO: 1452) | 1492R (5'-GGTTACCTTGTT ACGACTT-3') (SEQ ID NO: 1453) | Full length of the bacterial 16S rDNA, from position 8-1507. |

| Primer 1 | Primer 2 | Target |
|---|---|---|
| ITS1 (5'-TCCGTAGGTGAACCTGCGG- 3') (SEQ ID NO: 1454) | ITS2 (5' - GCTGCGTTCTTCATCGATGC- 3') (SEQ ID NO.: 1455) | ~240 bp ITS1 region of fungal genome |
| SR1R (5' - TACCTGGTTGATTCTGCCAGT- 3') (SEQ ID NO: 1456) | SR6 (5' - TGTTACGACTTTTACTT- 3')(SEQ ID NO: 1457) | Small subunit (18s) of the fungal rDNA gene |
| ITS1F (5'-CTTGGTCATTTAGAGGAAGTAA- 3')(SEQ ID NO: 1458) | ITS4 (5'-TCCTCCGCTTATTGATATGC-3')(SEQ ID NO: 1459) | ~600-1000 bp ITS region of fungal genomes (J Microbiol Methods. 2007 October; 71(1): 7-14. Epub 2007 Jul. 5. |

To decrease background noise due to the non-specific binding of primers to DNA, the thermocycler is programmed for a touchdown-PCR, which increases specificity of the reaction at higher temperatures and increases the efficiency towards the end by lowering the annealing temperature. Below is an example of the conditions for a typical Touchdown PCR.

| Step # | Cycle | Temperature | Time |
|---|---|---|---|
| 1 | Initial Denaturalization | 98° C.* | 5 m |
| 2 | Denaturalization | 98° C.* | 30 s |
| 3 | Annealing | Predicted optimal Tm for the primer set +10° C., minus 1° C./cycle | 30 s |
| 4 | Elongation | 72° C.* | 1 m/1 Kb |
| 5 | GoTo Step 2 × 10 times | | |
| 6 | Denaturalization | 98° C.* | 30 s |
| 7 | Annealing | Predicted optimal Tm for the primer set | 30 s |
| 8 | Elongation | 72° C.* | 1 m/1 Kb |
| 9 | GoTo Step 6 × 20 times | | |
| 10 | Final Elongation | 72° C.* | 5 m |
| 11 | Cool Down | 4° C. | 5 m |

*Or the temperature specified by the DNA polymerase manufacturer for this step.

PCR reactions are purified to remove primers, dNTPs, and other components by methods known in the art, for example by the use of commercially available PCR clean-up kits, or 3M sodium acetate and chilled absolute ethanol as described below:
  1. For each 20 µL of PCR product, the following mixture is prepared and maintained cool in a 1.5 mL Tube.
  2 µL of 3M sodium acetate (NaOAc) pH 4.5
  40 µL chilled absolute ethanol.
  2. Transfer the PCR product (20 µl) into the tube containing the mixture.
  3. Vortex the tube and then store it at −20 for 30-50 min.
  4. Spin for 30 min at maximum speed 14.000 rpm.
  5. Remove the supernatant carefully without disturbing the pellet. (Do not touch the bottom of the tube)
  6. Wash the pellet with 100 µl of chilled 70% ethanol and centrifuge at ~13,000RCF for 5 min.
  7. Remove the supernatant and then dry the pellet using a vacuum centrifuge or by leaving the tube open in a biosafety hood.
  8. Resuspend the pellet in 30 µL in sterile water.

DNA amplicons are sequenced using methods known in the art, for example Sanger sequencing (Johnston-Monje D, Rairada M N (2011) PLoS ONE 6(6): e20396) using one of the two primers used for amplification.

The resulting sequences are aligned as query sequences with the publicly available databases GenBank nucleotide, RDP (Wang, Q, G. M. Garrity, J. M. Tiedje, and J. R. Cole. 2007. Appl Environ Microbiol. 73 (16):5261-7.), UNITE (Abarenkov, Nilsson et al. New Phytologist 2010; Volume 186: 281-285.) and PlutoF (Evol Bioinform Online. 2010; 6: 189-196.). RDP is specifically compiled and used for bacterial 16s classification. UNITE and PlutoF are specifically compiled and used for identification of fungi. In all the cases, the strains are identified to species level if their sequences are more than 95% similar to any identified accession from all databases analyzed (Zimmerman, Naupaka B., and Peter M Vitousek. 109.32 (2012): 13022-13027.). When the similarity percentage is between 90-97%, the strain is classified at genus, family, order, class, subdivision or phylum level depending on the information displayed in databases used. Isolates with lower similarity values (from 30-90%) are classified as unknown or uncultured depending on the information displayed after BLAST analysis. To support the molecular identification, fungal taxa are confirmed by inducing sporulation on PDA or V8 agar plates and using reported morphological criteria for identification of fruiting bodies structure and shape (Ainsworth, G. Geoffrey Clough. *Ainsworth and Bisby's Dictionary of the Fungi*. CABI, 2008). Bacterial taxa are confirmed by using reported morphological criteria in specialized differential media for the particular taxon, or by biochemical differentiation tests, as described by the Bergey's Manual of Systematic Microbiology (Whitman, William B., et al., eds. Bergey's Manual® of systematic bacteriology. Vols. 1-5. Springer, 2012).

Culture-Independent Characterization of Fungal and Bacterial Communities in Seeds or Plants Example Description To understand the diversity of culturable and unculturable microbial (bacterial and fungal) taxa that reside inside of seeds or plants of agriculturally-relevant cultivars, landraces, and ancestral wild varieties, microbial DNA is extracted from surface sterilized seed or plant parts, followed by amplification of conserved genomic regions like the ribosomal DNA loci. Amplified DNA represents a "snapshot" of the full microbial community inside seeds or plants.

Experimental Description

To obtain microbial DNA from seeds, plants or plant parts, the seeds, plants or plant parts are surface sterilized under aseptic conditions as described herein. Microbial DNA from seeds, plants, or plant parts is extracted using methods known in the art, for example using commercially available Seed-DNA or plant DNA extraction kits, or the following method.

1. A sample of each kind of seed or plant tissue is placed in a cold-resistant container and 10-50 mL of liquid nitrogen is applied. The seeds or plant tissues are then macerated to a powder.
2. Genomic DNA is extracted from each seed or plant tissue preparation, following a chloroform:isoamyl alcohol 24:1 protocol (Sambrook et al. 1989).

Fungal-specific primers are used to amplify the ITS (Internal Transcribed Spacer) region of nuclear ribosomal DNA (Schoch. Conrad L., et al. *Proceedings of the National Academy of Sciences* 109.16 (2012): 6241-6246.). Bacterial specific primers are used to amplify region of the 16s rDNA gene of the bacterial genome (Caporaso, J. Gregory, et al. The ISME journal 6.8 (2012): 1621-1624.). Sequences obtained through NGS platforms are analyzed against databases, such as the ones mentioned herein.

Some of the primer pairs used for this analysis are detailed below:

| Primer 1 | Primer 2 | Target |
|---|---|---|
| V4_515F (see above) | V4_806R (see above) | The 4$^{th}$ Variable region of the bacterial 16S rDNA |
| 27F (see above) | 1492R (see above) | Full length of the bacterial 16S rDNA, from position 8-1507. |
| ITS1 (see above) | ITS2 (see above) | ~240 bp ITS1 region of fungal genome |
| SR1R (see above) | SR6 (see above) | Small subunit (18s) of the fungal rDNA gene |
| ITS1F (5'-CTTGGTCATTTAGAGGAAGTAA-3')(SEQ ID NO: 1458) | ITS4 (5'-TCCTCCGCTTATTGATATGC-3')(SEQ ID NO: 1459) | ~600-1000 bp ITS region of fungal genomes (J Microbiol Methods. 2007 October; 71(1): 7-14. Epub 2007 Jul. 5. |
| ITS5 (Universal)(5'-GGAAGTAAAAGTCGTAACAAGG-3')(SEQ ID NO: 1460) | ITS4Asco (Ascomycota-specific): 5' CGTTACTRRGGCAATCCCTGTTG3' (SEQ ID NO: 1461) or ITS4Basidio (Basidiomycota-specific): 5' GCRCGGAARACGCTTCTC 3' (SEQ ID NO: 1462); or ITS4Chytrid (Chytridiomycota-specific): 5' TTTTCCCGTTTCATTCGCCA 3' (SEQ ID NO: 1463); or ITS4Oo (Oomycota-specific): 5' ATAGACTACAATTCGCC 3' (SEQ ID NO: 1464); or ITS4Zygo (Zygomycota-specific): 5' AAAACGTWTCTTCAAA 3' (SEQ ID NO: 1465). | ~500 bp fragment from different fungal Phyla depending on primer combination used. Liliya G. Nikolcheva, Felix Bärlocher Mycological Progress 01/2004; 3(1):41-49. |
| SSUmAf - (equimolar mix of 2 degenerate primers) and SSUmCf equimolar mix of 3 degenerate primers) | LSUmAr (equimolar mix of 4 degenerate primers) and LSUmBr (equimolar mix of 5 degenerate primers) | 1000-1600 bp fragment of the Glomerycota (albuscular mycorrhizae) genome comprising partial SSU, whole internal transcribed spacer (ITS) rDNA region and partial LSU. Manuela Krüger, Herbert, Claudia Krüger and Arthur Schüßler. (2009) DNA-based species level detection of Glomeromycota: one PCR primer set for all arbuscular mycorrhizal fungi. New Phytol. 183(1): 212-23. |
| Arch 340F (5'-CCCTAYGGGGYGCASCAG-3')(SEQ ID NO: 1466) | Arch 1000R (5'-GAGARGWRGTGCATGGCC-3')(SEQ ID NO: 1467) | ~660 bp product of the 18S from Archaea (Gantner, S., et al. (2011). Journal of microbiological methods, 84(1), 12-18.) |
| 27F-Degen (5'-AGRRTTYGATYMTGGYTYAG-3')(SEQ ID NO: 1468) and 799f(5'-AACMGGATTAGATACCCKG-3')(SEQ ID NO: 1470) | 27F-Degen (5'-HGGHTACCTTGTTACGACTT-3')(SEQ ID NO: 1469) | Full length of the bacterial 16S rDNA, from position 8-1507. Johnston-Monje D, Raizada MN (2011) PLoS ONE 6(6): e20396. |

As an alternative to next generation sequencing, Terminal Restricition Fragment Length Polymorphism, (TRFLP) can be performed, essentially as described in Johnston-Monje, D. and Raizada et al [PLoS ONE 6(6): e20396 (2011)]. Group specific, fluorescently labeled primers are used to amplify diagnostic regions of genes in the microbial population. This fluorescently labeled PCR product is cut by a restriction enzyme chosen for heterogeneous distribution in the PCR product population. The enzyme cut mixture of fluorescently labeled and unlabeled DNA fragments is then submitted for sequence analysis on a Sanger sequence platform such as the Applied Biosystems 3730 DNA Analyzer.

Determination of the Plant Pathogenic Potential of Microbial Isolates

Since a microbe which confers positive traits to one cultivar might be a pathogenic agent in a different plant species, a general assay is used to determine the pathogenic potential of the isolates. Surface and interior-sterilized seeds are germinated in water agar, and once the plant develops its first set of leaves, are inoculated with the isolate. Alternatively, the plants are inoculated as seeds. For inoculation the microbial isolate is grown on solid media, and inoculated into a plant or onto a seed via any of the methods described herein. Plants are allowed to grow under ideal conditions for 2-3 weeks and any pathogenic effect of the introduced microbe is evaluated against uninoculated control plants.

Testing for Microbial Traits In Vitro

Examples below are adapted from: Johnston-Monje D, Raizada M N (2011) PLoS ONE 6(6): e20396, which is incorporated herein by reference in its entirety.

Assay for Growth on Nitrogen Free LGI Media.

All glassware is cleaned with 6 M HCl before media preparation. A new 96 deep-well plate (2 mL well volume) is filled with 1 mL/well of sterile LGI broth [per L, 50 g Sucrose, 0.01 g $FeCl_3$-$6H_2O$, 0.8 g $K_3PO_4$, 0.2 g $MgSO_4$-$7H_2O$, 0.002 g $Na_2MoO_4$-$2H_2O$, pH 7.5]. Bacteria are inoculated with a flame-sterilized 96 pin replicator. The plate is sealed with a breathable membrane, incubated at 25° C. with gentle shaking for 5 days, and OD600 readings taken.

ACC Deaminase Activity Assay.

Microbes are assayed for growth with ACC as their sole source of nitrogen. Prior to media preparation all glassware is cleaned with 6 M HCl. A 2 M filter sterilized solution of ACC (#1373A, Research Organics, USA) is prepared in water. 1 μl/mL of this is added to autoclaved LGI broth (see above), and 1 mL aliquots are placed in a new 96 well plate. The plate is sealed with a breathable membrane, incubated at 25° C. with gentle shaking for 5 days, and OD600 readings taken. Only wells that are significantly more turbid than their corresponding nitrogen free LGI wells are considered to display ACC deaminase activity.

Mineral Phosphate Solubilization Assay.

Microbes are plated on tricalcium phosphate media. This is prepared as follows: 10 g/L glucose, 0.373 g/L $NH_4NO_3$, 0.41 g/L $MgSO_4$, 0.295 g/L NaCl, 0.003 $FeCl_3$, 0.7 g/L $Ca_3HPO_4$ and 20 g/L Agar, pH 6, then autoclaved and poured into 150 mm plates. After 3 days of growth at 25° C. in darkness, clear halos are measured around colonies able to solubilize the tricalcium phosphate.

RNAse Activity Assay.

1.5 g of torula yeast RNA (#R6625, Sigma) is dissolved in 1 mL of 0.1 M $Na_2HPO_4$ at pH 8, filter sterilized and added to 250 mL of autoclaved R2A agar media which is poured into 150 mm plates. The bacteria from a glycerol stock plate are inoculated using a flame-sterilized 96 pin replicator, and incubated at 25° C. for 3 days. On day three, plates are flooded with 70% perchloric acid (#311421, Sigma) for 15 minutes and scored for clear halo production around colonies.

Acetoin and Diacetyl Production Assay.

1 mL of autoclaved R2A broth supplemented with 0.5% glucose is aliquoted into a 96 deep well plate (#07-200-700, Fisher). The bacteria from a glycerol stock plate are inoculated using a flame-sterilized 96 pin replicator, sealed with a breathable membrane, then incubated for 5 days with shaking (200 rpm) at 25° C. At day 5, 100 μl aliquots of culture are removed and placed into a 96 well white fluorometer plate, along with 100 μl/well of Barritt's Reagents A and B which are prepared by mixing 5 g/L creatine mixed 3:1 (v/v) with freshly prepared alpha-naphthol (75 g/L in 2.5 M sodium hydroxide). After 15 minutes, plates are scored for red or pink colouration against a copper coloured negative control.

Auxin Production Assay.

R2A agar media, supplemented with L-tryptophan to a final concentration of 5 mM, is autoclaved and poured into 150 mm plates. Using a 96 pin plate replicator, all microbes are inoculated onto the fresh plate from a 96 well plate glycerol stock. The plate is incubated at 25° C. for 3 days, then overlaid with a nitrocellulose membrane, and put in a fridge at 4° C. overnight, allowing bacteria and their metabolites to infiltrate into the paper. The next day, the nitrocellulose membrane is removed and placed for 30 min on Whatman #2 filter papers saturated with Salkowski reagent (0.01 M ferric chloride in 35% perchloric acid, #311421, Sigma). Dark pink halos around colonies are visualized in the membrane by background illumination using a light table.

Siderophore Production Assay.

To ensure no contaminating iron is carried over from previous experiments, all glassware is deferrated with 6 M HCl and water prior to media preparation. In this cleaned glassware, R2A agar media, which is iron limited, is prepared and poured into 150 mm Petri dishes and inoculated with bacteria using a 96 pin plate replicator. After 3 days of incubation at 25° C., plates are overlaid with O-CAS overlay. Again using the cleaned glassware, 1 liter of O-CAS overlay is made by mixing 60.5 mg of Chrome azurol S (CAS), 72.9 mg of hexadecyltrimethyl ammonium bromide (HDTMA), 30.24 g of finely crushed Piperazine-1,4-bis-2-ethanesulfonic acid (PIPES) with 10 mL of 1 mM $FeCl_3.6H_2O$ in 10 mM HCl solvent. The PIPES had to be finely powdered and mixed gently with stirring (not shaking) to avoid producing bubbles, until a dark blue colour is achieved. Melted 1% agarose is then added to pre-warmed O-CAS just prior pouring the overlay in a proportion of 1:3 (v/v). After 15 minutes, colour change is scored by looking for purple halos (catechol type siderophores) or orange colonies (hydroxamate siderophores).

Pectinase Activity Assay.

Adapting a previous protocol 0.2% (w/v) of citrus pectin (#76280, Sigma) and 0.1% triton X-100 are added to R2A media, autoclaved and poured into 150 mm plates. Bacteria are inoculated using a 96 pin plate replicator. After 3 days of culturing in the darkness at 25° C., pectinase activity is visualized by flooding the plate with Gram's iodine. Positive colonies are surrounded by clear halos.

Cellulase Activity Assay.

Adapting a previous protocol, 0.2% carboxymethylcellulose (CMC) sodium salt (#C5678, Sigma) and 0.1% triton X-100 are added to R2A media, autoclaved and poured into 150 mm plates. Bacteria are inoculated using a 96 pin plate replicator. After 3 days of culturing in the darkness at 25° C., cellulose activity is visualized by flooding the plate with Gram's iodine. Positive colonies are surrounded by clear halos.

Antibiosis Assay.

Bacteria are inoculated using a 96 pin plate replicator onto 150 mm Petri dishes containing R2A agar, then grown for 3 days at 25° C. At this time, colonies of either $E.$ $coli$ DH5α (gram negative tester), $Bacillus$ $subtillus$ ssp. $Subtilis$ (gram positive tester), or yeast strain AH109 (fungal tester) are resuspended in 1 mL of 50 mM $Na_2HPO_4$ buffer to an $OD_{600}$ of 0.2, and 30 µl of this is mixed with 30 mL of warm LB agar. This is quickly poured completely over a microbe array plate, allowed to solidify and incubated at 37° C. for 16 hours. Antibiosis is scored by looking for clear halos around microbial colonies.

Generating/Isolating Endophytes Compatible with Agrochemicals

The application of pesticides against fungal pathogens of agriculturally-relevant plants is a common practice in agriculture to ensure higher yields. One method of pesticide delivery is to cover the seeds with a coating with pesticides. Although pesticides are meant to deter the growth and propagation of pathogenic microorganisms, they may also affect endophyte populations residing inside of the seed. For this purpose, conferring compatibility mechanisms to endophytic fungi providing beneficial properties which are sensitive to these compounds is desirable for the maintenance of endophytes in the seeds.

Compatibility with pesticides can be intrinsic (naturally pesticide compatible fungi, for example) or acquired (due to mutations in the genetic material of the microorganism, or to the introduction of exogenous DNA by natural DNA transfer).

Fungicides used as protectants are effective only on the seed surface, providing protection against seed surface-borne pathogens and providing some level of control of soil-borne pathogens. These products generally have a relatively short residual. Protectant fungicides such as captan, maneb, thiram, or fludioxonil help control many types of soil-borne pathogens, except root rotting organisms. Systemic fungicides are absorbed into the emerging seedling and inhibit or kill susceptible fungi inside host plant tissues. Systemic fungicides used for seed treatment include the following: azoxystrobin, carboxin, mefenoxam, metalaxyl, thiabendazole, trifloxystrobin, and various triazole fungicides, including difenoconazole, ipconazole, tebuconazole, and triticonazole. Mefenoxam and metalaxyl are primarily used to target the oomycetes such as species of $Pythium$ and $Phytophthora$.

Strobilurin analogues, such as azoxystrobin, inhibit mitochondrial respiration by blocking electron transfer at the cytochrome bc1 complex. Phenylamides, including metalaxyl, interfere with RNA synthesis in target fungi. Oxathiin systemic fungicides like carboxin inhibits the incorporation of phenylalanine into protein and of uracil into RNA. Azole fungicides BAS 480F, flusilazole, and tebuconazole are inhibitors of sterol 14α-demethylase, and block sterol biosynthesis.

Determination of Intrinsic Resilience Against Agrochemicals of Bacteria Cultured from Seeds To test the intrinsic resilience pesticides of bacteria isolated as described herein, minimum inhibitory concentration (MIC) assays are performed on all isolated bacteria of interest, as described in Wiegand, Irith, Kai Hilpert, and Robert E W Hancock. Nature protocols 3.2 (2008): 163-175, which is incorporated herein by reference in its entirety. Briefly, known concentrations of bacterial cells or spores are used to inoculate plates containing solid media with different concentrations of the pesticide, or to inoculate liquid media containing different concentrations of the pesticide (in a 96-well plate). The pesticides are used at the concentration recommended by the manufacturer for seed coating, and two-fold dilutions down to 0.000125 (12 two-fold dilutions). Growth is assessed after incubation for a defined period of time (16-20 h) and compared to cultures grown in the same manner without any pesticides as control. The MIC value is determined as described in Wiegand, Irith, Kai Hilpert, and Robert E W Hancock. Nature protocols 3.2 (2008): 163-175.

Determination of Intrinsic Resilience Against Agrochemicals of Fungi Cultured from Seeds To test the intrinsic resilience against pesticides of the fungi isolated as described in this application, minimum inhibitory concentration (MIC) assays are performed on all isolated fungi of interest, as described in Mohiddin, F. A., and M. R. Khan. African Journal of Agricultural Research 8.43 (2013): 5331-5334 (incorporated herein by reference in its entirety), with the following changes: Briefly, double strength potato dextrose agar is prepared containing different concentrations of each pesticide. The pesticides are applied at the concentration recommended by the manufacturer, and also in two fold dilutions to 0.000125× (12 two-fold dilutions). Thereafter, the plates are seeded centrally with a 3 mm disc of 4 days old culture of each fungus that had been centrifuged and rinsed twice in sterile phosphate buffer. PDA plates without a fungicide but inoculated with the fungi serve as a control. The inoculated plates are incubated at 25±2° C. for 5 days. The radial growth of the colony in each treatment is measured and the percent inhibition of growth is calculated as described by Mohiddin, F. A., and M. R. Khan. African Journal of Agricultural Research 8.43 (2013): 5331-5334 (incorporated herein by reference in its entirety). Fungal isolates are classified as resilience against the particular pesticide if their maximum tolerance concentration (MTC) is 2× or above the concentration of pesticides recommended to be used in seed coatings.-

Generating Fungal Species with Compatibility with Commercial Pesticides Coated onto Seeds When a fungal strain of interest that provides a beneficial property to its plant host is found to be sensitive to a commercially-relevant pesticide, pesticide-compatible variants of the strains need to be generated for use in this application. Generation of compatibility to multiple pesticides or cocktails of pesticides is accomplished by sequentially selecting compatible variants to each individual pesticide and then confirming compatibility with a combination of the pesticides. After each round of selection, fungi are tested for their ability to form symbiotic relationships with the plants and to confirm that they provide a beneficial property on the plant as did the parental strain, with or without application of the pesticide product as described herein.

Generation and isolation of pesticide-compatible strains derived from endophytic strains isolated from seeds and shown to provide beneficiary traits to plants is performed as described by Shapiro-Ilan, David I., et al. Journal of invertebrate pathology 81.2 (2002): 86-93 (incorporated herein by reference in its entirety), with some changes. Briefly, spores of the isolated fungi are collected and solutions containing between ~$1\times10^3$ spores are used to inoculate potato dextrose agar (PDA) plates containing 2, 5, and 10 times the MTC of the particular strain. Plates are incubated for 1-5 days and a single colony from the highest concentration of pesticide which allows growth is inoculated onto a fresh plate with the same pesticide concentration 7 consecutive times. After compatibility has been established, the strain is inoculated onto PDA plates 3 consecutive times and then inoculated onto a PDA plate containing the pesticide to confirm that the compatibility trait is permanent.

Alternatively, if this method fails to provide a compatible strain, a spore suspension is treated with ethyl methanesulfonate to generate random mutants, similarly as described by Leonard, Cory A., Stacy D. Brown, and J. Russell Hayman. International journal of microbiology 2013 (2013), Article ID 901697 (incorporated herein by reference in its entirety) and spores from this culture are used in the experiment detailed above.

To develop fungal endophytes compatible with multiple pesticides or cocktails of pesticides, spores of a strain compatible with one or more pesticides are used to select for variants to a new pesticide as described above. Strains developed this way are tested for retention of the pesticide-compatibility traits by inoculating these strains onto PDA plates containing each single pesticide or combinations of pesticides.

Generating Bacterial Species with Compatibility to Commercial Pesticides Coated onto Seeds When a bacterial strain of interest is found to be sensitive to a commercially-relevant pesticide, generation of pesticide-compatible variants of the strains can be generated for use in this application. Generation of compatible with multiple pesticides or cocktails of pesticides is accomplished by first sequentially selecting variants compatible with incrementally higher concentrations of each individual pesticide (as described by Thomas, Louise, et al. Journal of Hospital Infection 46.4 (2000): 297-303, which is incorporated herein by reference in its entirety). To develop bacterial endophytes compatible with multiple pesticides or cocktails of pesticides, bacterial cells of a strain compatible with one or more pesticides is used to select for variants to a new pesticide as described above. Strains developed this way are tested for retention of the pesticide-compatible traits by inoculating these strains onto PDA plates containing each single pesticide or combinations of pesticides.

After each round of selection, bacteria are tested for their ability to live within plants and for their ability to provide the same beneficial property to the plant as did the parental strain, with or without application of the pesticide product to the plants as described herein.

Generation of Pesticide-Compatible Bacteria by Insertion of a Resistance Plasmid Many bacterial plasmids that confer compatible pesticides have been described in the literature (Don, R. H., and J. M. Pemberton. Journal of Bacteriology 145.2 (1981): 681-686; and Fisher, P. R., J. Appleton, and J. M. Pemberton. *Journal of bacteriology* 135.3 (1978): 798-804, each of which is incorporated herein by reference in its entirety)

For cases in which obtaining naturally occurring compatible bacteria is not feasible, use of these plasmids is a possible way to develop endophytic strains compatible with multiple pesticides.

For example, a *Pseudomonas fluorescens* strain that provides anti-nematode properties to plants but is sensitive to the pesticides 2,4-dichlorophenoxyacetic acid and 4-chloro-2-methylphenoxyacetic can be transformed with the plasmid pJP2 (isolated from *Alcaligenes eutrophus*) which provides transmissible compatible with these compounds, as described by Don and Pemberton, 1981. Briefly, plasmids are transferred by conjugation to *Pseudomonas*, using the method described in Haas, Dieter, and Bruce W. Holloway. Molecular and General Genetics 144.3 (1976): 243-251 (incorporated herein by reference in its entirety).

After the generation of bacteria carrying pesticide-compatibility conferring plasmids, these endophytes are tested for their ability to live inside plant tissues and for their ability to provide the same beneficial property to the plant as it did for the parental strain, with or without application of the pesticide product to the plants as described herein.

Growth & Scale-Up of Bacteria for Inoculation on Solid Media

The bacterial isolates are grown by loop-inoculation of a single colony into R2A broth (supplemented with appropriate antibiotics) in 100 mL flasks. The bacterial culture is incubated at 30±2° C. for 2 days at 180 rpm in a shaking incubator (or under varying temperatures and shaking speeds as appropriate). This liquid suspension is then used to inoculate heat sterilized vermiculite powder which is premixed with sterile R2A broth (without antibiotics), resulting in a soil like mixture of particles and liquid. This microbial powder is then incubated for an additional couple of days at 30±2° C. with daily handshaking to aerate the moist powder and allow bacterial growth. Microbially inoculated vermiculite powder is now ready for spreading on to soil or onto plant parts. Alternatively, the R2A broth is used to inoculate Petri dishes containing R2A or another appropriate nutrient agar where lawns of bacteria are grown under standard conditions and the solid colonies scraped off, resuspended in liquid and applied to plants as desired.

Growth & Scale-Up of Fungi for Inoculation on Solid Media Once a fungal isolate has been characterized, conditions are optimized for growth in the lab and scaled-up to provide sufficient material for assays. For example, the medium used to isolate the fungus is supplemented with nutrients, vitamins, co-factors, plant-extracts, and other supplements that can decrease the time required to grow the fungal isolate or increase the yield of mycelia and/or spores the fungal isolate produces. These supplements can be found in the literature or through screening of different known media additives that promote the growth of all fungi or of the particular fungal taxa.

To scale up the growth of fungal isolates, isolates are grown from a frozen stock on several Petri dishes containing media that promotes the growth of the particular fungal isolate and the plates are incubated under optimal environmental conditions (temperature, atmosphere, light). After mycelia and spore development, the fungal growth is scraped and resuspended in 0.05M Phosphate buffer (pH 7.2, 10 mL/plate). Disposable polystyrene Bioassay dishes (500 $cm^2$, Thermo Scientific Nunc UX-01929-00) are prepared with 225 mL of autoclaved media with any required supplements added to the media, and allowed to solidify. Plates are stored at room temperature for 2-5 days prior to inoculation to confirm sterility. 5 mL of the fungal suspension is spread over the surface of the agar in the Bioassay plate in a biosafety cabinet, plates are allowed to dry for 1 h, and they are then incubated for 2-5 days, or until mycelia and/or spores have developed.

A liquid fungal suspension is then created via the following. Fungal growth on the surface of the agar in the Bioassay plates are then scraped and resuspended in 0.05M Phosphate buffer (pH 7.2). OD600 readings are taken using a spectrometer and correlated to previously established OD600/CFU counts to estimate fungal population densities, and the volume adjusted with additional sodium phosphate buffer to result in 100 mL aliquots of fungi at a density of approximately $10^6$-$10^{11}$ spores/mL. This suspension may or may not be filtered to remove mycelia and can be used to create a liquid microbial formulation as described herein to apply the fungal isolate onto a plant, plant part, or seed.

Growth & Scale-Up of Bacteria for Inoculation in Liquid Media

Bacterial strains are grown by loop-inoculation of one single colony into R2A broth (amended with the appropriate antibiotics) in 100 L flasks. The bacterial culture is incubated at 30±2° C. for 2 days at 180 rpm in a shaking incubator (or under varying temperatures and shaking speeds as appropriate). The bacteria are pelleted by centrifugation and resuspended in sterile 0.1 M sodium phosphate. $OD_{600}$ readings are taken using a spectrometer and correlated to previously established $OD_{600}$/CFU counts to estimate bacterial population densities, and the volume adjusted with additional sodium phosphate buffer to result in 100 mL aliquots of bacteria at a density of $1\times10^8$ cells/mL. To help break surface tension, aid bacterial entry into plants and provide microbes for some energy for growth, 10 μL of Silwet L-77 surfactant and 1 g of sucrose is added to each 100 mL aliquot (resulting in 0.01% v/v and 1% v/v concentrations, respectively) in a similar way as in the protocol for *Agrobacterium*-mediated genetic transformation of *Arabidopsis thaliana* seed [Clough, S., Bent, A. (1999) The Plant Journal 16(6): 735-743].

Growth & Scale-Up of Fungi for Inoculation in Liquid Media

Once a fungal isolate has been characterized, conditions are optimized for growth in the lab and scaled-up to provide enough material for assays. For example, the medium used to isolate the fungi is supplemented with nutrients, vitamins, co-factors, plant-extracts, and/or other supplements that can decrease the time required to grow the fungal isolate and/or increase the yield of mycelia and/or spores the fungal isolate produces. These supplements can be found in the literature or through screening of different known media additives that promote the growth of all fungi or of the particular fungal taxa.

To scale up the growth of fungal isolates, isolates are grown from a frozen stock on Petri dishes containing media that promotes the growth of the particular fungal isolate and the plates are incubated under optimal environmental conditions (temperature, atmosphere, light). After mycelia and spore development, the fungal growth is scraped and resuspended in 0.05M Phosphate buffer (pH 7.2, 10 mL/plate). 1 liter of liquid media selected to grow the fungal culture is prepared in 2 L glass flasks and autoclaved and any required supplements added to the media. These are stored at room temperature for 2-5 days prior to inoculation to confirm sterility. 1 mL of the fungal suspension is added aseptically to the media flask, which is then incubated for 2-5 days, or until growth in the liquid media has reached saturation. $OD_{600}$ readings are taken using a spectrometer and correlated to previously established $OD_{600}$/CFU counts to estimate fungal population densities, and the volume adjusted with additional sodium phosphate buffer to result in 100 mL aliquots of fungi at a density of approximately $10^6$-$10^{11}$ spores/mL. This suspension may or may not be filtered to remove mycelia and can be used to create a liquid microbial formulation as described herein to apply the fungal isolate onto a plant, plant part, or seed.

Creation of Liquid Microbial Formulations or Preparations for the Application of Microbes to Plants Bacterial or fungal cells are cultured in liquid nutrient broth medium to between $10^2$-$10^{12}$ CFU/mL. The cells are separated from the medium and suspended in another liquid medium if desired. The microbial formulation may contain one or more bacterial or fungal strains. The resulting formulation contains living cells, lyophilized cells, or spores of the bacterial or fungal strains. The formulation may also contain water, nutrients, polymers and binding agents, surfactants or polysaccharides such as gums, carboxymethylcellulose and polyalcohol derivatives. Suitable carriers and adjuvants can be solid or liquid and include natural or regenerated mineral substances, solvents, dispersants, wetting agents, tackifiers, thickeners, binders or fertilizers. Compositions can take the form of aqueous solutions, oil-in-water emulsions, or water-in-oil emulsions. Small amounts of insoluble material can optionally be present, for example in suspension in the medium, but it is generally preferred to minimize the presence of such insoluble material.

Inoculation of Plants by Coating Microbes Directly onto Seed

Seed is treated by coating it with a liquid microbial formulation (prepared as described herein) comprising microbial cells and other formulation components, directly onto the seed surface at the rate of $10^2$-$10^8$ microbial CFU per seed. Seeds are soaked in liquid microbial formulation for 1, 2, 3, 5, 10, 12, 18 or 24 hours or 2, 3, or 5 days. After soaking in microbial formulation, seeds are planted in growing containers or in an outdoor field. Seeds may also be coated with liquid microbial formulation by using an auger or a commercial batch treater. One or more microbial formulations or other seed treatments are applied concurrently or in sequence. Treatment is applied to the seeds using a variety of conventional treatment techniques and machines, such as fluidized bed techniques, augers, the roller mill method, rotostatic seed treaters, and drum coaters. Other methods, such as spouted beds may also be useful. The seeds are pre-sized before coating. Optionally the microbial formulation is combined with an amount of insecticide, herbicide, fungicide, bactericide, or plant growth regulator, or plant micro- or macro-nutrient prior to or during the coating process. After coating, the seeds are typically dried and then transferred to a sizing machine for grading before planting. Following inoculation, colonization of the plants or seeds produced therefrom is confirmed via any of the various methods described herein. Growth promotion or stress resilience benefits to the plant are tested via any of the plant growth testing methods described herein.

Inoculation of Plants with a Combination of Two or More Microbes

Seeds can be coated with bacterial or fungal endophytes. This method describes the coating of seeds with two or more bacterial or fungal strains. The concept presented here involves simultaneous seed coating of two microbes (e.g., both a gram negative endophytic bacterium *Burkholderia phytofirmans* and a gram positive endophytic bacterium *Bacillus mojavensis*). Optionally, both microbes are genetically transformed by stable chromosomal integration as follows. *Bacillus mojavensis* are transformed with a construct with a constitutive promoter driving expression of a synthetic operon of GFPuv and spectinomycin resistance genes, while *Burkholderia phytofirmans* are transformed with a construct with a constitutive promoter driving expression of the lac operon with an appended spectinomycin resistance gene. Seeds are coated with a prepared liquid formulation of the two microbes the various methods described herein. Various concentrations of each endophyte in the formulation is applied, from $10^2$/seed to about $10^8$/seed. Following inoculation, colonization of the plants or seeds produced therefrom may be confirmed via any of the various methods described herein. Growth promotion or stress resilience benefits to the plant are tested via any of the plant growth testing methods described herein.

Culturing to Confirm Colonization of Plant by Bacteria

The presence in the seeds or plants of GFPuv or gusA-labeled endophytes can be detected by colony counts from mashed seed material and germinated seedling tissue using R2A plates amended with 5-Bromo-4-chloro-3-indolyl β-D-glucuronide (X-glcA, 50 μg/mL), IPTG (50 μg/mL) and the antibiotic spectinomycin (100 μg/mL). Alternatively, bacterial or fungal endophytes not having received transgenes can also be detected by isolating microbes from plant, plant tissue or seed homogenates (optionally surface-sterilized) on antibiotic free media and identified visually by colony morphotype and molecular methods described herein. Representative colony morphotypes are also used in colony PCR and sequencing for isolate identification via ribosomal gene sequence analysis as described herein. These trials are repeated twice per experiment, with 5 biological samples per treatment.

Culture-Independent Methods to Confirm Colonization of the Plant or Seeds by Bacteria or Fungi Example Description One way to detect the presence of endophytes on or within plants or seeds is to use quantitative PCR (qPCR). Internal colonization by the endophyte can be demonstrated by using surface-sterilized plant tissue (including seed) to extract total DNA, and isolate-specific fluorescent MGB probes and amplification primers are used in a qPCR reaction. An increase in the product targeted by the reporter probe at each PCR cycle therefore causes a proportional increase in fluorescence due to the breakdown of the probe and release of the reporter. Fluorescence is measured by a quantitative PCR instrument and compared to a standard curve to estimate the number of fungal or bacterial cells within the plant.

Experimental Description

The design of both species-specific amplification primers, and isolate-specific fluorescent probes are well known in the art. Plant tissues (seeds, stems, leaves, flowers, etc.) are pre-rinsed and surface sterilized using the methods described herein.

Total DNA is extracted using methods known in the art, for example using commercially available Plant-DNA extraction kits, or the following method.

1. Tissue is placed in a cold-resistant container and 10-50 mL of liquid nitrogen is applied. Tissues are then macerated to a powder.
2. Genomic DNA is extracted from each tissue preparation, following a chloroform:isoamyl alcohol 24:1 protocol (Sambrook, Joseph, Edward F. Fritsch, and Thomas Maniatis. *Molecular cloning*. Vol. 2. New York: Cold spring harbor laboratory press, 1989.).

Quantitative PCR is performed essentially as described by Gao, Zhan, et al. *Journal of clinical microbiology* 48.10 (2010): 3575-3581 with primers and probe(s) specific to the desired isolate using a quantitative PCR instrument, and a standard curve is constructed by using serial dilutions of cloned PCR products corresponding to the specie-specific PCR amplicon produced by the amplification primers. Data are analyzed using instructions from the quantitative PCR instrument's manufacturer software.

As an alternative to qPCR, Terminal Restriction Fragment Length Polymorphism, (TRFLP) can be performed, essentially as described in Johnston-Monje D, Raizada M N (2011) PLoS ONE 6(6): e20396. Group specific, fluorescently labelled primers are used to amplify a subset of the microbial population, especially bacteria, especially fungi, especially archaea, especially viruses. This fluorescently labelled PCR product is cut by a restriction enzyme chosen for heterogeneous distribution in the PCR product population. The enzyme cut mixture of fluorescently labelled and unlabeled DNA fragments is then submitted for sequence analysis on a Sanger sequence platform such as the Applied Biosystems 3730 DNA Analyzer.

Immunological Methods to Detect Microbes in Seeds and Vegetative Tissues

A polyclonal antibody is raised against specific bacteria X or fungus Y strains via standard methods. A polyclonal antibody is also raised against specific GUS and GFP proteins via standard methods. Enzyme-linked immunosorbent assay (ELISA) and immunogold labeling is also conducted via standard methods, briefly outlined below.

Immunofluorescence microscopy procedures involve the use of semi-thin sections of seed or seedling or adult plant tissues transferred to glass objective slides and incubated with blocking buffer (20 mM Tris (hydroxymethyl)-aminomethane hydrochloride (TBS) plus 2% bovine serum albumin, pH 7.4) for 30 min at room temperature. Sections are first coated for 30 min with a solution of primary antibodies and then with a solution of secondary antibodies (goat anti-rabbit antibodies) coupled with fluorescein isothiocyanate (FITC) for 30 min at room temperature. Samples are then kept in the dark to eliminate breakdown of the light-sensitive FITC. After two 5-min washings with sterile potassium phosphate buffer (PB) (pH 7.0) and one with double-distilled water, sections are sealed with mounting buffer (100 mL 0.1 M sodium phosphate buffer (pH 7.6) plus 50 mL double-distilled glycerine) and observed under a light microscope equipped with ultraviolet light and a FITC Texas-red filter.

Ultrathin (50- to 70-nm) sections for TEM microscopy are collected on pioloform-coated nickel grids and are labeled with 15-nm gold-labeled goat anti-rabbit antibody. After being washed, the slides are incubated for 1 h in a 1:50 dilution of 5-nm gold-labeled goat anti-rabbit antibody in IGL buffer. The gold labeling is then visualized for light microscopy using a BioCell silver enhancement kit. Toluidine blue (0.01%) is used to lightly counterstain the gold-labeled sections. In parallel with the sections used for immunogold silver enhancement, serial sections are collected on uncoated slides and stained with 1% toluidine blue. The sections for light microscopy are viewed under an optical microscope, and the ultrathin sections are viewed by TEM.

Characterization of Uniformity of Endophytes in a Population of Seeds

To test for the homogeneity of endophytes either on the surface or colonizing the interior tissues in a population of seeds, seeds are tested for the presence of the microbes by culture-dependent and/or—independent methods. Seeds are obtained, surface sterilized and pulverized, and the seed homogenate is divided and used to inoculate culture media or to extract DNA and perform quantitative PCR. The homogeneity of colonization in a population of seeds is assessed through detection of specific microbial strains via these methods and comparison of the culture-dependent and culture-independent results across the population of seeds. Homogeneity of colonization for a strain of interest is rated based on the total number of seeds in a population that contain a detectable level of the strain, on the uniformity across the population of the number of cells or CFU of the strain present in the seed, or based on the absence or presence of other microbial strains in the seed.

Experimental Description

Surface sterilized seeds are obtained as described herein. For culture-dependent methods of microbial-presence confirmation, bacterial and fungi are obtained from seeds essentially as described herein with the following modification. Seed homogenate is used to inoculate media containing selective and/or differential additives that will allow to identification of a particular microbe.

For qPCR, total DNA of each seed is extracted using methods known in the art, as described herein.

Characterization of Homogeneity of Colonization in Population of Plants

To test for the homogeneity of microorganisms (including endophytes) colonizing the interior in a population of plants, tissues from each plant are tested for the presence of the microbes by culture-dependent and/or—independent methods. Tissues are obtained, surface sterilized and pulverized, and the tissue material is divided and used to inoculate culture media or to extract DNA and perform quantitative PCR. The homogeneity of colonization in a population of plants is assessed through detection of specific microbial strains via these methods and comparison of the culture-dependent and culture-independent results across the population of plants or their tissues. Homogeneity of colonization for a strain of interest is rated based on the total number of plants in a population that contain a detectable level of the strain, on the uniformity across the population of the number of cells or CFU of the strain present in the plant tissue, or based on the absence or presence of other microbial strains in the plant.

Experimental Description

Surface sterilized plant tissues are obtained as described herein. For culture-dependent methods of microbial-presence confirmation, bacterial and fungi are obtained from plant tissues essentially as described herein with the following modification. Plant tissue homogenate is used to inoculate media containing selective and/or differential additives that will allow identification of a particular microbe.

For qPCR, total DNA of each plant tissue is extracted using methods known in the art, as described herein.

Testing for Beneficial and Inhibitory Effects of Endophytes

Testing for Germination Enhancement in Normal Conditions

Standard Germination Tests are used to assess the ability of the endophyte to enhance the seeds' germination and early growth. Briefly, 400 seeds which are coated with the endophyte as described elsewhere are placed in between wet brown paper towels (8 replicates with 50 seeds each). An equal number of seeds obtained from control plants that do not contain the microbe is treated in the same way. The paper towels are placed on top of 1×2 feet plastic trays and maintained in a growth chamber set at 25° C. and 70% humidity for 7 days. The proportion of seeds that germinate successfully is compared between the seeds coming from microbe-colonized plants with those coming from controls.

Testing for Germination Enhancement Under Biotic Stress

A modification of the method developed by Hodgson [Am. Potato. J. 38: 259-264 (1961)] is used to test germination enhancement in microbe-colonized seeds under biotic stress. Biotic stress is understood as a concentration of inocula in the form of cell (bacteria) or spore suspensions (fungus) of a known pathogen for a particular crop (e.g., *Pantoea stewartii* or *Fusarium graminearum* for *Zea mays* L.). Briefly, for each level of biotic stress, 400 seeds, the interiors of which are colonized by microbial strains, and 400 seed controls (lacking the microbial strains), are placed in between brown paper towels: 8 replicates with 50 seeds each for each treatment (microbe-colonized and control). Each one of the replicates is placed inside a large petri dish (150 mm in diameter). The towels are then soaked with 10 mL of pathogen cell or spore suspension at a concentration of $10^4$ to $10^8$ cells/spores per mL. Each level corresponds with an order of magnitude increment in concentration (thus, 5 levels). The petri dishes are maintained in a growth chamber set at 25° C. and 70% humidity for 7 days. The proportion of seeds that germinate successfully is compared between the seeds coming from microbe-colonized plants with those coming from controls for each level of biotic stress.

Testing for Germination Enhancement Under Drought Stress

Polyethylene glycol (PEG) is an inert, water-binding polymer with a non-ionic and virtually impermeable long chain [Couper and Eley, J. Polymer Sci., 3: 345-349 (1984)] that accurately mimics drought stress under dry-soil conditions. The higher the concentration of PEG, the lower the water potential achieved, thus inducing higher water stress in a watery medium. To determine germination enhancement in seeds, the interiors of which are colonized by microbial strains, the effect of osmotic potential on germination is tested at a range of water potential representative of drought conditions following Perez-Fernandez et al. [J. Environ. Biol. 27: 669-685 (2006)]. The range of water potentials simulates those that are known to cause drought stress in a range of cultivars and wild plants, (−0.05 MPa to −5 MPa) [Craine et al., Nature Climate Change 3: 63-67 (2013)]. The appropriate concentration of polyethylene glycol (6000) required to achieve a particular water potential is determined following Michel and Kaufmann (Plant Physiol., 51: 914-916 (1973)) and further modifications by Hardegree and Emmerich (Plant Physiol., 92, 462-466 (1990)). The final equation used to determine amounts of PEG is: $\psi=0.130$ $[PEG]^2 T-13.7 [PEG]^2$; where the osmotic potential ($\psi$) is a function of temperature (T). Germination experiments are conducted in 90 mm diameter petri dishes. Replicates consist of a Petri dish, watered with 10 mL of the appropriate solution and 20 seeds floating in the solution. 400 seeds, the interiors of which are colonized by microbial strains are tested, in addition to 400 seed controls (lacking the microbial strains), totaling 40 petri dishes. To prevent large variations in $\psi$, dishes are sealed with parafilm and the PEG solutions are renewed weekly by pouring out the existing PEG in the petri dish and adding the same amount of fresh solution. Petri dishes are maintained in a growth chamber set at 25° C., 16:8 hour light:dark cycle, 70% humidity, and least 120 µE/m²/s light intensity. The proportion of seeds that germinate successfully after two weeks is compared between the seeds coming from inoculated plants and those coming from controls.

Testing for Germination Enhancement in Heat Conditions

Standard Germination Tests are used to determine if a microbe colonizing the interior of a seed protects maize against heat stress during germination. Briefly, 400 seeds, the interiors of which are colonized by microbial strains are placed in between wet brown paper towels (8 replicates with 50 seeds each). An equal number of seeds obtained from control plants that lack the microbe is treated in the same way. The paper towels are placed on top of 1×2 ft plastic trays and maintained in a growth chamber set at 16:8 hour light:dark cycle, 70% humidity, and at least 120 µE/m2/s light intensity for 7 days. A range of high temperatures (from 35° C. to 45° C., with increments of 2 degrees per assay) is tested to assess the germination of microbe-colonized seeds at each temperature. The proportion of seeds that germinate successfully is compared between the seeds coming from microbe-colonized plants and those coming from controls.

Testing for Germination Enhancement in Cold Conditions

Standard Germination Tests are used to determine if a microbe colonizing the interior of a seed protects maize against cold stress during germination. Briefly, 400 seeds, the interiors of which are colonized by microbial strains are placed in between wet brown paper towels (8 replicates with 50 seeds each). An equal number of seeds obtained from control plants that lack the microbe is treated in the same way. The paper towels are placed on top of 1×2 ft plastic trays and maintained in a growth chamber set at 16:8 hour light:dark cycle, 70% humidity, and at least 120 µE/m2/s light intensity for 7 days. A range of low temperatures (from 0° C. to 10° C., with increments of 2 degrees per assay) is tested to assess the germination of microbe-colonized seeds at each temperature. The proportion of seeds that germinate successfully is compared between the seeds coming from microbe-colonized plants and those coming from controls.

Testing for Germination Enhancement in High Salt Concentrations

Germination experiments are conducted in 90 mm diameter petri dishes. Replicates consist of a Petri dish, watered with 10 mL of the appropriate solution and 20 seeds floating in the solution. 400 seeds, the interiors of which are colonized by microbial strains, and 400 seed controls (lacking the microbial strains) are tested in this way (40 petri dishes total). To prevent large variations in salt concentration due to evaporation, dishes are sealed with parafilm and the saline solutions are renewed weekly by pouring out the existing saline solution in the petri dish and adding the same amount of fresh solution. A range of saline solutions (100-500 mM NaCl) is tested for to assess the germination of microbe-colonized seeds at varying salt levels. Petri dishes are maintained in a growth chamber set at 25° C., 16:8 hour light:dark cycle, 70% humidity, and at least 120 µE/m2/s light intensity. The proportion of seeds that germinates successfully after two weeks is compared between the seeds coming from inoculated plants and those coming from controls.

Testing for Germination Enhancement in Soils with High Metal Content

Standard Germination Tests are used to determine if a microbe colonizing the interior of a seed protects maize against stress due to high soil metal content during germination. Briefly, 400 seeds of maize, the interiors of which are colonized by microbial strains, are placed in between wet brown paper towels (8 replicates with 50 seeds each). An equal number of seeds obtained from control plants that lack the microbe (microbe-free) is treated in the same way. The paper towels are placed on top of 1×2 ft plastic trays with holes to allow water drainage. The paper towels are covered with an inch of sterile sand. For each metal to be tested, the sand needs to be treated appropriately to ensure the release and bioavailability of the metal. For example, in the case of aluminum, the sand is watered with pH 4.0+~1 g/Kg soil $Al^{+3}$ (~621 uM). The trays are maintained in a growth chamber set at 25° C. and 70% humidity for 7 days. The proportion of seeds that germinates successfully is compared between the seeds coming from microbe-colonized plants and those coming from controls.

Testing for Growth Promotion in Growth Chamber in Normal Conditions

Soil is made from a mixture of 60% Sunshine Mix #5 (Sun Gro; Bellevue, Wash., USA) and 40% vermiculite. To determine if a particular microbe colonizing the interior of seeds is capable of promoting plant growth under normal conditions, 24 pots are prepared in two 12-pot no-hole flat trays with 28 grams of dry soil in each pot, and 2 L of filtered water is added to each tray. The water is allowed to soak into the soil and the soil surface is misted before seeding. For each seed-microbe combination, 12 pots are seeded with 3-5 seeds colonized by the microbe and 12 pots are seeded with 3-5 seeds lacking the microbe (microbe-free plants). The seeded pots are covered with a humidity dome and kept in the dark for 3 days, after which the pots are transferred to a growth chamber set at 25° C., 16:8 hour light:dark cycle, 70% humidity, and at least 120 µE/m2/s light intensity. The humidity domes are removed on day 5, or when cotyledons are fully expanded. After removal of the domes, each pot is irrigated to saturation with 0.5× Hoagland's solution, then allowing the excess solution to drain. Seedlings are then thinned to 1 per pot. In the following days, the pots are irrigated to saturation with filtered water, allowing the excess water to drain after about 30 minutes of soaking, and the weight of each 12-pot flat tray is recorded weekly. Canopy area is measured at weekly intervals. Terminal plant height, average leaf area and average leaf length are measured at the end of the flowering stage. The plants are allowed to dry and seed weight is measured. Significance of difference in growth between microbe-colonized plants and controls lacking the microbe is assessed with the appropriate statistical test depending on the distribution of the data at $p<0.05$.

Testing for Growth Promotion in Growth Chamber Under Biotic Stress

Soil is made from a mixture of 60% Sunshine Mix #5 (Sun Gro; Bellevue, Wash., USA) and 40% vermiculite. To determine if a particular microbe colonizing the interior of seeds is capable of promoting plant growth in the presence of biotic stress, 24 pots are prepared in two 12-pot no-hole flat trays with 28 grams of dry soil in each pot, and 2 L of filtered water is added to each tray. The water is allowed to soak into the soil before planting. For each seed-microbe combination test, 12 pots are seeded with 3-5 seeds colonized by the microbe and 12 pots are seeded with 3-5 seeds lacking the microbe (microbe-free plants). The seeded pots are covered with a humidity dome and kept in the dark for 3 days, after which the pots are transferred to a growth chamber set at 25° C., 16:8 hour light:dark cycle, 70% humidity, and at least 120 µE/m2/s light intensity. The humidity domes are removed on day 5, or when cotyledons are fully expanded. After removal of the domes, each pot is irrigated to saturation with 0.5× Hoagland's solution, allowing the excess solution to drain. Seedlings are then thinned to 1 per pot. In the following days, the pots are irrigated to saturation with filtered water, allowing the excess water to drain after about 30 minutes of soaking.

Several methods of inoculation are used depending on the lifestyle of the pathogen. For leaf pathogens (e.g., *Pseudomonas syringeae* or *Colletotrichum graminicola*), a suspension of cells for bacteria ($10^8$ cell/mL) or spores for fungi ($10^7$ spores/mL) is applied with an applicator on the adaxial surface of each of the youngest fully expanded leaves. Alternatively for fungal pathogens that do not form conidia easily, two agar plugs containing mycelium (~4 mm in diameter) are attached to the adaxial surface of each of the youngest leaves on each side of the central vein. For vascular pathogens (e.g., *Pantoea stewartii* or *Fusarium moniliforme*), the suspension of cells or spores is directly introduced into the vasculature (5-10 µL) through a minor injury inflected with a sterile blade. Alternatively, the seedlings can be grown hydroponically in the cell/spore or mycelium suspension. To test the resilience of the plant-microbe combination against insect stresses, such as thrips or aphids, plants are transferred to a specially-designated growth chamber containing the insects. Soil-borne insect or nematode pathogens are mixed into or applied topically to the potting soil. In all cases, care is taken to contain the fungal, insect, nematode or other pathogen and prevent release outside of the immediate testing area.

The weight of each 12-pot flat tray is recorded weekly. Canopy area is measured at weekly intervals. Terminal plant height, average leaf area and average leaf length are measured at the cease of flowering. The plants are allowed to dry and seed weight is measured. Significance of difference in growth between microbe-colonized plants and controls lacking the microbe is assessed with the appropriate statistical test depending on the distribution of the data at $p<0.05$.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11166465B2). An electronic copy of the "Sequence Listing" will also be available from the USPTO upon request and payment of the fee set forth in 37 CFR 1.19(b)(3).

What is claimed is:

1. A method of treating a cereal agricultural plant, comprising mechanically or manually contacting a cereal agricultural plant with an agricultural formulation comprising an agriculturally acceptable carrier and a purified bacterial population that comprises a seed bacterial endophyte of the genus *Enterobacter* that is heterologous to a seed of the cereal agricultural plant, and has a 16S nucleic acid sequence that is at least 99% identical to a 16S nucleic acid sequence selected from the group consisting of SEQ ID NO: 541, 595, 540, and 550, and is capable of producing an auxin or acetoin, wherein the endophyte is heterologously disposed to the cereal agricultural plant in an amount effective to colonize the contacted cereal plant, wherein the contacted cereal plant has increased growth as compared to a reference cereal plant grown under the same conditions.

2. The method of claim 1, wherein the seed bacterial endophyte is obtainable from an interior seed compartment.

3. The method of claim 1, wherein the seed bacterial endophyte is obtainable from an exterior surface of a seed.

4. The method of claim 1, wherein the seed bacterial endophyte is obtainable from a different cultivar, variety or crop as compared to the seed of the cereal agricultural plant.

5. The method of claim 1, wherein the seed bacterial endophyte colonizes the roots of the contacted cereal plant.

6. The method of claim 1, wherein the seed bacterial population includes two or more bacterial endophytes.

7. The method of claim 1, wherein the seed bacterial endophyte is obtained from rice seed, maize seed, wheat seed, or barley seed.

8. The method of claim 1, wherein the agricultural formulation further comprises a purified fungal population.

9. The method of claim 1, wherein the increased growth occurs under conditions of biotic stress.

10. The method of claim 9, wherein the biotic stress is selected from the group consisting of nematode stress, insect herbivory stress, fungal pathogen stress, bacterial pathogen stress, and viral pathogen stress.

11. The method of claim 1, wherein the contacted cereal plant has a larger amount of lateral roots and root-hairs as compared to the reference cereal plant.

12. The method of claim 1, wherein the contacted cereal plant has increased shoot length as compared to the reference cereal plant.

13. The method of claim 1, wherein the contacted cereal plant has increased seedling weight as compared to the reference cereal plant.

14. The method of claim 1, wherein the contacted cereal plant has increased shoot biomass as compared to the reference cereal plant.

15. The method of claim 1, wherein the contacted cereal plant has increased nitrogen use efficiency as compared to the reference cereal plant.

16. The method of claim 1, wherein the contacted cereal plant has increased root biomass as compared to the reference cereal plant.

17. The method of claim 1, wherein the seed bacterial endophyte of the genus *Enterobacter* has a 16S nucleic acid sequence that is 100% identical to the 16S nucleic acid sequence selected from the group consisting of SEQ ID NO: 541, 595, 540, and 550.

18. The method of claim 1, wherein the effective amount is at least $10^2$ CFU/ml in a liquid formulation or $10^3$ CFU/g in a non-liquid formulation.

19. The method of claim 1, wherein the cereal agricultural plant is a seedling.

20. The method of claim 1, wherein the method of contacting the cereal agricultural plant with the formulation is selected from the group consisting of spraying, immersing, coating, dusting, encapsulating, and dipping.

* * * * *